US012583898B2

(12) United States Patent
Kley et al.

(10) Patent No.: US 12,583,898 B2
(45) **Date of Patent: *Mar. 24, 2026**

(54) THERAPEUTIC INTERFERON ALPHA 1 PROTEINS

(71) Applicants: Orionis Biosciences, Inc., Waltham, MA (US); Orionis Biosciences BV, Zwijnaarde (BE)

(72) Inventors: Nikolai Kley, Waltham, MA (US); Erik Depla, Zwijnaarde (BE); Lennart Zabeau, Zwijnaarde (BE); Jan Tavernier, Zwijnaarde (BE)

(73) Assignees: Orionis Biosciences, Inc., Waltham, MA (US); Orionis Biosciences BV, Zwijnaarde (BE)

( * ) Notice: Subject to any disclaimer, the term of this patent is extended or adjusted under 35 U.S.C. 154(b) by 71 days.

This patent is subject to a terminal disclaimer.

(21) Appl. No.: 17/813,985

(22) Filed: Jul. 21, 2022

(65) Prior Publication Data

US 2023/0103946 A1 Apr. 6, 2023

Related U.S. Application Data

(63) Continuation of application No. 16/832,995, filed on Mar. 27, 2020, now Pat. No. 11,440,943.

(60) Provisional application No. 62/906,431, filed on Sep. 26, 2019, provisional application No. 62/825,569, filed on Mar. 28, 2019.

(51) Int. Cl.

| | |
|---|---|
| ***C07K 14/56*** | (2006.01) |
| ***A61K 38/00*** | (2006.01) |
| ***C07K 16/28*** | (2006.01) |

(52) U.S. Cl.

CPC .......... *C07K 14/56* (2013.01); *C07K 16/2818* (2013.01); *C07K 16/2827* (2013.01); *C07K 16/2851* (2013.01); *C07K 16/2887* (2013.01); *A61K 38/00* (2013.01); *C07K 2317/22* (2013.01); *C07K 2317/24* (2013.01); *C07K 2317/31* (2013.01); *C07K 2317/52* (2013.01); *C07K 2317/569* (2013.01); *C07K 2319/30* (2013.01); *C07K 2319/70* (2013.01)

(58) Field of Classification Search

None

See application file for complete search history.

(56) References Cited

U.S. PATENT DOCUMENTS

| | | | | |
|---|---|---|---|---|
| 5,661,009 | A | 8/1997 | Stabinsky | |
| 5,914,254 | A | 6/1999 | Mascarenhas et al. | |
| 8,980,267 | B2 | 3/2015 | Grewal et al. | |
| 9,139,634 | B2 | 9/2015 | Morrison et al. | |
| 9,492,562 | B2 | 11/2016 | Tavernier et al. | |
| 9,534,056 | B2 | 1/2017 | Grewal et al. | |
| 9,732,135 | B2 | 8/2017 | Tavernier et al. | |
| 9,878,014 | B2 | 1/2018 | Tavernier et al. | |
| 9,914,759 | B2 | 3/2018 | Tavernier et al. | |
| 9,932,409 | B2 | 4/2018 | Tavernier et al. | |
| 10,034,919 | B2 | 7/2018 | Tavernier et al. | |
| 10,035,835 | B2 | 7/2018 | Tavernier et al. | |
| 10,072,059 | B2 | 9/2018 | Tavernier et al. | |
| 10,407,480 | B2 | 9/2019 | Tavernier et al. | |
| 10,640,542 | B2 | 5/2020 | Tavernier et al. | |
| 11,440,943 | B2 * | 9/2022 | Kley | C07K 16/2851 |
| 2002/0193569 | A1 | 12/2002 | Hanna | |
| 2010/0028341 | A1 | 2/2010 | Hermans et al. | |
| 2010/0172868 | A1 | 7/2010 | Morrison et al. | |
| 2010/0297076 | A1 | 11/2010 | Morrison et al. | |
| 2011/0020273 | A1 | 1/2011 | Chang et al. | |
| 2011/0081341 | A1 | 4/2011 | Honjo et al. | |
| 2011/0104112 | A1 | 5/2011 | Morrison et al. | |
| 2011/0224407 | A1 | 9/2011 | Langer et al. | |
| 2011/0274658 | A1 | 11/2011 | Silver et al. | |
| 2012/0288477 | A1 | 11/2012 | Wang | |
| 2013/0183298 | A1 | 7/2013 | Le et al. | |
| 2013/0230517 | A1 | 9/2013 | Grewal et al. | |
| 2014/0248238 | A1 | 9/2014 | Wilson, Jr. et al. | |
| 2014/0348789 | A1 | 11/2014 | Tavernier et al. | |
| 2015/0139951 | A1 | 5/2015 | Grewal et al. | |
| 2018/0186894 | A1 | 7/2018 | Tavernier et al. | |
| 2018/0333465 | A1 | 11/2018 | Tavernier et al. | |
| 2018/0334488 | A1 | 11/2018 | Tavernier et al. | |
| 2018/0334489 | A1 | 11/2018 | Tavernier et al. | |
| 2019/0010199 | A1 | 1/2019 | Tavernier et al. | |
| 2019/0023795 | A1 | 1/2019 | Tveita | |
| 2019/0071500 | A1 | 3/2019 | Kley et al. | |
| 2019/0092871 | A1 | 3/2019 | Tavernier et al. | |

(Continued)

FOREIGN PATENT DOCUMENTS

| | | | |
|---|---|---|---|
| CN | 103319608 | B | 8/2014 |
| EP | 1739090 | A2 | 1/2007 |

(Continued)

OTHER PUBLICATIONS

Goel et al. Plasticity within the Antigen-Combining Site May Manifest as Molecular Mimicry in the Humoral Immune Response. 1 J. Immunol. 173(12)7358-7367, 2004.*

(Continued)

*Primary Examiner* — Nora M Rooney

(74) *Attorney, Agent, or Firm* — Morgan, Lewis & Bockius LLP

(57) ABSTRACT

The present invention relates, in part, to chimeric proteins or chimeric protein complexes, such as Fc-based chimeric protein complexes, comprising interferon alpha 1, or a variant thereof, and their use as therapeutic agents.

9 Claims, 41 Drawing Sheets

Specification includes a Sequence Listing.

(56) References Cited

U.S. PATENT DOCUMENTS

| | | | |
|---|---|---|---|
| 2019/0144553 | A1 | 5/2019 | Kley et al. |
| 2019/0194284 | A1 | 6/2019 | Kley et al. |
| 2019/0202934 | A1 | 7/2019 | Tavernier et al. |
| 2019/0351021 | A1 | 11/2019 | Tavernier et al. |
| 2019/0352406 | A1 | 11/2019 | Tavernier et al. |
| 2019/0367575 | A1 | 12/2019 | Tavernier et al. |
| 2019/0367604 | A1 | 12/2019 | Kley et al. |
| 2020/0071414 | A1 | 3/2020 | Kley et al. |
| 2020/0087411 | A1 | 3/2020 | Kley et al. |
| 2020/0231674 | A1 | 7/2020 | Kley et al. |

FOREIGN PATENT DOCUMENTS

| | | | |
|---|---|---|---|
| EP | 2343081 | A1 | 7/2011 |
| WO | WO 91/02754 | | 3/1991 |
| WO | WO 2003/033720 | A2 | 4/2003 |
| WO | 2006/004959 | A2 | 1/2006 |
| WO | WO 2006/053883 | A1 | 5/2006 |
| WO | WO 2006/115800 | A2 | 11/2006 |
| WO | WO 2006/120580 | A2 | 11/2006 |
| WO | WO 2007/110231 | A2 | 10/2007 |
| WO | WO 2008/014612 | A1 | 2/2008 |
| WO | WO 2008/124086 | A2 | 10/2008 |
| WO | WO 2009/003145 | A1 | 12/2008 |
| WO | WO 2009/039409 | A1 | 3/2009 |
| WO | WO 2010/036918 | A2 | 4/2010 |
| WO | WO 2010/066740 | A1 | 6/2010 |
| WO | WO 2011/020783 | A2 | 2/2011 |
| WO | WO 2011/029870 | A1 | 3/2011 |
| WO | WO 2012/170072 | A1 | 12/2012 |
| WO | WO 2013/059885 | A2 | 5/2013 |
| WO | WO 2013/107791 | A1 | 7/2013 |
| WO | WO 2013/134138 | A1 | 9/2013 |
| WO | WO 2014/164680 | A1 | 10/2014 |
| WO | WO 2015/007520 | A1 | 1/2015 |
| WO | WO 2015/007536 | A1 | 1/2015 |
| WO | WO 2015/007542 | A1 | 1/2015 |
| WO | WO 2015/007903 | A1 | 1/2015 |
| WO | WO 2017/077382 | A1 | 5/2017 |
| WO | 2017/134301 | A1 | 8/2017 |
| WO | 2017/134305 | A1 | 8/2017 |
| WO | WO 2017/134302 | A2 | 8/2017 |
| WO | WO 2017/194782 | A2 | 11/2017 |
| WO | WO 2019/032662 | A1 | 2/2019 |
| WO | WO 2019/032663 | A1 | 2/2019 |
| WO | WO 2019/148089 | A1 | 8/2019 |
| WO | WO 2019/152979 | A1 | 8/2019 |
| WO | WO 2019/191519 | A1 | 10/2019 |
| WO | WO 2020/033646 | A1 | 2/2020 |
| WO | WO 2020/097350 | A1 | 5/2020 |
| WO | WO 2020/132189 | A1 | 6/2020 |

OTHER PUBLICATIONS

Kahn et al. 'Adjustable Locks and Flexible Keys: Plasticity of Epitope-Paratope Interactions in Germline Antibodies.' J. Immunol. 192:5398-5405, 2014.*

Poosarla et al. 'Computational De Novo Design of Antibodies Binding to a Peptide With High Affinity.' Biotech. Bioeng. 114(6): 1331-1342, 2017.*

Acres, et al., "Fusokine Interleukin-2/Interleukin-18, a Novel Potent Innate and Adaptive Immune Stimulator with Decreased Toxicity," Cancer Res., vol. 65, No. 20, pp. 9536-9546, 2005.

Baba, et al., "Identification of CCR6, the Specific Receptor for a Novel Lymphocyte-Directed CC Chemokine LARC," The Journal of Biological Chemistry, vol. 272, No. 23, pp. 14893-14898, 1997.

Bansal, et al., "Targeted Recombinant Fusion Proteins of IFNγ and Mimetic IFNγ with PDGFβR Bicyclic Peptide Inhibits Liver Fibrogenesis in Vivo," PLOS One, vol. 9, No. 2, 10 pages, 2014.

Barbara, et al., "Dissociation of TNF-α cytotoxic and proinflammatory activities by p55 receptor-and p75 receptor-selective TNF-α mutants," EMBO Journal, vol. 13, No. 4, pp. 843-850, 1994.

Beilharz, et al., "Antiviral and Antiproliferative Activities of Interferon-α: The Role of Cysteine Residues," Journal of Interferon Research, vol. 6, pp. 677-685, 1986.

Bork, et al., "Go hunting in sequence databases but watch out for the traps." Trends in Genetics, vol. 12, pp. 125-427, 1996.

Bork, "Powers and Pitfalls in Sequence Analysis: The 70% Hurdle," Genome Research, vol. 10, pp. 398-400, 2000.

Boschert, et al., "Single chain TNF derivatives with individually mutated receptor binding sites reveal differential stoichiometry of ligand receptor complex formation for TNFR1 and TNFR2," Cellular Signalling 22 (7):1088-1096, 2010.

Bremer, et al., "Superior activity of fusion protein scFvRit:sFasL over cotreatment with rituximab and Fas agonists," Cancer Res. 68: 597-604, 2008.

Camacho, et al., "Structure of an Interleukin-1β Mutant With Reduced Bioactivity Shows Multiple Subtle Changes in Conformation That Affect Protein-Protein Recognition," Biochemistry, vol. 32, No. 34, pp. 8749-8757, 1993.

Coulstock, et al., "Liver-Targeting of Interferon-Alpha with Tissue Specific Domain Antibodies," PLOS ONE, vol. 8, No. 2, pp. 1-11, 2013.

De Bruyn, et al., "Antibody-Based Fusion Proteins to Target Death Receptors in Cancer," Cancer Letters, vol. 332, pp. 175-183, 2013.

Deffar, et al., "Nanobodies—The New Concept in Antibody Engineering," African Journal of Biotechnology, vol. 8, No. 12, pp. 2645-2652, 2009.

Dijkmans, et al., "Murine Interferon-γ Interleukin-1 Fusion Proteins Used as Antigens for the Generation of Hybridomas Producing Monoclonal Anti-Interleukin-1 Antibodies," Cytokine, vol. 3, No. 2, pp. 134-140, 1991.

Dimitrov, "Engineered CH2 Domains (Nanoantibodies)," mAbs, Landes Bioscience, vol. 1, No. 1, pp. 26-28, 2009.

Ebbinghaus, et al., "Engineered vascular-targeting antibody-interferon-gamma fusion protein for cancer therapy," Int. J. Cancer: vol. 116, No. 2, pp. 304-313, 2005.

Frey, et al., "Antibody-Based Targeting of Interferon-Alpha to the Tumor Neovasculature: A Critical Evaluation," ntegrative Biology, vol. 3, pp. 468-478, 2011.

Garcin, et al., "High Efficiency cell-specific targeting of cytokine activity," Nature Communications, vol. 5, No. 8, 9 pages, 2014.

Garlanda, et al., "The Interleukin-1 Family: Back to the Future," Immunity, 39 (6): pp. 1003-1018, Dec. 12, 2013.

Guo, et al., "Empowering therapeutic antibodies with IFN-α for cancer immunotherapy," PLOS ONE, 13 pages, Aug. 8, 2019.

Hemmerle, et al., "The Dose-Dependent Tumor Targeting of Antibody-IFN Fusion Proteins Reveals an Unexpected Receptor-Trapping Mechanism In Vivo," Cancer Immunology Research, vol. 2, No. 6, pp. 559-568, 2014.

Holler, et al., "Two Adjacent Trimeric Fas Ligands are Required for Fas Signaling and Formation of a Death-Inducing Signaling Complex," Molecular and Cellular Biology, vol. 23, No. 4, pp. 1428-1440, 2003.

Huang, et al., "A Trimeric Anti-HER2/neu ScFv and Tumor Necrosis Factor-[alpha] Fusion Protein Induces HER2/Neu Signaling and Facilitates Repair of Injured Epithelia," The Journal of Pharmacology and Experimental Therapeutics, vol. 316, No. 3, pp. 983-991, 2006.

International Search Report & Written Opinion, PCT Application No. PCT/EP2013/050787, dated Jun. 6, 2017, 4 pages.

International Search Report & Written Opinion, PCT Application No. PCT/EP2017/065143, dated Jul. 11, 2017, 8 pages.

International Search Report & Written Opinion, PCT Application No. PCT/EP2017/061544, dated Oct. 20, 2017, 21 pages.

International Search Report & Written Opinion, PCT Appl. No. PCT/EP2017/077193, dated Mar. 21, 2018, 11 pages.

International Search Report & Written Opinion, PCT Appl. No. PCT/US2018/016857, dated Apr. 24, 2018, 11 pages.

International Search Report & Written Opinion, PCT Appl. No. PCT/US2020/025411, dated Jul. 9, 2020, 12 pages.

Krippner-Heidenreich, et al., "Single-Chain TNF, a TNF Derivative with Enhanced Stability and Antitumoral Activity," The Journal of Immunology, vol. 180, pp. 8176-8183, 2008.

(56) References Cited

OTHER PUBLICATIONS

Loetscher, et al., "Human Tumor Necrosis Factor α (TNFα) Mutants with Exclusive Specificity for 55-kDA or 75-kDa TNF Receptors," Journal of Biological Chemistry, American Society For Biochemistry and Molecular Biology, US, vol. 268, No. 35, pp. 26350-26357, 1993.
Masci, et al., "New and Modified Interferon alfas: Preclinical and Clinical Data," Current Oncology Reports, vol. 5, pp. 108-113, 2003.
Ngo, et al., "Computational Complexity, Protein Structure Prediction, and the Levinthal Paradox. The Protein Folding Problem and Tertiary Structure Prediction," Edited by: Mertz et al., (Birkhauser, Boston), pp. 491-495, 1994.
Pan, et al., "Mutation of the IFNAR-1 Receptor Binding Site of Human IFN-α2 Generates Type I IFN Competitive Antagonists," Biochemistry, vol. 47, pp. 12018-12027, 2008.
Patris, et al., "Nanoimmunoassay onto a screen printed electrode for HER2 breast cancer biomarker determination," Talanta, 2014, vol. 130, pp. 164-170, 2014.
Penafuerte, et al., "The Human Ortholog of Granulocyte Macrophage Colony-Stimulating Factor and Interleukin-2 fusion Protein Induces Potent Ex Vivo Natural Killer Cell Activation and Maturation," Cancer Res, vol. 69, No. 23, pp. 9020-9028, 2009.
Piehler, et al., "New Structural and Functional Aspects of the Type I Inteferon-Receptor Interaction Revealed by Comprehensive Mutational Analysis of the Binding Interface," Journal of Biological Chemistry, vol. 275, No. 51, pp. 40425-40433, Dec. 22, 2000.
Rafei, et al., "A MCP1 Fusokine with CCR2-Specific Tumoricidal Activity," Molecular Cancer, vol. 10, No. 121, pp. 1-11, 2011.
Rafei, et al., "An Engineered GM-CSF-CCL2 Fusokine Is A Potent Inhibitor of CCR2-Driven Inflammation as Demonstrated in a Murine Model of Inflammatory Arthritis," The Journal of Immunology, vol. 183, pp. 1759-1766, 2009.
Roisman, et al., "Structure of the Interferon-Receptor Complex Determined by Distant Constraints from Double Mutant Cycles and Flexible Docking," PNAS, vol. 98, No. 23, pp. 13231-13236, 2001.
Rovero, et al., "Insertion of the DNA for the 163-171 Peptide of IL 1 II Enables a DNA Vaccine Encoding $p185^{neu}$ to inhibit Mammary Carcinogenesis in Her-2/neu Transgenic BALB/c Mice," Gene Therapy, vol. 8, pp. 447-452, 2001.
Runkel, et al., "Systematic Mutational Mapping of Sites on Human Interferon-β-1a That Are Important for Receptor Binding and Functional Activity," Biochemistry, vol. 39, No. 10, pp. 2538-2551, 2000.
Schutyser, et al., "The CC Chemokine CCL20 and its Receptor CCR6," Cytokine & Growth Factor Reviews, vol. 14, pp. 409-426, 2003.
Vaneycken, et al., "Preclinical Screening of Anti-HER2 Nanobodies for Molecular Imaging of Breast Cancer", The ASEB Journal, vol. 25, pp. 2433-2446, 2011.
Van Pesch, et al., "Characterization of the Murine Alpha Interferon Gene Family," Journal of Virology, vol. 78, No. 15, pp. 8219-8228, Aug. 2004.
Weber, et al., "Single Amino Acid Changes that Render Human IFN-α2 Biologically Active on Mouse Cells," The EMBO Journal, vol. 6, No. 3, pp. 591-598, 1987.
Wells, "Additivity of Mutational Effects in Proteins," Biochemistry, vol. 29, No. 37, pp. 8509-8517, 1990.
Wesolowski, et al., "Single Domain Antibodies: Promising Experimental and Therapeutic Tools in Infection and Immunity," Med. Microbiol. Immunol., vol. 198, pp. 157-174, 2009.
Yan, et al., "Definition of the Interferon-α Receptor-binding Domain on the TYK2 Kinase," The Journal of Biological Chemistry, vol. 273, No. 15, Feb. 13, 1998, 7 pages.
Franciane Paul, "Ciblage de l'activite de l'interferon alpha: de la preuve de concept a l'activite biologique", Apr. 20, 2017, English Abstract on p. 6.

* cited by examiner

Fig. 2E
Fig. 2F
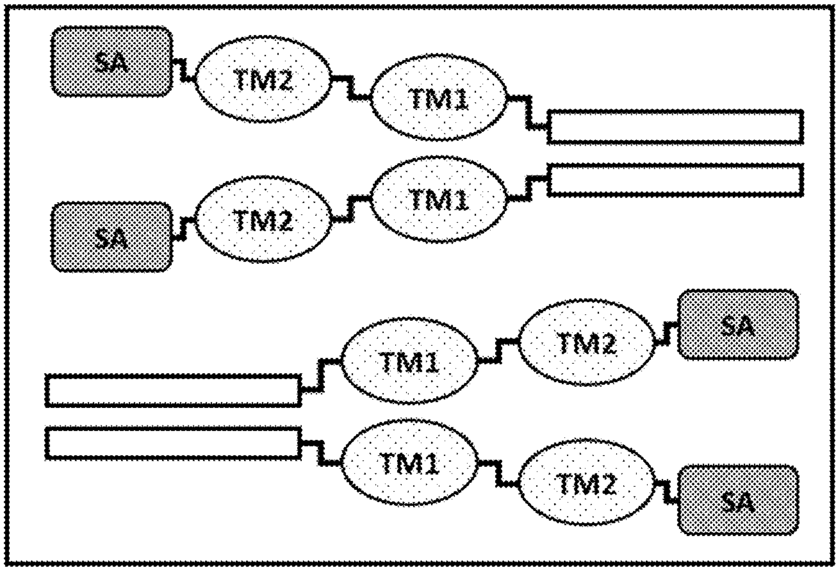
Fig. 2G
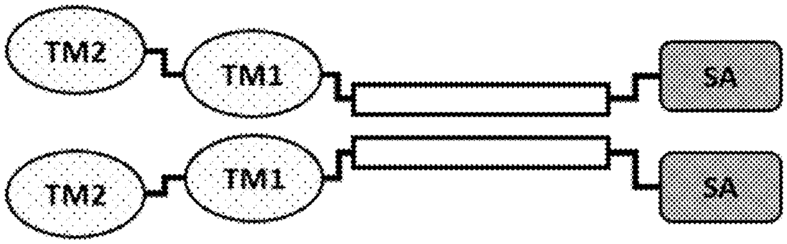
Fig. 2H
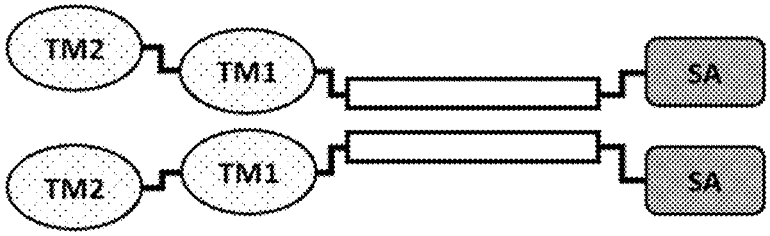

*IFNa2*

*R1CHCL50-Fc3 + Fc4-hIFNa1_C86S*
*(P-1479 + P-2213)*

*R1CHCL50-Fc3 + Fc4-hIFNa1_C86Y*
*(P-1479 + P-2216)*

*R1CHCL50-Fc3 + Fc4-hIFNa1_C86S_A146G*
*(P-1479 + P-2214)*

SEQUENCE LISTING

```
Sequence total quantity: 303
SEQ ID NO: 1            moltype = AA  length = 166
FEATURE                 Location/Qualifiers
REGION                  1..166
                        note = Synthetic Sequence (wild type IFN-alpha1)
source                  1..166
                        mol_type = protein
                        organism = synthetic construct
SEQUENCE: 1
CDLPETHSLD NRRTLMLLAQ MSRISPSSCL MDRHDFGFPQ EEFDGNQFQK APAISVLHEL  60
IQQIFNLFTT KDSSAAWDED LLDKFCTELY QQLNDLEACV MQEERVGETP LMNADSILAV  120
KKYFRRITLY LTEKKYSPCA WEVVRAEIMR SLSLSTNLQE RLRRKE                 166

SEQ ID NO: 2            moltype =   length =
SEQUENCE: 2
000

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype =   length =
SEQUENCE: 6
000

SEQ ID NO: 7            moltype = AA  length = 447
FEATURE                 Location/Qualifiers
REGION                  1..447
                        note = Synthetic Sequence
source                  1..447
                        mol_type = protein
                        organism = synthetic construct
SEQUENCE: 7
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 8            moltype = AA  length = 218
FEATURE                 Location/Qualifiers
REGION                  1..218
                        note = Synthetic Sequence
source                  1..218
                        mol_type = protein
                        organism = synthetic construct
SEQUENCE: 8
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 9            moltype = AA  length = 440
FEATURE                 Location/Qualifiers
REGION                  1..440
                        note = Synthetic Sequence
source                  1..440
                        mol_type = protein
                        organism = synthetic construct
SEQUENCE: 9
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
```

-continued

```
MHEALHNHYT QKSLSLSLGK                                         440

SEQ ID NO: 10          moltype = AA  length = 214
FEATURE                Location/Qualifiers
REGION                 1..214
                       note = Synthetic Sequence
source                 1..214
                       mol_type = protein
                       organism = synthetic construct
SEQUENCE: 10
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                         214

SEQ ID NO: 11          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 11
EIVLTQSPSS LSASVGDRVT ITCSARSSVS YMHWYQQKPG KAPKLLIYRT SNLASGVPSR  60
FSGSGSGTDF TLTINSLQPE DFATYYCQQR SSFPLTFGGG TKLEIK             106

SEQ ID NO: 12          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 12
EIVLTQSPSS LSASVGDRVT ITCSARSSVS YMHWFQQKPG KAPKLWIYRT SNLASGVPSR  60
FSGSGSGTDY TLTINSLQPE DFATYYCQQR SSFPLTFGGG TKLEIK             106

SEQ ID NO: 13          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 13
EIVLTQSPSS LSASVGDRVT ITCSARSSVS YMHWFQQKPG KAPKLWIYRT SNLASGVPSR  60
FSGSGSGTDY CLTINSLQPE DFATYYCQQR SSFPLTFGGG TKLEIK             106

SEQ ID NO: 14          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 14
EIVLTQSPSS LSASVGDRVT ITCSARSSVS YMHWFQQKPG KAPKLWIYRT SNLASGVPSR  60
FSGSGSGTSY CLTINSLQPE DFATYYCQQR SSFPLTFGGG TKLEIK             106

SEQ ID NO: 15          moltype = AA  length = 117
FEATURE                Location/Qualifiers
REGION                 1..117
                       note = Synthetic Sequence
source                 1..117
                       mol_type = protein
                       organism = synthetic construct
SEQUENCE: 15
QVQLVQSGSE LKKPGASVKI SCKASGYSFS NYGMNWVRQA PGQGLQWMGW INTDSGESTY  60
AEEFKGRFVF SLDTSVSTAY LQITSLTAED TGMYFCAKVG YDALDYWGQG TLVTVSS     117

SEQ ID NO: 16          moltype = AA  length = 117
FEATURE                Location/Qualifiers
REGION                 1..117
                       note = Synthetic Sequence
source                 1..117
                       mol_type = protein
                       organism = synthetic construct
SEQUENCE: 16
QVQLVQSGSE LKKPGASVKI SCKASGYTFT NYGMNWVRQA PGQGLQWMGW INTDSGESTY  60
```

-continued

```
AEEFKGRFVF SLDTSVSTAY LQITSLTAED TGMYFCAKVG YDALDYWGQG TLVTVSS     117

SEQ ID NO: 17          moltype = AA  length = 117
FEATURE                Location/Qualifiers
REGION                 1..117
                       note = Synthetic Sequence
source                 1..117
                       mol_type = protein
                       organism = synthetic construct
SEQUENCE: 17
QVQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 18          moltype = AA  length = 117
FEATURE                Location/Qualifiers
REGION                 1..117
                       note = Synthetic Sequence
source                 1..117
                       mol_type = protein
                       organism = synthetic construct
SEQUENCE: 18
QIQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 19          moltype = AA  length = 117
FEATURE                Location/Qualifiers
REGION                 1..117
                       note = Synthetic Sequence
source                 1..117
                       mol_type = protein
                       organism = synthetic construct
SEQUENCE: 19
QIQLVQSGSE LKKPGASVKI SCKASGYTFT NYGMNWVKQA PGQGLKWMGW INTDSGESTY  60
AEEFKGRFAF SLDTSVNTAY LQITSLNAED TGMYFCVRVG YDALDYWGQG TLVTVSS     117

SEQ ID NO: 20          moltype = AA  length = 254
FEATURE                Location/Qualifiers
REGION                 1..254
                       note = Synthetic Sequence
source                 1..254
                       mol_type = protein
                       organism = synthetic construct
SEQUENCE: 20
LFTVTVPKEL YIIEHGSNVT LECNFDTGSH VNLGAITASL QKVENDTSPH RERATLLEEQ  60
LPLGKASFHI PQVQVRDEGQ YQCIIIYGVA WDYKYLTLKV KASYRKINTH ILKVPETDEV  120
ELTCQATGYP LAEVSWPNVS VPANTSHSRT PEGLYQVTSV LRLKPPPGRN FSCVFWNTHV  180
RELTLASIDL QSQMEPRTHP TWLLHIFIPF CIIAFIFIAT VIALRKQLCQ KLYSSKDTTK  240
RPVTTTKREV NSAI                                                    254

SEQ ID NO: 21          moltype = AA  length = 453
FEATURE                Location/Qualifiers
REGION                 1..453
                       note = Synthetic Sequence
source                 1..453
                       mol_type = protein
                       organism = synthetic construct
SEQUENCE: 21
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT WEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                                453

SEQ ID NO: 22          moltype = AA  length = 22
FEATURE                Location/Qualifiers
REGION                 1..22
                       note = Synthetic Sequence
SITE                   8
                       note = MISC_FEATURE - A branch with sequence SNTSESF
source                 1..22
                       mol_type = protein
                       organism = synthetic construct
SEQUENCE: 22
SNTSESFKFR VTQLAPKAQI KE                                           22

SEQ ID NO: 23          moltype = AA  length = 119
```

```
FEATURE                Location/Qualifiers
REGION                 1..119
                       note = Synthetic Sequence
source                 1..119
                       mol_type = protein
                       organism = synthetic construct
SEQUENCE: 23
EVQLQQSGPV LVKPGASVKM SCKASGYTFT DYYMNWVKQS HGKSLEWIGN INPYNGGTTY  60
NQKFKGKATL TVDKSSRTAY MEINSLTSED SAVYYCARGR IYDGSLDYWG QGTALTVSS   119

SEQ ID NO: 24          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 24
DIQMTQFPSS LCASQGGKVT VTCKASQDIN NYMAWYQHKP GKGPRLLIHY TSTLLSGIPS  60
RFSGSGSGRD YSFSISNLEP EDIATYYCLQ YDNLWTFGGG TKLEIK                 106

SEQ ID NO: 25          moltype = AA  length = 116
FEATURE                Location/Qualifiers
REGION                 1..116
                       note = Synthetic Sequence
source                 1..116
                       mol_type = protein
                       organism = synthetic construct
SEQUENCE: 25
QVQLQQSGAE LAKPGASVRL SCKASGYTFT NYWMHWVKQR PGQGLEWIGH INPSSGFTTY  60
NQNFKDKATL TADKSSNTAY MQLSSLTYED SAVYFCARED YDVDYWGQGT TLTVSS      116

SEQ ID NO: 26          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 26
DIVMTQSQKF MSTSVGDRVS VTCKASQSVD TNVAWYQQKP GQSPKALIFS ASYRYSGVPD  60
RFTGSGSGTD FTLTINSVQS EDLAEYFCQQ YNSYPYTFGS GTKLEIK                107

SEQ ID NO: 27          moltype = AA  length = 122
FEATURE                Location/Qualifiers
REGION                 1..122
                       note = Synthetic Sequence
source                 1..122
                       mol_type = protein
                       organism = synthetic construct
SEQUENCE: 27
EVQLVESGGG LVKPGGSLKL SCAASGFTFS DYGMHWVRQA PEKGLEWVAY ISSGSYTIYY  60
TDTVKGRFTI SRDNAKNTLF LQMTSLRSED TAMYYCARRG YGSFYEYYFD YWGQGTTLTV  120
SS                                                                 122

SEQ ID NO: 28          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 28
QIVLTQSPAL MSASPGEKVT MTCSASSSVS YMYWYQQKPR SSPKPWIYLT SNLASGVPAR  60
FSGSGSGTSY SLTISSMEAE DAATYYCQQW SSNPFTFGSG TKLEIK                 106

SEQ ID NO: 29          moltype = AA  length = 119
FEATURE                Location/Qualifiers
REGION                 1..119
                       note = Synthetic Sequence
source                 1..119
                       mol_type = protein
                       organism = synthetic construct
SEQUENCE: 29
EVQLVESGGG LVQAGKSLRL SCAASGSIFS IHAMGWFRQA PGKEREFVAA ITWSGGITYY  60
EDSVKGRFTI SRDNAKNTVY LQMNSLKPED TAIYYCAADR AESSWYDYWG QGTQVTVSS   119

SEQ ID NO: 30          moltype = AA  length = 119
FEATURE                Location/Qualifiers
```

-continued

```
REGION                  1..119
                        note = Synthetic Sequence
source                  1..119
                        mol_type = protein
                        organism = synthetic construct
SEQUENCE: 30
EVQLVESGGG LVQAGGSLRL SCAASGSIAS IHAMGWFRQA PGKEREFVAV ITWSGGITYY  60
ADSVKGRFTI SRDNAKNTVY LQMNSLKPED TAIYYCAGDK HQSSWYDYWG QGTQVTVSS   119

SEQ ID NO: 31           moltype = AA  length = 119
FEATURE                 Location/Qualifiers
REGION                  1..119
                        note = Synthetic Sequence
source                  1..119
                        mol_type = protein
                        organism = synthetic construct
SEQUENCE: 31
EVQLVESGGG LVQAGGSLRL SCAASGSISS IHAMGWFRQA PGKEREFVAA ITWSGGITYY  60
ADSLKGRFTI SRDNAKNTGY LQMNSLKPED TAIYYCAADR AQSSWYDYWG QGTQVTVSS   119

SEQ ID NO: 32           moltype = AA  length = 119
FEATURE                 Location/Qualifiers
REGION                  1..119
                        note = Synthetic Sequence
source                  1..119
                        mol_type = protein
                        organism = synthetic construct
SEQUENCE: 32
EVQLVESGGG LVQAGGSLGL SCAASGSIFS INAMAWFRQA PGKEREFVAL ISWSGGSTYY  60
EDSVKGRFTI SRDNAKNTVY LQMNSLKPED TAIYYCAADR VDSNWYDYWG QGTQVTVSS   119

SEQ ID NO: 33           moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 33
EVQLVESGGG LVQAGGSLRL SCAASGRAFS SGTMGWFRRA PGKEREFVAS IPWSGGRIYY  60
ADSVKGRFTI SRDNAQNTVY LQMNSLKPED TAVYYCAVKE RSTGWDFASW GQCTQVTVSS  120

SEQ ID NO: 34           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 34
QVQLVQSGAE LKQPGASVKM SCKASGYSFT SSWIHWVKQA PGQGLEWIGY IYPSTGFTEY  60
NQKFKDRATL TADKSTSTAY MELSSLRSED SAVYYCARWR DSSGYHAMDY WGQGTSVTVS  120
S                                                                  121

SEQ ID NO: 35           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 35
QVQLVQSGAE VKQPGASVKM SCKASGYSFT SSWIHWVKQA PGQGLEWIGY IYPSTGFTEY  60
NQKFKDRATL TADKSTSTAY MELSSLRSED TAVYYCARWR DSSGYHAMDY WGQGTSVTVS  120
S                                                                  121

SEQ ID NO: 36           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 36
QVQLVQSGHE VKQPGASVKM SCKASGYSFT SSWIHWVKQA PGQGLEWIGY IYPSTGFTEY  60
NQKFKDRATL TADKSTSTAY MELSSLRSED TAVYYCARWR DSSGYHAMDY WGQGTLVTVS  120
S                                                                  121

SEQ ID NO: 37           moltype = AA  length = 121
```

-continued

```
FEATURE                Location/Qualifiers
REGION                 1..121
                       note = Synthetic Sequence
source                 1..121
                       mol_type = protein
                       organism = synthetic construct
SEQUENCE: 37
QVQLVQSGHE VKQPGASVKM SCKASGYSFT SSWIHWVRQA PGQGLEWIGY IYPSTGFTEY  60
NQKFKDRATL TADKSTSTAY MELSSLRSED TAVYYCARWR DSSGYHAMDY WGQGTLVTVS  120
S                                                                 121

SEQ ID NO: 38          moltype = AA  length = 121
FEATURE                Location/Qualifiers
REGION                 1..121
                       note = Synthetic Sequence
source                 1..121
                       mol_type = protein
                       organism = synthetic construct
SEQUENCE: 38
QVQLVQSGHE VKQPGASVKV SCKASGYSFT SSWIHWVRQA PGQGLEWIGY IYPSTGFTEY  60
NQKFKDRATI TADKSTSTAY MELSSLRSED TAVYYCARWR DSSGYHAMDY WGQGTLVTVS  120
S                                                                 121

SEQ ID NO: 39          moltype = AA  length = 111
FEATURE                Location/Qualifiers
REGION                 1..111
                       note = Synthetic Sequence
source                 1..111
                       mol_type = protein
                       organism = synthetic construct
SEQUENCE: 39
DIVLTQSPAS LTLSPGQRLT ISCRASQSVS TSGYSYMHWY QQKPDQSPKL LIKFGSNLES  60
GIPARFSGSG SGTDFTLTIS SLEEEDFATY YCQHSWEIPY TFGQGTKLEI K           111

SEQ ID NO: 40          moltype = AA  length = 111
FEATURE                Location/Qualifiers
REGION                 1..111
                       note = Synthetic Sequence
source                 1..111
                       mol_type = protein
                       organism = synthetic construct
SEQUENCE: 40
DIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K           111

SEQ ID NO: 41          moltype = AA  length = 111
FEATURE                Location/Qualifiers
REGION                 1..111
                       note = Synthetic Sequence
source                 1..111
                       mol_type = protein
                       organism = synthetic construct
SEQUENCE: 41
EIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K           111

SEQ ID NO: 42          moltype = AA  length = 111
FEATURE                Location/Qualifiers
REGION                 1..111
                       note = Synthetic Sequence
source                 1..111
                       mol_type = protein
                       organism = synthetic construct
SEQUENCE: 42
DIVLTQSPAT LSLSPGQRLT ISCRASQSVS TSGYSYMHWY QQKPDQSPKL LIKFGSNLES  60
GIPARFSGSG SGTDFTLTIS SLEPEDFAVY YCQHSWEIPY TFGQGTKLEI K           111

SEQ ID NO: 43          moltype = AA  length = 451
FEATURE                Location/Qualifiers
REGION                 1..451
                       note = Synthetic Sequence
source                 1..451
                       mol_type = protein
                       organism = synthetic construct
SEQUENCE: 43
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
```

```
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 44           moltype = AA  length = 215
FEATURE                 Location/Qualifiers
REGION                  1..215
                        note = Synthetic Sequence
source                  1..215
                        mol_type = protein
                        organism = synthetic construct
SEQUENCE: 44
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 45           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 45
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                 121

SEQ ID NO: 46           moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 46
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK              108

SEQ ID NO: 47           moltype = AA  length = 448
FEATURE                 Location/Qualifiers
REGION                  1..448
                        note = Synthetic Sequence
source                  1..448
                        mol_type = protein
                        organism = synthetic construct
SEQUENCE: 47
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 48           moltype = AA  length = 214
FEATURE                 Location/Qualifiers
REGION                  1..214
                        note = Synthetic Sequence
source                  1..214
                        mol_type = protein
                        organism = synthetic construct
SEQUENCE: 48
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 49           moltype = AA  length = 450
FEATURE                 Location/Qualifiers
REGION                  1..450
                        note = Synthetic Sequence
source                  1..450
                        mol_type = protein
                        organism = synthetic construct
SEQUENCE: 49
```

-continued

```
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                 450

SEQ ID NO: 50          moltype = AA  length = 216
FEATURE                Location/Qualifiers
REGION                 1..216
                       note = Synthetic Sequence
source                 1..216
                       mol_type = protein
                       organism = synthetic construct
SEQUENCE: 50
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                          216

SEQ ID NO: 51          moltype = AA  length = 123
FEATURE                Location/Qualifiers
REGION                 1..123
                       note = Synthetic Sequence
source                 1..123
                       mol_type = protein
                       organism = synthetic construct
SEQUENCE: 51
QVQLVQSGAE VKKPGSSVKV SCKTSGDTFS TYAISWVRQA PGQGLEWMGG IIPIFGKAHY  60
AQKFQGRVTI TADESTSTAY MELSSLRSED TAVYFCARKF HFVSGSPFGM DVWGQGTTVT  120
VSS                                                              123

SEQ ID NO: 52          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 52
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK               106

SEQ ID NO: 53          moltype = AA  length = 117
FEATURE                Location/Qualifiers
REGION                 1..117
                       note = Synthetic Sequence
source                 1..117
                       mol_type = protein
                       organism = synthetic construct
SEQUENCE: 53
QVQLVQSGAE VKKPGASVKV SCKASGYTFT DYGFSWVRQA PGQGLEWMGW ITAYNGNTNY  60
AQKLQGRVTM TTDTSTSTVY MELRSLRSDD TAVYYCARDY FYGMDVWGQG TTVTVSS    117

SEQ ID NO: 54          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 54
EIVLTQSPAT LSLSPGERAT LSCRASQSVS SYLVWYQQKP GQAPRLLIYD ASNRATGIPA  60
RFSGSGSGTD FTLTISSLEP EDFAVYYCQQ RSNWPRTFGQ GTKVEIK              107

SEQ ID NO: 55          moltype = AA  length = 118
FEATURE                Location/Qualifiers
REGION                 1..118
                       note = Synthetic Sequence
source                 1..118
                       mol_type = protein
                       organism = synthetic construct
SEQUENCE: 55
QVQLVQSGAE VKKPGASVKV SCKASGYTFT SYDVHWVRQA PGQRLEWMGW LHADTGITKF  60
SQKFQGRVTI TRDTSASTAY MELSSLRSED TAVYYCARER IQLWFDYWGQ GTLVTVSS   118

SEQ ID NO: 56          moltype = AA  length = 107
```

-continued

```
FEATURE                 Location/Qualifiers
REGION                  1..107
                        note = Synthetic Sequence
source                  1..107
                        mol_type = protein
                        organism = synthetic construct
SEQUENCE: 56
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK                107

SEQ ID NO: 57           moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 57
QVQLVQSGAE VKKPGSSVKV SCKVSGGIFS TYAINWVRQA PGQGLEWMGG IIPIFGTANH  60
AQKFQGRVTI TADESTSTAY MELSSLRSED TAVYYCARDQ GIAAALFDYW GQGTLVTVSS  120

SEQ ID NO: 58           moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 58
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK               108

SEQ ID NO: 59           moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 59
EVQLVESGGG LVQPGRSLRL SCAVSGFTFD DYVVHWVRQA PGKGLEWVSG ISGNSGNIGY  60
ADSVKGRFTI SRDNAKNSLY LQMNSLRAED TALYYCAVPF DYWGQGTLVT VSS         113

SEQ ID NO: 60           moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 60
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK                107

SEQ ID NO: 61           moltype = AA  length = 123
FEATURE                 Location/Qualifiers
REGION                  1..123
                        note = Synthetic Sequence
source                  1..123
                        mol_type = protein
                        organism = synthetic construct
SEQUENCE: 61
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HFVSGSPFGM DVWGQGTTVT  120
VSS                                                                123

SEQ ID NO: 62           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 62
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                 106

SEQ ID NO: 63           moltype = AA  length = 123
FEATURE                 Location/Qualifiers
```

-continued

```
REGION              1..123
                    note = Synthetic Sequence
source              1..123
                    mol_type = protein
                    organism = synthetic construct
SEQUENCE: 63
QVQLVQSGAE VKKPGSSVKV SCKTSGGTFS SYAISWVRQA PGQGLEWMGG IIPIFGKAHY  60
AQKFQGRVTI TADESTTTAY MELSSLRSED TAVYYCARKY DYVSGSPFGM DVWGQGTTVT  120
VSS                                                               123

SEQ ID NO: 64       moltype = AA  length = 106
FEATURE             Location/Qualifiers
REGION              1..106
                    note = Synthetic Sequence
source              1..106
                    mol_type = protein
                    organism = synthetic construct
SEQUENCE: 64
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 65       moltype = AA  length = 121
FEATURE             Location/Qualifiers
REGION              1..121
                    note = Synthetic Sequence
source              1..121
                    mol_type = protein
                    organism = synthetic construct
SEQUENCE: 65
QVQLVQSGAE VKKPGSSVKV SCKASGGTFS SYAINWVRQA PGQGLEWMGG IIPIFGSANY  60
AQKFQDRVTI TADESTSAAY MELSSLRSED TAVYYCARDS SGWSRYYMDV WGQGTTVTVS  120
S                                                                 121

SEQ ID NO: 66       moltype = AA  length = 106
FEATURE             Location/Qualifiers
REGION              1..106
                    note = Synthetic Sequence
source              1..106
                    mol_type = protein
                    organism = synthetic construct
SEQUENCE: 66
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPFGGG TKVEIK                106

SEQ ID NO: 67       moltype = AA  length = 123
FEATURE             Location/Qualifiers
REGION              1..123
                    note = Synthetic Sequence
source              1..123
                    mol_type = protein
                    organism = synthetic construct
SEQUENCE: 67
QVQLVQSGAE VKEPGSSVKV SCKASGGTFN SYAISWVRQA PGQGLEWMGG IIPLFGIAHY  60
AQKFQGRVTI TADESTNTAY MDLSSLRSED TAVYYCARKY SYVSGSPFGM DVWGQGTTVT  120
VSS                                                               123

SEQ ID NO: 68       moltype = AA  length = 106
FEATURE             Location/Qualifiers
REGION              1..106
                    note = Synthetic Sequence
source              1..106
                    mol_type = protein
                    organism = synthetic construct
SEQUENCE: 68
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TRLEIK                106

SEQ ID NO: 69       moltype = AA  length = 121
FEATURE             Location/Qualifiers
REGION              1..121
                    note = Synthetic Sequence
source              1..121
                    mol_type = protein
                    organism = synthetic construct
SEQUENCE: 69
EVQLVESGGG LVQPGRSLRL SCAASGITFD DYGMHWVRQA PGKGLEWVSG ISWNRGRIEY  60
ADSVKGRFTI SRDNAKNSLY LQMNSLRAED TALYYCAKGR FRYFDWFLDY WGQGTLVTVS  120
S                                                                 121
```

-continued

```
SEQ ID NO: 70          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 70
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPFTFGP GTKVDIK               107

SEQ ID NO: 71          moltype = AA  length = 118
FEATURE                Location/Qualifiers
REGION                 1..118
                       note = Synthetic Sequence
source                 1..118
                       mol_type = protein
                       organism = synthetic construct
SEQUENCE: 71
EVKLQESGPS LVKPSQTLSL TCSVTGYSIT SDYWNWIRKF PGNKLEYVGY ISYTGSTYYN  60
PSLKSRISIT RDTSKNQYYL QLNSVTSEDT ATYYCARYGG WLSPFDYWGQ GTTLTVSS    118

SEQ ID NO: 72          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 72
DIVMTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK               107

SEQ ID NO: 73          moltype = AA  length = 120
FEATURE                Location/Qualifiers
REGION                 1..120
                       note = Synthetic Sequence
source                 1..120
                       mol_type = protein
                       organism = synthetic construct
SEQUENCE: 73
EVQLQESGPG LVAPSQSLSI TCTVSGFSLT TYSINWIRQP PGKGLEWLGV MWAGGGTNSN  60
SVLKSRLIIS KDNSKSQVFL KMNSLQTDDT ARYYCARYYG NSPYYAIDYW GQGTSVTVSS  120

SEQ ID NO: 74          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 74
DIVTTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK               107

SEQ ID NO: 75          moltype = AA  length = 118
FEATURE                Location/Qualifiers
REGION                 1..118
                       note = Synthetic Sequence
source                 1..118
                       mol_type = protein
                       organism = synthetic construct
SEQUENCE: 75
EVKLQESGPS LVKPSQTLSL TCSVTGYSII SDYWNWIRKF PGNKLEYLGY ISYTGSTYYN  60
PSLKSRISIT RDTSKNQYYL QLNSVTTEDT ATYYCARRGG WLLPFDYWGQ GTTLTVSS    118

SEQ ID NO: 76          moltype = AA  length = 113
FEATURE                Location/Qualifiers
REGION                 1..113
                       note = Synthetic Sequence
source                 1..113
                       mol_type = protein
                       organism = synthetic construct
SEQUENCE: 76
DIVMTQSPSS LAVSVGEKVS MGCKSSQSLL YSSNQKNSLA WYQQKPGQSP KLLIDWASTR  60
ESGVPDRFTG SGSGTDFTLT ISSVKAEDLA VYYCQQYYGY PLTFGAGTKL ELK         113

SEQ ID NO: 77          moltype = AA  length = 118
FEATURE                Location/Qualifiers
```

-continued

```
REGION                  1..118
                        note = Synthetic Sequence
source                  1..118
                        mol_type = protein
                        organism = synthetic construct
SEQUENCE: 77
EVKLQESGPS LVKPGASVKL SCKASGYTFT SYDINWVKQR PGQGLEWIGW IFPRDNNTKY  60
NENFKGKATL TVDTSSTTAY MELHSLTSED SAVYFCTKEN WVGDFDYWGQ GTTLTLSS    118

SEQ ID NO: 78           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 78
DIVMTQSPAI MSASPGEKVT MTCSASSSIR YMHWYQQKPG TSPKRWISDT SKLTSGVPAR  60
FSGSGSGTSY ALTISSMEAE DAATYYCHQR SSYPWTFGGG TKLEIK                 106

SEQ ID NO: 79           moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 79
EVQLQQSGPD LVTPGASVRI SCQASGYTFP DYYMNWVKQS HGKSLEWIGD IDPNYGGTTY  60
NQKFKGKAIL TVDRSSSTAY MELRSLTSED SAVYYCARGA LTDWGQGTSL TVSS        114

SEQ ID NO: 80           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 80
QIVLSQSPAI LSASPGEKVT MTCRASSSVS YIYWFQQKPG SSPKPWIYAT FNLASGVPAR  60
FSGSGSGTSY SLTISRVETE DAATYYCQQW SNNPLTFGAG TKLELK                 106

SEQ ID NO: 81           moltype = AA  length = 115
FEATURE                 Location/Qualifiers
REGION                  1..115
                        note = Synthetic Sequence
source                  1..115
                        mol_type = protein
                        organism = synthetic construct
SEQUENCE: 81
EVQLVQSGPE LKKPGASVKM SCKASGYTFT SYVMHWVKQA PGQRLEWIGY VNPFNDGTKY  60
NEMFKGRATL TSDKSTSTAY MELSSLRSED SAVYYCARQA WGYPWGQGTL VTVSS       115

SEQ ID NO: 82           moltype = AA  length = 115
FEATURE                 Location/Qualifiers
REGION                  1..115
                        note = Synthetic Sequence
source                  1..115
                        mol_type = protein
                        organism = synthetic construct
SEQUENCE: 82
EVQLVQSGAE VKKPGASVKM SCKASGYTFT SYVMHWVKQA PGQRLEWIGY VNPFNDGTKY  60
NEMFKGRATL TSDKSTSTAY MELSSLRSED TAVYYCARQA WGYPWGQGTL VTVSS       115

SEQ ID NO: 83           moltype = AA  length = 115
FEATURE                 Location/Qualifiers
REGION                  1..115
                        note = Synthetic Sequence
source                  1..115
                        mol_type = protein
                        organism = synthetic construct
SEQUENCE: 83
EVQLVQSGAE VKKPGASVKM SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 84           moltype = AA  length = 115
FEATURE                 Location/Qualifiers
REGION                  1..115
                        note = Synthetic Sequence
```

```
source                  1..115
                        mol_type = protein
                        organism = synthetic construct
SEQUENCE: 84
EVQLVQSGAE VKKPGASVKV SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 85           moltype = AA  length = 115
FEATURE                 Location/Qualifiers
REGION                  1..115
                        note = Synthetic Sequence
source                  1..115
                        mol_type = protein
                        organism = synthetic construct
SEQUENCE: 85
EVQLVQSGAE VKKPGASVKV SCKASGYTFT SYVMHWVRQA PGQRLEWIGY VNPFNDGTKY  60
NEMFKGRATI TSDKSTSTAY MELSSLRSED TAVYYCARQA WGYPWGQGTL VTVSS       115

SEQ ID NO: 86           moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 86
DIVLTQSPAS LALSPGERAT LSCRATESVE YYGTSLVQWY QQKPGQPPKL LIYAASSVDS  60
GVPSRFSGSG SGTDFTLTIN SLEEEDAAMY FCQQSRRVPY TFGQGTKLEI K           111

SEQ ID NO: 87           moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 87
DIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 88           moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 88
EIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 89           moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 89
DIVLTQSPAT LSLSPGERAT LSCRATESVE YYGTSLVQWY QQKPGQPPKL LIYAASSVDS  60
GVPSRFSGSG SGTDFTLTIN SLEAEDAATY FCQQSRRVPY TFGQGTKLEI K           111

SEQ ID NO: 90           moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 90
EVQLVESGGG LVKPGGSLRL SCAASGFTFS TYSMNWVRQA PGKGLEWVSS ISSSGDYIYY  60
ADSVKGRFTI SRDNAKNSLF LQMNSLKAED TAVYYCARDL VTSMVAFDYW GQGTLVTVSS  120

SEQ ID NO: 91           moltype = AA  length = 108
FEATURE                 Location/Qualifiers
REGION                  1..108
                        note = Synthetic Sequence
source                  1..108
                        mol_type = protein
```

-continued

```
                        organism = synthetic construct
SEQUENCE: 91
SYELTQPPSV SVSPGQAARI TCSGDALPQK YVFWYQQKSG QAPVLVIYED SKRPSGIPER  60
FSGSSSGTMA TLTISGAQVE DEADYYCYST DRSGNHRVFG GGTRLTVL               108

SEQ ID NO: 92           moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 92
EVQLVESGGG LVQPGGSLRL SCAASGFTFS SYWMSWVRQA PGKGLEWVAN IKQDGGEQYY  60
VDSVKGRFTI SRDNAKNSLY LQMNSLRAED TAVYYCARDW NYGYYDMDVW GQGTTVTVSS  120

SEQ ID NO: 93           moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 93
EIVLTQSPGT LSLSPGERAT LSCRASQSVS SNYLAWFQQK PGQAPRLLIF GTSSRATGIP  60
DRFSGSGSGT DFTLTISRLE PEDFAVYYCQ QYGSSIFTFG PGTKVDIK               108

SEQ ID NO: 94           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 94
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 95           moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 95
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTEVEIK               108

SEQ ID NO: 96           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 96
EVQLLESGGG LVQPGGSLRL SCAASGFTFS NYAMSWVRQA PGKGLEWVSA IRGSGGSTYY  60
ADSVKGRFTI SRDNSKNTLY LQMNSLRAED TAVYYCAKDL HYDSSGYLDY WGQGTLVTVS  120
S                                                                  121

SEQ ID NO: 97           moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 97
DIQMTQSPSS VSASVGDRVT ITCRASQGIR SWLAWYQQKP GKAPKLLIYA ISRLQSGVPS  60
RFSGSGSGTD FTLTISSLQP EDFATYYCQQ ANSFPLTFGG GTKVEIK                107

SEQ ID NO: 98           moltype = AA  length = 119
FEATURE                 Location/Qualifiers
REGION                  1..119
                        note = Synthetic Sequence
source                  1..119
                        mol_type = protein
```

```
                        organism = synthetic construct
SEQUENCE: 98
EVQLVESGGG LVQPGGSLRL SCAASGFTFS SYWMSWVRQA PGKGLEWVAN IKQDGGEKYY  60
VDSVKGRFTI SRDNAKNSLF LQMNSLRAED TAVYYCARVQ LYSDYFDYWG QGTLVTVSS   119

SEQ ID NO: 99           moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 99
DIQMTQSPSS VSASVGDRVT ITCRASQGIS SWLAWYQQKS GKAPKLLIYA ASGLQSGVPS  60
RFSGSGSGTD FTLTISSLQP EDLATYYCQQ SHSLPPTFGQ GTKVEIK                107

SEQ ID NO: 100          moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 100
EVQLLESGGD LVQPGGSLRL SCAASGFTFN SYAMSWVRQA PGKGLEWVST ISGSGGFTFS  60
ADSVKGRFTI SRDNSKNTLF LQMNSLRVED SAVYSCAKVL VGFNNGCWDY WGQGTLVTVS  120
S                                                                  121

SEQ ID NO: 101          moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 101
SYVLTQPPSV SVAPGQTARI TCGGNNIGSK SVHWYQQKPG QAPVLVVYDD SDRPSGIPER  60
FSGSNSGNTA TLTISRVEAG DEADYYCQVW DSSNDHVVFG GGTKLTVL               108

SEQ ID NO: 102          moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 102
EVQLVESGGG LVKPGGSLRL SCAASGFTFS TYSMNWVRQA PGKGLEWVSS ISSSGDYIYY  60
ADSVKGRFTI SRDNAKNSLY LQMNSLRAED TAVYYCARDL VTSMVAFDYW GQGTLVTVSS  120

SEQ ID NO: 103          moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 103
SYELTQPPSV SVSPGQTARI TCSGDALPQK YVFWYQQKSG QAPVLVIYED SKRPSGIPER  60
FSGSSSGTMA TLTISGAQVE DEADYYCYST DRSGNHRVFG GGTKLTVL               108

SEQ ID NO: 104          moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 104
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 105          moltype = AA  length = 108
FEATURE                 Location/Qualifiers
REGION                  1..108
                        note = Synthetic Sequence
source                  1..108
                        mol_type = protein
```

-continued

```
                         organism = synthetic construct
SEQUENCE: 105
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK              108

SEQ ID NO: 106           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 106
QVQLVQSGAE VKKPGASVKV SCKASGYTFT SYWMYWVRQA TGQGLEWMGR IDPNSGSTKY  60
NEKFKNRFTI SRDDSKNTAY LQMNSLKTED TAVYYCARDY RKGLYAMDYW GQGTTVTVSS  120

SEQ ID NO: 107           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 107
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120

SEQ ID NO: 108           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 108
EVQLVQSGAE VKKPGESLRI SCKGSGYTFT SYWMYWVRQA PGQGLEWMGR IDPNSGSTKY  60
NEKFKNRVTI SVDTSKNQFS LKLSSVTAAD TAVYYCARDY RKGLYAMDYW GQGTTVTVSS  120

SEQ ID NO: 109           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 109
EVQLVQSGAE VKKPGATVKI SCKVSGYTFT SYWMYWIRQS PSRGLEWLGR IDPNSGSTKY  60
NEKFKNRLTI SKDTSKNQVV LTMTNMDPVD TATYYCARDY RKGLYAMDYW GQGTTVTVSS  120

SEQ ID NO: 110           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 110
EVQLVQSGAE VKKPGESLRI SCKGSGYTFT SYWMYWIRQP PGKGLEWIGR IDPNSGSTKY  60
NEKFKNRVTI TADKSTSTAY MELSSLRSED TAVYYCARDY RKGLYAMDYW GQGTTVTVSS  120

SEQ ID NO: 111           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 111
QVQLVQSGAE VKKPGASVKV SCKASGYTFT SYWMYWIRQS PSRGLEWLGR IDPNSGSTKY  60
NEKFKNRFTI SRDDSKNTAY LQMNSLKTED TAVYYCARDY RKGLYAMDYW GQGTTVTVSS  120

SEQ ID NO: 112           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 112
```

-continued

```
EVQLVQSGAE VKKPGESLRI SCKGSGYTFT SYWMYWVRQA RGQRLEWIGR IDPNSGSTKY  60
NEKFKNRLTI SKDTSKNQVV LTMTNMDPVD TATYYCARDY RKGLYAMDYW GQGTTVTVSS  120

SEQ ID NO: 113         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 113
QITLKESGPT LVKPTQTLTL TCTFSGYTFT SYWMYWVRQA PGKGLEWVSR IDPNSGSTKY  60
NEKFKNRVTI TADKSTSTAY MELSSLRSED TAVYYCARDY RKGLYAMDYW GQGTTVTVSS  120

SEQ ID NO: 114         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 114
EVQLVQSGAE VKKPGATVKI SCKVSGYTFT SYWMYWVRQA RGQRLEWIGR IDPNSGSTKY  60
NEKFKNRFTI SRDNSKNTLY LQMNSLRAED TAVYYCARDY RKGLYAMDYW GQGTTVTVSS  120

SEQ ID NO: 115         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 115
DIVMTQTPLS LPVTPGEPAS ISCKASQDVG TAVAWYLQKP GQSPQLLIYW ASTRHTGIPA  60
RFSGSGSGTE FTLTISSLQS EDFAVYYCQQ YNSYPLTFGQ GTKVEIK                107

SEQ ID NO: 116         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 116
DIQMTQSPSS LSASVGDRVT ITCKASQDVG TAVAWYLQKP GQSPQLLIYW ASTRHTGVPS  60
RFSGSGSGTD FTLTISSLQP EDFATYYCQQ YNSYPLTFGQ GTKVEIK                107

SEQ ID NO: 117         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 117
EIVLTQSPDF QSVTPKEKVT ITCKASQDVG TAVAWYLQKP GQSPQLLIYW ASTRHTGVPD  60
RFSGSGSGTD FTLKISRVEA EDVGVYYCQQ YNSYPLTFGQ GTKVEIK                107

SEQ ID NO: 118         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 118
EIVLTQSPDF QSVTPKEKVT ITCKASQDVG TAVAWYLQKP GQSPQLLIYW ASTRHTGVPS  60
RFSGSGSGTD FTFTISSLQP EDIATYYCQQ YNSYPLTFGQ GTKVEIK                107

SEQ ID NO: 119         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 119
EIVLTQSPAT LSLSPGERAT LSCKASQDVG TAVAWYLQKP GQSPQLLIYW ASTRHTGIPP  60
RFSGSGYGTD FTLTINNIES EDAAYYFCQQ YNSYPLTFGQ GTKVEIK                107
```

```
SEQ ID NO: 120          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 120
DVVMTQSPLS LPVTLGQPAS ISCKASQDVG TAVAWYQQKP GQAPRLLIYW ASTRHTGVPS  60
RFSGSGSGTE FTLTISSLQP DDFATYYCQQ YNSYPLTFGQ GTKVEIK              107

SEQ ID NO: 121          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 121
DIQMTQSPSS LSASVGDRVT ITCKASQDVG TAVAWYQQKP GQAPRLLIYW ASTRHTGVPS  60
RFSGSGSGTD FTFTISSLQP EDIATYYCQQ YNSYPLTFGQ GTKVEIK              107

SEQ ID NO: 122          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 122
AIQLTQSPSS LSASVGDRVT ITCKASQDVG TAVAWYLQKP GQSPQLLIYW ASTRHTGVPS  60
RFSGSGSGTD FTFTISSLEA EDAATYYCQQ YNSYPLTFGQ GTKVEIK              107

SEQ ID NO: 123          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 123
EIVLTQSPDF QSVTPKEKVT ITCKASQDVG TAVAWYQQKP GQAPRLLIYW ASTRHTGVPS  60
RFSGSGSGTE FTLTISSLQP DDFATYYCQQ YNSYPLTFGQ GTKVEIK              107

SEQ ID NO: 124          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 124
EVKLVESGGG LVKPGGSLKL SCAASGFIFR SYGMSWVRQT PEKRLEWVAS ISSGGSTYYP  60
DSVKGRFTIS RDNARNILYL QMSSLRSEDT AMYDCARGYD SGFAYWGQGT LVTVSE     116

SEQ ID NO: 125          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 125
EVKLVESGGG LVKPGGSLKL SCAASGFTFR SYGMSWVRQT PEKRLEWVAS ISSGGTTYYP  60
DSVKGRFIIS RDNARNILYL QMSSLRSEDT AMYYCAKGYD SGFAYWGQGT LVIVSA     116

SEQ ID NO: 126          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 126
QVQLKQSGPG LVQPSQSLSI TCTVSGFSLT TYGVHWVRQS PGKGLEWLGV IWRGVTTDYN  60
AAFMSRLTIT KDNSKSQVFF KMNSLQANDT AIYYCARLGF YAMDYWGQGT SVTVSS     116

SEQ ID NO: 127          moltype = AA  length = 116
```

```
FEATURE               Location/Qualifiers
REGION                1..116
                      note = Synthetic Sequence
source                1..116
                      mol_type = protein
                      organism = synthetic construct
SEQUENCE: 127
QVQLKQSGPG LVQPSQSLSI TCTVSGFSLT SYGVHWVRQS PGKGLEWLGV IWSGGVTDYN  60
AAFISRLSIS KDNSKSQVFF KMNSLQANDT AIYYCARLGF YAMDYWGQGT SVTVSS      116

SEQ ID NO: 128        moltype = AA  length = 119
FEATURE               Location/Qualifiers
REGION                1..119
                      note = Synthetic Sequence
source                1..119
                      mol_type = protein
                      organism = synthetic construct
SEQUENCE: 128
EVKLFESGGG LVQPGGSLKL SCVASGFDFS TYWMHWVRQA PGQGLEWIGQ INPDSTTINY  60
APSLKDRFII SRDNAKNTLF LQMSKVRSED TALYYCAKPG DYGYDFDCWG QGTTLTVSS   119

SEQ ID NO: 129        moltype = AA  length = 119
FEATURE               Location/Qualifiers
REGION                1..119
                      note = Synthetic Sequence
source                1..119
                      mol_type = protein
                      organism = synthetic construct
SEQUENCE: 129
EVQLQESGPS LVKPSQTLSL TCSVTGDSIT SGYWNWIRKF PGNKLEYMGY ISYSGSTYYN  60
PSLKSRISIT RDTSKNQYYL QLNSVTTEDT ATYYCARSLL WFSTGFAYWG QGTLVTVSA   119

SEQ ID NO: 130        moltype = AA  length = 116
FEATURE               Location/Qualifiers
REGION                1..116
                      note = Synthetic Sequence
source                1..116
                      mol_type = protein
                      organism = synthetic construct
SEQUENCE: 130
QVQLKQSGPG LVQPSQSLSI TCTVSGFSLT SYGVHWVRQS PGKGLEWLGV IWSGGITDYN  60
AAFKSRLSIS KDNSKSQVFF KMNSLQANDT AIYFCARLGF YAMDYWGQGT SVTVSS      116

SEQ ID NO: 131        moltype = AA  length = 116
FEATURE               Location/Qualifiers
REGION                1..116
                      note = Synthetic Sequence
source                1..116
                      mol_type = protein
                      organism = synthetic construct
SEQUENCE: 131
EVKLVESGGG LVKPGGSLKL SCAASGFTFR SYGMSWARQI PEKRLEWVAS ISSGGTTYYL  60
GSVQGRFTIS RDNARNILYL QMSSLRSEDT AMYYCARGYD AGFAYWGQGT LVSVSE      116

SEQ ID NO: 132        moltype = AA  length = 117
FEATURE               Location/Qualifiers
REGION                1..117
                      note = Synthetic Sequence
source                1..117
                      mol_type = protein
                      organism = synthetic construct
SEQUENCE: 132
EVQLQESGPS LVKPSQTLSL TCSVTGDSIT SGYWTWIRKF PGNKLEYMGY ISYTGSTYYN  60
PSLKSRISIS RDTSKSQYYL QLNSVTTEDT ATYYCARQRD WLGFAYWGQG TLVTVSA     117

SEQ ID NO: 133        moltype = AA  length = 116
FEATURE               Location/Qualifiers
REGION                1..116
                      note = Synthetic Sequence
source                1..116
                      mol_type = protein
                      organism = synthetic construct
SEQUENCE: 133
EEKLVESGGG LVKPGGSLKL SCAASGFSFS SYGMSWVRQT PEKRLEWVAS ISSGGSIYYP  60
DSVKGRFTIS RDNARNILYL QMSSLRSEDT AMYYCARGYD AGFAFWGQGT LVTASA      116

SEQ ID NO: 134        moltype = AA  length = 116
FEATURE               Location/Qualifiers
REGION                1..116
```

-continued

```
                        note = Synthetic Sequence
source                  1..116
                        mol_type = protein
                        organism = synthetic construct
SEQUENCE: 134
QITLKESGPT LVKPTQTLTL TCTVSGFSLS TYGVHWIRQP PGKALEWLGV IWRGVTTDYN  60
AAFMSRLTIT KDNSKNQVVL TMNNMDPVDT ATYYCARLGF YAMDYWGQGT LVTVSS      116

SEQ ID NO: 135          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 135
EVQLVESGGG LVKPGGSLRL SCAASGFIFR SYGMSWVRQA PGKGLEWVAS ISSGGSTYYP  60
DSVKGRFTIS RDNAKNSLYL QMNSLRAEDT AVYDCARGYD SGFAYWGQGT LVTVSS      116

SEQ ID NO: 136          moltype = AA  length = 112
FEATURE                 Location/Qualifiers
REGION                  1..112
                        note = Synthetic Sequence
source                  1..112
                        mol_type = protein
                        organism = synthetic construct
SEQUENCE: 136
DIVLTQSPAS LAVSLGQRAT ISCRASQSVS TSSSSFMHWY QQKPGQPPKL LIKYASNLES  60
GVPARFSGSG SGTDFTLNIH PVEEEDTATY YCQHSWEIPY TFGGGTKLEI KR          112

SEQ ID NO: 137          moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 137
DIVLTQSPPS LAVSLGQRAT ISCRASQSVS TSSSSYMHWY QQKPGQPPKL LIKYASNLES  60
GVPARFSGSG SGTDFTLNIH PVEEEDTATY YCQHSWEIPY TFGGGTKLEI K           111

SEQ ID NO: 138          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 138
SIVMTQTPKF LLVSAGDRVT ITCKASQSVS NDVAWYQQKP GQSPKLLIYY AANRYTGVPD  60
RFTGSGYGTD FTFTISIVQA EDLAVYFCQQ DYTSPYTFGG GTKLEIK                107

SEQ ID NO: 139          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 139
SIVMTQTPKF LLVSAGDRVT ITCKASQSVS NDVGWYQQKP GQSPKLLIYY ASNRYSGVPD  60
RFTGSGYGTD FTFTISTVQA EDLAVYFCQQ DYTSPYTFGG GTKLEIK                107

SEQ ID NO: 140          moltype = AA  length = 112
FEATURE                 Location/Qualifiers
REGION                  1..112
                        note = Synthetic Sequence
source                  1..112
                        mol_type = protein
                        organism = synthetic construct
SEQUENCE: 140
DVLMTQTPLY LPVSLGDQAS ISCRSSQIIV HSNANTYLEW FLQKPGQSPK LLIYKVSNRF  60
SGVPDRFSGS GSGTDFTLKI SRVEAEDLGV YYCFQGSHVP YTFGGGTKLE IK          112

SEQ ID NO: 141          moltype = AA  length = 108
FEATURE                 Location/Qualifiers
REGION                  1..108
                        note = Synthetic Sequence
source                  1..108
```

```
                        mol_type = protein
                        organism = synthetic construct
SEQUENCE: 141
QIVLTQSPAI MSASPGEKVT LTCSASSSVS SSYLYWNQQK PGSSPKVWIY NTSNLASGVP  60
ARFSGSGSGT SYSLTISSME AEDAASYFCH QWRSYPPTLG AGTKLELK               108

SEQ ID NO: 142          moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 142
QIVLTQSPAI MSASPGEKVT MTCSANSSVS YMHWYQQKSG TSPKRWIYDT SKLASGVPAR  60
FSGSGSGTSY SLTISSMGAE DAATYYCQQW SSNPWTFGGG TKLEIK                 106

SEQ ID NO: 143          moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 143
DIVLTQSPAS LAVSLGQRAT ISCRASQSVS TSSYSYMHWY QQKPGQPPKL LIKYASNLES  60
GVPARFSGSG SGTDFTLNIH PVEEEDTATY YCQNSWEIPY TFGGGTKLEI K           111

SEQ ID NO: 144          moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 144
DIVMTQTPSS LAVSLGEKVT MSCKSSQSLL YSSNQKNSLA WYQQKPGQSP KLLIYWASNR  60
ESGVPDRFTG SSSGTDFTLT ISSVKAEDLA VYYCQQYYSY PLTFGAGTKL ELK        113

SEQ ID NO: 145          moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 145
DIVLTQSPAS LAVSLGQRAT ISCRASQSVS TSSYSYVHWY QQKPGQPPKL LIKYASNLES  60
GVPARFSGSG SGTDFTLNIH PVEEEDTATY YCQHSWEIPY TFGGGTKLEI K           111

SEQ ID NO: 146          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 146
DIQMTQSPSS LSASVGDRVT ITCKASQSVS NDVAWYQQKP GKAPKLLIYY AANRYTGVPD  60
RFSGSGYGTD FTFTISSLQP EDIATYFCQQ DYTSPYTFGQ GTKLEIK               107

SEQ ID NO: 147          moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 147
DIVLTQSPAS LAVSPGQRAT ITCRASQSVS TSSSSFMHWY QQKPGQPPKL LIKYASNLES  60
GVPARFSGSG SGTDFTLTIN PVEANDTANY YCQHSWEIPY TFGQGTKLEI K           111

SEQ ID NO: 148          moltype = AA  length = 117
FEATURE                 Location/Qualifiers
REGION                  1..117
                        note = Synthetic Sequence
source                  1..117
                        mol_type = protein
                        organism = synthetic construct
```

```
SEQUENCE: 148
EVQLVQSGAE VKKPGESLRI SCKGSGYTFT TYWMHWVRQA TGQGLEWMGN IYPGTGGSNF  60
DEKFKNRVTI TADKSTSTAY MELSSLRSED TAVYYCTRWT TGTGAYWGQG TTVTVSS     117

SEQ ID NO: 149         moltype = AA  length = 117
FEATURE                Location/Qualifiers
REGION                 1..117
                       note = Synthetic Sequence
source                 1..117
                       mol_type = protein
                       organism = synthetic construct
SEQUENCE: 149
EVQLVQSGAE VKKPGESLRI SCKGSGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 150         moltype = AA  length = 117
FEATURE                Location/Qualifiers
REGION                 1..117
                       note = Synthetic Sequence
source                 1..117
                       mol_type = protein
                       organism = synthetic construct
SEQUENCE: 150
QVQLVQSGAE VKKPGASVKV SCKASGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 151         moltype = AA  length = 117
FEATURE                Location/Qualifiers
REGION                 1..117
                       note = Synthetic Sequence
source                 1..117
                       mol_type = protein
                       organism = synthetic construct
SEQUENCE: 151
EVQLVQSGAE VKKPGESLRI SCKGSGYTFT TYWMHWVRQA PGQGLEWMGN IYPGTGGSNF  60
DEKFKNRFTI SRDNSKNTLY LQMNSLRAED TAVYYCTRWT TGTGAYWGQG TTVTVSS     117

SEQ ID NO: 152         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 152
EIVLTQSPAT LSLSPGERAT LSCKSSQSLL DSGNQKNFLT WYQQKPGQAP RLLIYWASTR  60
ESGVPSRFSG SGSGTEFTLT ISSLQPDDFA TYYCQNDYSY PYTFGQGTKV EIK         113

SEQ ID NO: 153         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 153
DIQMTQSPSS LSASVGDRVT ITCKSSQSLL DSGNQKNFLT WYQQKPGQAP RLLIYWASTR  60
ESGIPPRFSG SGYGTDFTLT INNIESEDAA YYFCQNDYSY PYTFGQGTKV EIK         113

SEQ ID NO: 154         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 154
EIVLTQSPAT LSLSPGERAT LSCKSSQSLL DSGNQKNFLT WYQQKPGKAP KLLIYWASTR  60
ESGVPSRFSG SGSGTDFTFT ISSLQPEDIA TYYCQNDYSY PYTFGQGTKV EIK         113

SEQ ID NO: 155         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 155
DIVMTQTPLS LPVTPGEPAS ISCKSSQSLL DSGNQKNFLT WYQQKPGQAP RLLIYWASTR  60
```

-continued

```
ESGVPSRFSG SGSGTDFTFT ISSLEAEDAA TYYCQNDYSY PYTFGQGTKV EIK         113

SEQ ID NO: 156         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 156
EIVLTQSPAT LSLSPGERAT LSCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113

SEQ ID NO: 157         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 157
EIVLTQSPDF QSVTPKEKVT ITCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 158         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 158
EIVLTQSPAT LSLSPGERAT LSCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 159         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 159
DIQMTQSPSS LSASVGDRVT ITCKSSQSLL DSGNQKNFLT WYLQKPGQSP QLLIYWASTR  60
ESGVPSRFSG SGSGTDFTFT ISSLEAEDAA TYYCQNDYSY PYTFGQGTKV EIK         113

SEQ ID NO: 160         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 160
DVVMTQSPLS LPVTLGQPAS ISCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113

SEQ ID NO: 161         moltype = AA  length = 118
FEATURE                Location/Qualifiers
REGION                 1..118
                       note = Synthetic Sequence
source                 1..118
                       mol_type = protein
                       organism = synthetic construct
SEQUENCE: 161
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSA    118

SEQ ID NO: 162         moltype = AA  length = 108
FEATURE                Location/Qualifiers
REGION                 1..108
                       note = Synthetic Sequence
source                 1..108
                       mol_type = protein
                       organism = synthetic construct
SEQUENCE: 162
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108
```

-continued

```
SEQ ID NO: 163          moltype = AA  length = 126
FEATURE                 Location/Qualifiers
REGION                  1..126
                        note = Synthetic Sequence
source                  1..126
                        mol_type = protein
                        organism = synthetic construct
SEQUENCE: 163
EVQLVESGGG LVQPGGSLRL SCAASGFTLD YYAIGWFRQA PGKEREWASS ISSSDGSTYY  60
ADSVKGRFTI SRDNAKNTVF LQMNSLKPED TAVYSCAASQ APITIATMMK PFYDYWGQGT  120
QVTVSS                                                             126

SEQ ID NO: 164          moltype = AA  length = 123
FEATURE                 Location/Qualifiers
REGION                  1..123
                        note = Synthetic Sequence
source                  1..123
                        mol_type = protein
                        organism = synthetic construct
SEQUENCE: 164
EVQLVESGGG LVQPGGSLRL SCAASGFTLD YYAKCWFRQA PGKEREWVSC ISSSDGSTYY  60
ADSVKGRFTI SRDNAKNTVY LQMNSLKPED TAVYFCAARH GGPLTVEYFF DYWGQGTQVT  120
VSS                                                                123

SEQ ID NO: 165          moltype = AA  length = 124
FEATURE                 Location/Qualifiers
REGION                  1..124
                        note = Synthetic Sequence
source                  1..124
                        mol_type = protein
                        organism = synthetic construct
SEQUENCE: 165
EVQLVESGGG LVQPGGSLRL SCAASGFTFD YYAIGWFRQA PGKAREGVSC ISGGDNSTYY  60
ADSVKGRFTI SRDNAKNTVY LQMNSLKPED TAVYYCATGG WKYCSGYDPE YIYWGQGTQV  120
TVSS                                                               124

SEQ ID NO: 166          moltype = AA  length = 115
FEATURE                 Location/Qualifiers
REGION                  1..115
                        note = Synthetic Sequence
source                  1..115
                        mol_type = protein
                        organism = synthetic construct
SEQUENCE: 166
EVQLVESGGG LVQAGGSLRL SCAASGSTFS QYDVGWYRQA PGKQRELVAF SSSGGRTIYP  60
DSVKGRFTFS RDNTKNTVYL QMTSLKPEDT AVYYCKIDWY LNSYWGQGTQ VTVSS       115

SEQ ID NO: 167          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 167
EVQLVESGGG LVQAGGSLRL SCAASGVDAS NSAMGWYRQA PGKQREWVAR ITGGGLIAYT  60
DSVKGRFTIS RDNAKSTVYL QMNSLEPEDT AVYYCNTINS RDGWGQGTQV TVSS        114

SEQ ID NO: 168          moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 168
EVQLVESGGG LVQAGGSLTI SCAASGITFS DSIVSWYRRA RGKQREWVAG ISNGGTTKYA  60
ESVLGRFTIS RDNAKNNVYL QMNGLNPEDT AVYLCKVRQY WGQGTQVTVS S           111

SEQ ID NO: 169          moltype = AA  length = 130
FEATURE                 Location/Qualifiers
REGION                  1..130
                        note = Synthetic Sequence
source                  1..130
                        mol_type = protein
                        organism = synthetic construct
SEQUENCE: 169
EVQLVESGGG LVQAGGSLRL SCAASESTVL INAMGWYRQA PGKQRELVAS ISSGGSTNYA  60
DSVKGRFTIS RDNAKNTVYL QMNSLKPEDT AVYYCNADVY PQDYGLGYVE GKVYYGHDYW  120
```

-continued

```
GTGTLVTVSS                                                  130

SEQ ID NO: 170          moltype = AA  length = 119
FEATURE                 Location/Qualifiers
REGION                  1..119
                        note = Synthetic Sequence
source                  1..119
                        mol_type = protein
                        organism = synthetic construct
SEQUENCE: 170
EVQLVESGGG LVQAGGSLRL SCAASGSTFS NYVSNYAMGW GRQAPGTQRE LVASISNGDT  60
TNYADSVKGR FTISRDNAKN TVYLQMNSLK PEDTAVYYCF EHQVAGLTWG QGTQVTVSS   119

SEQ ID NO: 171          moltype = AA  length = 118
FEATURE                 Location/Qualifiers
REGION                  1..118
                        note = Synthetic Sequence
SITE                    27
                        note = misc_feature - Xaa can be any naturally occurring
                         amino acid
SITE                    32
                        note = misc_feature - Xaa can be any naturally occurring
                         amino acid
SITE                    75
                        note = misc_feature - Xaa can be any naturally occurring
                         amino acid
source                  1..118
                        mol_type = protein
                        organism = synthetic construct
SEQUENCE: 171
EVQLVESGGG LVQAGGSLRL SCVASGXALK IXVMGWYRQA PGKQRELVAA ITSGGRTNYS  60
DSVKGRFTIS GDNAXNTVYL QMNSLKSEDT AVYYCREWNS GYPPVDYWGQ GTQVTVSS    118

SEQ ID NO: 172          moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 172
EVQLVESGGG LVQAGGSLRL SCAASGRTFS SGTMGWFRRA PGKEREFVAS IPWSGGRTYY  60
ADSVKDRFTI SRDNAQNTVF LQMNSLKPED TAVYYCAFKE RSTGWDFASW GQGIQVTVSS  120

SEQ ID NO: 173          moltype = AA  length = 127
FEATURE                 Location/Qualifiers
REGION                  1..127
                        note = Synthetic Sequence
source                  1..127
                        mol_type = protein
                        organism = synthetic construct
SEQUENCE: 173
EVQLVESGGG LVQTGGSLRL SCAASGFTLD YYGIGWFRQA PGKEREGVSF ISGSDGSTYY  60
AESVKGRFTI SRDKAKNTVY LQMNSLKPED TAVYYCAADP WGPPSIATMT SYEYKHWGQG  120
TQVTVSS                                                     127

SEQ ID NO: 174          moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 174
EVQLVESGGG LVQPGGSLRL SCAASGFTFS TYTMIWLRRA PGKGFEWVST IDKDGNTNYV  60
DSVKGRFAVS RDNTKNTLYL QMNSLKPEDT AMYYCTKHGS SARGQGTRVT VSS         113

SEQ ID NO: 175          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 175
EVQLVESGGG LVEPGGSLRL SCVASGFTFS SYDMSWVRQA PGKGLEWVST INSGGGITYR  60
GSVKGRFTIS RDNAKNTLYL QMNSLKPEDT AVYYCENGGS SYRRGQGTQV TVSS        114

SEQ ID NO: 176          moltype = AA  length = 114
```

-continued

```
FEATURE                 Location/Qualifiers
REGION                  1..114
                        note = Synthetic Sequence
source                  1..114
                        mol_type = protein
                        organism = synthetic construct
SEQUENCE: 176
QVQLVQSGAE LKKPGASVKM SCKASGYTFT GYTMHWVKQA PGQGLEWIGY INPRSGYTEY  60
NQKFKDRTTL TADKSTSTAY MELSSLRSED SAVYYCARPW FAYWGQGTLV TVSS        114

SEQ ID NO: 177          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 177
QVQLVQSGAE VKKPGASVKM SCKASGYTFT GYTMHWVKQA PGQGLEWIGY INPRSGYTEY  60
NQKFKDRTTL TADKSTSTAY MELSSLRSED TAVYYCARPW FAYWGQGTLV TVSS        114

SEQ ID NO: 178          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 178
QVQLVQSGAE VKKPGASVKM SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 179          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 179
QVQLVQSGAE VKKPGASVKV SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 180          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 180
QVQLVQSGAE VKKPGASVKV SCKASGYTFT GYTMHWVRQA PGQGLEWIGY INPRSGYTEY  60
NQKFKDRTTI TADKSTSTAY MELSSLRSED TAVYYCARPW FAYWGQGTLV TVSS        114

SEQ ID NO: 181          moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 181
DIVMTQSPAS LTVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 182          moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 182
DIVMTQSPAS LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 183          moltype = AA  length = 113
FEATURE                 Location/Qualifiers
REGION                  1..113
```

```
                        note = Synthetic Sequence
source                  1..113
                        mol_type = protein
                        organism = synthetic construct
SEQUENCE: 183
DIVMTQSPAF LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 184          moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 184
DIVMTQSPAF LSVTPGEKVT ITCKSSQSLL NSGNQKNYLT WYQQKPGQPP KLLIYWASTR  60
ESGVPDRFSG SGSGTDFTLT ISSLQAEDVA VYYCQNDYSY PLTFGQGTKL EIK         113

SEQ ID NO: 185          moltype = AA  length = 450
FEATURE                 Location/Qualifiers
REGION                  1..450
                        note = Synthetic Sequence
source                  1..450
                        mol_type = protein
                        organism = synthetic construct
SEQUENCE: 185
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSSA  120
KTTAPSVYPL APVCGGTTGS SVTLGCLVKG YFPEPVTLTW NSGSLSSGVH TFPAVLQSDL  180
YTLSSSVTVT SSTWPSQSIT CNVAHPASST KVDKKIEPRP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 186          moltype = AA  length = 213
FEATURE                 Location/Qualifiers
REGION                  1..213
                        note = Synthetic Sequence
source                  1..213
                        mol_type = protein
                        organism = synthetic construct
SEQUENCE: 186
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRADT APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213

SEQ ID NO: 187          moltype = AA  length = 449
FEATURE                 Location/Qualifiers
REGION                  1..449
                        note = Synthetic Sequence
source                  1..449
                        mol_type = protein
                        organism = synthetic construct
SEQUENCE: 187
EVQLLESGGG LVQPGGSLRL SCAASGFTFS SFPMAWVRQA PGKGLEWVST ISTSGGRTYY  60
RDSVKGRFTI SRDNSKNTLY LQMNSLRAED TAVYYCAKFR QYSGGFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYAS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 188          moltype = AA  length = 216
FEATURE                 Location/Qualifiers
REGION                  1..216
                        note = Synthetic Sequence
source                  1..216
                        mol_type = protein
                        organism = synthetic construct
SEQUENCE: 188
DIQLTQPNSV STSLGSTVKL SCTLSSGNIE NNYVHWYQLY EGRSPTTMIY DDDKRPDGVP  60
DRFSGSIDRS SNSAFLTIHN VAIEDEAIYF CHSYVSSFNV FGGGTKLTVL RQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216
```

-continued

```
SEQ ID NO: 189          moltype = AA  length = 449
FEATURE                 Location/Qualifiers
REGION                  1..449
                        note = Synthetic Sequence
source                  1..449
                        mol_type = protein
                        organism = synthetic construct
SEQUENCE: 189
QVQLVQSGGG VVQPGRSLRL SCKASGYTFT RYTMHWVRQA PGKGLEWIGY INPSRGYTNY  60
NQKVKDRFTI SRDNSKNTAF LQMDSLRPED TGVYFCARYY DDHYCLDYWG QGTPVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 190          moltype = AA  length = 213
FEATURE                 Location/Qualifiers
REGION                  1..213
                        note = Synthetic Sequence
source                  1..213
                        mol_type = protein
                        organism = synthetic construct
SEQUENCE: 190
DIQMTQSPSS LSASVGDRVT ITCSASSSVS YMNWYQQTPG KAPKRWIYDT SKLASGVPSR  60
FSGSGSGTDY TFTISSLQPE DIATYYCQQW SSNPFTFGQG TKLQITRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 191          moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 191
QVQLVQSGAE VKKPGASVKV SCKASGYTFI SYTMHWVRQA PGQGLEWMGY INPRSGYTHY  60
NQKLKDKATL TADKSASTAY MELSSLRSED TAVYYCARSA YYDYDGFAYW GQGTLVTVSS  120

SEQ ID NO: 192          moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 192
DIQMTQSPSS LSASVGDRVT ITCSASSSVS YMNWYQQKPG KAPKRLIYDT SKLASGVPSR  60
FSGSGSGTDF TLTISSLQPE DFATYYCQQW SSNPPTFGGG TKVEIK                 106

SEQ ID NO: 193          moltype = AA  length = 118
FEATURE                 Location/Qualifiers
REGION                  1..118
                        note = Synthetic Sequence
source                  1..118
                        mol_type = protein
                        organism = synthetic construct
SEQUENCE: 193
QVQLVESGGG VVQPGRSLRL SCAASGFKFS GYGMHWVRQA PGKGLEWVAV IWYDGSKKYY  60
VDSVKGRFTI SRDNSKNTLY LQMNSLRAED TAVYYCARQM GYWHFDLWGR GTLVTVSS    118

SEQ ID NO: 194          moltype = AA  length = 118
FEATURE                 Location/Qualifiers
REGION                  1..118
                        note = Synthetic Sequence
source                  1..118
                        mol_type = protein
                        organism = synthetic construct
SEQUENCE: 194
QVQLVQSGGG VVQSGRSLRL SCAASGFKFS GYGMHWVRQA PGKGLEWVAV IWYDGSKKYY  60
VDSVKGRFTI SRDNSKNTLY LQMNSLRGED TAVYYCARQM GYWHFDLWGR GTLVTVSS    118

SEQ ID NO: 195          moltype = AA  length = 108
FEATURE                 Location/Qualifiers
REGION                  1..108
                        note = Synthetic Sequence
source                  1..108
```

```
                        mol_type = protein
                        organism = synthetic construct
SEQUENCE: 195
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPLTFG GGTKVEIK               108

SEQ ID NO: 196          moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 196
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPLTFG GGTKVEIK               108

SEQ ID NO: 197          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 197
EVKLVESGGG LVQPGGSLRL SCAASGFTFN TYAMNWVRQA PGKGLEWVAR IRSKYNNYAT  60
YYADSVKDRF TISRDDSKSS LYLQMNNLKT EDTAMYYCVR HGNFGNSYVS WFAYWGQGTL  120
VTVSS                                                              125

SEQ ID NO: 198          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 198
EVKLVESGGG LVKPGRSLRL SCAASGFTFN TYAMNWVRQA PGKGLEWVAR IRSKYNNYAT  60
YYADSVKDRF TISRDDSKSI LYLQMNNLKT EDTAMYYCVR HGNFGNSYVS WFAYWGQGTL  120
VTVSS                                                              125

SEQ ID NO: 199          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 199
EVKLVESGGG LVKPGRSLRL SCAASGFTFN TYAMNWVRQA PGKGLEWVAR IRSKYNNYAT  60
YYADSVKDRF TISRDDSKSI LYLQMNSLKT EDTAMYYCVR HGNFGNSYVS WFAYWGQGTL  120
VTVSS                                                              125

SEQ ID NO: 200          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 200
EVKLVESGGG LVKPGRSLRL SCAASGFTFN TYAMNWVRQA PGKGLEWVAR IRSKYNNYAT  60
YYADSVKDRF TISRDDSKSI LYLQMNSLKT EDTAMYYCVR HGNFGNSYVS WFAYWGQGTM  120
VTVSS                                                              125

SEQ ID NO: 201          moltype = AA  length = 109
FEATURE                 Location/Qualifiers
REGION                  1..109
                        note = Synthetic Sequence
source                  1..109
                        mol_type = protein
                        organism = synthetic construct
SEQUENCE: 201
QAVVTQEPSF SVSPGGTVTL TCRSSTGAVT TSNYANWVQQ TPGQAFRGLI GGTNKRAPGV  60
PARFSGSLIG DKAALTITGA QADDESIYFC ALWYSNLWVF GGGTKLTVL              109

SEQ ID NO: 202          moltype = AA  length = 109
FEATURE                 Location/Qualifiers
REGION                  1..109
```

-continued

```
                         note = Synthetic Sequence
source                   1..109
                         mol_type = protein
                         organism = synthetic construct
SEQUENCE: 202
QAVVTQEPSF SVSPGGTVTL TCRSSTGAVT TSNYANWVQQ TPGQAFRGLI GGTNKRAPGV  60
PARFSGSILG NKAALTITGA QADDESIYFC ALWYSNLWVF GGGTKLTVL             109

SEQ ID NO: 203           moltype = AA  length = 109
FEATURE                  Location/Qualifiers
REGION                   1..109
                         note = Synthetic Sequence
source                   1..109
                         mol_type = protein
                         organism = synthetic construct
SEQUENCE: 203
QAVVTQEPSF SVSPGGTVTL TCRSSTGAVT TSNYANWVQQ TPGQAFRGLI GGTNKRAPGV  60
PARFSGSILG NKAALTITGA QADDESDYYC ALWYSNLWVF GGGTKLTVL             109

SEQ ID NO: 204           moltype = AA  length = 119
FEATURE                  Location/Qualifiers
REGION                   1..119
                         note = Synthetic Sequence
source                   1..119
                         mol_type = protein
                         organism = synthetic construct
SEQUENCE: 204
QVQLVQSGSE LKKPGASVKM SCKASGYTFT RYTMHWVRQA PGKGLEWIGY INPSRGYTNY  60
NQKFKDRATL TTDKSTSTAY MQLSSLRSED TAVYYCARYY DDHYSLDYWG QGTLVTVSS   119

SEQ ID NO: 205           moltype = AA  length = 106
FEATURE                  Location/Qualifiers
REGION                   1..106
                         note = Synthetic Sequence
source                   1..106
                         mol_type = protein
                         organism = synthetic construct
SEQUENCE: 205
QIVLTQSPAT LSLSPGERAT MSCSASSSVS YMNWYQQKPG KAPKRWIYDT SKLASGVPSR  60
FRGSGSGTDY TLTISSLQPE DFATYYCQQW SSNPFTFGGG TKVEIK                106

SEQ ID NO: 206           moltype = AA  length = 125
FEATURE                  Location/Qualifiers
REGION                   1..125
                         note = Synthetic Sequence
source                   1..125
                         mol_type = protein
                         organism = synthetic construct
SEQUENCE: 206
ELQLVESGGG VVQPGRSLRL SCAASGFTFS SYGMHWVRQA PGKGLEWVAV ISYDGSNKYY  60
ADSVKGRFTI SRDNSKNTLY LQMNSLRSED TAVYYCARLS PYCTNGVCWD AFDIWGQGTM  120
VTVSS                                                             125

SEQ ID NO: 207           moltype = AA  length = 122
FEATURE                  Location/Qualifiers
REGION                   1..122
                         note = Synthetic Sequence
source                   1..122
                         mol_type = protein
                         organism = synthetic construct
SEQUENCE: 207
ELQLVESGGG LVKPGRSLRL SCTASGFTFG DYAMSWFRQA PGKGLEWVGF IRSKAYGGTT  60
EYAASVKGRF TISRDDSKSI AYLQMNSLKT EDTAVYYCTP QLWLLQDAFD IWGQGTMVTV  120
SS                                                                122

SEQ ID NO: 208           moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 208
ELQLVESGPG LVKPSGTLSL TCAVSGGSIS SRNWWSWVRQ PPGKGLEWIG DIYHSGSTNY  60
NPSLKSRVTI SVDKSKNQFS LKLSSVTAAD TAVYYCASGY TSCRDAFDIW GQGTMVTVSS  120

SEQ ID NO: 209           moltype = AA  length = 126
FEATURE                  Location/Qualifiers
REGION                   1..126
```

```
                          note = Synthetic Sequence
source                    1..126
                          mol_type = protein
                          organism = synthetic construct
SEQUENCE: 209
ELQLVEWGAG LLKPSETLSL TCAVYGGSFS GYYWSWIRQP PGKGLEWIGE INHSGSTNYN  60
PSLKSRVTIS VDTSKNQFSL KLSSVTAADT AVYYCARGRG RFLGWLLGGS NWFDPWGQGT  120
LVTVSS                                                             126

SEQ ID NO: 210            moltype = AA  length = 119
FEATURE                   Location/Qualifiers
REGION                    1..119
                          note = Synthetic Sequence
source                    1..119
                          mol_type = protein
                          organism = synthetic construct
SEQUENCE: 210
ELQLVEWGAG LLKPSETLSL TCAVYGGSFS GYYWSWIRQP PGKGLEWIGE INHSGSTNYN  60
PSLKSRVTIS VDTSKNQFSL KLSSVTAADT AVYYCARGPD RMGHGFDIWG QGTMVTVSS   119

SEQ ID NO: 211            moltype = AA  length = 127
FEATURE                   Location/Qualifiers
REGION                    1..127
                          note = Synthetic Sequence
source                    1..127
                          mol_type = protein
                          organism = synthetic construct
SEQUENCE: 211
ELQLVESGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA RDRRRIAARQ YYGMDVWGQG  120
TTVTVSS                                                            127

SEQ ID NO: 212            moltype = AA  length = 121
FEATURE                   Location/Qualifiers
REGION                    1..121
                          note = Synthetic Sequence
source                    1..121
                          mol_type = protein
                          organism = synthetic construct
SEQUENCE: 212
ELQLVESGGG LVQPGGSLRL SCAASGFTFS SYAMGWVRQA PGKGLEWVSA VSGSGGSTYY  60
ADSVKGRFTI SRDNSKNTLY LQMNSLRAED TAVYYCAKAK FLGHYYGMDV WGQGTTVTVS  120
S                                                                  121

SEQ ID NO: 213            moltype = AA  length = 123
FEATURE                   Location/Qualifiers
REGION                    1..123
                          note = Synthetic Sequence
source                    1..123
                          mol_type = protein
                          organism = synthetic construct
SEQUENCE: 213
ELQLVESGPV LVKPTDTLTL TCTVSGFSLN NPRMGVSWIR QPPGKTLEWL AHIFPSDAKA  60
HSASLKSRLT ISKDTSKSQV VPTMTNMDPV DTATYYCARI LGEYYPPAWF DPWGQGTLVT  120
VSS                                                                123

SEQ ID NO: 214            moltype = AA  length = 107
FEATURE                   Location/Qualifiers
REGION                    1..107
                          note = Synthetic Sequence
source                    1..107
                          mol_type = protein
                          organism = synthetic construct
SEQUENCE: 214
ELQMTQSPSS LSASVGDRVS ITCRASQTIS NYLNWYQLKP GKAPKLLIYA ASTLQSEVPT  60
RFSGSGSGTD FTLTISGLHP EDFATYYCQQ FNSYPRTFGQ GTKVEIK                107

SEQ ID NO: 215            moltype = AA  length = 107
FEATURE                   Location/Qualifiers
REGION                    1..107
                          note = Synthetic Sequence
source                    1..107
                          mol_type = protein
                          organism = synthetic construct
SEQUENCE: 215
ELQMTQSPSS LSASVGDRVT ITCRASQGIS NYLAWYQQKP GKVPKLLIYA ASTLQSGVPS  60
RFSGSGSGTD FTLTISSLQP EDFATYYCQQ SYSTPPTFGQ GTKLEIK                107

SEQ ID NO: 216            moltype = AA  length = 107
```

-continued

```
FEATURE                Location/Qualifiers
REGION                 1..107
                       note = Synthetic Sequence
source                 1..107
                       mol_type = protein
                       organism = synthetic construct
SEQUENCE: 216
ELVMTQSPSS LSASVGDRVT ITCRASQGIG NYLAWYQQKP GQPPKMLIYW ASIRESGVPD  60
RFSGSGSGTD FTLTISSLQA EDVAVYYCQQ YYSNPQTFGQ GTKVEIK                107

SEQ ID NO: 217         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 217
ELVMTQSPSS LSASVGDRVT ITCRASQGIS NYLNWYQQKP GKAPKLLIYD ASNLETGVPS  60
RFSGSGSGTD FTLTISSLQP EDFATYYCQQ SYSTPYTFGQ GTKVDIK                107

SEQ ID NO: 218         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 218
ELQMTQSPSS LSASVGDRVT ITCRASQSIS SYLNWYQQKS GKAPKLLIYA ASSLQSGVPS  60
RFSGSGSGTD FTLTISSLQP EDFATYYCQQ SYSSPWTFGQ GTKVEIK                107

SEQ ID NO: 219         moltype = AA  length = 108
FEATURE                Location/Qualifiers
REGION                 1..108
                       note = Synthetic Sequence
source                 1..108
                       mol_type = protein
                       organism = synthetic construct
SEQUENCE: 219
ELVLTQSPGT LSLSPGERAT LSCRASQSVS SNYLAWYQQK PGQAPRLLIY GASSRATGIP  60
DRFSGSGSGT DFTLTISSLQ PEDVATYYCQ KYNSAPLTFG GGTKVEIK               108

SEQ ID NO: 220         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 220
ELQMTQSPSS LSASVGDRVT ITCRASQSIS SYLNWYQQKP GKAPKLLIYA ASSLQSGVPS  60
RFSGSGSGTE FTLTISSLQP EDFATYYCLQ HNAYPYTFGQ GTKVEIK                107

SEQ ID NO: 221         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 221
ELVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYLKI PYTFGQGTKV EIK        113

SEQ ID NO: 222         moltype = AA  length = 119
FEATURE                Location/Qualifiers
REGION                 1..119
                       note = Synthetic Sequence
source                 1..119
                       mol_type = protein
                       organism = synthetic construct
SEQUENCE: 222
QVQLVQSGAE VKKPGASVKV SCKASGYTFT RYTMHWVRQA PGQGLEWMGY INPSRGYTNY  60
NQKFKDRVTM TTDTSISTAY MELSRLRSDD TAVYYCARYY DDHYCLDYWG QGTLVTVSS   119

SEQ ID NO: 223         moltype = AA  length = 119
FEATURE                Location/Qualifiers
REGION                 1..119
```

-continued

```
                        note = Synthetic Sequence
source                  1..119
                        mol_type = protein
                        organism = synthetic construct
SEQUENCE: 223
QVQLVQSGAE VKKPGASVKV SCKASGYTFT RYTMHWVRQA PGQGLEWMGY INPSRGYTNY  60
NQKFKDRVTM TTDTSISTAY MELSRLRSDD TAVYYCARYY DDHYSLDYWG QGTLVTVSS   119

SEQ ID NO: 224          moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 224
EIVLTQSPAT LSLSPGERAT LSCSASSSVS YMNWYQQKPG QAPRLLIYDT SKLASGVPAH  60
FRGSGSGTDY TLTISSLEPE DFAVYYCQQW SSNPFTFGQG TKVEIK                 106

SEQ ID NO: 225          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 225
EVQLVESGGG LVQPGGSLRL SCAASGFTFS TYAMNWVRQA PGKGLEWVGR IRSKYNNYAT  60
YYADSVKDRF TISRDDSKNS LYLQMNSLKT EDTAVYYCAR HGNFGNSYVS WFAYWGQGTL  120
VTVSS                                                              125

SEQ ID NO: 226          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 226
EVQLVESGGG LVQPGGSLRL SCAASGFTFS TYAMNWVRQA PGKGLEWVGR IRSKYNNYAT  60
YYADSVKDRF TISRDDSKNS LYLQMNSLKT EDTAVYYCAR HGNFGNSYVS WFAYWGQGTL  120
VTVSS                                                              125

SEQ ID NO: 227          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 227
EVQLVESGGG LVQPGGSLRL SCAASGFTFS TYAMNWVRQA PGKGLEWVGR IRSKYNNYAT  60
YYADSVKDRF TISRDDSKNS LYLQMNSLKT EDTAVYYCAR HGNFGNSYVS YFAYWGQGTL  120
VTVSS                                                              125

SEQ ID NO: 228          moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 228
EVQLVESGGG LVQPGGSLRL SCAASGFTFS TYAMNWVRQA PGKGLEWVGR IRSKYNNYAT  60
YYADSVKDRF TISRDDSKNS LYLQMNSLKT EDTAVYYCAR HGNFGNSYVS HFAYWGQGTL  120
VTVSS                                                              125

SEQ ID NO: 229          moltype = AA  length = 110
FEATURE                 Location/Qualifiers
REGION                  1..110
                        note = Synthetic Sequence
source                  1..110
                        mol_type = protein
                        organism = synthetic construct
SEQUENCE: 229
DIQMTQSPSS LSASVGDRVT ITCRSSTGAV TTSNYANWVQ QKPGKAPKGL IGGTNKRAPG  60
VPSRFSGSLI GDKATLTISS LQPEDFATYY CALWYSNLWV FGQGTKVEIK             110

SEQ ID NO: 230          moltype = AA  length = 110
```

```
FEATURE                Location/Qualifiers
REGION                 1..110
                       note = Synthetic Sequence
source                 1..110
                       mol_type = protein
                       organism = synthetic construct
SEQUENCE: 230
DIQMTQSPSS LSASVGDRVT ITCRSSTGAV TTSNYANWVQ QKPGKAPKGL IGGTNKRAPG  60
VPARFSGSGS GTDFTLTISS LQPEDFATYY CALWYSNLWV FGQGTKVEIK            110

SEQ ID NO: 231         moltype = AA  length = 110
FEATURE                Location/Qualifiers
REGION                 1..110
                       note = Synthetic Sequence
source                 1..110
                       mol_type = protein
                       organism = synthetic construct
SEQUENCE: 231
DIQMTQSPSS LSASVGDRVT ITCRSSTGAV TTSNYANWVQ QKPGKAPKAL IGGTNKRAPG  60
VPSRFSGSLI GDKATLTISS LQPEDFATYY CALWYSNLWV FGQGTKVEIK            110

SEQ ID NO: 232         moltype = AA  length = 110
FEATURE                Location/Qualifiers
REGION                 1..110
                       note = Synthetic Sequence
source                 1..110
                       mol_type = protein
                       organism = synthetic construct
SEQUENCE: 232
DIQMTQSPSS LSASVGDRVT ITCRSSTGAV TTSNYANWVQ QKPGKAPKGL IGGTNKRAPG  60
VPSRFSGSLI GDKATLTISS LQPEDFATYY CALWYSNLWV FGQGTKVEIK            110

SEQ ID NO: 233         moltype = AA  length = 165
FEATURE                Location/Qualifiers
REGION                 1..165
                       note = Synthetic Sequence
source                 1..165
                       mol_type = protein
                       organism = synthetic construct
SEQUENCE: 233
CDLPQTHSLG SRRTLMLLAQ MRKISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 234         moltype = AA  length = 165
FEATURE                Location/Qualifiers
REGION                 1..165
                       note = Synthetic Sequence
source                 1..165
                       mol_type = protein
                       organism = synthetic construct
SEQUENCE: 234
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 235         moltype = AA  length = 165
FEATURE                Location/Qualifiers
REGION                 1..165
                       note = Synthetic Sequence
source                 1..165
                       mol_type = protein
                       organism = synthetic construct
SEQUENCE: 235
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRC DKPRR                 165

SEQ ID NO: 236         moltype = AA  length = 165
FEATURE                Location/Qualifiers
REGION                 1..165
                       note = Synthetic Sequence
source                 1..165
                       mol_type = protein
                       organism = synthetic construct
SEQUENCE: 236
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRS LTRKD                 165
```

```
SEQ ID NO: 237          moltype = AA  length = 157
FEATURE                 Location/Qualifiers
REGION                  1..157
                        note = Synthetic Sequence
source                  1..157
                        mol_type = protein
                        organism = synthetic construct
SEQUENCE: 237
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL  120
GGVFQLEKGD RLSAEINRPD YLDFAESGQV YFGIIAL                           157

SEQ ID NO: 238          moltype = AA  length = 171
FEATURE                 Location/Qualifiers
REGION                  1..171
                        note = Synthetic Sequence
source                  1..171
                        mol_type = protein
                        organism = synthetic construct
SEQUENCE: 238
LPGVGLTPSA AQTARQHPKM HLAHSNLKPA AHLIGDPSKQ NSLLWRANTD RAFLQDGFSL  60
SNNSLLVPTS GIYFVYSQVV FSGKAYSPKA TSSPLYLAHE VQLFSSQYPF HVPLLSSQKM  120
VYPGLQEPWL HSMYHGAAFQ LTQGDQLSTH TDGIPHLVLS PSTVFFGAFA L           171

SEQ ID NO: 239          moltype = AA  length = 281
FEATURE                 Location/Qualifiers
REGION                  1..281
                        note = Synthetic Sequence
source                  1..281
                        mol_type = protein
                        organism = synthetic construct
SEQUENCE: 239
MAMMEVQGGP SLGQTCVLIV IFTVLLQSLC VAVTYVYFTN ELKQMQDKYS KSGIACFLKE  60
DDSYWDPNDE ESMNSPCWQV KWQLRQLVRK MILRTSEETI STVQEKQQNI SPLVRERGPQ  120
RVAAHITGTR GRSNTLSSPN SKNEKALGRK INSWESSRSG HSFLSNLHLR NGELVIHEKG  180
FYYIYSQTYF RFQEEIKENT KNDKQMVQYI YKYTSYPDPI LLMKSARNSC WSKDAEYGLY  240
SIYQGGIFEL KENDRIFVSV TNEHLIDMDH EASFFGAFLV G                      281

SEQ ID NO: 240          moltype = AA  length = 153
FEATURE                 Location/Qualifiers
REGION                  1..153
                        note = Synthetic Sequence
source                  1..153
                        mol_type = protein
                        organism = synthetic construct
SEQUENCE: 240
APVRSLNCTL RDSQQKSLVM SGPYELKALH LQGQDMEQQV VFSMSFVQGE ESNDKIPVAL  60
GLKEKNLYLS CVLKDDKPTL QLESVDPKNY PKKKMEKRFV FNKIEINNKL EFESAQFPNW  120
YISTSQAENM PVFLGGTKGG QDITDFTMQF VSS                               153

SEQ ID NO: 241          moltype = AA  length = 133
FEATURE                 Location/Qualifiers
REGION                  1..133
                        note = Synthetic Sequence
source                  1..133
                        mol_type = protein
                        organism = synthetic construct
SEQUENCE: 241
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 242          moltype = AA  length = 129
FEATURE                 Location/Qualifiers
REGION                  1..129
                        note = Synthetic Sequence
source                  1..129
                        mol_type = protein
                        organism = synthetic construct
SEQUENCE: 242
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
REKYSKCSS                                                          129

SEQ ID NO: 243          moltype = AA  length = 185
FEATURE                 Location/Qualifiers
REGION                  1..185
                        note = Synthetic Sequence
```

```
source                  1..185
                        mol_type = protein
                        organism = synthetic construct
SEQUENCE: 243
APVPPGEDSK DVAAPHRQPL TSSERIDKQI RYILDGISAL RKETCNKSNM CESSKEALAE  60
NNLNLPKMAE KDGCFQSGFN EETCLVKIIT GLLEFEVYLE YLQNRFESSE EQARAVQMST  120
KVLIQFLQKK AKNLDAITTP DPTTNASLTT KLQAQNQWLQ DMTTHLILRS FKEFLQSSLR  180
ALRQM                                                             185

SEQ ID NO: 244          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 244
SPGPVPPSTA LRELIEELVN ITQNQKAPLC NGSMVWSINL TAGMYCAALE SLINVSGCSA  60
IEKTQRMLSG FCPHKVSAGQ FSSLHVRDTK IEVAQFVKDL LLHLKKLFRE GRFN        114

SEQ ID NO: 245          moltype = AA  length = 194
FEATURE                 Location/Qualifiers
REGION                  1..194
                        note = Synthetic Sequence
source                  1..194
                        mol_type = protein
                        organism = synthetic construct
SEQUENCE: 245
MAAEPVEDNC INFVAMKFID NTLYFIAEDD ENLESDYFGK LESKLSVIRN LNDQVLFIDQ  60
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NEDL                                                   194

SEQ ID NO: 246          moltype = AA  length = 270
FEATURE                 Location/Qualifiers
REGION                  1..270
                        note = Synthetic Sequence
source                  1..270
                        mol_type = protein
                        organism = synthetic construct
SEQUENCE: 246
MKPKMKYSTN KISTAKWKNT ASKALCFKLG KSQQKAKEVC PMYFMKLRSG LMIKKEACYF  60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
GVKDNHLALI KVDSSENLCT ENILFKLSET                                  270

SEQ ID NO: 247          moltype = AA  length = 193
FEATURE                 Location/Qualifiers
REGION                  1..193
                        note = Synthetic Sequence
source                  1..193
                        mol_type = protein
                        organism = synthetic construct
SEQUENCE: 247
MGVHECPAWL WLLLSLLSLP LGLPVLGAPP RLICDSRVLE RYLLEAKEAE NITTGCAEHC  60
SLNENITVPD TKVNFYAWKR MEVGQQAVEV WQGLALLSEA VLRGQALLVN SSQPWEPLQL  120
HVDKAVSGLR SLTTLLRALG AQKEAISPPD AASAAPLRTI TADTFRKLFR VYSNFLRGKL  180
KLYTGEACRT GDR                                                    193

SEQ ID NO: 248          moltype = AA  length = 166
FEATURE                 Location/Qualifiers
REGION                  1..166
                        note = Synthetic Sequence
source                  1..166
                        mol_type = protein
                        organism = synthetic construct
SEQUENCE: 248
APPRLICDSR VLERYLLEAK EAENITTGCA EHCSLNENIT VPDTKVNFYA WKRMEVGQQA  60
VEVWQGLALL SEAVLRGQAL LVNSSQPWEP LQLHVDKAVS GLRSLTTLLR ALGAQKEAIS  120
PPDAASAAPL RTITADTFRK LFRVYSNFLR GKLKLYTGEA CRTGDR                166

SEQ ID NO: 249          moltype = AA  length = 5
FEATURE                 Location/Qualifiers
REGION                  1..5
                        note = Synthetic Sequence
source                  1..5
                        mol_type = protein
                        organism = synthetic construct
```

-continued

```
SEQUENCE: 249
GGGGS                                                         5

SEQ ID NO: 250          moltype = AA  length = 10
FEATURE                 Location/Qualifiers
REGION                  1..10
                        note = Synthetic Sequence
source                  1..10
                        mol_type = protein
                        organism = synthetic construct
SEQUENCE: 250
GGGGSGGGGS                                                    10

SEQ ID NO: 251          moltype = AA  length = 15
FEATURE                 Location/Qualifiers
REGION                  1..15
                        note = Synthetic Sequence
source                  1..15
                        mol_type = protein
                        organism = synthetic construct
SEQUENCE: 251
GGGGSGGGGS GGGGS                                              15

SEQ ID NO: 252          moltype = AA  length = 20
FEATURE                 Location/Qualifiers
REGION                  1..20
                        note = Synthetic Sequence
source                  1..20
                        mol_type = protein
                        organism = synthetic construct
SEQUENCE: 252
GGGGSGGGGS GGGGSGGGGS                                         20

SEQ ID NO: 253          moltype = AA  length = 25
FEATURE                 Location/Qualifiers
REGION                  1..25
                        note = Synthetic Sequence
source                  1..25
                        mol_type = protein
                        organism = synthetic construct
SEQUENCE: 253
GGGGSGGGGS GGGGSGGGGS GGGGS                                   25

SEQ ID NO: 254          moltype = AA  length = 30
FEATURE                 Location/Qualifiers
REGION                  1..30
                        note = Synthetic Sequence
source                  1..30
                        mol_type = protein
                        organism = synthetic construct
SEQUENCE: 254
GGGGSGGGGS GGGGSGGGGS GGGGSGGGGS                              30

SEQ ID NO: 255          moltype = AA  length = 35
FEATURE                 Location/Qualifiers
REGION                  1..35
                        note = Synthetic Sequence
source                  1..35
                        mol_type = protein
                        organism = synthetic construct
SEQUENCE: 255
GGGGSGGGGS GGGGSGGGGS GGGGSGGGGS GGGGS                        35

SEQ ID NO: 256          moltype = AA  length = 40
FEATURE                 Location/Qualifiers
REGION                  1..40
                        note = Synthetic Sequence
source                  1..40
                        mol_type = protein
                        organism = synthetic construct
SEQUENCE: 256
GGGGSGGGGS GGGGSGGGGS GGGGSGGGGS GGGGSGGGGS                   40

SEQ ID NO: 257          moltype = AA  length = 16
FEATURE                 Location/Qualifiers
REGION                  1..16
                        note = Synthetic Sequence
source                  1..16
                        mol_type = protein
```

```
                        organism = synthetic construct
SEQUENCE: 257
GGSGGSGGGG SGGGGS                                                   16

SEQ ID NO: 258          moltype = AA  length = 8
FEATURE                 Location/Qualifiers
REGION                  1..8
                        note = Synthetic Sequence
source                  1..8
                        mol_type = protein
                        organism = synthetic construct
SEQUENCE: 258
GGGGGGGG                                                            8

SEQ ID NO: 259          moltype = AA  length = 6
FEATURE                 Location/Qualifiers
REGION                  1..6
                        note = Synthetic Sequence
source                  1..6
                        mol_type = protein
                        organism = synthetic construct
SEQUENCE: 259
GGGGGG                                                              6

SEQ ID NO: 260          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 260
EAAAK                                                               5

SEQ ID NO: 261          moltype = AA  length = 10
FEATURE                 Location/Qualifiers
REGION                  1..10
                        note = Synthetic Sequence
source                  1..10
                        mol_type = protein
                        organism = synthetic construct
SEQUENCE: 261
EAAAKEAAAK                                                          10

SEQ ID NO: 262          moltype = AA  length = 15
FEATURE                 Location/Qualifiers
REGION                  1..15
                        note = Synthetic Sequence
source                  1..15
                        mol_type = protein
                        organism = synthetic construct
SEQUENCE: 262
EAAAKEAAAK EAAAK                                                    15

SEQ ID NO: 263          moltype = AA  length = 12
FEATURE                 Location/Qualifiers
REGION                  1..12
                        note = Synthetic Sequence
source                  1..12
                        mol_type = protein
                        organism = synthetic construct
SEQUENCE: 263
AEAAAKEAAA KA                                                       12

SEQ ID NO: 264          moltype = AA  length = 17
FEATURE                 Location/Qualifiers
REGION                  1..17
                        note = Synthetic Sequence
source                  1..17
                        mol_type = protein
                        organism = synthetic construct
SEQUENCE: 264
AEAAAKEAAA KEAAAKA                                                  17

SEQ ID NO: 265          moltype = AA  length = 22
FEATURE                 Location/Qualifiers
REGION                  1..22
                        note = Synthetic Sequence
source                  1..22
```

```
                        mol_type = protein
                        organism = synthetic construct
SEQUENCE: 265
AEAAAKEAAA KEAAAKEAAA KA                                                    22

SEQ ID NO: 266          moltype = AA  length = 27
FEATURE                 Location/Qualifiers
REGION                  1..27
                        note = Synthetic Sequence
source                  1..27
                        mol_type = protein
                        organism = synthetic construct
SEQUENCE: 266
AEAAAKEAAA KEAAAKEAAA KEAAAKA                                               27

SEQ ID NO: 267          moltype = AA  length = 46
FEATURE                 Location/Qualifiers
REGION                  1..46
                        note = Synthetic Sequence
source                  1..46
                        mol_type = protein
                        organism = synthetic construct
SEQUENCE: 267
AEAAAKEAAA KEAAAKEAAA KALEAEAAAK EAAAKEAAAK EAAAKA                          46

SEQ ID NO: 268          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 268
PAPAP                                                                       5

SEQ ID NO: 269          moltype = AA  length = 18
FEATURE                 Location/Qualifiers
REGION                  1..18
                        note = Synthetic Sequence
source                  1..18
                        mol_type = protein
                        organism = synthetic construct
SEQUENCE: 269
KESGSVSSEQ LAQFRSLD                                                         18

SEQ ID NO: 270          moltype = AA  length = 14
FEATURE                 Location/Qualifiers
REGION                  1..14
                        note = Synthetic Sequence
source                  1..14
                        mol_type = protein
                        organism = synthetic construct
SEQUENCE: 270
EGKSSGSGSE SKST                                                             14

SEQ ID NO: 271          moltype = AA  length = 12
FEATURE                 Location/Qualifiers
REGION                  1..12
                        note = Synthetic Sequence
source                  1..12
                        mol_type = protein
                        organism = synthetic construct
SEQUENCE: 271
GSAGSAAGSG EF                                                               12

SEQ ID NO: 272          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 272
GGGSE                                                                       5

SEQ ID NO: 273          moltype = AA  length = 5
FEATURE                 Location/Qualifiers
REGION                  1..5
                        note = Synthetic Sequence
```

```
source                  1..5
                        mol_type = protein
                        organism = synthetic construct
SEQUENCE: 273
GSESG                                                                       5

SEQ ID NO: 274          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 274
GSEGS                                                                       5

SEQ ID NO: 275          moltype = AA  length = 35
FEATURE                 Location/Qualifiers
REGION                  1..35
                        note = Synthetic Sequence
source                  1..35
                        mol_type = protein
                        organism = synthetic construct
SEQUENCE: 275
GEGGSGEGSS GEGSSSEGGG SEGGGSEGGG SEGGS                                      35

SEQ ID NO: 276          moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 276
CPPC                                                                        4

SEQ ID NO: 277          moltype = AA  length = 166
FEATURE                 Location/Qualifiers
REGION                  1..166
                        note = Synthetic Sequence (Human IFN-beta)
source                  1..166
                        mol_type = protein
                        organism = synthetic construct
SEQUENCE: 277
MSYNLLGFLQ RSSNFQCQKL LWQLNGRLEY CLKDRMNFDI PEEIKQLQQF QKEDAALTIY  60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRN                 166

SEQ ID NO: 278          moltype = AA  length = 167
FEATURE                 Location/Qualifiers
REGION                  1..167
                        note = Synthetic Sequence (Consensus interferon)
source                  1..167
                        mol_type = protein
                        organism = synthetic construct
SEQUENCE: 278
MCDLPQTHSL GNRRALILLA QMRRISPFSC LKDRHDFGFP QEEFDGNQFQ KAQAISVLHE  60
MIQQTFNLFS TKDSSAAWDE SLLEKFYTEL YQQLNDLEAC VIQEVGVEET PLMNVDSILA  120
VKKYFQRITL YLTEKKYSPC AWEVVRAEIM RSFSLSTNLQ ERLRRKE                167

SEQ ID NO: 279          moltype = AA  length = 166
FEATURE                 Location/Qualifiers
REGION                  1..166
                        note = Synthetic Sequence (Consensus Interferon without
                         methionine atthe beginning)
source                  1..166
                        mol_type = protein
                        organism = synthetic construct
SEQUENCE: 279
CDLPQTHSLG NRRALILLAQ MRRISPFSCL KDRHDFGFPQ EEFDGNQFQK AQAISVLHEM  60
IQQTFNLFST KDSSAAWDES LLEKFYTELY QQLNDLEACV IQEVGVEETP LMNVDSILAV  120
KKYFQRITLY LTEKKYSPCA WEVVRAEIMR SFSLSTNLQE RLRRKE                 166

SEQ ID NO: 280          moltype = AA  length = 166
FEATURE                 Location/Qualifiers
REGION                  1..166
                        note = Synthetic Sequence (IFN-Con2 (Consensus Interferon
                         Variant 2))
source                  1..166
```

```
                         mol_type = protein
                         organism = synthetic construct
SEQUENCE: 280
CDLPQTHSLG NRRTLMLLAQ MRRISPFSCL KDRHDFGFPQ EEFDGNQFQK AQAISVLHEM  60
IQQTFNLFST KDSSAAWDES LLEKFYTELY QQLNDLEACV IQEVGVEETP LMNVDSILAV  120
KKYFQRITLY LTEKKYSPCA WEVVRAEIMR SFSLSTNLQE RLRRKE                 166

SEQ ID NO: 281           moltype = AA  length = 166
FEATURE                  Location/Qualifiers
REGION                   1..166
                         note = Synthetic Sequence (IFN-Con3 (Consensus Interferon
                          Variant 3))
source                   1..166
                         mol_type = protein
                         organism = synthetic construct
SEQUENCE: 281
CDLPQTHSLG NRRALILLAQ MRRISPFSCL KDRHDFGFPQ EEFDGNQFQK AQAISVLHEM  60
IQQTFNLFST KDSSAAWDES LLEKFYTELY QQLNDLEACV IQEVGVEETP LMNEDSILAV  120
RKYFQRITLY LTEKKYSPCA WEVVRAEIMR SFSLSTNLQE RLRRKE                 166

SEQ ID NO: 282           moltype = AA  length = 167
FEATURE                  Location/Qualifiers
REGION                   1..167
                         note = Synthetic Sequence (Consensus Interferon Variant)
source                   1..167
                         mol_type = protein
                         organism = synthetic construct
SEQUENCE: 282
MCDLPQTHSL GNRRALILLA QMRRISPFSC LKDRHDFGFP QEEFDGNQFQ KAQAISVLHE  60
MIQQTFNLFS TKDSSAAWDE SLLEKFYTEL YQQLNDLEAC VIQEVGVEET PLMNEDSILA  120
VRKYFQRITL YLTEKKYSPC AWEVVRAEIM RSFSLSTNLQ ERLRRKE                167

SEQ ID NO: 283           moltype = AA  length = 167
FEATURE                  Location/Qualifiers
REGION                   1..167
                         note = Synthetic Sequence (Consensus Interferon Variant)
source                   1..167
                         mol_type = protein
                         organism = synthetic construct
SEQUENCE: 283
MCDLPQTHSL GNRRALILLA QMRRISPFSC LKDRHDFGFP QEEFDGNQFQ KAQAISVLHE  60
MIQQTFNLFS TKDSSAAWDE SLLEKFYTEL YQQLNDLEAC VIQEVGVEET PLMNEDSILA  120
VRKYFQRITL YLTEKKYSPC AWEVVRAEIM RSFSLCTNLQ ERLRRKE                167

SEQ ID NO: 284           moltype = AA  length = 6
FEATURE                  Location/Qualifiers
REGION                   1..6
                         note = Synthetic Sequence (human IFN-alpha2a)
source                   1..6
                         mol_type = protein
                         organism = synthetic construct
SEQUENCE: 284
EEFGNQ                                                            6

SEQ ID NO: 285           moltype = AA  length = 7
FEATURE                  Location/Qualifiers
REGION                   1..7
                         note = Synthetic Sequence (human IFN-alpha2a)
source                   1..7
                         mol_type = protein
                         organism = synthetic construct
SEQUENCE: 285
EEFDGNQ                                                           7

SEQ ID NO: 286           moltype = AA  length = 356
FEATURE                  Location/Qualifiers
REGION                   1..356
                         note = Synthetic Sequence (IFN-alpha1 AFN)
source                   1..356
                         mol_type = protein
                         organism = synthetic construct
SEQUENCE: 286
QVQLQESGGG LAQAGGSLRL SCAASGRTFS MGWFRQAPGK EREFVAAITY SGGSPYYASS  60
VRGRFTISRD NAKNTVYLQM NSLKPEDTAV YYCAANPTYG SDWNAENWGQ GTQVTVSSVD  120
GGSGGSGGSG GSGGSGGSRS GGSGGSGGSG GSGGSGGSGG SGGSGGSGGS GGSGGSGGSA  180
AACDLPETHS LDNRRTLMLL AQMSRISPSS CLMDRHDFGF PQEEFDGNQF QKAPAISVLH  240
ELIQQIFNLF TTKDSSAAWD EDLLDKFCTE LYQQLNDLEA CVMQEERVGE TPLMNADSIL  300
AVKKYFRRIT LYLTEKKYSP CAWEVVRAEI MRSLSLSTNL QERLRRKELE HHHHHH      356
```

```
SEQ ID NO: 287         moltype = AA  length = 356
FEATURE                Location/Qualifiers
REGION                 1..356
                       note = Synthetic Sequence (IFN-alpha2 AFN)
source                 1..356
                       mol_type = protein
                       organism = synthetic construct
SEQUENCE: 287
QVQLQESGGG LAQAGGSLRL SCAASGRTFS MGWFRQAPGK EREFVAAITY SGGSPYYASS  60
VRGRFTISRD NAKNTVYLQM NSLKPEDTAV YYCAANPTYG SDWNAENWGQ GTQVTVSSVD  120
GGSGGSGGSG GSGGSGGSRS GGSGGSGGSG GSGGSGGSGG SGGSGGSGGS GGSGGSGGSA  180
AAMCDLPQTH SLGSRRTLML LAQMRRISLF SCLKDRHDFG FPQEEFGNQF QKAETIPVLH  240
EMIQQIFNLF STKDSSAAWD ETLLDKFYTE LYQQLNDLEA CVIQGVGVTE TPLMKEDSIL  300
AVRKYFQRIT LYLKEKKYSP CAWEVVRAEI MRSFSLSTNL QESLRSKELE HHHHHH      356

SEQ ID NO: 288         moltype = AA  length = 118
FEATURE                Location/Qualifiers
REGION                 1..118
                       note = Synthetic Sequence
source                 1..118
                       mol_type = protein
                       organism = synthetic construct
SEQUENCE: 288
QVQLQESGGG LAQAGGSLRL SCAASGRTFS MGWFRQAPGK EREFVAAITY SGGSPYYASS  60
VRGRFTISRD NAKNTVYLQM NSLKPEDTAV YYCAANPTYG SDWNAENWGQ GTQVTVSS    118

SEQ ID NO: 289         moltype = AA  length = 397
FEATURE                Location/Qualifiers
REGION                 1..397
                       note = Synthetic Sequence
REGION                 1..397
                       note = MISC_FEATURE - mature Flt3-L_linker_humanIFNa1
source                 1..397
                       mol_type = protein
                       organism = synthetic construct
SEQUENCE: 289
TQDCSFQHSP ISSDFAVKIR ELSDYLLQDY PVTVASNLQD EELCGGLWRL VLAQRWMERL  60
KTVAGSKMQG LLERVNTEIH FVTKCAFQPP PSCLRFVQTN ISRLLQETSE QLVALKPWIT  120
RQNFSRCLEL QCQPDSSTLP PPWSPRPLEA TAPTAVDGGS GGSGGSGGSG GSGGSGGSGG  180
SGGSGGSGGS GGSGGSGGSG GSGGSGGSGG SGGSAAACDL PETHSLDNRR TLMLLAQMSR  240
ISPSSCLMDR HDFGFPQEEF DGNQFQKAPA ISVLHELIQQ IFNLFTTKDS SAAWDEDLLD  300
KFCTELYQQL NDLEACVMQE ERVGETPLMN ADSILAVKKY FRRITLYLTE KKYSPCAWEV  360
VRAEIMRSLS LSTNLQERLR RKELEGGSHH HHHHHH                            397

SEQ ID NO: 290         moltype = AA  length = 402
FEATURE                Location/Qualifiers
REGION                 1..402
                       note = Synthetic Sequence
REGION                 1..402
                       note = MISC_FEATURE - R1CHCL50-20*GGS-human IgG1 Fc
source                 1..402
                       mol_type = protein
                       organism = synthetic construct
SEQUENCE: 290
QVQLVESGGG LVHPGGSLRL SCAASGSFSS INVMGWYRQA PGKERELVAR ITNLGLPNYA  60
DSVTGRFTIS RDNAKNTVYL QMNSLKPEDT AVYYCYLVAL KAEYWGQGTQ VTVSSGGSGG  120
SGGSGGSGGS GGSGGSGGSG GSGGSGGSGG SGGSGGSGGS GGSGGSGGSG GSGGSDKTHT  180
CPPCPAPEAA GGPSVFLFPP KPKDTLMISR TPEVTCVVVD VSHEDPEVKF NWYVDGVEVH  240
NAKTKPREEQ YNSTYRVVSV LTVLHQDWLN GKEYKCQVSN KALPAPIEKT ISKAKGQPRE  300
PQVCTLPPSR DELTKNQVSL SCAVKGFYPS DIAVEWESNG QPENNYKTTP PVLDSDGSFF  360
LVSKLTVDKS RWQQGNVFSC SVMHEALHNH YTQKSLSLSP GK                     402

SEQ ID NO: 291         moltype = AA  length = 453
FEATURE                Location/Qualifiers
REGION                 1..453
                       note = Synthetic Sequence
REGION                 1..453
                       note = MISC_FEATURE - human IgG1 Fc
source                 1..453
                       mol_type = protein
                       organism = synthetic construct
SEQUENCE: 291
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGS GGSGGSGGSG  240
GSGGSGGSGG SGGSGGSGGS GGSGGSGGSG GSGGSGGSGG SGGSGGSCDL PETHSLDNRR  300
TLMLLAQMSR ISPSSCLMDR HDFGFPQEEF DGNQFQKAPA ISVLHELIQQ IFNLFTTKDS  360
SAAWDEDLLD KFCTELYQQL NDLEACVMQE ERVGETPLMN ADSILAVKKY FRRITLYLTE  420
```

-continued

```
KKYSPCAWEV VRAEIMRSLS LSTNLQERLR RKE                       453

SEQ ID NO: 292          moltype = AA  length = 114
FEATURE                 Location/Qualifiers
REGION                  1..114
                        note = Synthetic Sequence (wild type IL-15)
source                  1..114
                        mol_type = protein
                        organism = synthetic construct
SEQUENCE: 292
NWVNVISDLK KIEDLIQSMH IDATLYTESD VHPSCKVTAM KCFLLELQVI SHESGDTDIH  60
DTVENLIILA NNILSSNGNI TESGCKECEE LEEKNIKEFL QSFVHIVQMF INTS        114

SEQ ID NO: 293          moltype = AA  length = 357
FEATURE                 Location/Qualifiers
REGION                  1..357
                        note = Synthetic Sequence
source                  1..357
                        mol_type = protein
                        organism = synthetic construct
SEQUENCE: 293
QVQLVESGGG LVHPGGSLRL SCAASGSFSS INVMGWYRQA PGKERELVAR ITNLGLPNYA  60
DSVTGRFTIS RDNAKNTVYL QMNSLKPEDT AVYYCYLVAL KAEYWGQGTQ VTVSSGGSGG  120
SGGSGGSGGS DKTHTCPPCP APEAAGGPSV FLFPPKPKDT LMISRTPEVT CVVVDVSHED  180
PEVKFNWYVD GVEVHNAKTK PREEQYNSTY RVVSVLTVLH QDWLNGKEYK CQVSNKALPA  240
PIEKTISKAK GQPREPQVCT LPPSRDELTK NQVSLSCAVK GFYPSDIAVE WESNGQPENN  300
YKTTPPVLDS DGSFFLVSKL TVDKSRWQQG NVFSCSVMHE ALHNHYTQKS LSLSPGK     357

SEQ ID NO: 294          moltype = AA  length = 423
FEATURE                 Location/Qualifiers
REGION                  1..423
                        note = Synthetic Sequence
source                  1..423
                        mol_type = protein
                        organism = synthetic construct
SEQUENCE: 294
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGS GGSGGSGGSG  240
GSGGSGGSGG SGGSGGSCDL PETHSLDNRR TLMLLAQMSR ISPSSCLMDR HDFGFPQEEF  300
DGNQFQKAPA ISVLHELIQQ IFNLFTTKDS SAAWDEDLLD KFSTELYQQL NDLEACVMQE  360
ERVGETPLMN ADSILAVKKY FRRITLYLTE KKYSPCAWEV VRAEIMRSLS LSTNLQERLR  420
RKE                                                        423

SEQ ID NO: 295          moltype = AA  length = 423
FEATURE                 Location/Qualifiers
REGION                  1..423
                        note = Synthetic Sequence
source                  1..423
                        mol_type = protein
                        organism = synthetic construct
SEQUENCE: 295
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGS GGSGGSGGSG  240
GSGGSGGSGG SGGSGGSCDL PETHSLDNRR TLMLLAQMSR ISPSSCLMDR HDFGFPQEEF  300
DGNQFQKAPA ISVLHELIQQ IFNLFTTKDS SAAWDEDLLD KFSTELYQQL NDLEACVMQE  360
ERVGETPLMN ADSILAVKKY FRRITLYLTE KKYSPCAWEV VRGEIMRSLS LSTNLQERLR  420
RKE                                                        423

SEQ ID NO: 296          moltype = AA  length = 423
FEATURE                 Location/Qualifiers
REGION                  1..423
                        note = Synthetic Sequence
source                  1..423
                        mol_type = protein
                        organism = synthetic construct
SEQUENCE: 296
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGS GGSGGSGGSG  240
GSGGSGGSGG SGGSGGSCDL PETHSLDNRR TLMLLAQMSR ISPSSCLMDR HDFGFPQEEF  300
DGNQFQKAPA ISVLHELIQQ IFNLFTTKDS SAAWDEDLLD KFSTELYQQL NDLEACVMQE  360
ERVGETPLMN ADSILAVKKY FRRITLYLTE KKYSPCAWEV VRAEIVRSLS LSTNLQERLR  420
RKE                                                        423
```

-continued

```
SEQ ID NO: 297         moltype = AA  length = 423
FEATURE                Location/Qualifiers
REGION                 1..423
                       note = Synthetic Sequence
source                 1..423
                       mol_type = protein
                       organism = synthetic construct
SEQUENCE: 297
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGS GGSGGSGGSG  240
GSGGSGGSGG SGGSGGSCDL PETHSLDNRR TLMLLAQMSR ISPSSCLMDR HDFGFPQEEF  300
DGNQFQKAPA ISVLHELIQQ IFNLFTTKDS SAAWDEDLLD KFYTELYQQL NDLEACVMQE  360
ERVGETPLMN ADSILAVKKY FRRITLYLTE KKYSPCAWEV VRAEIMRSLS LSTNLQERLR  420
RKE                                                               423

SEQ ID NO: 298         moltype = AA  length = 423
FEATURE                Location/Qualifiers
REGION                 1..423
                       note = Synthetic Sequence
source                 1..423
                       mol_type = protein
                       organism = synthetic construct
SEQUENCE: 298
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGS GGSGGSGGSG  240
GSGGSGGSGG SGGSGGSCDL PETHSLDNRR TLMLLAQMSR ISPSSCLMDR HDFGFPQEEF  300
DGNQFQKAPA ISVLHELIQQ IFNLFTTKDS SAAWDEDLLD KFYTELYQQL NDLEACVMQE  360
ERVGETPLMN ADSILAVKKY FRRITLYLTE KKYSPCAWEV VRGEIMRSLS LSTNLQERLR  420
RKE                                                               423

SEQ ID NO: 299         moltype = AA  length = 423
FEATURE                Location/Qualifiers
REGION                 1..423
                       note = Synthetic Sequence
source                 1..423
                       mol_type = protein
                       organism = synthetic construct
SEQUENCE: 299
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGS GGSGGSGGSG  240
GSGGSGGSGG SGGSGGSCDL PETHSLDNRR TLMLLAQMSR ISPSSCLMDR HDFGFPQEEF  300
DGNQFQKAPA ISVLHELIQQ IFNLFTTKDS SAAWDEDLLD KFYTELYQQL NDLEACVMQE  360
ERVGETPLMN ADSILAVKKY FRRITLYLTE KKYSPCAWEV VRAEIVRSLS LSTNLQERLR  420
RKE                                                               423

SEQ ID NO: 300         moltype = AA  length = 227
FEATURE                Location/Qualifiers
REGION                 1..227
                       note = Synthetic Sequence
source                 1..227
                       mol_type = protein
                       organism = synthetic construct
SEQUENCE: 300
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CQVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 301         moltype = AA  length = 357
FEATURE                Location/Qualifiers
REGION                 1..357
                       note = Synthetic Sequence
source                 1..357
                       mol_type = protein
                       organism = synthetic construct
SEQUENCE: 301
DVQLVESGGG LVQPGGSLRL SCTASGTIFS INRMDWFRQA PGKQRELVAL ITSGGTPAYA  60
DSAKGRFTIS RDNSKNTVYL QMNSLRPEDT AVYYCHVSSG VYNYWGQGTL VTVSSGGSGG  120
SGGSGGSGGS DKTHTCPPCP APEAAGGPSV FLFPPKPKDT LMISRTPEVT CVVVDVSHED  180
PEVKFNWYVD GVEVHNAKTK PREEQYNSTY RVVSVLTVLH QDWLNGKEYK CQVSNKALPA  240
PIEKTISKAK GQPREPQVCT LPPSRDELTK NQVSLSCAVK GFYPSDIAVE WESNGQPENN  300
YKTTPPVLDS DGSFFLVSKL TVDKSRWQQG NVFSCSVMHE ALHNHYTQKS LSLSPGK     357
```

-continued

```
SEQ ID NO: 302          moltype = AA  length = 356
FEATURE                 Location/Qualifiers
REGION                  1..356
                        note = Synthetic Sequence
source                  1..356
                        mol_type = protein
                        organism = synthetic construct
SEQUENCE: 302
DVQLVESGGG LVQPGGSLRL SCAASGKIFS GNHMGWYRQA PGKQRELVGI ITSGGITDYA  60
DSVKGRFTIS RDNSKNTVYL QMNSLRPEDT AVYYCNVRDR TIWWGQGTLV TVSSGGSGGS  120
GGSGGSGGSD KTHTCPPCPA PEAAGGPSVF LFPPKPKDTL MISRTPEVTC VVVDVSHEDP  180
EVKFNWYVDG VEVHNAKTKP REEQYNSTYR VVSVLTVLHQ DWLNGKEYKC QVSNKALPAP  240
IEKTISKAKG QPREPQVCTL PPSRDELTKN QVSLSCAVKG FYPSDIAVEW ESNGQPENNY  300
KTTPPVLDSD GSFFLVSKLT VDKSRWQQGN VFSCSVMHEA LHNHYTQKSL SLSPGK      356

SEQ ID NO: 303          moltype = AA  length = 532
FEATURE                 Location/Qualifiers
REGION                  1..532
                        note = Synthetic Sequence
source                  1..532
                        mol_type = protein
                        organism = synthetic construct
SEQUENCE: 303
DVQLQESGGG LVQPGGSLRL SCTASGTIFS INRMDWFRQA PGKQRELVAL ITSGGTPAYA  60
DSAKGRFTIS RDNSKNTVYL QMNSLRPEDT AVYYCHVSSG VYNYWGQGTL VTVSSGGSGG  120
SGGSGGSGGS GGSGGSGGSG GSGGSGGSGG SGGSGGSGGS GGSGGSGGSG GSGGSDVQLV  180
ESGGGLVQPG GSLRLSCTAS GTIFSINRMD WFRQAPGKQR ELVALITSGG TPAYADSAKG  240
RFTISRDNSK NTVYLQMNSL RPEDTAVYYC HVSSGVYNYW GQGTLVTVSS GGSGGSGGSG  300
GSGGSDKTHT CPPCPAPEAA GGPSVFLFPP KPKDTLMISR TPEVTCVVVD VSHEDPEVKF  360
NWYVDGVEVH NAKTKPREEQ YNSTYRVVSV LTVLHQDWLN GKEYKCQVSN KALPAPIEKT  420
ISKAKGQPRE PQVCTLPPSR DELTKNQVSL SCAVKGFYPS DIAVEWESNG QPENNYKTTP  480
PVLDSDGSFF LVSKLTVDKS RWQQGNVFSC SVMHEALHNH YTQKSLSLSP GK          532
```

THERAPEUTIC INTERFERON ALPHA 1 PROTEINS

CROSS-REFERENCE TO RELATED APPLICATIONS

This application is a continuation of U.S. patent application Ser. No. 16/832,995, filed Mar. 27, 2020 (now U.S. U.S. Pat. No. 11,440,943), which claims the benefit of and priority to U.S. Provisional Patent Application No. 62/906,431 filed Sep. 26, 2019, and to U.S. Provisional Patent Application No. 62/825,569 filed Mar. 28, 2019, the contents of which are hereby incorporated by reference in their entirety.

FIELD

The present invention relates, in part, to chimeric proteins, or chimeric protein complexes (including Fc-based chimeric protein complexes) comprising interferon alpha 1 (IFNα1) or variants thereof and their use as therapeutic agents.

SEQUENCE LISTING

The contents of the text file submitted electronically herewith are incorporated herein by reference in their entirety. A computer readable XML format copy of the Sequence Listing (filename: ORN-057C1_114384-5057.xml, date recorded: Jul. 21, 2022; file size: 415,023 bytes).

BACKGROUND

Type I interferons (IFNs) form a family of multifunctional cytokines that play major roles in the immune responses and other biological processes. The human type I IFNs comprises 13 distinct non-allelic alpha subtypes, one beta subtype, and one omega subtype. Type I interferons all appear to bind a common receptor, type I interferon-α/β receptor (IFNAR), composed of the IFNAR1 and IFNAR2 subunits, albeit to different extents. Upon binding of type I IFNs, IFNAR activates the JAK-STAT signaling pathway to elicit various biological effects. Differential activities of IFN subtypes have been reported and, accordingly, differentially used in clinically for the treatment of various diseases and disorders, including, e.g., viral hepatitis (IFN-α2), multiple sclerosis and cancer therapy (e.g., IFN-β or IFNα2). The assembly of a IFN-IFNAR ligand-receptor complex initiates activation of several signal transduction pathways that, depending upon the cell type, IFN subtype engaging with IFNAR and the type of receptor-activation associated signal (amplitude, duration etc.) modify cellular differentiation and/or functions. While type I interferons share the property of engaging IFNAR, they can do so to varying degrees, and, consequently, can also have non-redundant functions. These are related, at least in part, to differences in the type and quality of signal response they elicit upon engaging IFNAR. This is relevant to various type I IFN responses, such as immune stimulatory, antiproliferative, antiviral and other biological effects. IFNα2 is among the most potent IFNAR-binding ligands and IFNAR signaling activators. Various efforts have been reported in the generation of even more potent IFNAR binders for potential therapeutic use.

In contrast to other type I IFNs, Interferon alpha 1 (IFNα1) is a member of the type I interferon family that is characterized by a markedly lower affinity for the IFNAR2 receptor (20-fold lower binding affinity for IFNAR2 compared to IFN-α2; Jaks et al., J. Mol. Biol. 2007; 366:525-534). It is deemed to be the weakest, naturally occurring human IFNAR-binding type I IFN ligand and IFNAR signaling activator among the type I IFN family (Moll et al., Cytokine 2011; 53:52-59). These characteristics, among others, have contributed to a longtime lack of general interest in and pursuit of IFNα1 as a potential therapeutic agent. The efficacy of type I IFNs in clinical practice is limited by ineffective dosing due to significant systemic toxicity and side effects, including flu-like syndrome, depression, hepatotoxicity, autoimmune disease, thyroid dysfunction, and weight loss. It could therefore be highly worthwhile to localize and target IFN activity toward only the cellular population that should be treated with IFN (e.g., infected organ or tumor mass) or activated by IFN (e.g., subsets of immune cells). Accordingly, there remains a need for safe and effective IFNα1-based therapeutics with improved pharmacokinetic and therapeutic properties and minimal toxicity profiles.

SUMMARY

Accordingly, in some aspects, the present invention relates to chimeric proteins and chimeric protein complexes, including Fc-based chimeric protein complexes, comprising wild type IFNα1, or variants thereof, as a signaling agent. The term variants as used herein includes IFNα1 mutants. In an embodiment, the IFNα1 comprises an amino acid sequence of SEQ ID NO: 1 or variants thereof.

The present disclosure concerns, in part, findings that chimeric proteins or chimeric protein complexes comprising wild type IFNα1, and variants thereof, exhibit substantially reduced IFNAR-activation signaling activity compared to wild type IFNα1. This reduced IFNAR-activation signaling activity, however, can be induced and/or restored at a target cell when directed to such a cell through a targeting moiety. Surprisingly, the induced IFNα1 activity at a target cell, achieved through targeting of chimeric proteins or chimeric protein complexes comprising IFNα1, or variants thereof, may be similar or greater at the target cell than that of wild type IFNα1. Furthermore, and equally surprising, the targeted IFNα1 activity of the chimeric protein or chimeric protein complexes comprising IFNα1, or variants thereof, may be similar to or even greater than that of wild type IFNα2, which is among the most potent natural type I IFNs (e.g., ~10-100 fold more potent than wild type IFNα1, e.g., depending on cell type). Importantly, the IFNα1 chimeric proteins and chimeric protein complexes comprising IFNα1 described herein, exhibit substantial and surprising selectivity for target cells versus non-target cells, and substantially more than, for example, achieved with targeted wild type IFNα2 chimeric protein(s). In summary, a unique combination of highly potent and highly cell target-selective IFNAR-signaling activation can be achieved with IFNα1 compositions, and variants thereof, described herein. Accordingly, in various embodiments, the present invention relates to target-selective IFNAR-activators with a high therapeutic index, as well as excellent pharmaceutical properties, for use in the treatment of various diseases, including cancer, infectious disease, and autoimmune disease.

In some embodiments the incorporation of wild type IFNα1 in a chimeric protein or chimeric protein complex, such as, for example, through genetic fusion or attachment (e.g. the formation of a complex), reduces the biological activity of IFNα1 (sometimes referred to as "attenuated by fusion"). For example, wild type IFNα1 incorporated in chimeric proteins or chimeric protein complexes may have reduced affinity and/or activity compared to wild type IFNα1 interferon for a therapeutic receptor. In an embodiment, the therapeutic receptor is the interferon-α/β receptor (IFNAR), which is composed of the IFNAR1 and IFNAR2 subunits. In some embodiments, the loss in affinity and/or activity of wild type IFNα1 for a therapeutic receptor, e.g., IFNAR, can be induced and restored upon directing or targeting of the chimeric protein or chimeric protein complex comprising IFNα1 to a target cell through a targeting moiety. In some embodiments, the induction and restoration of IFNα1-mediated IFNAR-activation at a target cell may reach a level that is similar to or higher than IFNAR-activation achieved with wild type (non-chimeric) IFNα1. In some embodiments, the IFNα1 is a variant that comprises one or more mutations which reduce undesired disulphide pairings to improve product homogeneity and pharmaceutical properties of the chimeric protein or chimeric protein complexes, while simultaneously maintaining or avoiding substantial loss of IFNAR-activation of the modified IFNα1 compared to wild type IFNα1 in the context of chimeric proteins or chimeric protein complexes, including maintaining or avoiding substantial loss of restoration and induction of IFNAR-activation by the modified IFNα1 when directed or targeted to a target cell through a targeting moiety.

In some embodiments, the IFNα1 is modified, i.e., is a variant and comprises one or more mutations in IFNα1. In some embodiments, the one or more mutations reduce the biological activity of the IFNα1 (sometime referred to as "attenuated by mutation"). For example, the one or more mutations may reduce the affinity and/or activity of the IFNα1 interferon for a therapeutic receptor. In an embodiment, the therapeutic receptor is the interferon-α/β receptor (IFNAR), which is composed of the IFNAR1 and IFNAR2 subunits. In an embodiment, the modified IFNα1 comprises one or more mutations that reduce its affinity and/or activity for IFNAR1. In another embodiment, the modified IFNα1 comprises one or more mutations that reduce its affinity and/or activity for IFNAR2. In an embodiment, the modified IFNα1 comprises one or more mutations that reduce its affinity and/or activity for IFNAR1 and comprises one or more mutations that reduce its affinity and/or activity for IFNAR2. In some embodiments, the loss in affinity and/or activity of the modified IFNα1 ("attenuated by mutation") for a therapeutic receptor, e.g., IFNAR1, IFNAR2 and/or IFNAR, can be induced and restored upon directing or targeting of the chimeric protein or chimeric protein complex comprising the modified IFNα1 to a target cell through a targeting moiety. In some embodiments, the modified IFNα1 variant ("attenuated by mutation") that comprises one or more mutations that reduce its affinity and/or activity for IFNAR1, IFNAR2 and/or IFNAR, further comprises one or more mutations that reduce undesired disulphide pairings to improve product homogeneity and pharmaceutical properties of the chimeric protein or chimeric protein complexes, while simultaneously maintaining or avoiding substantial loss of induction and/or restoration of IFNAR-activation activity by the modified IFNα1 ("attenuated by mutation") when directed/targeted to a target cell through a targeting moiety.

In some embodiments, the chimeric proteins and chimeric protein complexes, including Fc-based chimeric protein complexes, comprises one or more additional signaling agents, e.g., without limitation, an interferon, an interleukin, and a tumor necrosis factor, that may be modified. In various embodiments, the chimeric proteins and chimeric protein complexes, including Fc-based chimeric protein complexes, of the invention provides improved safety and/or therapeutic activity and/or pharmacokinetic profiles (e.g., increased serum half-life) compared to an untargeted and/or unmodified IFNα1 or an unmodified, wild type IFN-α, such as, IFN-α2a or IFN-α2b.

In various embodiments, the chimeric proteins and chimeric protein complexes, including Fc-based chimeric protein complexes, comprise one or more targeting moieties which have recognition domains (e.g. antigen recognition domains, including without limitation various antibody formats, inclusive of single-domain antibodies) which specifically bind to a target (e.g. antigen, receptor) of interest. In various embodiments, the targeting moieties have recognition domains that specifically bind to a target (e.g. antigen, receptor) of interest, including those found on one or more immune cells, which can include, without limitation, T cells, cytotoxic T lymphocytes, T helper cells, T regulatory cells (Tregs), natural killer (NK) cells, natural killer T (NKT) cells, anti-tumor and tumor macrophages (e.g. M1 and M2 macrophages), B cells, B regulatory (Breg) cells, neutrophils, monocytes, myeloid derived cells, and dendritic cells. In various embodiments, the targeting moieties have recognition domains that specifically bind to a target (e.g. antigen, receptor) of interest, including those found on one or more tumor cells, endothelial cells, epithelial cells, mesenchymal cells, stromal cells or other cell types that are characteristic of and/or unique for specific organs and/or tissues, including those specifically associated with disease. In some embodiments, the recognition domains specifically bind to a target (e.g. antigen, receptor) of interest and effectively recruit one or more immune cells. In some embodiments, the targets (e.g. antigens, receptors) of interest can be found on one or more tumor cells. In some embodiments, the present chimeric proteins, chimeric protein complexes, including Fc-based chimeric protein complexes, may recruit an immune cell, e.g., an immune cell that can kill and/or suppress a tumor cell, or modulate other immune cells, to a site of action (such as, by way of non-limiting example, the tumor microenvironment). In some embodiments, the present chimeric proteins, chimeric protein complexes, including Fc-based chimeric protein complexes, may modulate an immune cell at a site of action, or recruit an immune cell to a site of action that is associated with an autoimmune disease, inflammatory disease, infection, metabolic and/or cardiovascular disease (such as, by way of non-limiting example, the disease microenvironment). In some embodiments, the recognition domains specifically bind to a target (e.g. antigen, receptor) of interest that is part of a non-cellular structure.

In various embodiments, the present chimeric proteins and chimeric protein complexes, including Fc-based chimeric protein complexes find use in the treatment of various diseases or disorders such as cancer, infections, immune disorders, autoimmune diseases, cardiovascular diseases, wound healing, ischemia-related diseases, neurodegenerative diseases, metabolic diseases and many other diseases and disorders, and the present invention encompasses various methods of treatment.

BRIEF DESCRIPTION OF THE DRAWINGS

FIGS. 1A-F, 2A-H, 3A-H, 4A-D, 5A-F, 6A-J, 7A-D, 8A-F, 9A-J, 10A-F, 11A-L, 12A-L, 13A-F, 14A-L, 15A-L, 16A-J, 17A-J, 18A-F, and 19A-F show various non-limiting illustrative schematics of the Fc-based chimeric protein complexes of the present invention. In embodiments, each schematic is a composition of the present invention. Where applicable in the figures, "TM" refers to a "targeting moiety" as described herein, "SA" refers to a "signaling agent" as described herein, "└┐" is an optional "linker" as described herein, the two long parallel rectangles are human Fc domains, e.g. from IgG1, from IgG2, or from IgG4, as described herein and optionally with effector knock-out and/or stabilization mutations as also described herein, and the two long parallel rectangles with one having a protrusion and the other having an indentation are human Fc domains, e.g. from IgG1, from IgG2, or from IgG4 as described herein, with knob-in-hole and/or ionic pair (a/k/a charged pairs, ionic bond, or charged residue pair) mutations as described herein and optionally with effector knock-out and/or stabilization mutations as also described herein.

FIGS. 1A-F show illustrative homodimeric 2-chain complexes. These figures show illustrative configurations for the homodimeric 2-chain complexes.

FIGS. 2A-H show illustrative homodimeric 2-chain complexes with two targeting moieties (TM) (as described herein, more targeting moieties may be present in some embodiments). In embodiments, the position of TM1 and TM2 are interchangeable. In embodiments, the constructs shown in the box (i.e., FIGS. 2G and 2H) have signaling agent (SA) between TM1 and TM2 or between TM1 and Fc.

FIGS. 3A-H show illustrative homodimeric 2-chain complexes with two signaling agents (as described herein, more signaling agents may be present in some embodiments). In embodiments, the position of SA1 and SA2 are interchangeable. In embodiments, the constructs shown in the box (i.e., FIGS. 3G and 3H) have TM between SA1 and SA2 or TM at N- or C-terminus.

FIGS. 4A-D show illustrative heterodimeric 2-chain complexes with split TM and SA chains, namely the TM on the knob chain of the Fc and the SA on hole chain of the Fc.

FIGS. 5A-F show illustrative heterodimeric 2-chain complexes with split TM and SA chains, namely with both TMs on the knob chain of the Fc and with SA on hole chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 6A-J show illustrative heterodimeric 2-chain complexes with split TM and SA chains, namely with TM on the knob chain of the Fc and with a SA on the hole chain of the Fc, with two signaling agents (as described herein, more signaling agents may be present in some embodiments). In these orientations and/or configurations, one SA is on the knob chain and one SA is on the hole chain. In embodiments, the position of SA1 and SA2 are interchangeable.

FIGS. 7A-D show illustrative heterodimeric 2-chain complexes with split TM and SA chains, namely the SA on the knob chain of the Fc and the TM on hole chain of the Fc.

FIGS. 8A-F show illustrative heterodimeric 2-chain complexes with split TM and SA chains, namely with SA on the knob chain of the Fc and both TMs on hole chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 9A-J show illustrative heterodimeric 2-chain complexes with split TM and SA chains, namely with SA on the knob chain of the Fc and TM on hole chain of the Fc, with two signaling agents (as described herein, more signaling agents may be present in some embodiments). In these orientations and/or configurations, one SA is on the knob chain and one SA is on the hole chain. In embodiments, the position of SA1 and SA2 are interchangeable.

FIGS. 10A-F show illustrative heterodimeric 2-chain complexes with TM and SA on the same chain, namely the SA and TM both on the knob chain of the Fc.

FIGS. 11A-L show illustrative heterodimeric 2-chain complexes with a TM and a SA on the same chain, namely with SA and with TM both on the knob chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 12A-L show illustrative heterodimeric 2-chain complexes with a TM and a SA on the same chain, namely with SA and with TM both on the knob chain of the Fc, with two signaling agents (as described herein, more signaling agents may be present in some embodiments). In embodiments, the position of SA1 and SA2 are interchangeable.

FIGS. 13A-F show illustrative heterodimeric 2-chain complexes with TM and SA on the same chain, namely the SA and TM both on the hole chain of the Fc.

FIGS. 14A-L show illustrative heterodimeric 2-chain complexes with a TM and a SA on the same chain, namely with SA and with TM both on the hole chain of the Fc, with two targeting moieties (as described herein, more targeting moieties are present in some embodiments). In embodiments, the position of TM1 and TM2 are interchangeable. In embodiments, TM1 and TM2 can be identical.

FIGS. 15A-L show illustrative heterodimeric 2-chain complexes with a TM and a SA on the same chain, namely with SA and with TM both on the hole chain of the Fc, with two signaling agents (as described herein, more signaling agents may be present in some embodiments). In embodiments, the position of SA1 and SA2 are interchangeable.

FIGS. 16A-J show illustrative heterodimeric 2-chain complexes with two targeting moieties (as described herein, more targeting moieties may be present in some embodiments) and with SA on knob Fc and TM on each chain. In embodiments, TM1 and TM2 can be identical.

FIGS. 17A-J show illustrative heterodimeric 2-chain complexes with two targeting moieties (as described herein, more targeting moieties may be present in some embodiments) and with SA on hole Fc and TM on each chain. In embodiments, TM1 and TM2 can be identical.

FIGS. 18A-F show illustrative heterodimeric 2-chain complexes with two signaling agents (as described herein, more signaling agents may be present in some embodiments) and with split SA and TM chains: SA on knob and TM on hole Fc.

FIGS. 19A-F show illustrative heterodimeric 2-chain complexes with two signaling agents (as described herein, more signaling agents may be present in some embodiments) and with split SA and TM chains: TM on knob and SA on hole Fc.

DETAILED DESCRIPTION

Figure 1A:
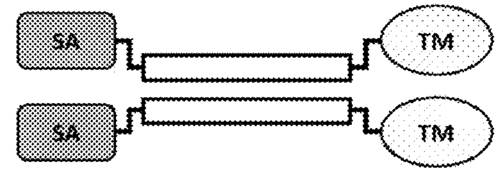
Figure 1B:
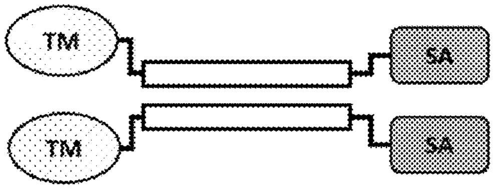
Figure 1C:
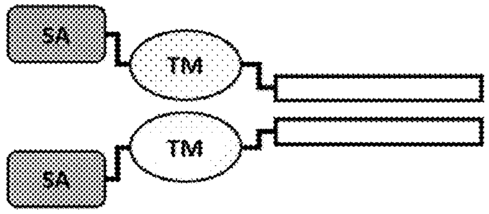
Figure 1D:
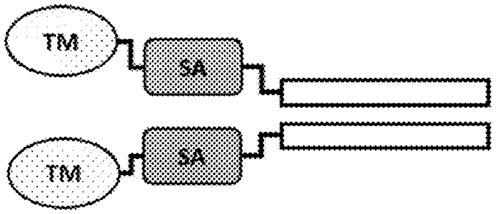
Figure 1E:
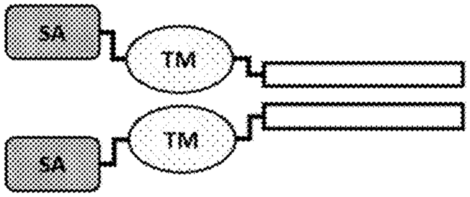
Figure 1F:
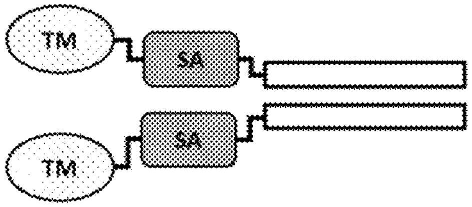
Figure 2A:
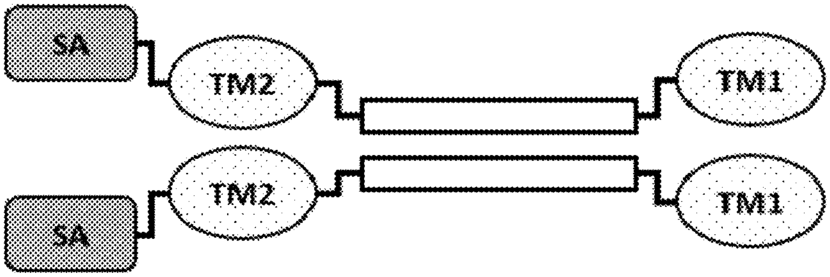
Figure 2B:
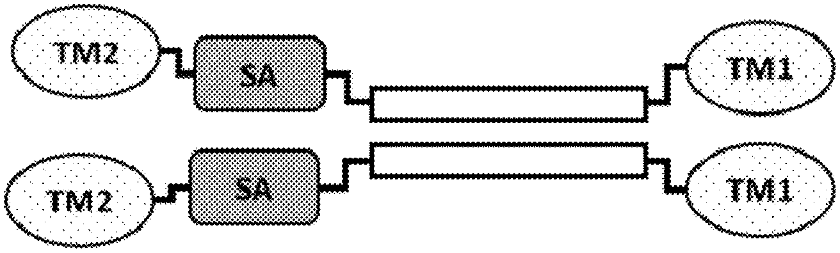
Figure 2C:
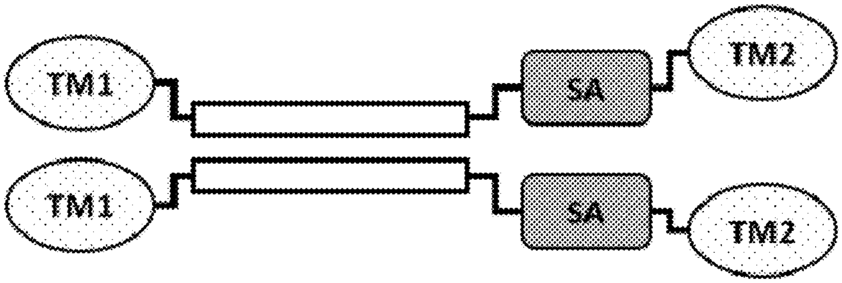
Figure 2D:
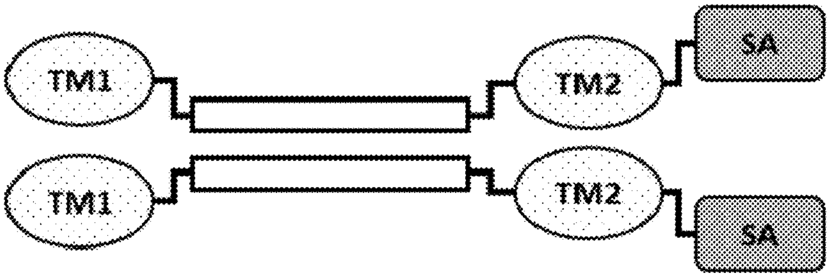
Figure 3A:
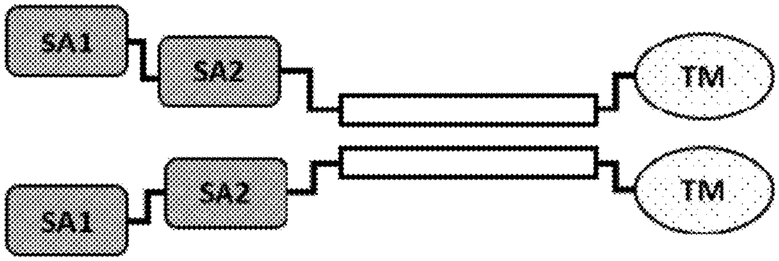
Figure 3B:
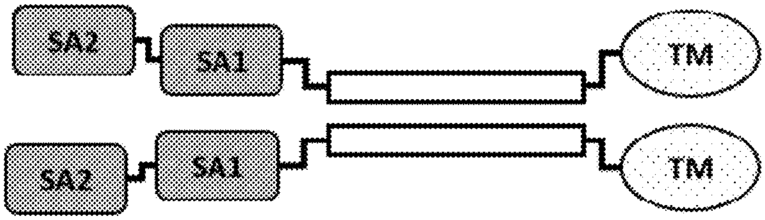
Figure 3C:
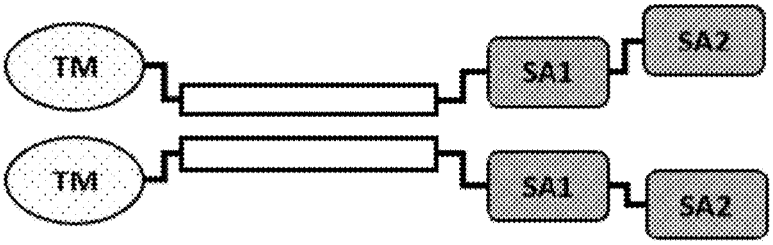
Figure 3D:
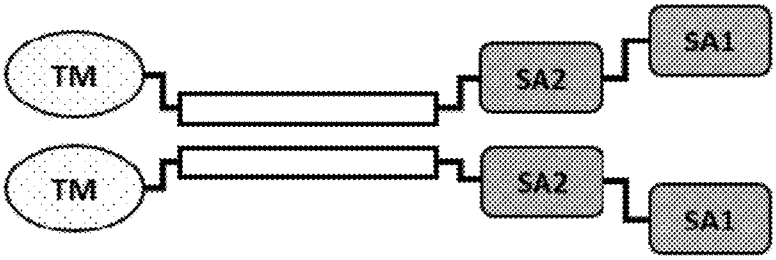
Figure 3E:
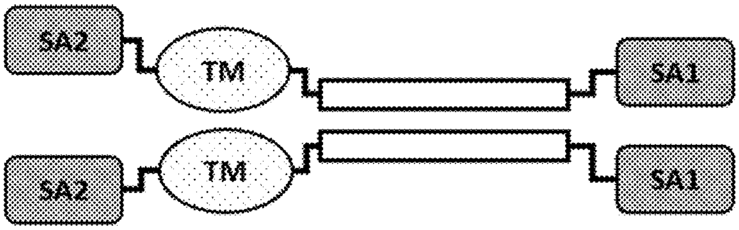
Figure 3F:
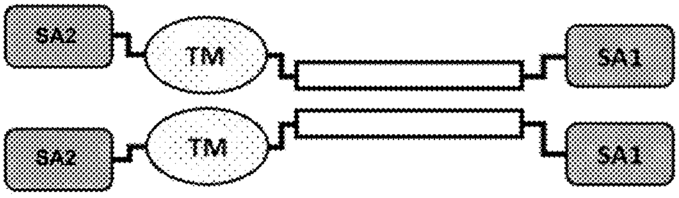
Figure 3G:
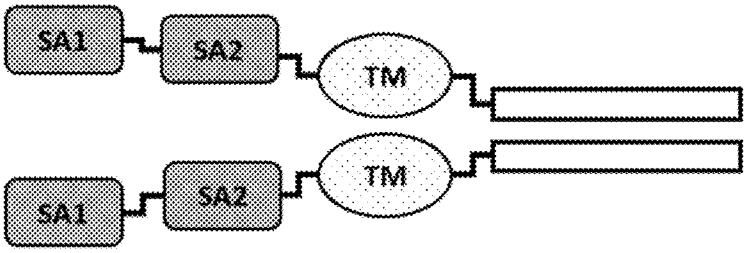
Figure 3H:
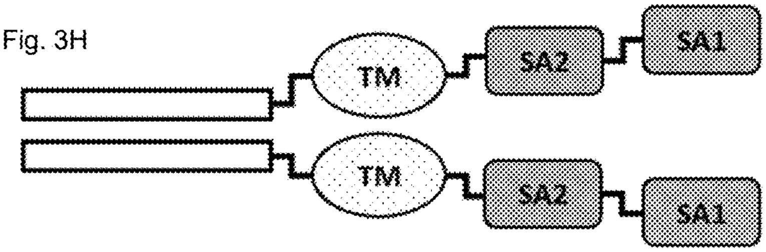
Figure 4A:
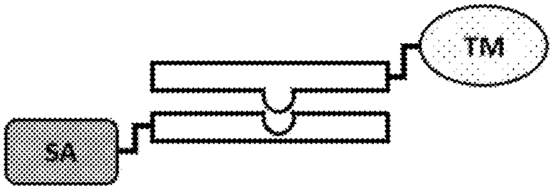
Figure 4B:
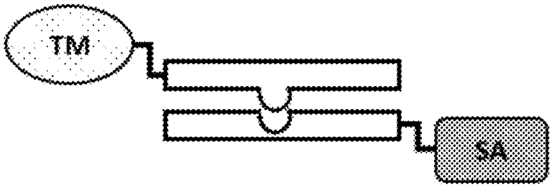
Figure 4C:
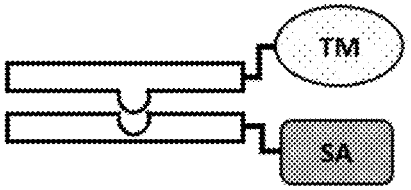
Figure 4D:
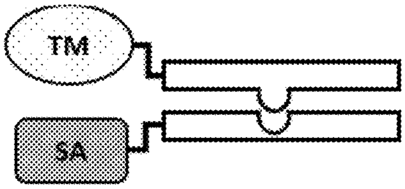
Figure 5A:
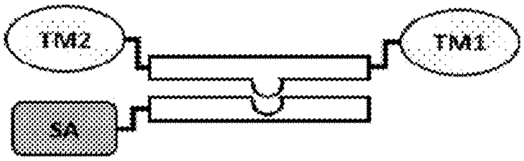
Figure 5B:
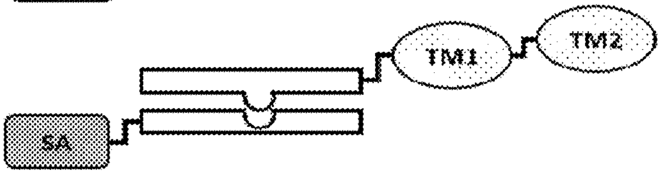
Figure 5C:
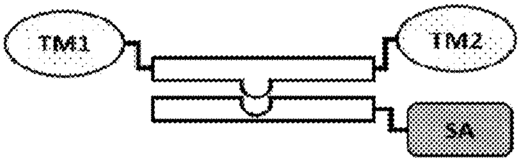
Figure 5D:
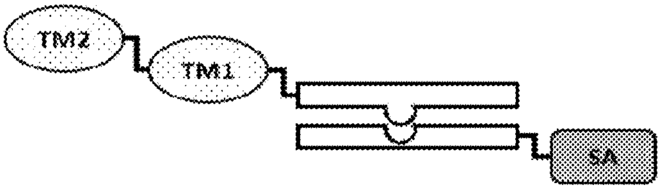
Figure 5E:
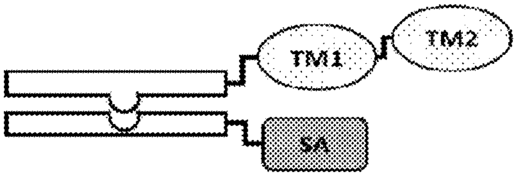
Figure 5F:
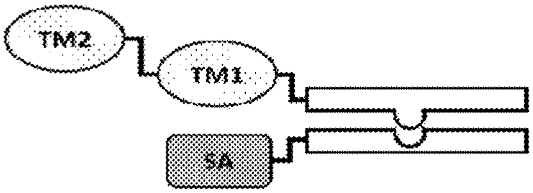
Figure 6A:
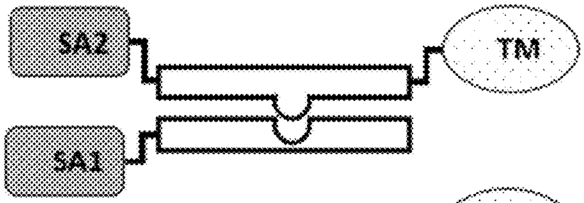
Figure 6B:
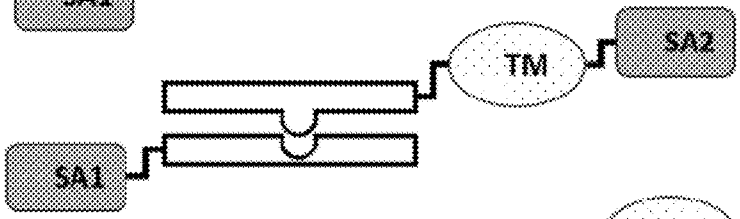
Figure 6C:
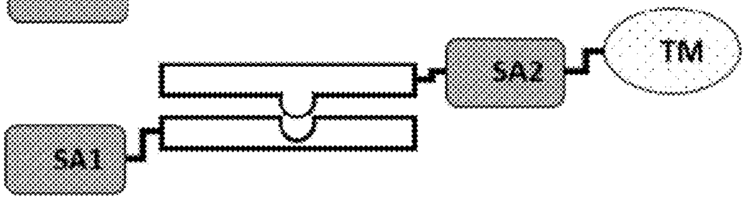
Figure 6D:
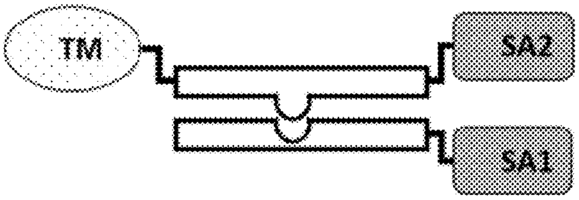
Figure 6E:
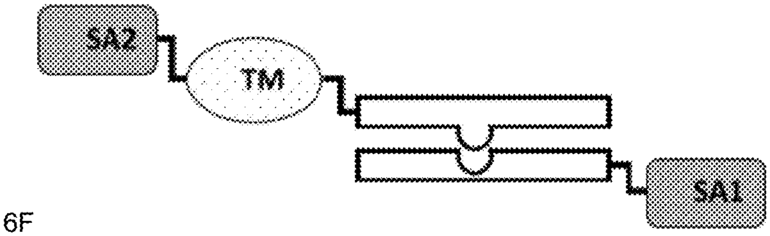
Figure 6F:
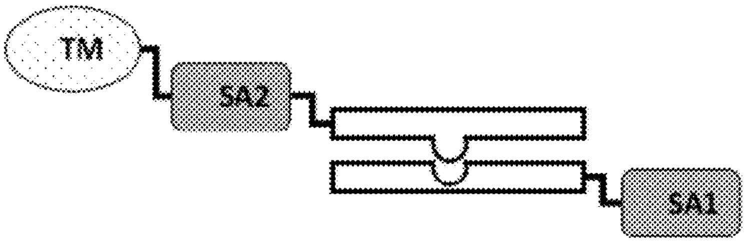
Figure 6G:
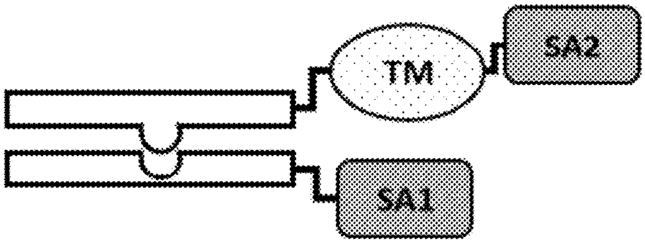
Figure 6H:
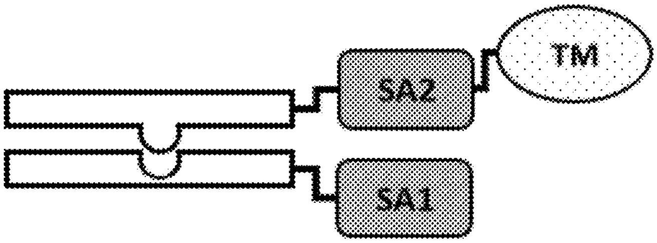
Figure 6I:
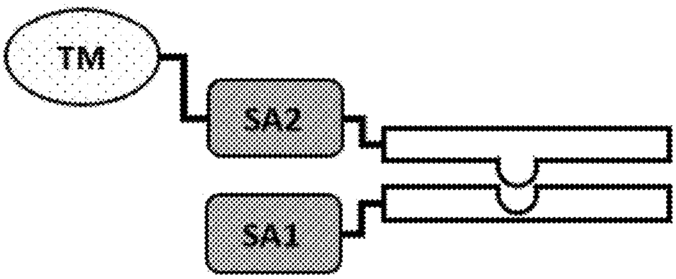
Figure 6J:
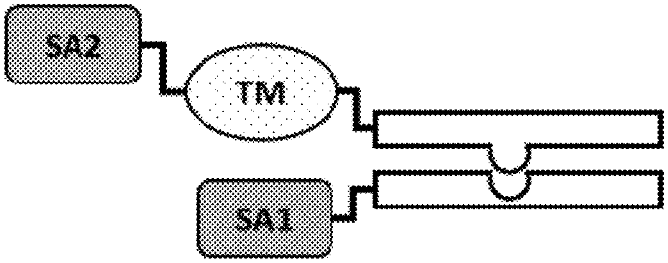

The present invention is based, in part, on the discovery that targeted chimeric proteins and chimeric protein complexes, such as Fc-based chimeric protein complexes, that include a IFNα1 exhibit substantially superior activity and/or target selectivity over a non-fused, wild type IFNα1, and exhibit beneficial therapeutic and pharmaceutical properties and reduced side effects. For example, the chimeric proteins or chimeric protein complexes, such as Fc-based chimeric protein complexes of the present invention are highly target selective, enable conditional and/or regulated modulation of IFNAR1/2 receptor signaling, and are highly active and/or long-acting active and/or long-acting while exhibiting minimal off-target effects and eliciting minimal side effects.

The present invention also provides pharmaceutical compositions that include the chimeric proteins, chimeric protein complexes (including Fc-based chimeric protein complexes), and/or nucleic acids encoding the chimeric proteins and chimeric protein complexes, including Fc-based chimeric protein complexes. The present invention also includes host cells that comprise the nucleic acids encoding the chimeric proteins and chimeric protein complexes, including Fc-based chimeric protein complexes. The present invention further includes the use of the chimeric proteins, the chimeric protein complexes (including Fc-based chimeric protein complexes), the nucleic acids encoding the chimeric proteins and chimeric protein complexes (including Fc-based chimeric protein complexes), the pharmaceutical compositions and/or the host cells as described herein for the treatment of various diseases.

Interferon-Alpha 1 or a Variant Thereof

In one aspect, the present invention provides a chimeric protein or chimeric protein complexes, such as Fc-based chimeric protein complexes that includes an engineered interferon. In one aspect, the present invention provides a chimeric protein or chimeric protein complexes, such as Fc-based chimeric protein complexes that include a wild type IFNα1. In various embodiments, the wild-type IFNα1 comprises the following amino acid sequence:

```
                                    (SEQ ID NO: 1)
CDLPETHSLDNRRTLMLLAQMSRISPSSCLMDRHDFGFPQEEFDGNQFQ

KAPAISVLHELIQQIFNLFTTKDSSAAWDEDLLDKFCTELYQQLNDLEA

CVMQEERVGETPLMNADSILAVKKYFRRITLYLTEKKYSPCAWEVVRAE

IMRSLSLSTNLQERLRRKE.
```

In various embodiments, the present invention provides a chimeric protein or chimeric protein complexes, such as Fc-based chimeric protein complexes that include a wild type IFNα1 fused to one or more targeting moities. In some embodiments the incorporation of wild type IFNα1 in a chimeric protein or chimeric protein complex, such as for example through genetic fusion or attachment, reduces the biological activity of IFNα1 ("attenuated by fusion IFNα1"). For example, wild type IFNα1 incorporated in chimeric proteins or chimeric protein complexes may have reduced affinity and/or activity compared to wild type IFN-α1 interferon for a therapeutic receptor. In an embodiment, the therapeutic receptor is the interferon-α/β receptor (IFNAR), which is composed of the IFNAR1 and IFNAR2 subunits. In some embodiments, the loss in affinity and/or activity of wild type IFNα1 for a therapeutic receptor, e.g., IFNAR, can be induced and restored upon directing or targeting of the chimeric protein or chimeric protein complex comprising IFNα1 to a target cell through a targeting moiety. In some embodiments, the induction and restoration of IFNα1-mediated IFNAR-activation at a target cell may reach a level that is similar to or higher than IFNAR-activation achieved with wild type (non-chimeric) IFNα1. In some embodiments, the IFNα1 is a variant that comprises one or more mutations which reduce undesired disulphide pairings to improve product homogeneity and pharmaceutical properties of the chimeric protein or chimeric protein complexes, while simultaneously maintaining or avoiding substantial loss of IFNAR-activation of the modified IFNα1 compared to wild type IFNα1 in the context of chimeric proteins or chimeric protein complexes, including maintaining or avoiding substantial loss of restoration and induction of IFNAR-activation by the modified IFNα1 when directed or targeted to a target cell through a targeting moiety. In some embodiments, the IFNα1 is a variant that comprises one or more mutations which reduce undesired disulphide pairings wherein the one or more mutations are, e.g., at amino acid positions C1, C29, C86, C99, or C139 with reference to SEQ ID NO: 1. In some embodiments, the mutation at position C86 can be, e.g., C86S or C86A or C86Y. These C86 mutants of IFNα1 are called reduced cysteine-based aggregation mutants. In some embodiment, the IFNα1 variant includes mutations at positions C1, C86 and C99 with reference to SEQ ID NO: 1. In embodiments, any of C1, C86 and C99 made be deleted or substituted.

In some embodiments, the IFN-α1 is modified, i.e., is a variant and comprises one or more mutations in IFNα1. In some embodiments, the one or more mutations reduce the biological activity of the IFN-α1 ("attenuated by mutation"). For example, the one or more mutations may reduce the affinity and/or activity of the IFN-α1 interferon for a therapeutic receptor. In an embodiment, the therapeutic receptor is the interferon-α/β receptor (IFNAR), which is composed of the IFNAR1 and IFNAR2 subunits. In an embodiment, the modified IFN-α1 comprises one or more mutations that reduce its affinity and/or activity for IFNAR1. In another embodiment, the modified IFN-α1 comprises one or more mutations that reduce its affinity and/or activity for IFNAR2. In an embodiment, the modified IFN-al comprises one or more mutations that reduce its affinity and/or activity for IFNAR1 and comprises one or more mutations that reduce its affinity and/or activity for IFNAR2. In some embodiments, the loss in affinity and/or activity of the modified IFNα1 ("attenuated by mutation") for a therapeutic receptor, e.g., IFNAR1, IFNAR2 and/or IFNAR, can be induced and restored upon directing or targeting of the chimeric protein or chimeric protein complex comprising the modified IFNα1 to a target cell through a targeting moiety, In some embodiments, the modified IFNα1 variant ("attenuated by mutation") that comprises one or more mutations that reduce its affinity and/or activity for IFNAR1, IFNAR2 and/or IFNAR, further comprises one or more mutations that reduce undesired disulphide pairings to improve product homogeneity and pharmaceutical properties of the chimeric protein or chimeric protein complexes, while simultaneously maintaining or avoiding substantial loss of induction and/or restoration of IFNAR-activation activity by the modified IFNα1 ("attenuated by mutation") when directed/targeted to a target cell through a targeting moiety. In some embodiments, the IFNα1 is a variant that comprises one or more mutations which reduce undesired disulphide pairings to improve product homogeneity and pharmaceutical properties of the chimeric protein or chimeric protein complexes, while simultaneously maintaining or avoiding substantial loss of IFNAR-activation of the modified IFNα1 compared to wild type IFNα1 in the context of chimeric proteins or chimeric protein complexes, including maintaining or avoiding substantial loss of restoration and induction of IFNAR-activation by the modified IFNα1 when directed or targeted to a target cell through a targeting moiety. In some embodiments, the IFNα1 is a variant that comprises one or more mutations which reduce undesired disulphide pairings wherein the one or more mutations are, e.g., at amino acid positions C1, C29, C86, C99, or C139 with reference to SEQ ID NO: 1. In some embodiments, the mutation at position C86 can be, e.g., C86S or C86A or C86Y. These C86 mutants of IFNα1 are called reduced cysteine-based aggregation mutants. In some embodiment, the IFNα1 variant includes mutations at positions C1, C86 and C99 with reference to SEQ ID NO: 1. In various embodiments, the chimeric protein or chimeric protein complexes, such as Fc-based chimeric protein complexes of the invention comprises a modified version of IFNα1, i.e., a IFNα1 variant including a IFNα1 mutant, as a signaling agent. In various embodiments, the IFNα1 variant encompasses mutants, functional derivatives, analogs, precursors, isoforms, splice variants, or fragments of the interferon.

Additional IFNα1 variant sequences are known in the art. In various embodiments the modified IFNα1 comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any known amino acid sequences of a IFNα1 interferon variant (e.g., about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In some embodiments, the IFNα1 variant comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any of the IFNα1 or IFNα1 variant sequences disclosed herein, e.g., SEQ ID NO: 1 (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the IFNα1 variant comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and 6-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In various embodiments, the IFNα1 is modified to have one or more mutations. In some embodiments, the mutations allow for the IFNα1 variant to have one or more of attenuated activity such as one or more of reduced binding affinity, reduced endogenous activity, and reduced specific bioactivity relative to unmutated, e.g., the wild type form of IFNα1 (e.g., the IFNα1 having an amino acid sequence of SEQ ID NO: 1). For instance, the one or more of attenuated activity such as reduced binding affinity, reduced endogenous activity, and reduced specific bioactivity relative to unmutated, e.g. the wild type form of IFNα1, may be at a therapeutic receptor such as IFNAR. Consequentially, in various embodiments, the mutations allow for the IFNα1 variant to have reduced systemic toxicity, reduced side effects, and reduced off-target effects relative to unmutated, e.g. the wild type form of IFNα1. In various embodiments, IFNα1 is modified to have a mutation that reduces its binding affinity or activity at a therapeutic receptor such as IFNAR. In some embodiments, the activity provided by IFNα1 is agonism at the therapeutic receptor (e.g. activation of a cellular effect at a site of therapy). For example, the IFNα1 may activate the therapeutic receptor. In such embodiments, the mutation results in IFNα1 variant to have reduced activating activity at the therapeutic receptor.

In some embodiments, the reduced affinity or activity of the modified IFNα1 at the therapeutic receptor is inducible or restorable by attachment to a targeting moiety or upon inclusion of a targeting moiety in a chimeric protein or a chimeric protein complex, e.g., a Fc-based chimeric protein complex as disclosed herein. In some embodiments, the activity of IFNα1 is reduced or attenuated by virtue of its fusion with another protein, including, in some instances, by fusion with targeting moieties as described herein. In other embodiments, the activity of IFNα1 is reduced or attenuated by modifying the IFNα1, e.g., by introducing mutations as described herein. In some embodiments, attenuation of the activity can be restored by attaching the IFNα1 to a targeting moiety or by the action of the attached targeting moiety. In embodiments, the targeting moiety—by virtue of its attachment or by its activity—induces IFNα1's activity.

In other embodiments, the reduced affinity or activity at the therapeutic receptor is not substantially inducible or restorable by attachment with the targeting moiety or upon inclusion in a chimeric protein or a chimeric protein complex, e.g., a Fc-based chimeric protein complex as disclosed herein. In various embodiments, the therapeutic chimeric proteins, the chimeric protein complexes, or Fc-based chimeric protein complexes of the present invention reduce off-target effects because the wild type IFNα1 or IFNα1 variant having one or more mutations, exhibit weak binding affinity or activity at a therapeutic receptor compared to wild type IFNα1 (non-fused). In various embodiments, this reduces side effects observed with, for example, the wild type form of IFNα1 or other type I interferons. In various embodiments, the IFNα1 construct and/or IFNα1 variant is substantially inactive en route to the site of therapeutic activity and has its effect substantially on specifically targeted cell types, which greatly reduces undesired cross-reactivities and side effects.

In various embodiments, the IFNα1 variant has one or more mutations that cause the IFNα1 variant to have attenuated or reduced affinity, e.g. binding (e.g. $K_D$) and/or activation (measurable as, for example, $K_A$ and/or $EC_{50}$) for one or more therapeutic receptors. In various embodiments, the reduced affinity at the therapeutic receptor allows for attenuation of activity and/or signaling from the therapeutic receptor.

In various embodiments, the IFNα1 variant has one or more mutations that reduce its binding to or its affinity for the IFNAR1 subunit of IFNAR. In one embodiment, the IFNα1 variant has reduced affinity and/or activity at IFNAR1.

In some embodiments, the IFNα1 variant has one or more mutations that reduce its binding to or its affinity for the IFNAR2 subunit of IFNAR. In some embodiments, the IFNα1 variant has one or more mutations that reduce its binding to or its affinity for both IFNAR1 and IFNAR2 subunits.

In some embodiments, the IFNα1 variant has one or more mutations that reduce its binding to or its affinity for IFNAR1 and one or more mutations that substantially reduce or ablate binding to or its affinity for IFNAR2. In some embodiments, chimeric proteins and chimeric protein complexes, such as or Fc-based chimeric protein complexes with such IFNα1 variant can provide target-selective IFNAR1 activity (e.g. IFNAR1 activity is inducible or restorable via targeting through the targeting moiety or upon inclusion in the Fc-based chimeric protein complex disclosed herein).

In some embodiments, the IFNα1 variant has one or more mutations that reduce its binding to or its affinity for IFNAR2 and one or more mutations that substantially reduce or ablate binding to or its affinity for IFNAR1. In some embodiments, chimeric proteins or chimeric protein complexes, such as Fc-based chimeric protein complexes with such IFNα1 variant can provide target-selective IFNAR2 activity (e.g. IFNAR2 activity is inducible or restorable via targeting through the targeting moiety or upon inclusion in the Fc-based chimeric protein complex disclosed herein).

In some embodiments, the IFNα1 variant has one or more mutations that reduce its binding to or its affinity for IFNAR1 and one or more mutations that reduce its binding to or its affinity for IFNAR2. In some embodiments, chimeric proteins or chimeric protein complexes, such as Fc-based chimeric protein complexes with such IFNα1 variant can provide target-selective IFNAR1 and/or IFNAR2 activity (e.g. IFNAR1 and/IFNAR2 activity is inducible or restorable via targeting through the targeting moiety or upon inclusion in the Fc-based chimeric protein complex disclosed herein).

In various embodiments, the IFNα1 variant has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the therapeutic receptor (e.g., IFNAR or any one of its subunits IFNAR1 and/or IFNAR2) relative to the wild type IFNα1. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type IFNα1.

In some embodiments, the IFNα1 variant comprises one or more mutations that cause the IFNα1 variant to have reduced affinity for a receptor. In some embodiments, the IFNα1 variant's binding affinity for a receptor is lower than the binding affinity of the targeting moiety for its receptor. In some embodiments, this binding affinity differential is between the IFNα1 variant/receptor and targeting moiety/receptor on the same cell. In some embodiments, this binding affinity, differential allows for the IFNα1 variant to have localized, on-target effects and to minimize off-target effects that underlie side effects that are observed with wild type IFNα1. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold less.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

In various embodiments, the chimeric protein complexes of the present invention include (a) an interferon alpha 1 (IFNα1) or a variant thereof, and (b) one or more targeting moieties, said targeting moieties comprising recognition domains which specifically bind to antigens or receptors of interest; wherein the IFNα1 or the variant thereof, and the one or more targeting moieties are connected with a domain that causes complexation (e.g. a complexation domain). In some embodiments, the chimeric protein complexes of the present invention further include one or more proteins or peptides that interact with each other (e.g. a complexation domain), e.g., using electrostatic interactions, hydrogen bonding, and/or the hydrophobic effect. In some embodiments, the chimeric protein complexes are homomers (e.g., that include two or more chimeric proteins as described herein comprising, e.g., interferon alpha 1 (IFNα1) or a variant thereof and one or more targeting moieties connected with one or more linkers). In some embodiments, the chimeric protein complexes are heteromers (e.g., that include one chimeric protein comprising interferon alpha 1 (IFNα1) or a variant thereof and one or more targeting moieties connected with one or more linkers and another protein). A variety of protein interaction domains (e.g. a complexation domains) have been employed to generate protein complexes and can be used for the purposes of making chimeric protein complexes of the present invention. In some embodiments, the chimeric protein complexes can be made by using leucine zippers, Jun and Fos family of proteins, helix-turn-helix self dimerizing peptides, tri- and tetrameric subdomains of collagen and p53 (see, e.g. methods of making protein complexes as described in U.S. Pat. No. 8,507,222, which is hereby incorporated by reference in its entirety). Other methods to make heteromeric complexes include charge based heterodimers as e.g. described by Chang et al. (PNAS 1984; 91:11408-11412) or heterodimerizing leucine zippers as described e.g. by Deng et al. (Chemistry & Biology 2008; 15:908-919) or designed heterodimers as described by Chen et al. (Nature 2019; 565: 106-111). In various embodiments, these chimeric protein complexes, are not Fc-based. In some embodiments, the variety of protein interaction domains can be used in place of Fc-domains described herein (in the context of Fc-based chimeric protein complexes) to form protein complexes.

In various embodiments, the chimeric protein complexes, such as Fc-based chimeric protein complex comprises a wild type signaling agent that has improved target selectivity and safety relative to a signaling agent which is not fused to an Fc, or a signaling agent which is not in the context of a complex, e.g., without limitation, a heterodimeric complex. In various embodiments, the chimeric protein complexes, such as Fc-based chimeric protein complex comprises a wild type signaling agent that has improved target selective activity relative to a signaling agent which is not fused to an Fc, or a signaling agent which is not in the context of a complex, e.g., without limitation, a heterodimeric complex. In various embodiments, the chimeric protein complexes, such as Fc-based chimeric protein complex allows for conditional activity.

In various embodiments, the chimeric protein complexes, such as Fc-based chimeric protein complex comprises a wild type signaling agent that has improved safety, e.g. reduced systemic toxicity, reduced side effects, and reduced off-target effects relative to a signaling agent which is not fused to an Fc, or a signaling agent which is not in the context of a complex, e.g., without limitation, a heterodimeric complex. In various embodiments, improved safety means that the present chimeric protein complexes, such as Fc-based chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window of the wild type signaling agent as compared to the signaling agent which is not fused to an Fc, or a signaling agent which is not in the context of a complex, e.g., without limitation, a heterodimeric complex.

In some embodiments, the reduced affinity or activity at the receptor is inducible or restorable by attachment with one or more of the targeting moieties as described herein or upon inclusion in the chimeric protein complexes, such as Fc-based chimeric protein complex disclosed herein.

In various embodiments, the chimeric protein complexes, such as Fc-based chimeric protein complex comprises a wild type signaling agent that has reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_I$ and/or $IC_{50}$), for one or more of its receptors. In various embodiments, the reduced affinity at the signaling agent's receptor allows for attenuation of activity. In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor as compared to the signaling agent which is not fused to an Fc, or a signaling agent which is not in the context of a complex, e.g., without limitation, a heterodimeric complex. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower as compared to the signaling agent which is not fused to an Fc, or a signaling agent which is not in the context of a complex, e.g., without limitation, a heterodimeric complex.

In various embodiments, the chimeric protein complexes, such as Fc-based chimeric protein complex comprises a wild type signaling agent that has reduced endogenous activity of the signaling agent to about 75%, or about 70%, or about 60%, or about 50%, or about 40%, or about 30%, or about 25%, or about 20%, or about 10%, or about 5%, or about 3%, or about 1%, e.g., as compared to the signaling agent which is not fused to an Fc, or a signaling agent which is not in the context of a complex, e.g., without limitation, a heterodimeric complex.

In various embodiments, the attenuated activity at the therapeutic receptor, the weakened affinity at the therapeutic receptor is inducible or restorable by attachment with a targeting moiety or upon inclusion in the chimeric protein complexes, such as Fc-based chimeric protein complex disclosed herein, having high affinity for an antigen at the site of therapeutic activity (e.g. an antibody or antibody format described herein). The targeting is realized by linking the IFNα1 or a variant thereof to a targeting moiety or upon its inclusion in the chimeric protein complexes, such as Fc-based chimeric protein complex as disclosed herein. In an embodiment, the IFNα1 or a variant thereof is linked to a targeting moiety through its amino-terminus. In another embodiment, the IFNα1 or a variant thereof is linked to a targeting moiety through its carboxy-terminus. In this way, the present chimeric proteins or chimeric protein complexes, such as Fc-based chimeric protein complexes provide, in some embodiments, localized, on-target, and controlled therapeutic action at the therapeutic receptor.

In some embodiments, the IFNα1 interferon is modified to have a mutation at one or more amino acids at positions L15, A19, R23, S25, L30, D32, R33, H34, Q40, D115, L118, K121, R126, E133, K134, K135, R145, A146, M149, R150, S153, L154, and N157 with reference to SEQ ID NO: 1. The mutations can optionally be a hydrophobic mutation and can be, e.g., selected from alanine, valine, leucine, and isoleucine. In some embodiments, the IFNα1 interferon is modified to have a one or more mutations selected from L15A, A19W, R23A, S25A, L30A, L30V, D32A, R33K, R33A, R33Q, H34A, Q40A, D115R, L118A, K121A, K121E, R126A, R126E, E133A, K134A, K135A, R145A, R145D, R145E, R145G, R145H, R145I, R145K, R145L, R145N, R145Q, R145S, R145T, R145V, R145Y, A146D, A146E, A146G, A146H, A146I, A146K, A146L, A146M, A146N, A146Q, A146R, A146S, A146T, A146V, A146Y, M149A, M149V, R150A, S153A, L154A, and N157A with reference to SEQ ID NO: 1. In some embodiments, the IFNα1 mutant comprises one or more multiple mutations selected from L30A/H58Y/E59N_Q62S, R33A/H58Y/E59N/Q62S, M149A/H58Y/E59N/Q62S, L154A/H58Y/E59N/Q62S, R145A/H58Y/E59N/Q62S, D115A/R121A, L118A/R121A, L118A/R121A/K122A, R121A/K122A, and R121E/K122E with reference to SEQ ID NO: 1.

In an embodiment, the IFNα1 interferon, or variant thereof, is modified to have one or more mutations at amino acid positions C1, C29, C86, C99, or C139 with reference to SEQ ID NO: 1. In this regard, Beilharz et al., Journal of interferon research 6.6 (1986): 677-685 (which is hereby incorporated by reference in its entirety) describes various mutations of IFNα1 that may be used introduced in the modified IFNα1 of the present invention. The mutation at position C86 can be, e.g., C86S or C86A or C86Y. These C86 mutants of IFNα1 are called reduced cysteine-based aggregation mutants. In some embodiment, the IFNα1 variant includes mutations at positions C1, C86 and C99 with reference to SEQ ID NO: 1.

Therapeutic Agents Comprising the Interferon or a Variant Thereof

Targeting Moiety Cellular Recruitment

In various embodiments, the chimeric proteins or chimeric protein complexes, such as Fc-based chimeric protein complexes of the present invention additionally comprise one or more targeting moieties having recognition domains which specifically bind to a target (e.g. antigen, receptor) of interest. In some embodiments, the chimeric protein or chimeric protein complexes, such as Fc-based chimeric protein complexes may comprise two, three, four, five, six, seven, eight, nine, ten or more targeting moieties. In illustrative embodiments, the chimeric proteins or chimeric protein complexes, such as Fc-based chimeric protein complexes of the invention comprise two or more targeting moieties. In such embodiments, the chimeric proteins or chimeric protein complexes, such as Fc-based chimeric protein complexes can target two different cells (e.g. to make a synapse) or the same cell (e.g. to get a more concentrated signaling agent effect). In some embodiments, the chimeric proteins or chimeric protein complexes, such as Fc-based chimeric protein complexes of the invention comprise IFNα1 or a variant thereof, a targeting moiety that is Flt3L and one targeting moiety that recognizes PD-1 or PD-L1. In some embodiments, the chimeric proteins or chimeric protein complexes, such as Fc-based chimeric protein complexes of the invention comprise IFNα1 or a variant thereof, a targeting moiety that is Flt3L and two targeting moieties that recognizes PD-1 or PD-L1.

In some embodiments, the chimeric proteins or chimeric protein complexes, such as Fc-based chimeric protein complexes of the invention comprise IFNα2 or a variant thereof, a targeting moiety that is Flt3L and one targeting moiety that recognizes PD-1 or PD-L1. In some embodiments, the chimeric proteins or chimeric protein complexes, such as Fc-based chimeric protein complexes of the invention comprise IFNα2 or a variant thereof, a targeting moiety that is Flt3L and two targeting moieties that recognizes PD-1 or PD-L1.

In various embodiments, the target (e.g. antigen, receptor) of interest can be found on one or more immune cells, which can include, without limitation, T cells, cytotoxic T lymphocytes, T helper cells, natural killer (NK) cells, natural killer T (NKT) cells, anti-tumor or tumor-associated macrophages (e.g. M1 or M2 macrophages), B cells, Breg cells, dendritic cells, or subsets thereof. In some embodiments, the recognition domains specifically bind to a target (e.g. antigen, receptor) of interest and effectively, directly or indirectly, recruit one of more immune cells. In some embodiments, the target (e.g. antigen, receptor) of interest can be found on one or more tumor cells. In some embodiments, the present chimeric proteins or chimeric protein complexes, such as Fc-based chimeric protein complexes may directly or indirectly recruit an immune cell, e.g., in some embodiments, to a therapeutic site (e.g. a locus with one or more disease cell or cell to be modulated for a therapeutic effect). In some embodiments, the present chimeric proteins or chimeric protein complexes such as Fc-based chimeric protein complexes may directly or indirectly recruit an immune cell, e.g. an immune cell that can kill and/or suppress a tumor cell, to a site of action (such as, by way of non-limiting example, the tumor microenvironment).

In various embodiments, the chimeric proteins or chimeric protein complexes such as Fc-based chimeric protein complexes have targeting moieties having recognition domains which specifically bind to a target (e.g. antigen, receptor) which is part of a non-cellular structure. In some embodiments, the antigen or receptor is not an integral component of an intact cell or cellular structure. In some embodiments, the antigen or receptor is an extracellular antigen or receptor. In some embodiments, the target is a non-proteinaceous, non-cellular marker, including, without limitation, nucleic acids, inclusive of DNA or RNA, such as, for example, DNA released from necrotic tumor cells or extracellular deposits such as cholesterol.

In some embodiments, the target (e.g. antigen, receptor) of interest is part of the non-cellular component of the stroma or the extracellular matrix (ECM) or the markers associated therewith. As used herein, stroma refers to the connective and supportive framework of a tissue or organ. Stroma may include a compilation of cells such as fibroblasts/myofibroblasts, glial, epithelia, fat, immune, vascular, smooth muscle, and immune cells along with the extracellular matrix (ECM) and extracellular molecules. In various embodiments, the target (e.g. antigen, receptor) of interest is part of the non-cellular component of the stroma such as the extracellular matrix and extracellular molecules. As used herein, the ECM refers to the non-cellular components present within all tissues and organs. The ECM is composed of a large collection of biochemically distinct components including, without limitation, proteins, glycoproteins, proteoglycans, and polysaccharides. These components of the ECM are usually produced by adjacent cells and secreted into the ECM via exocytosis. Once secreted, the ECM components often aggregate to form a complex network of macromolecules. In various embodiments, the chimeric proteins or chimeric protein complexes such as Fc-based chimeric protein chimeric proteins of the invention comprises a targeting moiety that recognizes a target (e.g., an antigen or receptor or non-proteinaceous molecule) located on any component of the ECM. Illustrative components of the ECM include, without limitation, the proteoglycans, the non-proteoglycan polysaccharides, fibers, and other ECM proteins or ECM non-proteins, e.g. polysaccharides and/or lipids, or ECM associated molecules (e.g. proteins or non-proteins, e.g. polysaccharides, nucleic acids and/or lipids).

In some embodiments, the targeting moiety recognizes a target (e.g. antigen, receptor) on ECM proteoglycans. Proteoglycans are glycosylated proteins. The basic proteoglycan unit includes a core protein with one or more covalently attached glycosaminoglycan (GAG) chains. Proteoglycans have a net negative charge that attracts positively charged sodium ions (Na+), which attracts water molecules via osmosis, keeping the ECM and resident cells hydrated. Proteoglycans may also help to trap and store growth factors within the ECM. Illustrative proteoglycans that may be targeted by the chimeric proteins or chimeric protein complexes such as Fc-based chimeric protein complexes of the invention include, but are not limited to, heparan sulfate, chondroitin sulfate, and keratan sulfate. In an embodiment, the targeting moiety recognizes a target (e.g. antigen, receptor) on non-proteoglycan polysaccharides such as hyaluronic acid.

In some embodiments, the targeting moiety recognizes a target (e.g. antigen, receptor) on ECM fibers. ECM fibers include collagen fibers and elastin fibers. In some embodiments, the targeting moiety recognizes one or more epitopes on collagens or collagen fibers. Collagens are the most abundant proteins in the ECM. Collagens are present in the ECM as fibrillar proteins and provide structural support to resident cells. In one or more embodiments, the targeting moiety recognizes and binds to various types of collagens present within the ECM including, without limitation, fibrillar collagens (types I, II, III, V, XI), facit collagens (types IX, XII, XIV), short chain collagens (types VIII, X), basement membrane collagens (type IV), and/or collagen types VI, VII, or XIII. Elastin fibers provide elasticity to tissues, allowing them to stretch when needed and then return to their original state. In some embodiments, the target moiety recognizes one or more epitopes on elastins or elastin fibers.

In some embodiments, the targeting moiety recognizes one or more ECM proteins including, but not limited to, a tenascin, a fibronectin, a fibrin, a laminin, or a nidogen/entactin.

In an embodiment, the targeting moiety recognizes and binds to tenascin. The tenascin (TN) family of glycoproteins includes at least four members, tenascin-C, tenascin-R, tenascin-X, and tenascin W. The primary structures of tenascin proteins include several common motifs ordered in the same consecutive sequence: amino-terminal heptad repeats, epidermal growth factor (EGF)-like repeats, fibronectin type III domain repeats, and a carboxyl-terminal fibrinogen-like globular domain. Each protein member is associated with typical variations in the number and nature of EGF-like and fibronectin type III repeats. Isoform variants also exist particularly with respect to tenascin-C. Over 27 splice variants and/or isoforms of tenascin-C are known. In a particular embodiment, the targeting moiety recognizes and binds to tenascin-CA1. Similarly, tenascin-R also has various splice variants and isoforms. Tenascin-R usually exists as dimers or trimers. Tenascin-X is the largest member of the tenascin family and is known to exist as trimers. Tenascin-W exists as trimers. In some embodiments, the targeting moiety recognizes one or more epitopes on a tenascin protein. In some embodiments, the targeting moiety recognizes the monomeric and/or the dimeric and/or the trimeric and/or the hexameric forms of a tenascin protein.

In an embodiment, the targeting moieties recognize and bind to fibronectin. Fibronectins are glycoproteins that connect cells with collagen fibers in the ECM, allowing cells to move through the ECM. Upon binding to integrins, fibronectins unfolds to form functional dimers. In some embodiments, the targeting moiety recognizes the monomeric and/or the dimeric forms of fibronectin. In some embodiments, the targeting moiety recognizes one or more epitopes on fibronectin. In illustrative embodiments, the targeting moiety recognizes fibronectin extracellular domain A (EDA) or fibronectin extracellular domain B (EDB). Elevated levels of EDA are associated with various diseases and disorders including psoriasis, rheumatoid arthritis, diabetes, and cancer. In some embodiments, the targeting moiety recognizes fibronectin that contains the EDA isoform and may be utilized to target the chimeric proteins or chimeric protein complexes such as Fc-based chimeric protein complexes to diseased cells including cancer cells. In some embodiments, the targeting moiety recognizes fibronectin that contains the EDB isoform. In various embodiments, such targeting moieties may be utilized to target the chimeric proteins or chimeric protein complexes such as Fc-based chimeric protein complexes to tumor cells including the tumor neovasculature.

In an embodiment, the targeting moiety recognizes and binds to fibrin. Fibrin is another protein substance often found in the matrix network of the ECM. Fibrin is formed by the action of the protease thrombin on fibrinogen which causes the fibrin to polymerize. In some embodiments, the targeting moiety recognizes one or more epitopes on fibrin. In some embodiments, the targeting moiety recognizes the monomeric as well as the polymerized forms of fibrin.

In an embodiment, the targeting moiety recognizes and binds to laminin. Laminin is a major component of the basal lamina, which is a protein network foundation for cells and organs. Laminins are heterotrimeric proteins that contain an α-chain, a β-chain, and a γ-chain. In some embodiments, the targeting moiety recognizes one or more epitopes on laminin. In some embodiments, the targeting moiety recognizes the monomeric, the dimeric as well as the trimeric forms of laminin.

In an embodiment, the targeting moiety recognizes and binds to a nidogen or entactin. Nidogens/entactins are a family of highly conserved, sulfated glycoproteins. They make up the major structural component of the basement membranes and function to link laminin and collagen IV networks in basement membranes. Members of this family include nidogen-1 and nidogen-2. In various embodiments, the targeting moiety recognizes an epitope on nidogen-1 and/or nidogen-2.

In various embodiments, the targeting moiety comprises an antigen recognition domain that recognizes an epitope present on any of the targets described herein. In an embodiment, the antigen-recognition domain recognizes one or more linear epitopes present on the protein. As used herein, a linear epitope refers to any continuous sequence of amino acids present on the protein. In another embodiment, the antigen-recognition domain recognizes one or more conformational epitopes present on the protein. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the targeting moiety may bind to the full-length and/or mature forms and/or isoforms and/or splice variants and/or fragments and/or any other naturally occurring or synthetic analogs, variants, or mutants of any of the targets described herein. In various embodiments, the targeting moiety may bind to any forms of the proteins described herein, including monomeric, dimeric, trimeric, tetrameric, heterodimeric, multimeric and associated forms. In various embodiments, the targeting moiety may bind to any post-translationally modified forms of the proteins described herein, such as glycosylated and/or phosphorylated forms.

In various embodiments, the targeting moiety comprises an antigen recognition domain that recognizes extracellular molecules such as DNA. In some embodiments, the targeting moiety comprises an antigen recognition domain that recognizes DNA. In an embodiment, the DNA is shed into the extracellular space from necrotic or apoptotic tumor cells or other diseased cells.

In various embodiments, the targeting moiety comprises an antigen recognition domain that recognizes one or more non-cellular structures associated with atherosclerotic plaques. Two types of atherosclerotic plaques are known. The fibro-lipid (fibro-fatty) plaque is characterized by an accumulation of lipid-laden cells underneath the intima of the arteries. Beneath the endothelium there is a fibrous cap covering the atheromatous core of the plaque. The core includes lipid-laden cells (macrophages and smooth muscle cells) with elevated tissue cholesterol and cholesterol ester content, fibrin, proteoglycans, collagen, elastin, and cellular debris. In advanced plaques, the central core of the plaque usually contains extracellular cholesterol deposits (released from dead cells), which form areas of cholesterol crystals with empty, needle-like clefts. At the periphery of the plaque are younger foamy cells and capillaries. A fibrous plaque is also localized under the intima, within the wall of the artery resulting in thickening and expansion of the wall and, sometimes, spotty localized narrowing of the lumen with some atrophy of the muscular layer. The fibrous plaque contains collagen fibers (eosinophilic), precipitates of calcium (hematoxylinophilic) and lipid-laden cells. In some embodiments, the targeting moiety recognizes and binds to one or more of the non-cellular components of these plaques such as the fibrin, proteoglycans, collagen, elastin, cellular debris, and calcium or other mineral deposits or precipitates. In some embodiments, the cellular debris is a nucleic acid, e.g. DNA or RNA, released from dead cells.

In various embodiments, the targeting moiety comprises an antigen recognition domain that recognizes one or more non-cellular structures found in the brain plaques associated with neurodegenerative diseases. In some embodiments, the targeting moiety recognizes and binds to one or more non-cellular structures located in the amyloid plaques found in the brains of patients with Alzheimer's disease. For example, the targeting moiety may recognize and bind to the peptide amyloid beta, which is a major component of the amyloid plaques. In some embodiments, the targeting moiety recognizes and binds to one or more non-cellular structures located in the brains plaques found in patients with Huntington's disease. In various embodiments, the targeting moiety recognizes and binds to one or more non-cellular structures found in plaques associated with other neurodegenerative or musculoskeletal diseases such as Lewy body dementia and inclusion body myositis.

In some embodiments, the chimeric proteins or chimeric protein complexes such as Fc-based chimeric protein complexes of the invention may have two or more targeting moieties that bind to non-cellular structures. In some embodiments, there are two targeting moieties and one targets a cell while the other targets a non-cellular structure. In various embodiments, the targeting moieties can directly or indirectly recruit cells, such as disease cells and/or effector cells. In some embodiments, the present chimeric proteins or chimeric protein complexes such as Fc-based chimeric protein complexes are capable of, or find use in methods involving, shifting the balance of immune cells in favor of immune attack of a tumor. For instance, the present chimeric proteins or chimeric protein complexes such as Fc-based chimeric protein complexes can shift the ratio of immune cells at a site of clinical importance in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), B cells, dendritic cells, or subsets thereof) and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present chimeric proteins or chimeric protein complexes such as Fc-based chimeric protein complexes are capable of increasing a ratio of effector T cells to regulatory T cells.

For example, in some embodiments, the recognition domains specifically bind to a target (e.g. antigen, receptor) associated with T cells. In some embodiments, the recognition domains directly or indirectly recruit T cells. In an embodiment, the recognition domains specifically bind to effector T cells. In some embodiments, the recognition domain directly or indirectly recruits effector T cells, e.g., in some embodiments, to a therapeutic site (e.g. a locus with one or more disease cell or cell to be modulated for a therapeutic effect). Illustrative effector T cells include cytotoxic T cells (e.g. αβTCR, $CD3^+$, $CD8^+$, $CD45RO^+$); $CD4^+$ effector T cells (e.g. αβ TCR, $CD3^+$, $CD4^+$, $CCR7^+$, CD62Lhi, IL-7R/$CD127^+$); $CD8^+$ effector T cells (e.g. αβ TCR, $CD3^+$, $CD8^+$, $CCR7^+$, CD62Lhi, IL-7R/$CD127^+$); effector memory T cells (e.g. CD62Llow, $CD44^+$, TCR, $CD3^+$, IL-7R/$CD127^+$, $IL\text{-}15R^+$, CCR7low); central memory T cells (e.g. $CCR7^+$, $CD62L^+$, $CD27^+$; or CCR7hi, $CD44^+$, CD62Lhi, TCR, $CD3^+$, IL-7R/$CD127^+$, $IL\text{-}15R^+$); $CD62L^+$ effector T cells; $CD8^+$ effector memory T cells (TEM) including early effector memory T cells ($CD27^+$ $CD62L^-$) and late effector memory T cells ($CD27^-CD62L^-$) (TemE and TemL, respectively); CD127(+)CD25(low/−) effector T cells; CD127(−)CD25(−) effector T cells; $CD8^+$ stem cell memory effector cells (TSCM) (e.g. CD44(low) CD62L(high)CD122(high)sca(+)); TH1 effector T-cells (e.g. $CXCR3^+$, $CXCR6^+$ and $CCR5^+$; or αβ TCR, $CD3^+$, $CD4^+$, $IL\text{-}12R^+$, $IFN\gamma R^+$, $CXCR3^+$), TH2 effector T cells (e.g. $CCR3^+$, $CCR4^+$ and $CCR8^+$; or αβ TCR, $CD3^+$, $CD4^+$, $IL\text{-}4R^+$, $IL\text{-}33R^+$, $CCR4^+$, $IL\text{-}17RB^+$, $CRTH2^+$); TH9 effector T cells (e.g. αβ TCR, $CD3^+$, $CD4^+$); TH17 effector T cells (e.g. αβ TCR, $CD3^+$, $CD4^+$, $IL\text{-}23R^+$, $CCR6^+$, $IL\text{-}1R^+$); $CD4^+CD45RO^+CCR7^+$ effector T cells, $ICOS^+$ effector T cells; $CD4^+CD45RO^+$CCR7(−) effector T cells; and effector T cells secreting IL-2, IL-4 and/or IFN-γ.

Illustrative T cell antigens of interest include, for example (and inclusive of the extracellular domains, where applicable): CD8, CD3, SLAMF4, IL-2Rα, 4-1BB/TNFRSF9, IL-2 R β, ALCAM, B7-1, IL-4 R, B7-H3, LAME/SLAMFS, CEACAM1, IL-6 R, CCR3, IL-7 Rα, CCR4, CXCRI/IL-S RA, CCR5, CCR6, IL-10R α, CCR 7, IL-I 0 R β, CCRS, IL-12 R β 1, CCR9, IL-12 R β 2, CD2, IL-13 R α 1, IL-13, CD3, CD4, ILT2/CDS5j, ILT3/CDS5k, ILT4/CDS5d, ILT5/CDS5a, lutegrin α 4/CD49d, CDS, Integrin α E/CD103, CD6, Integrin α M/CD 11 b, CDS, Integrin α X/CD11c, Integrin β 2/CDIS, KIR/CD15S, CD27/TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP β 1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD 102, TRAILR3/TNFRSF100, IFN-γR1, TRAILR4/TNFRSF10D, I FN-γ R2, TSLP, IL-1 R1 and TSLP R. In various embodiments, a targeting moiety of the chimeric proteins or chimeric protein complexes such as Fc-based chimeric protein complexes binds one or more of these illustrative T cell antigens.

By way of non-limiting example, in various embodiments, the present chimeric proteins or chimeric protein complexes such as Fc-based chimeric protein complexes have a targeting moiety directed against a checkpoint marker expressed on a T cell, e.g. one or more of PD-1, CD28, CTLA4, ICOS, BTLA, KIR, LAG3, CD137, OX40, CD27, CD40L, TIM3, and A2aR.

For example, in some embodiments, the recognition domains specifically bind to a target (e.g. antigen, receptor) associated with B cells. In some embodiments, the recognition domains directly or indirectly recruit B cells, e.g., in some embodiments, to a therapeutic site (e.g. a locus with one or more disease cell or cell to be modulated for a therapeutic effect). Illustrative B cell antigens of interest include, for example, CD10, CD19, CD20, CD21, CD22, CD23, CD24, CD37, CD38, CD39, CD40, CD70, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138, CDw150, CS1, and B-cell maturation antigen (BCMA). In various embodiments, a targeting moiety of the chimeric proteins or chimeric protein complexes such as Fc-based chimeric protein complexes binds one or more of these illustrative B cell antigens.

By way of further example, in some embodiments, the recognition domains specifically bind to a target (e.g. antigen, receptor) associated with Natural Killer cells. In some embodiments, the recognition domains directly or indirectly recruit Natural Killer cells, e.g., in some embodiments, to a therapeutic site (e.g. a locus with one or more disease cell or cell to be modulated for a therapeutic effect). Illustrative Natural Killer cell antigens of interest include, for example TIGIT, 2B4/SLAMF4, KIR2DS4, CD155/PVR, KIR3DL1, CD94, LMIR1/CD300A, CD69, LMIR2/CD300c, CRACC/SLAMF7, LMIR3/CD300LF, DNAM-1, LMIR5/CD300LB, Fc-epsilon RII, LMIR6/CD300LE, Fc-γ RI/CD64, MICA, Fc-γ RIIB/CD32b, MICB, Fc-γ RIIC/CD32c, MULT-1, Fc-γ RIIA/CD32a, Nectin-2/CD112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAM F6, Rae-1, Rae-1 α, Rae-1 β, Rae-1 delta, H60, Rae-1 epsilon, ILT2/CD85j, Rae-1 γ, ILT3/CD85k, TREM-1, ILT4/CD85d, TREM-2, ILT5/

CD85a, TREM-3, KIR/CD158, TREML1/TLT-1, KIR2DL1, ULBP-1, KIR2DL3, ULBP-2, KIR2DL4/CD158d and ULBP-3. In various embodiments, a targeting moiety of the chimeric proteins or chimeric protein complexes such as Fc-based chimeric protein complexes binds one or more of these illustrative NK cell antigens.

Also, in some embodiments, the recognition domains specifically bind to a target (e.g. antigen, receptor) associated with macrophages/monocytes. In some embodiments, the recognition domains directly or indirectly recruit macrophages/monocytes, e.g., in some embodiments, to a therapeutic site (e.g. a locus with one or more disease cell or cell to be modulated for a therapeutic effect). Illustrative macrophages/monocyte antigens of interest include, for example SIRP1a, B7-1/CD80, ILT4/CD85d, B7-H1, ILT5/CD85a, Common β Chain, Integrin α 4/CD49d, BLAME/SLAMF8, Integrin α X/CDIIc, CCL6/C10, Integrin β 2/CD18, CD155/PVR, Integrin β 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R α, TCCR/WSX-1, ICAM-2/CD102, TLR3, IFN-γ RI, TLR4, IFN-γ R2, TREM-I, IL-I RII, TREM-2, ILT2/CD85j, TREM-3, ILT3/CD85k, TREML1/TLT-1, 2B4/SLAMF 4, IL-10 R α, ALCAM, IL-10 R β, AminopeptidaseN/ANPEP, ILT2/CD85j, Common β Chain, ILT3/CD85k, Clq R1/CD93, ILT4/CD85d, CCR1, ILT5/CD85a, CCR2, Integrin α 4/CD49d, CCR5, Integrin α M/CDII b, CCR8, Integrin α X/CDIIc, CD155/PVR, Integrin β 2/CD18, CD14, Integrin β 3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF R α, Siglec-3/CD33, HVEM/TNFRSF14, SLAM, ICAM-1/CD54, TCCR/WSX-1, ICAM-2/CD102, TREM-I, IL-6 R, TREM-2, CXCRI/IL-8 RA, TREM-3 and TREMLI/TLT-1. In various embodiments, a targeting moiety of the chimeric proteins or chimeric protein complexes such as Fc-based chimeric protein complexes binds one or more of these illustrative macrophage/monocyte antigens.

Also, in some embodiments, the recognition domains specifically bind to a target (e.g. antigen, receptor) associated with dendritic cells. In some embodiments, the recognition domains directly or indirectly recruit dendritic cells, e.g., in some embodiments, to a therapeutic site (e.g. a locus with one or more disease cell or cell to be modulated for a therapeutic effect). Illustrative dendritic cell antigens of interest include, for example, CLEC9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin α 4/CD49d, Aag, Integrin β 2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, CLEC-8, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC/CLEC4C, SLAM, EMMPRIN/CD147, TCCR/WSX-1, Fc-γ R1/CD64, TLR3, Fc-γ RIIB/CD32b, TREM-1, Fc-γ RIIC/CD32c, TREM-2, Fc-y RIIA/CD32a, TREM-3, Fc-γ RIII/CD16, TREML1/TLT-1, ICAM-2/CD102 and Vanilloid R1. In various embodiments, a targeting moiety of the chimeric proteins or chimeric protein complexes such as Fc-based chimeric protein complexes binds one or more of these illustrative DC antigens.

In some embodiments, the recognition domains specifically bind to a target (e.g. antigen, receptor) on immune cells selected from, but not limited to, megakaryocytes, thrombocytes, erythrocytes, mast cells, basophils, neutrophils, myeloid cells, monocytes, eosinophils, or subsets thereof. In some embodiments, the recognition domains directly or indirectly recruit megakaryocytes, thrombocytes, erythrocytes, mast cells, basophils, neutrophils, myeloid cells, monocytes, eosinophils, or subsets thereof, e.g., in some embodiments, to a therapeutic site (e.g. a locus with one or more disease cell or cell to be modulated for a therapeutic effect). In some embodiments, the immune cell is selected from a T cell, a B cell, a dendritic cell, a macrophage, a neutrophil, a mast cell, a monocyte, a red blood cell, myeloid cell, myeloid derived suppressor cell, a NKT cell, and a NK cell, or derivatives thereof.

In some embodiments, the recognition domains specifically bind to a target (e.g. antigen, receptor) associated with megakaryocytes and/or thrombocytes. Illustrative megakaryocyte and/or thrombocyte antigens of interest include, for example, GP IIb/IIIa, GPIb, vWF, PF4, and TSP. In various embodiments, a targeting moiety of the chimeric proteins or chimeric protein complexes such as Fc-based chimeric protein complexes binds one or more of these illustrative megakaryocyte and/or thrombocyte antigens.

In some embodiments, the recognition domains specifically bind to a target (e.g. antigen, receptor) associated with erythrocytes. Illustrative erythrocyte antigens of interest include, for example, CD34, CD36, CD38, CD41a (platelet glycoprotein IIb/IIIa), CD41b (GPIIb), CD71 (transferrin receptor), CD105, glycophorin A, glycophorin C, c-kit, HLA-DR, H2 (MHC-II), and Rhesus antigens. In various embodiments, a targeting moiety of the chimeric proteins or chimeric protein complexes such as Fc-based chimeric protein complexes binds one or more of these illustrative erythrocyte antigens.

In some embodiments, the recognition domains specifically bind to a target (e.g. antigen, receptor) associated with mast cells. Illustrative mast cells antigens of interest include, for example, SCFR/CD117, $Fc_{\varepsilon}RI$, CD2, CD25, CD35, CD88, CD203c, C5R1, CMAI, FCERIA, FCER2, TPSABI. In various embodiments, a targeting moiety of the chimeric proteins or chimeric protein complexes such as Fc-based chimeric protein complexes binds one or more of these mast cell antigens.

In some embodiments, the recognition domains specifically bind to a target (e.g. antigen, receptor) associated with basophils. Illustrative basophils antigens of interest include, for example, $Fc_{\varepsilon}RI$, CD203c, CD123, CD13, CD107a, CD107b, and CD164. In various embodiments, a targeting moiety of the chimeric proteins or chimeric protein complexes such as Fc-based chimeric protein complexes binds one or more of these basophil antigens.

In some embodiments, the recognition domains specifically bind to a target (e.g. antigen, receptor) associated with neutrophils. Illustrative neutrophils antigens of interest include, for example, 7D5, CD10/CALLA, CD13, CD16 (FcRIII), CD18 proteins (LFA-1, CR3, and p150, 95), CD45, CD67, and CD177. In various embodiments, a targeting moiety of the chimeric proteins or chimeric protein complexes such as Fc-based chimeric protein complexes binds one or more of these neutrophil antigens.

In some embodiments, the recognition domains specifically bind to a target (e.g. antigen, receptor) associated with eosinophils. Illustrative eosinophils antigens of interest include, for example, CD35, CD44 and CD69. In various embodiments, a targeting moiety of the chimeric proteins or chimeric protein complexes such as Fc-based chimeric protein complexes binds one or more of these eosinophil antigens.

In various embodiments, the recognition domain may bind to any appropriate target, antigen, receptor, or cell surface markers known by the skilled artisan. In some embodiments, the antigen or cell surface marker is a tissue-specific marker. Illustrative tissue-specific markers include, but are not limited to, endothelial cell surface markers such as ACE, CD14, CD34, CDH5, ENG, ICAM2, MCAM, NOS3, PECAMI, PROCR, SELE, SELP, TEK, THBD, VCAMI, VWF; smooth muscle cell surface markers such as ACTA2, MYHIO, MYHI 1, MYH9, MYOCD; fibroblast (stromal) cell surface markers such as ALCAM, CD34, COLIAI, COL1A2, COL3A1, FAP, PH-4; epithelial cell surface markers such as CDID, K6IRS2, KRTIO, KRT13, KRT17, KRT18, KRT19, KRT4, KRT5, KRT8, MUCI, TACSTDI; neovasculature markers such as CD13, TFNA, Alpha-v beta-3 ($\alpha_v\beta_3$), E-selectin; and adipocyte surface markers such as ADIPOQ, FABP4, and RETN. In various embodiments, a targeting moiety of the chimeric proteins or chimeric protein complexes such as Fc-based chimeric protein complexes binds one or more of these antigens. In various embodiments, a targeting moiety of the chimeric proteins or chimeric protein complexes such as Fc-based chimeric protein complexes binds one or more of cells having these antigens.

In some embodiments, the recognition domains specifically bind to a target (e.g. antigen, receptor) associated with tumor cells. In some embodiments, the recognition domains directly or indirectly recruit tumor cells. For instance, in some embodiments, the direct or indirect recruitment of the tumor cell is to one or more effector cell (e.g. an immune cell as described herein) that can kill and/or suppress the tumor cell.

Tumor cells, or cancer cells refer to an uncontrolled growth of cells or tissues and/or an abnormal increase in cell survival and/or inhibition of apoptosis which interferes with the normal functioning of bodily organs and systems. For example, tumor cells include benign and malignant cancers, polyps, hyperplasia, as well as dormant tumors or micrometastases. Illustrative tumor cells include, but are not limited to cells of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Tumor cells, or cancer cells also include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative tumor antigens include, but are not limited to, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, a-fetoprotein, E-cadherin, $\alpha$-catenin, $\beta$-catenin and $\gamma$-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD47, CS1, CD38, ASGPR, CD56, CD70, CD74, CD138, AGS16, MUC1, GPNMB, Ep-CAM, PD-L1, PD-L2, PMSA, and BCMA (TNFRSF17). In various embodiments, a targeting moiety of the chimeric proteins or chimeric protein complexes such as Fc-based chimeric protein complexes binds one or more of these tumor antigens. In an embodiment, the chimeric proteins or chimeric protein complexes such as Fc-based chimeric protein complexes binds to HER2. In another embodiment, the chimeric proteins or chimeric protein complexes such as Fc-based chimeric protein complexes binds to PD-L2.

In some embodiments, the present chimeric proteins or chimeric protein complexes such as Fc-based chimeric protein complexes have (i) one or more of the targeting moieties which is directed against an immune cell selected from a T cell, a B cell, a dendritic cell, a macrophage, a NK cell, or subsets thereof and (ii) one or more of the targeting moieties which is directed against a tumor cell, along with any of the signaling agents (e.g., IFNα1 or a variant thereof) described herein. In one embodiment, the present chimeric proteins or chimeric protein complexes such as Fc-based chimeric protein complexes have (i) a targeting moiety directed against a T cell (including, without limitation an effector T cell) and (ii) a targeting moiety is directed against a tumor cell, along with any of the signaling agents described herein. In one embodiment, the present chimeric proteins or chimeric protein complexes such as Fc-based chimeric protein complexes have (i) a targeting moiety directed against a B cell and (ii) a targeting moiety is directed against a tumor cell, along with any of the signaling agents described herein. In one embodiment, the present chimeric proteins or chimeric protein complexes such as Fc-based chimeric protein complexes have (i) a targeting moiety directed against a dendritic cell and (ii) a targeting moiety is directed against a tumor cell, along with any of the signaling agents described herein. In one embodiment, the present chimeric proteins or chimeric protein complexes such as Fc-based chimeric protein complexes have (i) a targeting moiety directed against a macrophage and (ii) a targeting moiety is directed against a tumor cell, along with any of the signaling agents described herein. In one embodiment, the present chimeric proteins or chimeric protein complexes such as Fc-based chimeric protein complexes have (i) a targeting moiety directed against a NK cell and (ii) a targeting moiety is directed against a tumor cell, along with any of the signaling agents described herein.

By way of non-limiting example, in various embodiments, the present chimeric proteins or chimeric protein complexes such as Fc-based chimeric protein complexes have (i) a targeting moiety directed against a T cell, for example, mediated by targeting to CD8, SLAMF4, IL-2 R α, 4-1BB/TNFRSF9, IL-2 R β, ALCAM, B7-1, IL-4 R, B7-H3, BLAME/SLAMFS, CEACAM1, IL-6 R, CCR3, IL-7 Rα, CCR4, CXCRI/IL-S RA, CCR5, CCR6, IL-10R α, CCR 7, IL-I 0 R β, CCRS, IL-12 R β 1, CCR9, IL-12 R β 2, CD2, IL-13 R α 1, IL-13, CD3, CD4, ILT2/CDS5j, ILT3/CDS5k, ILT4/CDS5d, ILT5/CDS5a, lutegrin α 4/CD49d, CDS, Integrin a E/CD103, CD6, Integrin α M/CD 11 b, CDS, Integrin α X/CD11c, Integrin ↑ 2/CDIS, KIR/CD15S, CD27/TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP β 1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD 102, TRAILR3/TNFRSF10D, IFN-γR1, TRAILR4/TNFRSF10D, IFN-γ R2, TSLP, IL-1 R1, or TSLP R; and (ii) a targeting moiety is directed against a tumor cell, along with any of the signaling agents (e.g., IFNα1 or a variant thereof) described herein.

By way of non-limiting example, in various embodiments, the present chimeric proteins or chimeric protein complexes such as Fc-based chimeric protein complexes have a targeting moiety directed against (i) a checkpoint marker expressed on a T cell, e.g. one or more of PD-1, CD28, CTLA4, ICOS, BTLA, KIR, LAG3, CD137, OX40, CD27, CD40L, TIM3, and A2aR and (ii) a targeting moiety is directed against a tumor cell, along with any of the signaling agents described herein.

In various embodiments, the present chimeric proteins or chimeric protein complexes such as Fc-based chimeric protein complexes have one or more targeting moieties directed against PD-1. In some embodiments, the chimeric proteins or chimeric protein complexes such as Fc-based chimeric protein complexes have one or more targeting moieties which selectively bind a PD-1 polypeptide. In some embodiments, the chimeric proteins or chimeric protein complexes such as Fc-based chimeric protein complexes comprise one or more antibodies, antibody derivatives or formats, peptides or polypeptides, or fusion proteins that selectively bind a PD-1 polypeptide.

In an embodiment, the targeting moiety comprises the anti-PD-1 antibody pembrolizumab (aka MK-3475, KEYTRUDA), or fragments thereof. Pembrolizumab and other humanized anti-PD-1 antibodies are disclosed in Hamid, et al. (2013) New England Journal of Medicine 369 (2): 134-44, U.S. Pat. No. 8,354,509, and WO 2009/114335, the entire disclosures of which are hereby incorporated by reference. In illustrative embodiments, pembrolizumab or an antigen-binding fragment thereof for use in the methods provided herein comprises a heavy chain comprising the amino acid sequence of (SEQ ID NO: 7) and/or a light chain comprising the amino acid sequence of (SEQ ID NO: 8).

In an embodiment, the targeting moiety comprises the anti-PD-1 antibody, nivolumab (aka BMS-936558, MDX-1106, ONO-4538, OPDIVO), or fragments thereof. Nivolumab (clone 5C4) and other human monoclonal antibodies that specifically bind to PD-1 are disclosed in U.S. Pat. No. 8,008,449 and WO 2006/121168, the entire disclosures of which are hereby incorporated by reference. In illustrative embodiments, nivolumab or an antigen-binding fragment thereof comprises a heavy chain comprising the amino acid sequence of (SEQ ID NO: 9) and/or a light chain comprising the amino acid sequence of (SEQ ID NO: 10).

In an embodiment, the targeting moiety comprises the anti-PD-1 antibody pidilizumab (aka CT-011, hBAT or hBAT-1), or fragments thereof. Pidilizumab and other humanized anti-PD-I monoclonal antibodies are disclosed in US 2008/0025980 and WO 2009/101611, the entire disclosures of which are hereby incorporated by reference. In illustrative embodiments, the anti-PD-1 antibody or an antigen-binding fragment thereof for use in the methods provided herein comprises a light chain variable regions comprising an amino acid sequence selected from SEQ ID NOS: 15-18 of US 2008/0025980: SEQ ID No: 15 of US 2008/0025980 (SEQ ID NO: 11); SEQ ID No: 16 of US 2008/0025980 (SEQ ID NO: 12); SEQ ID No: 17 of US 2008/0025980 (SEQ ID NO: 13); and SEQ ID No: 18 of US 2008/0025980 (SEQ ID NO: 14); and/or a heavy chain comprising an amino acid sequence selected from SEQ ID NOS: 20-24 of US 2008/0025980: SEQ ID No: 20 of US 2008/0025980 (SEQ ID NO: 15); SEQ ID No: 21 of US 2008/0025980 (SEQ ID NO: 16); SEQ ID No: 22 of US 2008/0025980 (SEQ ID NO: 17); SEQ ID No: 23 of US 2008/0025980 (SEQ ID NO: 18); and SEQ ID No: 24 of US 2008/0025980 (SEQ ID NO: 19).

In an embodiment, the targeting moiety comprises a light chain comprising SEQ ID NO: 18 of US 2008/0025980 (SEQ ID NO: 14) and a heavy chain comprising SEQ ID NO: 22 of US 2008/0025980 (SEQ ID NO: 17).

In an embodiment, the targeting moiety comprises AMP-514 (aka MEDI-0680).

In an embodiment, the targeting moiety comprises the PD-L2-Fc fusion protein AMP-224, which is disclosed in WO2010/027827 and WO 2011/066342, the entire disclosures of which are hereby incorporated by reference. In such an embodiment, the targeting moiety may include a targeting domain which comprises SEQ ID NO:4 of WO2010/027827 (SEQ ID NO:20) and/or the B7-DC fusion protein which comprises SEQ ID NO:83 of WO2010/027827 (SEQ ID NO: 21).

In an embodiment, the targeting moiety comprises the peptide AUNP 12 or any of the other peptides disclosed in US 2011/0318373 or U.S. Pat. No. 8,907,053. For example, the targeting moiety may comprise AUNP 12 (i.e., Compound 8 or SEQ ID NO:49 of US 2011/0318373) which has the sequence of:

in US 2014/0044738, the entire disclosures of which are hereby incorporated by reference. In illustrative embodiments, 1E8 or an antigen-binding fragment thereof for use in the methods provided herein comprises a heavy chain variable region comprising the amino acid sequence of SEQ ID NO: 25) and/or a light chain variable region comprising the amino acid sequence of SEQ ID NO: 26.

In an embodiment, the targeting moiety comprises the anti-PD-1 antibody 1H3, or fragments thereof, as disclosed in US 2014/0044738, the entire disclosures of which are hereby incorporated by reference. In illustrative embodiments, 1H3 or an antigen-binding fragment thereof for use in the methods provided herein comprises a heavy chain variable region comprising the amino acid sequence of (SEQ ID NO: 27) and/or light chain variable region comprising the amino acid sequence of (SEQ ID NO: 28).

In an embodiment, the targeting moiety comprises a VHH directed against PD-1 as disclosed, for example, in U.S. Pat. No. 8,907,065 and WO 2008/071447, the entire disclosures of which are hereby incorporated by reference. In illustrative embodiments, the VHHs against PD-1 comprise SEQ ID NOS: 347-351 of U.S. Pat. No. 8,907,065 (SEQ ID No: 347 of U.S. Pat. No. 8,907,065 (SEQ ID NO: 29); SEQ ID No: 348 of U.S. Pat. No. 8,907,065 (SEQ ID NO:30); SEQ ID No: 349 of U.S. Pat. No. 8,907,065 (SEQ ID NO:31); SEQ ID No: 350 of U.S. Pat. No. 8,907,065 (SEQ ID NO:32); and SEQ ID No: 351 of U.S. Pat. No. 8,907,065 (SEQ ID NO:33)).

In an embodiment, the targeting moiety comprises any one of the anti-PD-1 antibodies, or fragments thereof, as disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID NOS: 25-29 of US2011/0271358 (SEQ ID No: 25 of US2011/0271358 (SEQ ID NO:34); SEQ ID No: 26 of US2011/0271358 (SEQ (SEQ ID NO: 22)

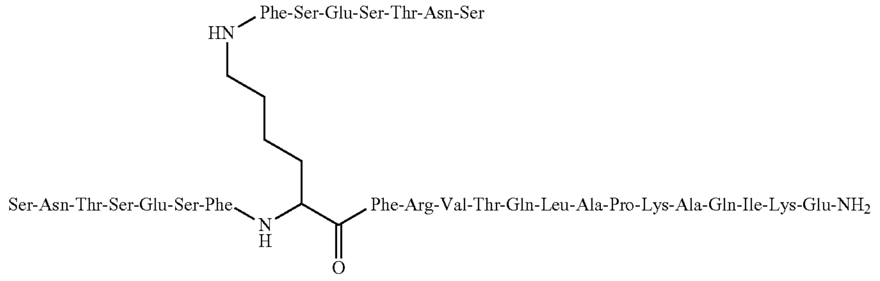

or:

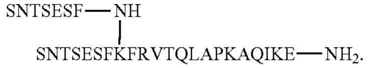

In an embodiment, the targeting moiety comprises the anti-PD-1 antibody 1E3, or fragments thereof, as disclosed in US 2014/0044738, the entire disclosures of which are hereby incorporated by reference. In illustrative embodiments, 1E3 or an antigen-binding fragment thereof for use in the methods provided herein comprises a heavy chain variable region comprising the amino acid sequence of (SEQ ID NO: 23); and/or a light chain variable region comprising the amino acid sequence of (SEQ ID NO: 24).

In an embodiment, the targeting moiety comprises the anti-PD-1 antibody 1E8, or fragments thereof, as disclosed ID NO:35); SEQ ID No: 27 of US2011/0271358 (SEQ ID NO:36); SEQ ID No: 28 of US2011/0271358 (SEQ ID NO:37); and SEQ ID No: 29 of US2011/0271358 (SEQ ID NO:38)); and/or a light chain comprising an amino acid sequence selected from SEQ ID NOS: 30-33 of US2011/0271358 (SEQ ID No: 30 of US2011/0271358 (SEQ ID NO:39); SEQ ID No: 31 of US2011/0271358 (SEQ ID NO:40); SEQ ID No: 32 of US2011/0271358 (SEQ ID NO:41); and SEQ ID No: 33 of US2011/0271358 (SEQ ID NO:42)).

In various embodiments, the present chimeric proteins or chimeric protein complexes such as Fc-based chimeric protein complexes comprise one or more antibodies directed against PD-1, or antibody fragments thereof, selected from TSR-042 (Tesaro, Inc.), REGN2810 (Regeneron Pharmaceuticals, Inc.), PDR001 (Novartis Pharmaceuticals), and BGB-A317 (BeiGene Ltd.)

In various embodiments, the present chimeric proteins or chimeric protein complexes such as Fc-based chimeric protein complexes have one or more targeting moieties directed against PD-L1. In some embodiments, the chimeric proteins or chimeric protein complexes such as Fc-based chimeric protein complexes have one or more targeting moieties which selectively bind a PD-L1 polypeptide. In some embodiments, the chimeric proteins or chimeric protein complexes such as Fc-based chimeric protein complexes comprise one or more antibodies, antibody derivatives or formats, peptides or polypeptides, or fusion proteins that selectively bind a PD-L1 polypeptide.

In an embodiment, the targeting moiety comprises the anti-PD-L1 antibody MEDI4736 (aka durvalumab), or fragments thereof. MEDI4736 is selective for PD-L1 and blocks the binding of PD-L1 to the PD-1 and CD80 receptors. MEDI4736 and antigen-binding fragments thereof for use in the methods provided herein comprises a heavy chain and a light chain or a heavy chain variable region and a light chain variable region. The sequence of MEDI4736 is disclosed in WO/2016/06272, the entire contents of which are hereby incorporated by reference. In illustrative embodiments, MEDI4736 or an antigen-binding fragment thereof for use in the methods provided herein comprises a heavy chain comprising the amino acid sequence of (SEQ ID NO:43); and/or a light chain comprising the amino acid sequence of (SEQ ID NO:44).

In illustrative embodiments, the MEDI4736 or an antigen-binding fragment thereof for use in the methods provided herein comprises a heavy chain variable region comprising the amino acid sequence of SEQ ID NO:4 of WO/2016/06272 (SEQ ID NO:45); and/or a light chain variable region comprising the amino acid sequence of SEQ ID NO:3 of WO/2016/06272 (SEQ ID NO:46).

In an embodiment, the targeting moiety comprises the anti-PD-L1 antibody atezolizumab (aka MPDL3280A, RG7446), or fragments thereof. In illustrative embodiments, atezolizumab or an antigen-binding fragment thereof for use in the methods provided herein comprises a heavy chain comprising the amino acid sequence of (SEQ ID NO:47); and/or a light chain comprising the amino acid sequence of (SEQ ID NO:48).

In an embodiment, the targeting moiety comprises the anti-PD-L1 antibody avelumab (aka MSB0010718C), or fragments thereof. In illustrative embodiments, avelumab or an antigen-binding fragment thereof for use in the methods provided herein comprises a heavy chain comprising the amino acid sequence of (SEQ ID NO:49); and/or a light chain comprising the amino acid sequence of (SEQ ID NO:50).

In an embodiment, the targeting moiety comprises the anti-PD-L1 antibody BMS-936559 (aka 12A4, MDX-1105), or fragments thereof, as disclosed in US 2013/0309250 and WO2007/005874, the entire disclosures of which are hereby incorporated by reference. In illustrative embodiments, BMS-936559 or an antigen-binding fragment thereof for use in the methods provided herein comprises a heavy chain variable region comprising the amino acid sequence of: (SEQ ID NO:51); and/or a light chain variable region comprising the amino acid sequence of (SEQ ID NO:52).

In an embodiment, the targeting moiety comprises the anti-PD-L1 antibody 3G10, or fragments thereof, as disclosed in US 2013/0309250 and WO2007/005874, the entire disclosures of which are hereby incorporated by reference. In illustrative embodiments, 3G10 or an antigen-binding fragment thereof for use in the methods provided herein comprises a heavy chain variable region comprising the amino acid sequence of (SEQ ID NO: 53); and/or a light chain variable region comprising the amino acid sequence of (SEQ ID NO: 54).

In an embodiment, the targeting moiety comprises the anti-PD-L1 antibody 10A5, or fragments thereof, as disclosed in US 2013/0309250 and WO2007/005874, the entire disclosures of which are hereby incorporated by reference. In illustrative embodiments, 10A5 or an antigen-binding fragment thereof for use in the methods provided herein comprises a heavy chain variable region comprising the amino acid sequence of (SEQ ID NO: 55); and/or a light chain variable region comprising the amino acid sequence of (SEQ ID NO: 56).

In an embodiment, the targeting moiety comprises the anti-PD-L1 antibody 5F8, or fragments thereof, as disclosed in US 2013/0309250 and WO2007/005874, the entire disclosures of which are hereby incorporated by reference. In illustrative embodiments, 5F8 or an antigen-binding fragment thereof for use in the methods provided herein comprises a heavy chain variable region comprising the amino acid sequence of (SEQ ID NO: 57); and/or a light chain variable region comprising the amino acid sequence of (SEQ ID NO: 58).

In an embodiment, the targeting moiety comprises the anti-PD-L1 antibody 10H10, or fragments thereof, as disclosed in US 2013/0309250 and WO2007/005874, the entire disclosures of which are hereby incorporated by reference. In illustrative embodiments, 10H10 or an antigen-binding fragment thereof for use in the methods provided herein comprises a heavy chain variable region comprising the amino acid sequence of (SEQ ID NO: 59); and/or a light chain variable region comprising the amino acid sequence of (SEQ ID NO: 60).

In an embodiment, the targeting moiety comprises the anti-PD-L1 antibody 1B12, or fragments thereof, as disclosed in US 2013/0309250 and WO2007/005874, the entire disclosures of which are hereby incorporated by reference. In illustrative embodiments, 1B12 or an antigen-binding fragment thereof for use in the methods provided herein comprises a heavy chain variable region comprising the amino acid sequence of (SEQ ID NO: 61); and/or a light chain variable region comprising the amino acid sequence of (SEQ ID NO: 62).

In an embodiment, the targeting moiety comprises the anti-PD-L1 antibody 7H1, or fragments thereof, as disclosed in US 2013/0309250 and WO2007/005874, the entire disclosures of which are hereby incorporated by reference. In illustrative embodiments, 7H1 or an antigen-binding fragment thereof for use in the methods provided herein comprises a heavy chain variable region comprising the amino acid sequence of (SEQ ID NO: 63); and/or a light chain variable region comprising the amino acid sequence of (SEQ ID NO: 64).

In an embodiment, the targeting moiety comprises the anti-PD-L1 antibody 11E6, or fragments thereof, as disclosed in US 2013/0309250 and WO2007/005874, the entire disclosures of which are hereby incorporated by reference. In illustrative embodiments, 11E6 or an antigen-binding fragment thereof for use in the methods provided herein comprises a heavy chain variable region comprising the amino acid sequence of (SEQ ID NO: 65); and/or a light chain variable region comprising the amino acid sequence of (SEQ ID NO: 66).

In an embodiment, the targeting moiety comprises the anti-PD-L1 antibody 12B7, or fragments thereof, as disclosed in US 2013/0309250 and WO2007/005874, the entire disclosures of which are hereby incorporated by reference. In illustrative embodiments, 12B7 or an antigen-binding fragment thereof for use in the methods provided herein comprises a heavy chain variable region comprising the amino acid sequence of (SEQ ID NO: 67); and/or a light chain variable region comprising the amino acid sequence of (SEQ ID NO: 68).

In an embodiment, the targeting moiety comprises the anti-PD-L1 antibody 13G4, or fragments thereof, as disclosed in US 2013/0309250 and WO2007/005874, the entire disclosures of which are hereby incorporated by reference. In illustrative embodiments, 13G4 or an antigen-binding fragment thereof for use in the methods provided herein comprises a heavy chain variable region comprising the amino acid sequence of (SEQ ID NO: 69); and/or a light chain variable region comprising the amino acid sequence of (SEQ ID NO: 70).

In an embodiment, the targeting moiety comprises the anti-PD-L1 antibody 1E12, or fragments thereof, as disclosed in US 2014/0044738, the entire disclosures of which are hereby incorporated by reference. In illustrative embodiments, 1E12 or an antigen-binding fragment thereof for use in the methods provided herein comprises a heavy chain variable region comprising the amino acid sequence of (SEQ ID NO: 71); and/or a light chain variable region comprising the amino acid sequence of (SEQ ID NO: 72).

In an embodiment, the targeting moiety comprises the anti-PD-L1 antibody 1F4, or fragments thereof, as disclosed in US 2014/0044738, the entire disclosures of which are hereby incorporated by reference. In illustrative embodiments, 1F4 or an antigen-binding fragment thereof for use in the methods provided herein comprises a heavy chain variable region comprising the amino acid sequence of (SEQ ID NO: 73); and/or a light chain variable region comprising the amino acid sequence of (SEQ ID NO: 74).

In an embodiment, the targeting moiety comprises the anti-PD-L1 antibody 2G11, or fragments thereof, as disclosed in US 2014/0044738, the entire disclosures of which are hereby incorporated by reference. In illustrative embodiments, 2G11 or an antigen-binding fragment thereof for use in the methods provided herein comprises a heavy chain variable region comprising the amino acid sequence of (SEQ ID NO: 75); and/or a light chain variable region comprising the amino acid sequence of (SEQ ID NO: 76).

In an embodiment, the targeting moiety comprises the anti-PD-L1 antibody 3B6, or fragments thereof, as disclosed in US 2014/0044738, the entire disclosures of which are hereby incorporated by reference. In illustrative embodiments, 3B6 or an antigen-binding fragment thereof for use in the methods provided herein comprises a heavy chain variable region comprising the amino acid sequence of (SEQ ID NO: 77); and/or a light chain variable region comprising the amino acid sequence of (SEQ ID NO: 78).

In an embodiment, the targeting moiety comprises the anti-PD-L1 antibody 3D10, or fragments thereof, as disclosed in US 2014/0044738 and WO2012/145493, the entire disclosures of which are hereby incorporated by reference. In illustrative embodiments, 3D10 or an antigen-binding fragment thereof for use in the methods provided herein comprises a heavy chain variable region comprising the amino acid sequence of (SEQ ID NO: 79); and/or a light chain variable region comprising the amino acid sequence of (SEQ ID NO: 80).

In an embodiment, the targeting moiety comprises any one of the anti-PD-L1 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 34-38 of US2011/0271358 (SEQ ID No: 34 of US2011/0271358 (SEQ ID NO: 81); SEQ ID No: 35 of US2011/0271358 (SEQ ID NO: 82); SEQ ID No: 36 of US2011/0271358 (SEQ ID NO: 83); SEQ ID No: 37 of US2011/0271358 (SEQ ID NO: 84); and SEQ ID No: 38 of US2011/0271358 (SEQ ID NO: 85)); and/or a light chain comprising an amino acid sequence selected from SEQ ID Nos: 39-42 of US2011/0271358 (SEQ ID No: 39 of US2011/0271358 (SEQ ID NO: 86); SEQ ID No: 40 of US2011/0271358 (SEQ ID NO: 87); SEQ ID No: 41 of US2011/0271358 (SEQ ID NO: 88); and SEQ ID No: 42 of US2011/0271358 (SEQ ID NO: 89)).

In an embodiment, the targeting moiety comprises the anti-PD-L1 antibody 2.7A4, or fragments thereof, as disclosed in WO 2011/066389, U.S. Pat. No. 8,779,108, and US2014/0356353, the entire disclosures of which are hereby incorporated by reference. In illustrative embodiments, 2.7A4 or an antigen-binding fragment thereof for use in the methods provided herein comprises a heavy chain variable region comprising the amino acid sequence of SEQ ID No: 2 of WO 2011/066389 (SEQ ID NO: 90); and/or a light chain variable region comprising the amino acid sequence of SEQ ID No: 7 of WO 2011/066389 (SEQ ID NO: 91).

In an embodiment, the targeting moiety comprises the anti-PD-L1 antibody 2.9D10, or fragments thereof, as disclosed in WO 2011/066389, U.S. Pat. No. 8,779,108, and US2014/0356353, the entire disclosures of which are hereby incorporated by reference. In illustrative embodiments, 2.9D10 or an antigen-binding fragment thereof for use in the methods provided herein comprises a heavy chain variable region comprising the amino acid sequence of SEQ ID No: 12 of WO 2011/066389 (SEQ ID NO: 92); and/or a light chain variable region comprising the amino acid sequence of SEQ ID No: 17 of WO 2011/066389 (SEQ ID NO: 93).

In an embodiment, the targeting moiety comprises the anti-PD-L1 antibody 2.14H9, or fragments thereof, as disclosed in WO 2011/066389, US8,779,108, and US2014/0356353, the entire disclosures of which are hereby incorporated by reference. In illustrative embodiments, 2.14H9 or an antigen-binding fragment thereof for use in the methods provided herein comprises a heavy chain variable region comprising the amino acid sequence of SEQ ID No: 22 of WO 2011/066389 (SEQ ID NO: 94); and/or a light chain variable region comprising the amino acid sequence of SEQ ID No: 27 of WO 2011/066389 (SEQ ID NO: 95).

In an embodiment, the targeting moiety comprises the anti-PD-L1 antibody 2.20A8, or fragments thereof, as disclosed in WO 2011/066389, U.S. Pat. No. 8,779,108, and US2014/0356353, the entire disclosures of which are hereby incorporated by reference. In illustrative embodiments, 2.20A8 or an antigen-binding fragment thereof for use in the methods provided herein comprises a heavy chain variable region comprising the amino acid sequence of SEQ ID No: 32 of WO 2011/066389 (SEQ ID NO: 96); and/or a light chain variable region comprising the amino acid sequence of SEQ ID No: 37 of WO 2011/066389 (SEQ ID NO: 97).

In an embodiment, the targeting moiety comprises the anti-PD-L1 antibody 3.15G8, or fragments thereof, as disclosed in WO 2011/066389, U.S. Pat. No. 8,779,108, and US2014/0356353, the entire disclosures of which are hereby incorporated by reference. In illustrative embodiments, 3.15G8 or an antigen-binding fragment thereof for use in the methods provided herein comprises a heavy chain variable region comprising the amino acid sequence of SEQ ID No: 42 of WO 2011/066389 (SEQ ID NO: 98); and/or a light chain variable region comprising the amino acid sequence of SEQ ID No: 47 of WO 2011/066389 (SEQ ID NO: 99).

In an embodiment, the targeting moiety comprises the anti-PD-L1 antibody 3.18G1, or fragments thereof, as disclosed in WO 2011/066389, U.S. Pat. No. 8,779,108, and US2014/0356353, the entire disclosures of which are hereby incorporated by reference. In illustrative embodiments, 3.18G1 or an antigen-binding fragment thereof for use in the methods provided herein comprises a heavy chain variable region comprising the amino acid sequence of SEQ ID No: 52 of WO 2011/066389 (SEQ ID NO:100); and/or a light chain variable region comprising the amino acid sequence of SEQ ID No: 57 of WO 2011/066389 (SEQ ID NO: 101).

In an embodiment, the targeting moiety comprises the anti-PD-L1 antibody 2.7A4OPT, or fragments thereof, as disclosed in WO 2011/066389, U.S. Pat. No. 8,779,108, and US2014/0356353, and US2014/0356353, the entire disclosures of which are hereby incorporated by reference. In illustrative embodiments, 2.7A4OPT or an antigen-binding fragment thereof for use in the methods provided herein comprises a heavy chain variable region comprising the amino acid sequence of SEQ ID No: 62 of WO 2011/066389 (SEQ ID NO:102); and/or a light chain variable region comprising the amino acid sequence of SEQ ID No: 67 of WO 2011/066389 (SEQ ID NO:103).

In an embodiment, the targeting moiety comprises the anti-PD-L1 antibody 2.14H9OPT, or fragments thereof, as disclosed in WO 2011/066389, U.S. Pat. No. 8,779,108, and US2014/0356353, the entire disclosures of which are hereby incorporated by reference. In illustrative embodiments, 2.14H9OPT or an antigen-binding fragment thereof for use in the methods provided herein comprises a heavy chain variable region comprising the amino acid sequence of SEQ ID No: 72 of WO 2011/066389 (SEQ ID NO:104); and/or a light chain variable region comprising the amino acid sequence of SEQ ID No: 77 of WO 2011/066389 (SEQ ID NO:105).

In an embodiment, the targeting moiety comprises any one of the anti-PD-L1 antibodies disclosed in WO2016/061142, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 18, 30, 38, 46, 50, 54, 62, 70, and 78 of WO2016/061142 (SEQ ID No: 18 of WO2016/061142 (SEQ ID NO:106); SEQ ID No: 30 of WO2016/061142 (SEQ ID NO:107); SEQ ID No: 38 of WO2016/061142 (SEQ ID NO:108); SEQ ID No: 46 of WO2016/061142 (SEQ ID NO:109); SEQ ID No: 50 of WO2016/061142 (SEQ ID NO:110); SEQ ID No: 54 of WO2016/061142 (SEQ ID NO:111); SEQ ID No: 62 of WO2016/061142 (SEQ ID NO:112); SEQ ID No: 70 of WO2016/061142 (SEQ ID NO:113); and SEQ ID No: 78 of WO2016/061142 (SEQ ID NO:114)); and/or a light chain comprising an amino acid sequence selected from SEQ ID Nos: 22, 26, 34, 42, 58, 66, 74, 82, and 86 of WO2016/061142 (SEQ ID No: 22 of WO2016/061142 (SEQ ID NO:115); SEQ ID No: 26 of WO2016/061142 (SEQ ID NO:116); SEQ ID No: 34 of WO2016/061142 (SEQ ID NO:117); SEQ ID No: 42 of WO2016/061142 (SEQ ID NO:118); SEQ ID No: 58 of WO2016/061142 (SEQ ID NO:119); SEQ ID No: 66 of WO2016/061142 (SEQ ID NO:120); SEQ ID No: 74 of WO2016/061142 (SEQ ID NO:121); SEQ ID No: 82 of WO2016/061142 (SEQ ID NO:122); and SEQ ID No: 86 of WO2016/061142 (SEQ ID NO:123)).

In an embodiment, the targeting moiety comprises any one of the anti-PD-L1 antibodies disclosed in WO2016/022630, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 2, 6, 10, 14, 18, 22, 26, 30, 34, 38, 42, and 46 of WO2016/022630 (SEQ ID No: 2 of WO2016/022630 (SEQ ID NO:124); SEQ ID No: 6 of WO2016/022630 (SEQ ID NO:125); SEQ ID No: 10 of WO2016/022630 (SEQ ID NO:126); SEQ ID No: 14 of WO2016/022630 (SEQ ID NO:127); SEQ ID No: 18 of WO2016/022630 (SEQ ID NO:128); SEQ ID No: 22 of WO2016/022630 (SEQ ID NO:129); SEQ ID No: 26 of WO2016/022630 (SEQ ID NO:130); SEQ ID No: 30 of WO2016/022630 (SEQ ID NO:131); SEQ ID No: 34 of WO2016/022630 (SEQ ID NO:132); SEQ ID No: 38 of WO2016/022630 (SEQ ID NO:133); SEQ ID No: 42 of WO2016/022630 (SEQ ID NO:134); and SEQ ID No: 46 of WO2016/022630 (SEQ ID NO:135)); and/or a light chain comprising an amino acid sequence selected from SEQ ID Nos: 4, 8, 12, 16, 20, 24, 28, 32, 36, 40, 44, and 48 of WO2016/022630 (SEQ ID No: 4 of WO2016/022630 (SEQ ID NO:136); SEQ ID No: 8 of WO2016/022630 (SEQ ID NO:137); SEQ ID No: 12 of WO2016/022630 (SEQ ID NO:138); SEQ ID No: 16 of WO2016/022630 (SEQ ID NO:139); SEQ ID No: 20 of WO2016/022630 (SEQ ID NO:140); SEQ ID No: 24 of WO2016/022630 (SEQ ID NO:141); SEQ ID No: 28 of WO2016/022630 (SEQ ID NO:142); SEQ ID No: 32 of WO2016/022630 (SEQ ID NO:143); SEQ ID No: 36 of WO2016/022630 (SEQ ID NO:144); SEQ ID No: 40 of WO2016/022630 (SEQ ID NO:145); SEQ ID No: 44 of WO2016/022630 (SEQ ID NO:146); and SEQ ID No: 48 of WO2016/022630 (SEQ ID NO:147)).

In an embodiment, the targeting moiety comprises any one of the anti-PD-L1 antibodies disclosed in WO2015/112900, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 38, 50, 82, and 86 of WO 2015/112900 (SEQ ID No: 38 of WO2015/112900 (SEQ ID NO:148); SEQ ID No: 50 of WO 2015/112900 (SEQ ID NO:149); SEQ ID No: 82 of WO 2015/112900 (SEQ ID NO:150); and SEQ ID No: 86 of WO 2015/112900 (SEQ ID NO:151)); and/or a light chain comprising an amino acid sequence selected from SEQ ID Nos: 42, 46, 54, 58, 62, 66, 70, 74, and 78 of WO 2015/112900 (SEQ ID No: 42 of WO2015/112900 (SEQ ID NO:152); SEQ ID No: 46 of WO 2015/112900: (SEQ ID NO:153); SEQ ID No: 54 of WO 2015/112900 (SEQ ID NO:154); SEQ ID No: 58 of WO 2015/112900 (SEQ ID NO:155); SEQ ID No: 62 of WO 2015/112900 (SEQ ID NO:156); SEQ ID No: 66 of WO 2015/112900 (SEQ ID NO:157); SEQ ID No: 70 of WO 2015/112900 (SEQ ID NO:158); SEQ ID No: 74 of WO 2015/112900 (SEQ ID NO:159); and SEQ ID No: 78 of WO 2015/112900 (SEQ ID NO:160)).

In an embodiment, the targeting moiety comprises any one of the anti-PD-L1 antibodies disclosed in WO 2010/077634 and U.S. Pat. No. 8,217,149, the entire disclosures of which are hereby incorporated by reference. In illustrative embodiments, the anti-PD-L1 antibody or an antigen-binding fragment thereof for use in the methods provided herein comprises a heavy chain region comprising the amino acid sequence of SEQ ID No: 20 of WO 2010/077634 (SEQ ID NO: 161); and/or a light chain variable region comprising the amino acid sequence of SEQ ID No: 21 of WO 2010/077634 (SEQ ID NO: 162).

In an embodiment, the targeting moiety comprises any one of the anti-PD-L1 antibodies obtainable from the hybridoma accessible under CNCM deposit numbers CNCM I-4122, CNCM I-4080 and CNCM I-4081 as disclosed in US 20120039906, the entire disclosures of which are hereby incorporated by reference.

In an embodiment, the targeting moiety comprises a VHH directed against PD-L1 as disclosed, for example, in U.S. Pat. No. 8,907,065 and WO 2008/071447, the entire disclosures of which are hereby incorporated by reference. In illustrative embodiments, the VHHs against PD-L1 comprise SEQ ID NOS: 394-399 of U.S. Pat. No. 8,907,065 (SEQ ID No: 394 of U.S. Pat. No. 8,907,065 (SEQ ID NO:163); SEQ ID No: 395 of U.S. Pat. No. 8,907,065 (SEQ ID NO:164); SEQ ID No: 396 of U.S. Pat. No. 8,907,065 (SEQ ID NO:165); SEQ ID No: 397 of U.S. Pat. No. 8,907,065 (SEQ ID NO:166); SEQ ID No: 398 of U.S. Pat. No. 8,907,065 (SEQ ID NO:167); and SEQ ID No: 399 of U.S. Pat. No. 8,907,065 (SEQ ID NO:168)).

In various embodiments, the present chimeric proteins or chimeric protein complexes such as Fc-based chimeric protein complexes have one or more targeting moieties directed against PD-L2. In some embodiments, the chimeric proteins or chimeric protein complexes such as Fc-based chimeric protein complexes have one or more targeting moieties which selectively bind a PD-L2 polypeptide. In some embodiments, the chimeric proteins or chimeric protein complexes such as Fc-based chimeric protein complexes comprise one or more antibodies, antibody derivatives or formats, peptides or polypeptides, or fusion proteins that selectively bind a PD-L2 polypeptide.

In an embodiment, the targeting moiety comprises a VHH directed against PD-L2 as disclosed, for example, in U.S. Pat. No. 8,907,065 and WO 2008/071447, the entire disclosures of which are hereby incorporated by reference. In illustrative embodiments, the VHHs against PD-L2 comprise SEQ ID Nos: 449-455 of U.S. Pat. No. 8,907,065 (SEQ ID No: 449 of U.S. Pat. No. 8,907,065 (SEQ ID NO:169); SEQ ID No: 450 of U.S. Pat. No. 8,907,065 (SEQ ID NO:170); SEQ ID No: 451 of U.S. Pat. No. 8,907,065 (SEQ ID NO:171); SEQ ID No: 452 of U.S. Pat. No. 8,907,065 (SEQ ID NO:172); SEQ ID No: 453 of U.S. Pat. No. 8,907,065 (SEQ ID NO:173); SEQ ID No: 454 of U.S. Pat. No. 8,907,065 (SEQ ID NO:174); and SEQ ID No: 455 of U.S. Pat. No. 8,907,065 (SEQ ID NO:175)).

In an embodiment, the targeting moiety comprises any one of the anti-PD-L2 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 43-47 of US2011/0271358 (SEQ ID No: 43 of US2011/0271358 (SEQ ID NO:176); SEQ ID No: 44 of US2011/0271358 (SEQ ID NO:177); SEQ ID No: 45 of US2011/0271358 (SEQ ID NO:178); SEQ ID No: 46 of US2011/0271358 (SEQ ID NO:179); and SEQ ID No: 47 of US2011/0271358 (SEQ ID NO:180)); and/or a light chain comprising an amino acid sequence selected from SEQ ID Nos: 48-51 of US2011/0271358 (SEQ ID No: 48 of US2011/0271358 (SEQ ID NO:181); SEQ ID No: 49 of US2011/0271358 (SEQ ID NO:182); SEQ ID No: 50 of US2011/0271358 (SEQ ID NO:183); and SEQ ID No: 51 of US2011/0271358 (SEQ ID NO:184)).

In various embodiments, the targeting moieties of the invention may comprise a sequence that targets PD-1, PD-L1, and/or PD-L2 which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity with any of the sequences disclosed herein).

In various embodiments, the targeting moieties of the invention may comprise any combination of heavy chain, light chain, heavy chain variable region, light chain variable region, complementarity determining region (CDR), and framework region sequences that target PD-1, PD-L1, and/or PD-L2 as disclosed herein.

Additional antibodies, antibody derivatives or formats, peptides or polypeptides, or fusion proteins that selectively bind or target PD-1, PD-L1 and/or PD-L2 are disclosed in WO 2011/066389, US 2008/0025980, US 2013/0034559, U.S. Pat. No. 8,779,108, US 2014/0356353, U.S. Pat. No. 8,609,089, US 2010/028330, US 2012/0114649, WO 2010/027827, WO 2011/066342, U.S. Pat. No. 8,907,065, WO 2016/062722, WO 2009/101611, WO2010/027827, WO 2011/066342, WO 2007/005874, WO 2001/014556, US2011/0271358, WO 2010/036959, WO 2010/077634, U.S. Pat. No. 8,217,149, US 2012/0039906, WO 2012/145493, US 2011/0318373, U.S. Pat. No. 8,779,108, US 20140044738, WO 2009/089149, WO 2007/00587, WO 2016061142, WO 2016,02263, WO 2010/077634, and WO 2015/112900, the entire disclosures of which are hereby incorporated by reference.

In one embodiment, the present chimeric proteins or chimeric protein complexes such as Fc-based chimeric protein complexes have (i) a targeting moiety directed against a T cell, for example, mediated by targeting to CD8 and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against CD8 on T cells and a second targeting moiety directed against PD-L1 or PD-L2 on tumor cells.

In one embodiment, the present chimeric proteins or chimeric protein complexes such as Fc-based chimeric protein complexes have (i) a targeting moiety directed against a T cell, for example, mediated by targeting to CD4 and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against CD4 on T cells and a second targeting moiety directed against PD-L1 or PD-L2 on tumor cells.

In one embodiment, the present chimeric proteins or chimeric protein complexes such as Fc-based chimeric protein complexes have (i) a targeting moiety directed against a T cell, for example, mediated by targeting to CD3, CXCR3, CCR4, CCR9, CD70, CD103, or one or more immune checkpoint markers and (ii) a targeting moiety is directed against a tumor cell, along with any of the signaling agents (e.g., IFNα1 interferon or a variant thereof) described herein. In an embodiment, the present chimeric proteins or chimeric protein complexes such as Fc-based chimeric protein complexes have a targeting moiety directed against CD3 on T cells and a second targeting moiety directed against PD-L1 or PD-L2 on tumor cells.

In some embodiments, the present chimeric proteins or chimeric protein complexes such as Fc-based chimeric protein complexes have one or more targeting moieties directed against CD3 expressed on T cells. In some embodiments, the chimeric proteins or chimeric protein complexes such as Fc-based chimeric protein complexes have one or more targeting moieties which selectively bind a CD3 polypeptide. In some embodiments, the chimeric proteins or chimeric protein complexes such as Fc-based chimeric protein complexes comprise one or more antibodies, antibody derivatives or formats, peptides or polypeptides, or fusion proteins that selectively bind a CD3 polypeptide.

In an embodiment, the targeting moiety comprises the anti-CD3 antibody muromonab-CD3 (aka Orthoclone OKT3), or fragments thereof. Muromonab-CD3 is disclosed in U.S. Pat. No. 4,361,549 and Wilde et al. (1996) 51:865-894, the entire disclosures of which are hereby incorporated by reference. In illustrative embodiments, muromonab-CD3 or an antigen-binding fragment thereof for use in the methods provided herein comprises a heavy chain comprising the amino acid sequence of (SEQ ID NO:185); and/or a light chain comprising the amino acid sequence of (SEQ ID NO:186).

In an embodiment, the targeting moiety comprises the anti-CD3 antibody otelixizumab, or fragments thereof. Otelixizumab is disclosed in U.S. Patent Publication No. 20160000916 and Chatenoud et al. (2012) 9:372-381, the entire disclosures of which are hereby incorporated by reference. In illustrative embodiments, otelixizumab or an antigen-binding fragment thereof for use in the methods provided herein comprises a heavy chain comprising the amino acid sequence of: SEQ ID NO:187; and/or a light chain comprising the amino acid sequence of SEQ ID NO:188.

In an embodiment, the targeting moiety comprises the anti-CD3 antibody teplizumab (AKA MGA031 and hOKT3γ1(Ala-Ala)), or fragments thereof. Teplizumab is disclosed in Chatenoud et al. (2012) 9:372-381, the entire disclosures of which are hereby incorporated by reference. In illustrative embodiments, teplizumab or an antigen-binding fragment thereof for use in the methods provided herein comprises a heavy chain comprising the amino acid sequence of SEQ ID NO:189; and/or a light chain comprising the amino acid sequence of SEQ ID NO:190.

In an embodiment, the targeting moiety comprises the anti-CD3 antibody visilizumab (AKA Nuvion®; HuM291), or fragments thereof. Visilizumab is disclosed in U.S. Pat. No. 5,834,597 and WO2004052397, and Cole et al., Transplantation (1999) 68:563-571, the entire disclosures of which are hereby incorporated by reference. In illustrative embodiments, visilizumab or an antigen-binding fragment thereof for use in the methods provided herein comprises a heavy chain variable region comprising the amino acid sequence of SEQ ID NO:191; and/or a light chain variable region comprising the amino acid sequence of SEQ ID NO:192.

In an embodiment, the targeting moiety comprises the anti-CD3 antibody foralumab (aka N1-0401), or fragments thereof. In various embodiments, the targeting moiety comprises any one of the anti-CD3 antibodies disclosed in US20140193399, U.S. Pat. No. 7,728,114, US20100183554, and U.S. Pat. No. 8,551,478, the entire disclosures of which are hereby incorporated by reference.

In illustrative embodiments, the anti-CD3 antibody or an antigen-binding fragment thereof for use in the methods provided herein comprises a heavy chain variable region comprising the amino acid sequence of SEQ ID Nos: 2 and 6 of U.S. Pat. No. 7,728,114 (SEQ ID No: 2 of U.S. Pat. No. 7,728,114 (SEQ ID NO:193) and SEQ ID No: 6 of U.S. Pat. No. 7,728,114 (SEQ ID NO:194)); and/or a light chain variable region comprising the amino acid sequence of SEQ ID NOs 4 and 8 of U.S. Pat. No. 7,728,114 (SEQ ID No: 4 of U.S. Pat. No. 7,728,114 (SEQ ID NO:195) and SEQ ID No: 8 of U.S. Pat. No. 7,728,114 (SEQ ID NO:196)).

In an embodiment, the targeting moiety comprises a heavy chain variable region comprising the amino acid sequence of SEQ ID NO:2 of U.S. Pat. No. 7,728,114 and a light chain variable region comprising the amino acid sequence of SEQ ID NO:4 of U.S. Pat. No. 7,728,114. In an embodiment, the targeting moiety comprises any one of the anti-CD3 antibodies disclosed in US2016/0168247, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 6-9 of US2016/0168247 (SEQ ID No: 6 of US2016/0168247 (SEQ ID NO:197); SEQ ID No: 7 of US2016/0168247 (SEQ ID NO:198); SEQ ID No: 8 of US2016/0168247 (SEQ ID NO:199); and SEQ ID No: 9 of US2016/0168247 (SEQ ID NO:200)); and/or a light chain comprising an amino acid sequence selected from SEQ ID Nos: 10-12 of US2016/0168247 (SEQ ID No: 10 of US2016/0168247 (SEQ ID NO:201); SEQ ID No: 11 of US2016/0168247 (SEQ ID NO:202); and SEQ ID No: 12 of US2016/0168247 (SEQ ID NO:203)).

In an embodiment, the targeting moiety comprises any one of the anti-CD3 antibodies disclosed in US2015/0175699, the entire contents of which are hereby incorporated by reference. In illustrative embodiments, the antibody or an antigen-binding fragment thereof for use in the methods provided herein comprises a heavy chain comprising an amino acid sequence selected from SEQ ID No: 9 of US2015/0175699 (SEQ ID NO:204); and/or a light chain comprising an amino acid sequence selected from SEQ ID No: 10 of US2015/0175699 (SEQ ID NO:205).

In an embodiment, the targeting moiety comprises any one of the anti-CD3 antibodies disclosed in U.S. Pat. No. 8,784,821, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 2, 18, 34, 50, 66, 82, 98 and 114 of U.S. Pat. No. 8,784,821 (SEQ ID No: 2 of U.S. Pat. No. 8,784,821 (SEQ ID NO:206); SEQ ID No: 18 of U.S. Pat. No. 8,784,821 (SEQ ID NO:207); SEQ ID No: 34 of U.S. Pat. No. 8,784,821 (SEQ ID NO:208); SEQ ID No: 50 of U.S. Pat. No. 8,784,821 (SEQ ID NO:209); SEQ ID No: 66 of U.S. Pat. No. 8,784,821 (SEQ ID NO:210); SEQ ID No: 82 of U.S. Pat. No. 8,784,821 (SEQ ID NO:211); SEQ ID No: 98 of U.S. Pat. No. 8,784,821 (SEQ ID NO:212); and SEQ ID No: 114 of U.S. Pat. No. 8,784,821 (SEQ ID NO:213)); and/or a light chain comprising an amino acid sequence selected from SEQ ID Nos: 10, 26, 42, 58, 74, 90, 106 and 122 of U.S. Pat. No. 8,784,821 (SEQ ID No: 10 of U.S. Pat. No. 8,784,821 (SEQ ID NO:214); SEQ ID No: 26 of U.S. Pat. No. 8,784,821 (SEQ ID NO:215); SEQ ID No: 42 of U.S. Pat. No. 8,784,821 (SEQ ID NO:216); SEQ ID No: 58 of U.S. Pat. No. 8,784,821 (SEQ ID NO:217); SEQ ID No: 74 of U.S. Pat. No. 8,784,821 (SEQ ID NO:218); SEQ ID No: 90 of U.S. Pat. No. 8,784,821 (SEQ ID NO:219); SEQ ID No: 106 of U.S. Pat. No. 8,784,821 (SEQ ID NO:220); and SEQ ID No: 122 of U.S. Pat. No. 8,784,821 (SEQ ID NO:221).

In an embodiment, the targeting moiety comprises any one of the anti-CD3 binding constructs disclosed in US20150118252, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 6 and 86 of US20150118252 (SEQ ID No: 6 of US20150118252 (SEQ ID NO:222) and SEQ ID No: 86 of US20150118252 (SEQ ID NO:223)) and/or a light chain comprising an amino acid sequence selected from SEQ ID No: 3 of US2015/0175699 (SEQ ID No: 3 of US20150118252 (SEQ ID NO:224)).

In an embodiment, the targeting moiety comprises any one of the anti-CD3 binding proteins disclosed in US2016/0039934, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 6-9 of US2016/0039934 (SEQ ID No: 6 of US2016/0039934 (SEQ ID NO:225); SEQ ID No: 7 of US2016/0039934 (SEQ ID NO:226); SEQ ID No: 8 of US2016/0039934 (SEQ ID NO:227); and SEQ ID No: 9 of US2016/0039934 (SEQ ID NO:228)); and/or a light chain comprising an amino acid sequence selected from SEQ ID Nos: 1-4 of US2016/0039934 (SEQ ID No: 1 of US2016/0039934 (SEQ ID NO:229); SEQ ID No: 2 of US2016/0039934 (SEQ ID NO:230); SEQ ID No: 3 of US2016/0039934 (SEQ ID NO:231); and SEQ ID No: 4 of US2016/0039934 (SEQ ID NO:232)).

In various embodiments, the targeting moieties of the invention may comprise a sequence that targets CD3 which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity with any of the sequences disclosed herein).

In various embodiments, the targeting moieties of the invention may comprise any combination of heavy chain, light chain, heavy chain variable region, light chain variable region, complementarity determining region (CDR), and framework region sequences that target CD3 as disclosed herein. In various embodiments, the targeting moieties of the invention may comprise any heavy chain, light chain, heavy chain variable region, light chain variable region, complementarity determining region (CDR), and framework region sequences of the CD3-specific antibodies including, but not limited to, X35-3, VIT3, BMA030 (BW264/56), CLB-T3/3, CRIS7, YTH12.5, FI 11-409, CLB-T3.4.2, TR-66, WT32, SPv-T3b, 11D8, XIII-141, XIII-46, XIII-87, 12F6, T3/RW2-808, T3/RW2-4B6, OKT3D, M-T301, SMC2, WT31 and F101.01. These CD3-specific antibodies are well known in the art and, inter alia, described in Tunnacliffe (1989), Int. Immunol. 1, 546-550, the entire disclosures of which are hereby incorporated by reference.

Additional antibodies, antibody derivatives or formats, peptides or polypeptides, or fusion proteins that selectively bind or target CD3 are disclosed in US Patent Publication No. 2016/0000916, U.S. Pat. Nos. 4,361,549, 5,834,597, 6,491,916, 6,406,696, 6,143,297, 6,750,325 and International Publication No. WO 2004/052397, the entire disclosures of which are hereby incorporated by reference.

In one embodiment, the present chimeric proteins or chimeric protein complexes such as Fc-based chimeric protein complexes have (i) a targeting moiety directed against a T cell, for example, mediated by targeting to PD-1 and (ii) a targeting moiety is directed against a tumor cell, along with any of the signaling agents (e.g., IFNα1 or a variant thereof) described herein.

By way of non-limiting example, in various embodiments, the present chimeric proteins or chimeric protein complexes such as Fc-based chimeric protein complexes have (i) a targeting moiety directed against a B cell, for example, mediated by targeting to CD10, CD19, CD20, CD21, CD22, CD23, CD24, CD37, CD38, CD39, CD40, CD70, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138, or CDw150; and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against CD20.

In one embodiment, the present chimeric proteins or chimeric protein complexes such as Fc-based chimeric protein complexes have (i) a targeting moiety directed against a B cell, for example, mediated by targeting to CD19, CD20 or CD70 and (ii) a targeting moiety is directed against a tumor cell, along with any of the signaling agents (e.g., IFNα1 or a variant thereof) described herein.

In one embodiment, the present chimeric proteins or chimeric protein complexes such as Fc-based chimeric protein complexes have (i) a targeting moiety directed against a B cell, for example, mediated by targeting to CD20 and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against CD20 on B cells and a second targeting moiety directed against PD-L1 or PD-L2 on tumor cells. By way of example, in some embodiments, the CD20 targeting moiety is a recombinant heavy-chain-only antibody (VHH) having the sequence of:

(SEQ ID NO: 288)
QVQLQESGGGLAQAGGSLRLSCAASGRTFSMGWFRQAPGKEREFVAAITY

SGGSPYYASSVRGRFTISRDNAKNTVYLQMNSLKPEDTAVYYCAANPTYG

SDWNAENWGQGTQVTVSS.

By way of non-limiting example, in various embodiments, the present chimeric proteins or chimeric protein complexes such as Fc-based chimeric protein complexes have (i) a targeting moiety directed against a NK cell, for example, mediated by targeting to 2B4/SLAM F4, KIR2DS4, CD155/PVR, KIR3DL1, CD94, LMIR1/CD300A, CD69, LMIR2/CD300c, CRACC/SLAMF7, LMIR3/CD300LF, DNAM-1, LMIR5/CD300LB, Fc-epsilon RII, LMIR6/CD300LE, Fc-γ RI/CD64, MICA, Fc-γ RIIB/CD32b, MICB, Fc-γ RIIC/CD32c, MULT-1, Fc-γ RIIA/CD32a, Nectin-2/CD112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAM F6, Rae-1, Rae-1 a, Rae-1 β, Rae-1 delta, H60, Rae-1 epsilon, ILT2/CD85j, Rae-1 γ, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d, or ULBP-3; and (ii) a targeting moiety is directed against a tumor cell, along with any of the signaling agents (e.g., IFNα1 or a variant thereof) described herein.

In one embodiment, the present chimeric proteins or chimeric protein complexes such as Fc-based chimeric protein complexes have (i) a targeting moiety directed against a NK cell, for example, mediated by targeting to Kir1alpha, DNAM-1 or CD64 and (ii) a targeting moiety is directed against a tumor cell, along with any of the signaling agents (e.g., IFNα1 or a variant thereof) described herein.

In one embodiment, the present chimeric proteins or chimeric protein complexes such as Fc-based chimeric protein complexes have (i) a targeting moiety directed against a NK cell, for example, mediated by targeting to KIR1 and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against KIR1 on NK cells and a second targeting moiety directed against PD-L1 or PD-L2 on tumor cells.

In one embodiment, the present chimeric proteins or chimeric protein complexes such as Fc-based chimeric protein complexes have (i) a targeting moiety directed against a NK cell, for example, mediated by targeting to TIGIT or KIR1 and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against TIGIT on NK cells and a second targeting moiety directed against PD-L1 or PD-L2 on tumor cells.

By way of non-limiting example, in various embodiments, the present chimeric proteins or chimeric protein complexes such as Fc-based chimeric protein complexes have (i) a targeting moiety directed against a dendritic cell, for example, mediated by targeting to CLEC-9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin α 4/CD49d, Aag, Integrin β 2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCR/WSX-1, Fc-γ R1/CD64, TLR3, Fc-γ RIIB/CD32b, TREM-1, Fc-γ RIIC/CD32c, TREM-2, Fc-γ RIIA/CD32a, TREM-3, Fc-γ RIII/CD16, TREML1/TLT-1, ICAM-2/CD102, or Vanilloid R1; and (ii) a targeting moiety is directed against a tumor cell, along with any of the signaling agents (e.g., IFNα1 or a variant thereof) described herein.

In one embodiment, the present chimeric proteins or chimeric protein complexes such as Fc-based chimeric protein complexes have (i) a targeting moiety directed against a dendritic cell, for example, mediated by targeting to CLEC-9A, DC-SIGN, CD64, CLEC4A, or DEC205 and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against CLEC9A on dendritic cells and a second targeting moiety directed against PD-L1 or PD-L2 on tumor cells.

In one embodiment, the present chimeric proteins or chimeric protein complexes such as Fc-based chimeric protein complexes have (i) a targeting moiety directed against a dendritic cell, for example, mediated by targeting to CLEC9A and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against CLEC9A on dendritic cells and a second targeting moiety directed against PD-L1 or PD-L2 on tumor cells.

In one embodiment, the present chimeric proteins or chimeric protein complexes such as Fc-based chimeric protein complexes have (i) a targeting moiety directed against a dendritic cell, for example, mediated by targeting to XCR1 and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against XCR1 on dendritic cells and a second targeting moiety directed against PD-L1 or PD-L2 on tumor cells.

In one embodiment, the present chimeric proteins or chimeric protein complexes such as Fc-based chimeric protein complexes have (i) a targeting moiety directed against a dendritic cell, for example, mediated by targeting to RANK and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complexes have a targeting moiety directed against RANK on dendritic cells and a second targeting moiety directed against PD-L1 or PD-L2 on tumor cells.

By way of non-limiting example, in various embodiments, the present chimeric proteins or chimeric protein complexes such as Fc-based chimeric protein complexes have (i) a targeting moiety directed against a monocyte/macrophage, for example, mediated by targeting to SIRP1a, B7-1/CD80, ILT4/CD85d, B7-H1, ILT5/CD85a, Common β Chain, Integrin α 4/CD49d, BLAME/SLAMF8, Integrin α X/CDIIc, CCL6/C10, Integrin β 2/CD18, CD155/PVR, Integrin β 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R α, TCCR/WSX-1, ICAM-2/CD102, TLR3, IFN-γ RI, TLR4, IFN-γ R2, TREM-I, IL-I RII, TREM-2, ILT2/CD85j, TREM-3, ILT3/CD85k, TREML1/TLT-1, 2B4/SLAMF 4, IL-10 R α, ALCAM, IL-10 R β, AminopeptidaseN/ANPEP, ILT2/CD85j, Common β Chain, ILT3/CD85k, Clq R1/CD93, ILT4/CD85d, CCR1, ILT5/CD85a, CCR2, CD206, Integrin α 4/CD49d, CCR5, Integrin α M/CDII b, CCR8, Integrin α X/CDIIc, CD155/PVR, Integrin β 2/CD18, CD14, Integrin β 3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF R α, Siglec-3/CD33, HVEM/TNFRSF14, SLAM, ICAM-1/CD54, TCCR/WSX-1, ICAM-2/CD102, TREM-I, IL-6 R, TREM-2, CXCRI/IL-8 RA, TREM-3, or TREMLI/TLT-1; and (ii) a targeting moiety is directed against a tumor cell, along with any of the signaling agents (e.g., IFNα1 or a variant thereof) described herein.

In one embodiment, the present chimeric proteins or chimeric protein complexes such as Fc-based chimeric protein complexes have (i) a targeting moiety directed against a monocyte/macrophage, for example, mediated by targeting to B7-H1, CD31/PECAM-1, CD163, CCR2, or Macrophage Mannose Receptor CD206 and (ii) a targeting moiety is directed against a tumor cell, along with any of the signaling agents (e.g., IFNα1 or a variant thereof) described herein.

In one embodiment, the present chimeric proteins or chimeric protein complexes such as Fc-based chimeric protein complex has (i) a targeting moiety directed against a monocyte/macrophage, for example, mediated by targeting to SIRP1a and (ii) a targeting moiety is directed against a tumor cell, along with any of the signaling agents (e.g., IFNα1 or a variant thereof) described herein. In an embodiment, the present chimeric proteins or chimeric protein complexes such as Fc-based chimeric protein complex has a targeting moiety directed against SIRP1a on macrophage cells and a second targeting moiety directed against PD-L1 or PD-L2 on tumor cells.

In various embodiments, the present chimeric proteins or chimeric protein complexes such as Fc-based chimeric protein complex has one or more targeting moieties directed against a checkpoint marker, e.g. one or more of PD-1/PD-L1 or PD-L2, CD28/CD80 or CD86, CTLA4/CD80 or CD86, ICOS/ICOSL or B7RP1, BTLA/HVEM, KIR, LAG3, CD137/CD137L, OX40/OX40L, CD27, CD40L, TIM3/Gal9, CD47, CD70, and A2aR. In one embodiment, the present chimeric proteins or chimeric protein complexes such as Fc-based chimeric protein complex has (i) a targeting moiety directed against a checkpoint marker on a T cell, for example, PD-1 and (ii) a targeting moiety directed against a tumor cell, for example, PD-L1 or PD-L2, along with any of the signaling agents (e.g., IFNα1 or a variant thereof) described herein. In an embodiment, the present chimeric proteins or chimeric protein complexes such as Fc-based chimeric protein complex has a targeting moiety directed against PD-1 on T cells and a second targeting moiety directed against PD-L1 on tumor cells. In another embodiment, the present chimeric proteins or chimeric protein complexes such as Fc-based chimeric protein complex has a targeting moiety directed against PD-1 on T cells and a second targeting moiety directed against PD-L2 on tumor cells.

In some embodiments, the present chimeric proteins or chimeric protein complexes such as Fc-based chimeric protein complex comprises two or more targeting moieties directed to the same or different immune cells. In some embodiments, the present chimeric proteins or chimeric protein complexes such as Fc-based chimeric protein complex has (i) one or more targeting moieties directed against an immune cell selected from a T cell, a B cell, a dendritic cell, a macrophage, a NK cell, or subsets thereof and (ii) one or more targeting moieties directed against either the same or another immune cell selected from a T cell, a B cell, a dendritic cell, a macrophage, a NK cell, or subsets thereof, along with any of the signaling agents (e.g., IFNα1 or a variant thereof) described herein.

In one embodiment, the present chimeric proteins or chimeric protein complexes such as Fc-based chimeric protein complex comprises one or more targeting moieties directed against a T cell and one or more targeting moieties directed against the same or another T cell. In one embodiment, the present chimeric proteins or chimeric protein complexes such as Fc-based chimeric protein complex comprises one or more targeting moieties directed against a T cell and one or more targeting moieties directed against a B cell. In one embodiment, the present chimeric proteins or chimeric protein complexes such as Fc-based chimeric protein complex comprises one or more targeting moieties directed against a T cell and one or more targeting moieties directed against a dendritic cell. In one embodiment, the present chimeric proteins or chimeric protein complexes such as Fc-based chimeric protein complex comprises one or more targeting moieties against a T cell and one or more targeting moieties directed against a macrophage. In one embodiment, the present chimeric proteins or chimeric protein complexes such as Fc-based chimeric protein complex comprises one or more targeting moieties against a T cell and one or more targeting moieties directed against a NK cell. For example, in an illustrative embodiment, the chimeric proteins or chimeric protein complexes such as Fc-based chimeric protein complex may include a targeting moiety against CD8 and a targeting moiety against Clec9A. In another illustrative embodiment, the chimeric proteins or chimeric protein complexes such as Fc-based chimeric protein complex may include a targeting moiety against CD8 and a targeting moiety against CD3. In another illustrative embodiment, the chimeric proteins or chimeric protein complexes such as Fc-based chimeric protein complex may include a targeting moiety against CD8 and a targeting moiety against PD-1.

In one embodiment, the present chimeric proteins or chimeric protein complexes such as Fc-based chimeric protein complex comprises one or more targeting moieties directed against a B cell and one or more targeting moieties directed against the same or another B cell. In one embodiment, the present chimeric proteins or chimeric protein complexes such as Fc-based chimeric protein complex comprises one or more targeting moieties directed against a B cell and one or more targeting moieties directed against a T cell. In one embodiment, the present chimeric proteins or chimeric protein complexes such as Fc-based chimeric protein complex comprises one or more targeting moieties directed against a B cell and one or more targeting moieties directed against a dendritic cell. In one embodiment, the present chimeric proteins or chimeric protein complexes such as Fc-based chimeric protein complex comprises one or more targeting moieties against a B cell and one or more targeting moieties directed against a macrophage. In one embodiment, the present chimeric proteins or chimeric protein complexes such as Fc-based chimeric protein complex comprises one or more targeting moieties against a B cell and one or more targeting moieties directed against a NK cell.

In one embodiment, the present chimeric proteins or chimeric protein complexes such as Fc-based chimeric protein complex comprises one or more targeting moieties directed against a dendritic cell and one or more targeting moieties directed against the same or another dendritic cell. In one embodiment, the present chimeric proteins or chimeric protein complexes such as Fc-based chimeric protein complex comprises one or more targeting moieties directed against a dendritic cell and one or more targeting moieties directed against a T cell. In one embodiment, the present chimeric proteins or chimeric protein complexes such as Fc-based chimeric protein complex comprises one or more targeting moieties directed against a dendritic cell and one or more targeting moieties directed against a B cell. In one embodiment, the present chimeric proteins or chimeric protein complexes such as Fc-based chimeric protein complex comprises one or more targeting moieties against a dendritic cell and one or more targeting moieties directed against a macrophage. In one embodiment, the present chimeric proteins or chimeric protein complexes such as Fc-based chimeric protein complex comprises one or more targeting moieties against a dendritic cell and one or more targeting moieties directed against a NK cell.

In one embodiment, the present chimeric proteins or chimeric protein complexes such as Fc-based chimeric protein complex comprises one or more targeting moieties directed against a macrophage and one or more targeting moieties directed against the same or another macrophage. In one embodiment, the present chimeric proteins or chimeric protein complexes such as Fc-based chimeric protein complex comprises one or more targeting moieties directed against a macrophage and one or more targeting moieties directed against a T cell. In one embodiment, the present chimeric proteins or chimeric protein complexes such as Fc-based chimeric protein complex comprises one or more targeting moieties directed against a macrophage and one or more targeting moieties directed against a B cell. In one embodiment, the present chimeric proteins or chimeric protein complexes such as Fc-based chimeric protein complex comprises one or more targeting moieties against a macrophage and one or more targeting moieties directed against a dendritic cell. In one embodiment, the present chimeric proteins or chimeric protein complexes such as Fc-based chimeric protein complex comprises one or more targeting moieties against a macrophage and one or more targeting moieties directed against a NK cell.

In one embodiment, the present chimeric proteins or chimeric protein complexes such as Fc-based chimeric protein complex comprises one or more targeting moieties directed against an NK cell and one or more targeting moieties directed against the same or another NK cell. In one embodiment, the present chimeric proteins or chimeric protein complexes such as Fc-based chimeric protein complex comprises one or more targeting moieties directed against an NK cell and one or more targeting moieties directed against a T cell. In one embodiment, the present chimeric proteins or chimeric protein complexes such as Fc-based chimeric protein complex comprises one or more targeting moieties directed against an NK cell and one or more targeting moieties directed against a B cell. In one embodiment, the present chimeric proteins or chimeric protein complexes such as Fc-based chimeric protein complex comprises one or more targeting moieties against an NK cell and one or more targeting moieties directed against a macrophage. In one embodiment, the present chimeric proteins or chimeric protein complexes such as Fc-based chimeric protein complex comprises one or more targeting moieties against an NK cell and one or more targeting moieties directed against a dendritic cell.

In one embodiment, the present chimeric proteins or chimeric protein complexes such as Fc-based chimeric protein complex comprises a targeting moiety directed against a tumor cell and a second targeting moiety directed against the same or a different tumor cell. In such embodiments, the targeting moieties may bind to any of the tumor antigens described herein.

In some embodiments, the chimeric proteins or chimeric protein complexes such as Fc-based chimeric protein complex of the invention comprises one or more targeting moieties having recognition domains that bind to a target (e.g. antigen, receptor) of interest including those found on one or more cells selected from adipocytes (e.g., white fat cell, brown fat cell), liver lipocytes, hepatic cells, kidney cells (e.g., kidney parietal cell, kidney salivary gland, mammary gland, etc.), duct cells (of seminal vesicle, prostate gland, etc.), intestinal brush border cells (with microvilli), exocrine gland striated duct cells, gall bladder epithelial cells, ductulus efferens nonciliated cells, epididymal principal cells, epididymal basal cells, endothelial cells, ameloblast epithelial cells (tooth enamel secretion), planum semilunatum epithelial cells of vestibular system of ear (proteoglycan secretion), organ of Corti interdental epithelial cells (secreting tectorial membrane covering hair cells), loose connective tissue fibroblasts, corneal fibroblasts (corneal keratocytes), tendon fibroblasts, bone marrow reticular tissue fibroblasts, nonepithelial fibroblasts, pericytes, nucleus pulposus cells of intervertebral disc, cementoblasts/cementocytes (tooth root bonelike ewan cell secretion), odontoblasts/odontocytes (tooth dentin secretion), hyaline cartilage chondrocytes, fibrocartilage chondrocytes, elastic cartilage chondrocytes, osteoblasts/osteocytes, osteoprogenitor cells (stem cell of osteoblasts), hyalocytes of vitreous body of eye, stellate cells of perilymphatic space of ear, hepatic stellate cells (Ito cell), pancreatic stelle cells, skeletal muscle cells, satellite cells, heart muscle cells, smooth muscle cells, myoepithelial cells of iris, myoepithelial cells of exocrine glands, exocrine secretory epithelial cells (e.g., salivary gland cells, mammary gland cells, lacrimal gland cells, sweat gland cells, sebaceious gland cells, prostate gland cells, gastric glad cells, pancreatic acinar cells, pneumocytes), a hormone secreting cells (e.g., pituitary cells, neurosecretory cells, gut and respiratory tract cells, thyroid gland cells, parathyroid glad cells, adrenal gland cells, Leydig cells of testes, pancreatic islet cells), keratinizing epithelial cells, wet stratified barrier epithelial cells, neuronal cells (e.g., sensory transducer cells, autonomic neuron cells, sense organ and peripheral neuron supporting cells, and central nervous system neurons and glial cells such as interneurons, principal cells, astrocytes, oligodendrocytes, and ependymal cells).

Targeting Moiety Formats

In various embodiments, the targeting moiety of the present chimeric proteins or chimeric protein complexes such as Fc-based chimeric protein complex is a protein-based agent capable of specific binding, such as an antibody or derivatives thereof. In an embodiment, the targeting moiety comprises an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the targeting moiety comprises antibody derivatives or formats. In some embodiments, the targeting moiety of the present chimeric proteins or chimeric protein complexes such as Fc-based chimeric protein complex is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterases; a plastic antibodies; a phylomer; a stradobodies; a maxibodies; an evibody; a fynomer, an armadillo repeat protein, a Kunitz domain, an avimer, an atrimer, a probody, an immunobody, a triomab, a troybody; a pepbody; a vaccibody, a UniBody; affimers, a DuoBody, a Fv, a Fab, a Fab', a $F(ab')_2$, a peptide mimetic molecule, or a synthetic molecule, as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In one embodiment, the targeting moiety comprises a single-domain antibody, such as VHH from, for example, an organism that produces VHH antibody such as a camelid, a shark, or a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains (CH2 and CH3). VHHs are commercially available under the trademark of NANOBODY or NANOBODIES.

In an embodiment, the targeting moiety comprises a VHH. In some embodiments, the VHH is a humanized VHH or camelized VHH.

In some embodiments, the VHH comprises a fully human VH domain, e.g. a HUMABODY (Crescendo Biologics, Cambridge, UK). In some embodiments, fully human VH domain, e.g. a HUMABODY is monovalent, bivalent, or trivalent. In some embodiments, the fully human VH domain, e.g. a HUMABODY is mono- or multi-specific such as monospecific, bispecific, or trispecific. Illustrative fully human VH domains, e.g. a HUMABODIES are described in, for example, WO 2016/113555 and WO2016/113557, the entire disclosure of which is incorporated by reference.

In various embodiments, the targeting moiety of the present chimeric proteins or chimeric protein complexes such as Fc-based chimeric protein complex is a protein-based agent capable of specific binding to a cell receptor, such as a natural ligand for the cell receptor. In various embodiments, the cell receptor is found on one or more immune cells, which can include, without limitation, T cells, cytotoxic T lymphocytes, T helper cells, natural killer (NK) cells, natural killer T (NKT) cells, anti-tumor macrophages (e.g. M1 macrophages), B cells, dendritic cells, or subsets thereof. In some embodiments, the cell receptor is found on megakaryocytes, thrombocytes, erythrocytes, mast cells, basophils, neutrophils, eosinophils, or subsets thereof.

In some embodiments, the targeting moiety is a natural ligand such as a chemokine. Illustrative chemokines that may be included in the chimeric proteins or chimeric protein complexes such as Fc-based chimeric protein complex of the invention include, but are not limited to, CCL1, CCL2, CCL4, CCL5, CCL6, CCL7, CCL8, CCL9, CCL10, CCL11, CCL12, CCL13, CCL14, CCL15, CCL16, CL17, CCL18, CCL19, CCL20, CCL21, CCL22, CCL23, CCL24, CLL25, CCL26, CCL27, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, CX3CL1, HCC-4, and LDGF-PBP. In an illustrative embodiment, the targeting moiety may be XCL1 which is a chemokine that recognizes and binds to the dendritic cell receptor XCR1. In another illustrative embodiment, the targeting moiety is CCL1, which is a chemokine that recognizes and binds to CCR8. In another illustrative embodiment, the targeting moiety is CCL2, which is a chemokine that recognizes and binds to CCR2 or CCR9. In another illustrative embodiment, the targeting moiety is CCL3, which is a chemokine that recognizes and binds to CCR1, CCRS, or CCR9. In another illustrative embodiment, the targeting moiety is CCL4, which is a chemokine that recognizes and binds to CCR1 or CCR5 or CCR9. In another illustrative embodiment, the targeting moiety is CCL5, which is a chemokine that recognizes and binds to CCR1 or CCR3 or CCR4 or CCR5. In another illustrative embodiment, the targeting moiety is CCL6, which is a chemokine that recognizes and binds to CCR1. In another illustrative embodiment, the targeting moiety is CCL7, which is a chemokine that recognizes and binds to CCR2 or CCR9. In another illustrative embodiment, the targeting moiety is CCL8, which is a chemokine that recognizes and binds to CCR1 or CCR2 or CCR2B or CCR5 or CCR9. In another illustrative embodiment, the targeting moiety is CCL9, which is a chemokine that recognizes and binds to CCR1. In another illustrative embodiment, the targeting moiety is CCL10, which is a chemokine that recognizes and binds to CCR1. In another illustrative embodiment, the targeting moiety is CCL11, which is a chemokine that recognizes and binds to CCR2 or CCR3 or CCR5 or CCR9. In another illustrative embodiment, the targeting moiety is CCL13, which is a chemokine that recognizes and binds to CCR2 or CCR3 or CCR5 or CCR9. In another illustrative embodiment, the targeting moiety is CCL14, which is a chemokine that recognizes and binds to CCR1 or CCR9. In another illustrative embodiment, the targeting moiety is CCL15, which is a chemokine that recognizes and binds to CCR1 or CCR3. In another illustrative embodiment, the targeting moiety is CCL16, which is a chemokine that recognizes and binds to CCR1, CCR2, CCR5, or CCR8. In another illustrative embodiment, the targeting moiety is CCL17, which is a chemokine that recognizes and binds to CCR4. In another illustrative embodiment, the targeting moiety is CCL19, which is a chemokine that recognizes and binds to CCR7. In another illustrative embodiment, the targeting moiety is CCL20, which is a chemokine that recognizes and binds to CCR6. In another illustrative embodiment, the targeting moiety is CCL21, which is a chemokine that recognizes and binds to CCR7. In another illustrative embodiment, the targeting moiety is CCL22, which is a chemokine that recognizes and binds to CCR4. In another illustrative embodiment, the targeting moiety is CCL23, which is a chemokine that recognizes and binds to CCR1. In another illustrative embodiment, the targeting moiety is CCL24, which is a chemokine that recognizes and binds to CCR3. In another illustrative embodiment, the targeting moiety is CCL25, which is a chemokine that recognizes and binds to CCR9. In another illustrative embodiment, the targeting moiety is CCL26, which is a chemokine that recognizes and binds to CCR3. In another illustrative embodiment, the targeting moiety is CCL27, which is a chemokine that recognizes and binds to CCR10. In another illustrative embodiment, the targeting moiety is CCL28, which is a chemokine that recognizes and binds to CCR3 or CCR10. In another illustrative embodiment, the targeting moiety is CXCL1, which is a chemokine that recognizes and binds to CXCR1 or CXCR2. In another illustrative embodiment, the targeting moiety is CXCL2, which is a chemokine that recognizes and binds to CXCR2. In another illustrative embodiment, the targeting moiety is CXCL3, which is a chemokine that recognizes and binds to CXCR2. In another illustrative embodiment, the targeting moiety is CXCL4, which is a chemokine that recognizes and binds to CXCR3B. In another illustrative embodiment, the targeting moiety is CXCL5, which is a chemokine that recognizes and binds to CXCR2. In another illustrative embodiment, the targeting moiety is CXCL6, which is a chemokine that recognizes and binds to CXCR1 or CXCR2. In another illustrative embodiment, the targeting moiety is CXCL8, which is a chemokine that recognizes and binds to CXCR1 or CXCR2. In another illustrative embodiment, the targeting moiety is CXCL9, which is a chemokine that recognizes and binds to CXCR3. In another illustrative embodiment, the targeting moiety is CXCL10, which is a chemokine that recognizes and binds to CXCR3. In another illustrative embodiment, the targeting moiety is CXCL11, which is a chemokine that recognizes and binds to CXCR3 or CXCR7. In another illustrative embodiment, the targeting moiety is CXCL12, which is a chemokine that recognizes and binds to CXCR4 or CXCR7. In another illustrative embodiment, the targeting moiety is CXCL13, which is a chemokine that recognizes and binds to CXCR5. In another illustrative embodiment, the targeting moiety is CXCL16, which is a chemokine that recognizes and binds to CXCR6. In another illustrative embodiment, the targeting moiety is LDGF-PBP, which is a chemokine that recognizes and binds to CXCR2. In another illustrative embodiment, the targeting moiety is XCL2, which is a chemokine that recognizes and binds to XCR1. In another illustrative embodiment, the targeting moiety is CX3CL1, which is a chemokine that recognizes and binds to CX3CR1.

In some embodiments, the targeting moiety is a natural ligand such as FMS-like tyrosine kinase 3 ligand (Flt3L) or a truncated region thereof (e.g., which is able to bind Flt3). In some embodiments, the targeting moiety is an extracellular domain of Flt3L. In some embodiments, the targeting moiety comprising a Flt3L domain, wherein the Flt3L domain is a single chain dimer, optionally where one Flt3L domain is connected to the other Flt3L domain via one or more linkers, wherein the linker is a flexible linker. In some embodiments, the targeting moiety of the present invention comprises Flt3L domain, wherein the Flt3L domain is a single chain dimer and an Fc domain, the Fc domain optionally having one or more mutations that reduces or eliminates one or more effector functions of the Fc domain, promotes Fc chain pairing in the Fc domain, and/or stabilizes a hinge region in the Fc domain. In some embodiments, the targeting moiety recognizes CD20. In some embodiments, the targeting moiety recognizes PD-L1. In some embodiments, the targeting moiety recognizes Clec9A.

In various embodiments, the present chimeric proteins or chimeric protein complexes such as Fc-based chimeric protein complex comprises targeting moieties in various combinations. In an illustrative embodiment, the present chimeric proteins or chimeric protein complexes such as Fc-based chimeric protein complex may comprise two targeting moieties, wherein both targeting moieties are antibodies or derivatives thereof. In another illustrative embodiment, the present chimeric proteins or chimeric protein complexes such as Fc-based chimeric protein complex may comprise two targeting moieties, wherein both targeting moieties are natural ligands for cell receptors. In a further illustrative embodiment, the present chimeric proteins or chimeric protein complexes such as Fc-based chimeric protein complex may comprise two targeting moieties, wherein one of the targeting moieties is an antibody or derivative thereof, and the other targeting moiety is a natural ligand for a cell receptor.

In various embodiments, the recognition domain of the present chimeric proteins or chimeric protein complexes such as Fc-based chimeric protein complex functionally modulates (by way of non-limitation, partially or completely neutralizes) the target (e.g. antigen, receptor) of interest, e.g. substantially inhibiting, reducing, or neutralizing a biological effect that the antigen has. For example, various recognition domains may be directed against one or more tumor antigens that are actively suppressing, or have the capacity to suppress, the immune system of, for example, a patient bearing a tumor. For example, in some embodiments, the present chimeric proteins or chimeric protein complexes such as Fc-based chimeric protein complex functionally modulates immune inhibitory signals (e.g. checkpoint inhibitors), for example, one or more of TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2. For example, in some embodiments, the present chimeric proteins or chimeric protein complexes such as Fc-based chimeric protein complex is engineered to disrupt, block, reduce, and/or inhibit the transmission of an immune inhibitory signal, by way of non-limiting example, the binding of PD-1 with PD-L1 or PD-L2 and/or the binding of CTLA-4 with one or more of AP2M1, CD80, CD86, SHP-2, and PPP2R5A.

In various embodiments, the recognition domain of the present chimeric proteins or chimeric protein complexes such as Fc-based chimeric protein complex binds but does not functionally modulate the target (e.g. antigen, receptor) of interest, e.g. the recognition domain is, or is akin to, a binding antibody. For instance, in various embodiments, the recognition domain simply targets the antigen or receptor but does not substantially inhibit, reduce or functionally modulate a biological effect that the antigen or receptor has. For example, some of the smaller antibody formats described above (e.g. as compared to, for example, full antibodies) have the ability to target hard to access epitopes and provide a larger spectrum of specific binding locales. In various embodiments, the recognition domain binds an epitope that is physically separate from an antigen or receptor site that is important for its biological activity (e.g. the antigen's active site).

Such non-neutralizing binding finds use in various embodiments of the present invention, including methods in which the present chimeric proteins or chimeric protein complexes such as Fc-based chimeric protein complex is used to directly or indirectly recruit active immune cells to a site of need via an effector antigen, such as any of those described herein. For example, in various embodiments, the present chimeric proteins or chimeric protein complexes such as Fc-based chimeric protein complex may be used to directly or indirectly recruit cytotoxic T cells via CD8 to a tumor cell in a method of reducing or eliminating a tumor (e.g. the chimeric proteins or chimeric protein complexes such as Fc-based chimeric protein complex may comprise an anti-CD8 recognition domain and a recognition domain directed against a tumor antigen). In such embodiments, it is desirable to directly or indirectly recruit CD8-expressing cytotoxic T cells but not to functionally modulate the CD8 activity. On the contrary, in these embodiments, CD8 signaling is an important piece of the tumor reducing or eliminating effect. By way of further example, in various methods of reducing or eliminating tumors, the present chimeric proteins or chimeric protein complexes such as Fc-based chimeric protein complex is used to directly or indirectly recruit dendritic cells (DCs) via CLEC9A (e.g. the chimeric proteins or chimeric protein complexes such as Fc-based chimeric protein complex may comprise an anti-CLEC9A recognition domain and a recognition domain directed against a tumor antigen). In such embodiments, it is desirable to directly or indirectly recruit CLEC9A-expressing DCs but not to functionally modulate the CLEC9A activity. On the contrary, in these embodiments, CLEC9A signaling is an important piece of the tumor reducing or eliminating effect.

In various embodiments, the recognition domain of the present chimeric proteins or chimeric protein complexes such as Fc-based chimeric protein complex binds to XCR1 e.g. on dendritic cells. For instance, the recognition domain, in some embodiments comprises all or part of XCL1 or a non-neutralizing anti-XCR1 agent.

In various embodiments, the recognition domain of the present chimeric proteins or chimeric protein complexes such as Fc-based chimeric protein complex binds to an immune modulatory antigen (e.g. immune stimulatory or immune inhibitory). In various embodiments, the immune modulatory antigen is one or more of 4-1BB, OX-40, HVEM, GITR, CD27, CD28, CD30, CD40, ICOS ligand; OX-40 ligand, LIGHT (CD258), GITR ligand, CD70, B7-1, B7-2, CD30 ligand, CD40 ligand, ICOS, ICOS ligand, CD137 ligand and TL1A. In various embodiments, such immune stimulatory antigens are expressed on a tumor cell. In various embodiments, the recognition domain of the present chimeric proteins or chimeric protein complexes such as Fc-based chimeric protein complex binds but does not functionally modulate such immune stimulatory antigens and therefore allows recruitment of cells expressing these antigens without the reduction or loss of their potential tumor reducing or eliminating capacity.

In various embodiments, the recognition domain of the present chimeric proteins or chimeric protein complexes such as Fc-based chimeric protein complex may be in the context of chimeric proteins or chimeric protein complexes such as Fc-based chimeric protein complex that comprises two recognition domains that have neutralizing activity, or comprises two recognition domains that have non-neutralizing (e.g. binding) activity, or comprises one recognition domain that has neutralizing activity and one recognition domain that has non-neutralizing (e.g. binding) activity.

Fc Domains

The fragment crystallizable domain (Fc domain) is the tail region of an antibody that interacts with Fc receptors located on the cell surface of cells that are involved in the immune system, e.g., B lymphocytes, dendritic cells, natural killer cells, macrophages, neutrophils, eosinophils, basophils, and mast cells. In IgG, IgA and IgD antibody isotypes, the Fc domain is composed of two identical protein fragments, derived from the second and third constant domains of the antibody's two heavy chains. In IgM and IgE antibody isotypes, the Fc domain contains three heavy chain constant domains (CH domains 2-4) in each polypeptide chain.

In some embodiments, the Fc-based chimeric protein of complex the present technology includes a Fc domain. In some embodiments, the Fc domains are from selected from IgG, IgA, IgD, IgM or IgE. In some embodiments, the Fc domains are from selected from IgG1, IgG2, IgG3, or IgG4.

In some embodiments, the Fc domains are from selected from human IgG, IgA, IgD, IgM or IgE. In some embodiments, the Fc domains are from selected from human IgG1, IgG2, IgG3, or IgG4.

In some embodiments, the Fc domains of the Fc-based chimeric protein complex comprise the CH2 and CH3 regions of IgG. In some embodiments, the IgG is human IgG. In some embodiments, the human IgG is selected from IgG1, IgG2, IgG3, or IgG4.

In some embodiments, the Fc domains comprise one or more mutations. In some embodiments, the mutation(s) to the Fc domains reduces or eliminates the effector function the Fc domains. In some embodiments, the mutated Fc domain has reduced affinity or binding to a target receptor. By way of example, in some embodiments, the mutation to the Fc domains reduces or eliminates the binding of the Fc domains to FcγR. In some embodiments, the FcγR is selected from FcγRI; FcγRIIa, 131 R/R; FcγRIIa, 131 H/H, FcγRIIb; and FcγRIII. In some embodiments, the mutation to the Fc domains reduces or eliminated binding to complement proteins, such as, e.g., C1q. In some embodiments, the mutation to the Fc domains reduces or eliminated binding to both FcγR and complement proteins, such as, e.g., C1q.

In some embodiments, the Fc domains comprise the LALA mutation to reduce or eliminate the effector function of the Fc domains. By way of example, in some embodiments, the LALA mutation comprises L234A and L235A substitutions in human IgG (e.g., IgG1) (wherein the numbering is based on the commonly used numbering of the CH2 residues for human IgG1 according to EU convention (PNAS, Edelman et al., 1969; 63 (1) 78-85)).

In some embodiments, the Fc domains of human IgG comprise a mutation at 46. to reduce or eliminate the effector function of the Fc domains. By way of example, in some embodiments, the mutations are selected from L234A, L234F, L235A, L235E, L235Q, K322A, K322Q, D265A, P329G, P329A, P331G, and P331S.

In some embodiments, the Fc domains comprise the FALA mutation to reduce or eliminate the effector function of the Fc domains. By way of example, in some embodiments, the FALA mutation comprises F234A and L235A substitutions in human IgG4.

In some embodiments, the Fc domains of human IgG4 comprise a mutation at one or more of F234, L235, K322, D265, and P329 to reduce or eliminate the effector function of the Fc domains. By way of example, in some embodiments, the mutations are selected from F234A, L235A, L235E, L235Q, K322A, K322Q, D265A, P329G, and P329A.

In some embodiments, the mutation(s) to the Fc domain stabilize a hinge region in the Fc domain. By way of example, in some embodiments, the Fc domain comprises a mutation at S228 of human IgG to stabilize a hinge region. In some embodiments, the mutation is S228P.

In some embodiments, the mutation(s) to the Fc domain promote chain pairing in the Fc domain. In some embodiments, chain pairing is promoted by ionic pairing (a/k/a charged pairs, ionic bond, or charged residue pair).

In some embodiments, the Fc domain comprises a mutation at one more of the following amino acid residues of IgG to promote of ionic pairing: D356, E357, L368, K370, K392, D399, and K409.

By way of example, in some embodiments, the human IgG Fc domain comprise one of the mutation combinations in Table 1 to promote of ionic pairing.

TABLE 1

| Substitution(s) on one Fc Chain | Substitution(s) on other Fc Chain |
|---|---|
| D356K D399K | K392D K409D |
| E357R L368R | K370D K409D |
| E357R L368K | K370D K409D |
| E357R D399K | K370D K409D |
| E357R | K370D |
| L368R D399K | K392D K409D |
| L368K D399K | K392D K409D |
| L368R D399K | K409D |
| L368K D399K | K409D |
| L368R | K409D |
| L368K | K409D |
| K370D K409D | E357R D399K |
| K370D K409D | E357R L368R |
| K370D K409D | E357R L368K |
| K370D K409D | E357R D399K |
| K370D K409D | E357R L368R |
| K370D K409D | E357R L368K |
| K370D | E357R |
| K370D | E357R |
| K392D K409D | D356K D399K |
| K392D K409D | L368R D399K |
| K392D K409D | L368K D399K |
| K392D K409D | D399K |
| D399K | K392D K409D |
| D399K | K409D |
| K409D | L368R |
| K409D | L368K |
| K409D | L368R D399K |
| K409D | L368K D399K |
| K409D | L368R |
| K409D | L368K |
| K409D | L368R D399K |
| K409D | L368K D399K |
| K409D | D399K |

In some embodiments, chain pairing is promoted by a knob-in-hole mutations. In some embodiments, the Fc domain comprises one or more mutations to allow for a knob-in-hole interaction in the Fc domain. In some embodiments, a first Fc chain is engineered to express the "knob" and a second Fc chain is engineered to express the complementary "hole." By way of example, in some embodiments, human IgG Fc domain comprises the mutations of Table 2 to allow for a knob-in-hole interaction.

TABLE 2

| Substitution(s) on one Fc Chain | Substitution(s) on other Fc Chain |
|---|---|
| T366Y | Y407T |
| T366Y/F405A | T394W/Y407T |
| T366W | Y407A |
| T366W | Y407V |
| T366Y | Y407A |
| T366Y | Y407V |
| T366Y | Y407T |

In some embodiments, the Fc domains in the Fc-based chimeric protein complexes of the present technology comprise any combination of the above disclosed mutations. By way of example, in some embodiments, the Fc domain comprises mutations that promote ionic pairing and/or a knob-in-hole interaction. By way of example, in some embodiments, the Fc domain comprises mutations that have one or more of the following properties: promote ionic pairing, induce a knob-in-hole interaction, reduce or eliminate the effector function of the Fc domain, and cause Fc stabilization (e.g. at hinge).

By way of example, in some embodiments, a human IgG Fc domains comprise mutations disclosed in Table 3, which promote ionic pairing and/or promote a knob-in-hole interaction in the Fc domain.

TABLE 3

| Substitution(s) on one Fc Chain | Substitution(s) on other Fc Chain |
|---|---|
| T366W K370D | E357R Y407A |
| T366W K370D | E357R Y407V |
| T366W K409D | L368R Y407A |
| T366W K409D | L368R Y407V |
| T366W K409D | L368K Y407A |
| T366W K409D | L368K Y407V |
| T366W K409D | L368R D399K Y407A |
| T366W K409D | L368R D399K Y407V |
| T366W K409D | L368K D399K Y407A |
| T366W K409D | L368K D399K Y407V |
| T366W K409D | D399K Y407A |
| T366W K409D | D399K Y407V |
| T366W K392D K409D | D399K Y407A |
| T366W K392D K409D | D399K Y407V |
| T366W K392D K409D | D356K D399K Y407A |
| T366W K392D K409D | D356K D399K Y407V |
| T366W K370D K409D | E357R D399K Y407A |
| T366W K370D K409D | E357R D399K Y407V |
| T366W K370D K409D | E357R L368R Y407A |
| T366W K370D K409D | E357R L368R Y407V |
| T366W K370D K409D | E357R L368K Y407A |
| T366W K370D K409D | E357R L368K Y407V |
| T366W K392D K409D | L368R D399K Y407A |
| T366W K392D K409D | L368R D399K Y407V |
| T366W K392D K409D | L368K D399K Y407A |
| T366W K392D K409D | L368K D399K Y407V |
| E357R T366W | K370D Y407A |
| E357R T366W | K370D Y407V |
| T366W L368R | Y407A K409D |
| T366W L368R | Y407V K409D |

TABLE 3-continued

| Substitution(s) on one Fc Chain | Substitution(s) on other Fc Chain |
|---|---|
| T366W L368K | Y407A K409D |
| T366W L368K | Y407V K409D |
| T366W L368R D399K | Y407A K409D |
| T366W L368R D399K | Y407V K409D |
| T366W L368K D399K | Y407A K409D |
| T366W L368K D399K | Y407V K409D |
| T366W D399K | Y407A K409D |
| T366W D399K | Y407V K409D |
| 1366W D399K | K392D Y407A K409D |
| T366W D399K | K392D Y407V K409D |
| T366W D356K D399K | K392D Y407A K409D |
| T366W D356K D399K | K392D Y407V K409D |
| E357R T366W D399K | K370D Y407A K409D |
| E357R T366W D399K | K370D Y407V K409D |
| E357R T366W L368R | K370D Y407A K409D |
| E357R T366W L368R | K370D Y407V K409D |
| E357R T366W L368K | K370D Y407A K409D |
| E357R T366W L368K | K370D Y407V K409D |
| T366W L368R D399K | K392D Y407A K409D |
| T366W L368R D399K | K392D Y407V K409D |
| T366W L368K D399K | K392D Y407A K409D |

By way of example, in some embodiments, a human IgG Fc domains comprise mutations disclosed in Table 4, which promote ionic pairing, promote a knob-in-hole interaction, or a combination thereof in the Fc domain. In embodiments, the "Chain 1" and "Chain 2" of Table 4 can be interchanged (e.g. Chain 1 can have Y407T and Chain 2 can have T366Y).

TABLE 4

| Chain 1 mutation | Chain 2 mutation | Reference | IgG |
|---|---|---|---|
| T366Y | Y407T | Ridgway et al., 1996 Protein Engineering, Design and Selection, Volume 9, Issue 7, 1 Jul. 1996, Pages 617-62 | IgG1 |
| T366Y/F405A | T394W/Y407T | Ridgway et al., 1996 Protein Engineering, Design and Selection, Volume 9, Issue 7, 1 Jul. 1996, Pages 617-62 | IgG1 |
| T366W | Y407A | Atwell et al., 1997 JMB Volume 270, Issue 1, 4 Jul. 1997, Pages 26-35 | IgG1 |
| T366W | T366S/L368V/Y407A | Atwell et al., 1997 JMB Volume 270, Issue 1, 4 Jul. 1997, Pages 26-35 | IgG1 |
| T366W | L368A/Y407A | Atwell et al., 1997 JMB Volume 270, Issue 1, 4 Jul. 1997, Pages 26-35 | IgG1 |
| T366W | T366S/L368A/Y407A | Atwell e fa/., 1997 JMB Volume 270, Issue 1, 4 Jul. 1997, Pages 26-35 | IgG1 |
| T366W | T366S/L368G/Y407V | Atwell et al., 1997 JMB Volume 270, Issue 1, 4 Jul. 1997, Pages 26-35 | IgG1 |
| T366W/D399C | T366S/L368A/K392C/Y407V | Merchant et al., 1998 Nature Biotechnology volume 16, pages 677-681 (1998) | IgG1 |
| T366W/K392C | T366S/L368A/D399C/Y407V | Merchant et al., 1998 Nature Biotechnology volume 16, pages 677-681 (1998) | IgG1 |
| S354C/T366W | Y349C/T366S/L368A/Y407V | Merchant et al., 1998 Nature Biotechnology volume 16, pages 677-681 (1998) | IgG1 |
| Y349C/T366W | S354C/T366S/L368A/Y407V | Merchant et al., 1998 Nature Biotechnology volume 16, pages 677-681 (1998) | IgG1 |
| E356C/T366W | Y349C/T366S/L368A/Y407V | Merchant et al., 1998 Nature Biotechnology volume 16, pages 677-681 (1998) | IgG1 |
| Y349C/T366W | E356C/T366S/L368A/Y407V | Merchant et al., 1998 Nature Biotechnology volume 16, pages 677 681 (1998) | IgG1 |

TABLE 4-continued

| Chain 1 mutation | Chain 2 mutation | Reference | IgG |
|---|---|---|---|
| E357C/T366W | Y349C/T366S/L368A/Y407V | Merchant et al., 1998 Nature Biotechnology volume 16, pages 677-681 (1998) | IgG1 |
| Y349C/T366W | E357C/T366S/L368A/Y407V | Merchant et al., 1998 Nature Biotechnology volume 16, pages 677-681 (1998) | IgG1 |
| D339R | K409E | Gunasekaran et al., 2010 The Journal of Biological Chemistry 285, 19637-19646. | IgG1 |
| D339K | K409E | Gunasekaran et al., 2010 The Journal of Biological Chemistry 285, 19637-19646. | IgG1 |
| D339R | K409D | Gunasekaran et al., 2010 The Journal of Biological Chemistry 285, 19637-19646. | IgG1 |
| D339K | K409D | Gunasekaran et al., 2010 The Journal of Biological Chemistry 285, 19637-19646. | IgG1 |
| D339K | K360D/K409E | Gunasekaran et al., 2010 The Journal of Biological Chemistry 285, 19637-19646. | IgG1 |
| D339K | K392D/K409E | Gunasekaran et al., 2010 The Journal of Biological Chemistry 285, 19637-19646. | IgG1 |
| D339K/E356K | K392D/K409E | Gunasekaran et al., 2010 The Journal of Biological Chemistry 285, 19637-19646. | IgG1 |
| D339K/E357K | K392D/K409E | Gunasekaran et al., 2010 The Journal of Biological Chemistry 285, 19637-19646. | IgG1 |
| D339K/E356K | K409E/K439D | Gunasekaran et al., 2010 The Journal of Biological Chemistry 285, 19637-19646. | IgG1 |
| D339K/E357K | K370D/K409E | Gunasekaran et al., 2010 The Journal of Biological Chemistry 285, 19637-19646. | IgG1 |
| D339K/E356K/E357K | K370D/K392D/K409E | Gunasekaran et al., 2010 The Journal of Biological Chemistry 285, 19637-19646. | IgG1 |
| S364H/F405A | Y349T/T394F | Moore etal., 2011 mAbs, 3:6, 546-557 | lIgG1 |
| S364H/T394F | Y349T/F405A | Moore etal., 2011 mAbs, 3:6, 546-557 | igd |
| D221R/P228R/K409R | D221E/P228E/L368E | Strop et al., 2012 JMB Volume 420, Issue 3, 13 Jul. 2012, Pages 204-219 | IgG1 |
| C223R/E225R/P228R/K409R | C223E/P228E/L368E | Strop et al., 2012 JMB Volume 420, Issue 3, 13 Jul. 2012, Pages 204-219 | igG2 |
| F405L | K409R | Labrijn et al., 2013 PNAS March 26, 2013. 110(13) 5145-5150 | igd |
| F405A/Y407V | T394W | Von Kreudenstein et al., 2013 mAbs Volume 5, 2013 - Issue 5, pp.644-654 | igd |
| F405A/Y407V | T366I/T394W | Von Kreudenstein et al., 2013 mAbs Volume 5, 2013 - Issue 5, pp.644-654 | Igd |
| F405A/Y407V | T366L/T394W | Von Kreudenstein et al., 2013 mAbs Volume 5, 2013 - Issue 5, pp.644-654 | Igd |
| F405A/Y407V | T366L/K392M/T394W | Von Kreudenstein et al., 2013 mAbs Volume 5, 2013 - Issue 5, pp.644-654 | Igd |
| L351Y/F405A/Y407V | T366L/K392M/T394W | Von Kreudenstein et al., 2013 mAbs Volume 5, 2013 - Issue 5, pp.644-654 | igd |
| T350V/L351Y/F405A/Y407V | T350V/T366L/K392M/T394W | Von Kreudenstein et al., 2013 mAbs Volume 5, 2013 - Issue 5, pp.644-654 | IgG1 |
| T350V/L351Y/F405A/Y407V | T350V/T366L/K392L/T394W | Von Kreudenstein et al., 2013 mAbs Volume 5, 2013 - Issue 5, pp.644-654 | IgG1 |
| K409W | D339V/F405T | Choi et al., 2013 PNAS Jan. 2, 2013. 110 (1) 270-275 | igd |
| K360E | Q347R | Choi et al., 2013 PNAS Jan. 2, 2013. 110 (1) 270-275 | IgG1 |
| K360E/K409W | D339V/Q347R/F405T | Choi et al., 2013 PNAS Jan. 2, 2013. 110 (1) 270-275 | igd |
| Y349C/K360E/K409W | D339V/Q347R/S354C/F405T | Choi et al., 2013 PNAS Jan. 2, 2013. 110 (1) 270-275 | IgG1 |
| K392A/K409D | E356K/D399K | Leaver-Fey et al., 2016 Structure Volume 24, Issue 4, 5 Apr. 2016, Pages 641-651 | IgG1 |
| T366W | T366S/L358A/Y407A | Leaver-Fey et al., 2016 Structure Volume 24, Issue 4, 5 Apr. 2016, Pages 641-651 | IgG1 |
| D339MNY407A | T336V/K409V | Leaver-Fey et al., 2016 Structure Volume 24, Issue 4, 5 Apr. 2016, Pages 641-651 | IgG1 |
| D339M/K360D/Y407A | T336V/E345R/Q347R/K409V | Leaver-Fey et al., 2016 Structure Volume 24, Issue 4, 5 Apr. 2016, Pages 641-651 | IgG1 |
| Y349S/T366V/K370Y/K409V | E357D/S364Q/Y407A | Leaver-Fey et al., 2016 Structure Volume 24, Issue 4, 5 Apr. 2016, Pages 641-651 | IgG1 |

TABLE 4-continued

| Chain 1 mutation | Chain 2 mutation | Reference | IgG |
|---|---|---|---|
| Y349S/T366M/K370Y/K409V | E356G/E357D/S364Q/Y407A | Leaver-Fey et al., 2016 Structure Volume 24, Issue 4, 5 Apr. 2016, Pages 641-651 | IgG1 |
| Y349S/T366M/K370Y/K409V | E357D/S364R/Y407A | Leaver-Fey et al., 2016 Structure Volume 24, Issue 4, 5 Apr. 2016, Pages 641-651 | IgG1 |

And any combination as described in Tables 1-3 of US20150284475A1

By way of example, in some embodiments, a human IgG Fc domains comprise mutations disclosed in Table 5, which reduce or eliminate FcγR and/or complement binding in the Fc domain. In embodiments, the Table 5 mutations are in both chains.

TABLE 5

| Chain 1 mutation | Reference | IgG |
|---|---|---|
| L234A/L235A | Alegre et al., 1994 Transplantation 57:1537-1543 | IgG1 |
| F234A/L235A | Alegre et al., 1994 Transplantation 57:1537-1543 | IgG4 |
| L235E | Morgan et al., 1995 Immunology. 1995 October; 86(2): 319-324. | IgG1 |
| L235E | Morgan et al., 1995 Immunology. 1995 October; 86(2): 319-324. | IgG4 |
| L235A | Morgan et al., 1995 Immunology. 1995 October; 86(2): 319-324. | IgG1 |
| G237A | Morgan et al., 1995 Immunology. 1995 October; 86(2): 319-324. | IgG1 |
| N297H | Tao and Morrison, J. Immunol. 1989; 143:2595-2601 | IgG1 |
| N297Q | Tao and Morrison, J. Immunol. 1989; 143:2595-2601 | IgG1 |
| N297K | Tao and Morrison, J. Immunol. 1989; 143:2595-2601 | IgG3 |
| N297Q | Tao and Morrison, J. Immunol. 1989; 143:2595-2601 | IgG3 |
| D265A | Idusogie et al., 2000 J Immunol Apr. 15, 2000, 164 (8) 4178-4184 | IgG1 |
| D270A, V, K | Idusogie et al., 2000 J Immunol Apr. 15, 2000, 164 (8) 4178-4184 | IgG1 |
| K322A, L, M, D, E | Idusogie et al., 2000 J Immunol Apr. 15, 2000, 164 (8) 4178-4184 | IgG1 |
| P329A, X | Idusogie et al., 2000 J Immunol Apr. 15, 2000, 164 (8) 4178-4184 | IgG1 |
| P331A, S, G, X | Idusogie et al., 2000 J Immunol Apr. 15, 2000, 164 (8) 4178-4184 | IgG1 |
| D265A | Idusogie et al., 2000 J Immunol Apr. 15, 2000, 164 (8) 4178-4184 | IgG1 |
| L234A | Hezareh et al., 2001 J. Virol. December 2001 vol. 75 no. 24 12161-12168 | IgG1 |
| L234A/L235A | Hezareh et al., 2001 J. Virol. December 2001 vol. 75 no. 24 12161-12168 | IgG1 |
| L234F/L235E/P331S | Oganesyan et al., 2008 Acta Cryst. (2008). D64, 700-704 | IgG1 |

TABLE 5-continued

| Chain 1 mutation | Reference | IgG |
|---|---|---|
| H268Q/V309L/A330S/P331S | An et al., 2009 mAbs Volume 1, 2009 - Issue 6, pp. 572-579 | IgG1 |
| G236R/L328R | Moore et al., 2011 mAbs Volume 3, 2011 - Issue 6, pp. 546-557 | IgG1 |
| N297G | Couch et al., 2013 Sci. Transl. Med., 5 (2013) 183ra57, 1-12 | IgG1 |
| N297G/D265A | Couch et al., 2013 Sci. Transl. Med., 5 (2013) 183ra57, 1-12 | IgG1 |
| V234A/G237A/P328S/H268A/V309L/A330S/P331S | Vafa et al., 2014 Methods Volume 65, Issue 1, 1 Jan. 2014, Pages 114-126 | IgG2 |
| L234A/L235A/P329G | Lo et al., 2016 The Journal of Biological Chemistry 292. 3900-3908 | IgG1 |
| N297D | Schlothauer et al., 2016 Protein Engineering, Design and Selection, Volume 29, Issue 10, 1 Oct. 2016, Pages 457-466 | IgG1 |
| S228P/L235E | Schlothauer et al., 2016 Protein Engineering, Design and Selection, Volume 29, Issue 10, 1 Oct. 2016, Pages 457-466 | IgG4 |
| S228P/L235E/P329G | Schlothauer et al., 2016 Protein Engineering, Design and Selection, Volume 29, Issue 10, 1 Oct. 2016, Pages 457-466 | IgG4 |
| L234F/L235A/K322Q | Borrok et al., 2017 J Pharm Sci April 2017 Volume 106, Issue 4, Pages 1008-1017 | IgG1 |
| L234F/L235Q/P331G | Borrok et al., 2017 J Pharm Sci April 2017 Volume 106, Issue 4, Pages 1008-1017 | IgG1 |
| L234F/L235Q/K322Q | Borrok et al., 2017 J Pharm Sci April 2017 Volume 106, Issue 4, Pages 1008-1017 | IgG1 |
| L234A/L235A/G237A/P328S/H268A/A330S/P331S | Tam et al., 2017 Open Access Antibodies 2017, 6(3), 12; doi: 10.3390/antib6030012 | IgG1 |
| S228P/F234A/L235A | Tam et al., 2017 Open Access Antibodies 2017, 6(3), 12; doi: 10.3390/antib6030012 | IgG4 |
| S228P/F234A/L235A/G237A/P238S | Tam et al., 2017 Open Access Antibodies 2017, 6(3), 12; doi: 10.3390/antib6030012 | IgG4 |
| S228P/F234A/L235A/G236[illegible]/G237A/P238S | Tam et al., 2017 Open Access Antibodies 2017, 6(3), 12; doi: 10.3390/antib6030012 | IgG4 |

In some embodiments, the Fc domains in the Fc-based chimeric protein complexes of the present technology are homodimeric, i.e., the Fc region in the chimeric protein complex comprises two identical protein fragments.

In some embodiments, the Fc domains in the Fc-based chimeric protein complexes of the present technology are heterodimeric, i.e., the Fc domain comprises two non-identical protein fragments.

In some embodiments, heterodimeric Fc domains are engineered using ionic pairing and/or knob-in-hole mutations described herein. In some embodiments, the heterodimeric Fc-based chimeric protein complexes have a trans orientation/configuration. In a trans orientation/configuration, the targeting moiety and signaling agent, e.g. IFNα1 are, in embodiments, not found on the same polypeptide chain in the present Fc-based chimeric protein complexes.

In some embodiments, the Fc domains includes or starts with the core hinge region of wild-type human IgG1, which contains the sequence Cys-Pro-Pro-Cys. In some embodiments, the Fc domains also include the upper hinge, or parts thereof (e.g., DKTHTCPPC; see WO 2009053368), EPKSCDKTHTCPPC, or EPKSSDKTHTCPPC; see Lo et al., Protein Engineering vol. 11 no. 6 pp. 495-500, 1998)).

Fc-Based Chimeric Protein Complexes

The Fc-based chimeric protein complexes of the present technology comprise at least one Fc domain disclosed herein, at least one signaling agent, e.g. IFNα1 (SA) disclosed herein, e.g. IFNα1, and at least one targeting moiety (TM) disclosed herein.

It is understood that, the present Fc-based chimeric protein complexes may encompass a complex of two fusion proteins, each comprising an Fc domain.

In some embodiments, the Fc-based chimeric protein complex is heterodimeric. In some embodiments, the heterodimeric Fc-based chimeric protein complex has a trans orientation/configuration. In some embodiments, the heterodimeric Fc-based chimeric protein complex has a cis orientation/configuration.

In some embodiments, heterodimeric Fc domains are engineered using ionic pairing and/or knob-in-hole mutations described herein. In some embodiments, the heterodimeric Fc-based chimeric protein complexes have a trans orientation.

In a trans orientation, the targeting moiety and signaling agent are, in embodiments, not found on the same polypeptide chain in the present Fc-based chimeric protein complexes. In a trans orientation, the targeting moiety and signaling agent are, in embodiments, found on separate polypeptide chains in the Fc-based chimeric protein complexes. In a cis orientation, the targeting moiety and signaling agent are, in embodiments, found on the same polypeptide chain in the Fc-based chimeric protein complexes.

In some embodiments, where more than one targeting moiety is present in the heterodimeric protein complexes described herein, one targeting moiety may be in trans orientation (relative to the signaling agent), whereas another targeting moiety may be in cis orientation (relative to the signaling agent). In some embodiments, the signaling agent and target moiety are on the same ends/sides (N-terminal or C-terminal ends) of an Fc domain. In some embodiments, the signaling agent and targeting moiety are on different sides/ends of a Fc domain (N-terminal and C-terminal ends).

In some embodiments, where more than one targeting moiety is present in the heterodimeric protein complexes described herein, the targeting moieties may be found on the same Fc chain or on two different Fc chains in the heterodimeric protein complex (in the latter case the targeting moieties would be in trans relative to each other, as they are on different Fc chains). In some embodiments, where more than one targeting moiety is present on the same Fc chain, the targeting moieties may be on the same or different sides/ends of a Fc chain (N-terminal or/and C-terminal ends).

In some embodiments, where more than one signaling agent is present in the heterodimeric protein complexes described herein, the signaling agents may be found on the same Fc chain or on two different Fc chains in the heterodimeric protein complex (in the latter case the signaling agents would be in trans relative to each other, as they are on different Fc chains). In some embodiments, where more than one signaling agent is present on the same Fc chain, the signaling agents may be on the same or different sides/ends of a Fc chain (N-terminal or/and C-terminal ends).

In some embodiments, where more than one signaling agent is present in the heterodimeric protein complexes described herein, one signaling agent may be in trans orientation (as relates to the targeting moiety), whereas another signaling agent may be in cis orientation (as relates to the targeting moiety).

In some embodiments, the heterodimeric Fc-based chimeric protein complex does not comprise the signaling agent, e.g. IFNα1 and targeting moiety on a single polypeptide.

In some embodiments, the Fc-based chimeric protein has an improved in vivo half-life relative to a chimeric protein lacking an Fc or a chimeric protein which is not a heterodimeric complex. In some embodiments, the Fc-based chimeric protein has an improved solubility, stability and other pharmacological properties relative to a chimeric protein lacking an Fc or a chimeric protein which is not a heterodimeric complex.

Heterodimeric Fc-based chimeric protein complexes are composed of two different polypeptides. In embodiments described herein, the targeting domain is on a different polypeptide than the signaling agent, e.g. IFNα1, and accordingly, proteins that contain only one targeting domain copy, and also only one signaling agent, e.g. IFNα1 copy can be made (this provides a configuration in which potential interference with desired properties can be controlled). Further, in embodiments, one targeting domain (e.g. VHH) only can avoid cross-linking of the antigen on the cell surface (which could elicit undesired effects in some cases). Further, in embodiments, one signaling agent, e.g. IFNα1 may alleviate molecular "crowding" and potential interference with avidity mediated induction or restoration of effector function in dependence of the targeting domain. Further, in embodiments, heterodimeric Fc-based chimeric protein complexes can have two targeting moieties and these can be placed on the two different polypeptides. For instance, in embodiments, the C-terminus of both targeting moieties (e.g. VHHs) can be masked to avoid potential autoantibodies or pre-existing antibodies (e.g. VHH autoantibodies or pre-existing antibodies). Further, in embodiments, heterodimeric Fc-based chimeric protein complexes, e.g. with the targeting domain on a different polypeptide than the signaling agent, e.g. IFNα1 (e.g. wild type signaling agent, e.g. wild type IFNα1), may favor "cross-linking" of two cell types (e.g. a tumor cell and an immune cell). Further, in embodiments, heterodimeric Fc-based chimeric protein complexes can have two signaling agent, each on different polypeptides to allow more complex effector responses.

Further, in embodiments, heterodimeric Fc-based chimeric protein complexes, e.g. with the targeting domain on a different polypeptide than the signaling agent, e.g. IFNα1, combinatorial diversity of targeting moiety and signaling agent, e.g. IFNα1 is provided in a practical manner. For instance, in embodiments, polypeptides with any of the targeting moieties described herein can be combined "off the shelf" with polypeptides with any of the signaling agents described herein to allow rapid generation of various combinations of targeting moieties and signaling agents in single Fc-based chimeric protein complexes.

In some embodiments, the Fc-based chimeric protein complex comprises one or more linkers. In some embodiments, the Fc-based chimeric protein complex includes a linker that connects the Fc domain, signaling agent, e.g. IFNα1(s) and targeting moiety(ies). In some embodiments, the Fc-based chimeric protein complex includes a linker that connects each signaling agent, e.g. IFNα1 and targeting moiety (or, if more than one targeting moiety, a signaling agent, e.g. IFNα1 to one of the targeting moieties). In some embodiments, the Fc-based chimeric protein complex includes a linker that connects each signaling agent, e.g. IFNα1 to the Fc domain. In some embodiments, the Fc-based chimeric protein complex includes a linker that connects each targeting moiety to the Fc domain. In some embodiments, the Fc-based chimeric protein complex includes a linker that connects a targeting moiety to another targeting moiety. In some embodiments, the Fc-based chimeric protein complex includes a linker that connects a signaling agent, e.g. IFNα1 to another signaling agent.

In some embodiments, a Fc-based chimeric protein complex comprises two or more targeting moieties. In such embodiments, the targeting moieties can be the same targeting moiety or they can be different targeting moieties.

In some embodiments, a Fc-based chimeric protein complex comprises two or more signaling agents. In such embodiments, the signaling agents can be the same targeting moiety or they can be different targeting moieties.

By way of example, in some embodiments, the Fc-based chimeric protein complex comprise a Fc domain, at least two signaling agents (SA), and at least two targeting moieties (TM), wherein the Fc domain, signaling agents, and targeting moieties are selected from any of the Fc domains, signaling agents, and targeting moieties disclosed herein. In some embodiments, the Fc domain is homodimeric.

In various embodiments, the Fc-based chimeric protein complex takes the form of any of the schematics of FIGS. 1A-F.

In various embodiments, the Fc-based chimeric protein complex takes the form of any of the schematics of FIGS. 2A-H.

In various embodiments, the Fc-based chimeric protein complex takes the form of any of the schematics of FIGS. 3A-H.

In various embodiments, the Fc-based chimeric protein complex takes the form of any of the schematics of FIGS. 4A-D.

In various embodiments, the Fc-based chimeric protein complex takes the form of any of the schematics of FIGS. 5A-F.

In various embodiments, the Fc-based chimeric protein complex takes the form of any of the schematics of FIGS. 6A-J.

In various embodiments, the Fc-based chimeric protein complex takes the form of any of the schematics of FIGS. 7A-D.

In various embodiments, the Fc-based chimeric protein complex takes the form of any of the schematics of FIGS. 8A-F.

In various embodiments, the Fc-based chimeric protein complex takes the form of any of the schematics of FIGS. 9A-J.

In various embodiments, the Fc-based chimeric protein complex takes the form of any of the schematics of FIGS. 10A-F.

In various embodiments, the Fc-based chimeric protein complex takes the form of any of the schematics of FIGS. 11A-L.

In various embodiments, the Fc-based chimeric protein complex takes the form of any of the schematics of FIGS. 12A-L.

In various embodiments, the Fc-based chimeric protein complex takes the form of any of the schematics of FIGS. 13A-F.

In various embodiments, the Fc-based chimeric protein complex takes the form of any of the schematics of FIGS. 14A-L.

In various embodiments, the Fc-based chimeric protein complex takes the form of any of the schematics of FIGS. 15A-L.

In various embodiments, the Fc-based chimeric protein complex takes the form of any of the schematics of FIGS. 16A-J.

In various embodiments, the Fc-based chimeric protein complex takes the form of any of the schematics of FIGS. 17A-J.

In various embodiments, the Fc-based chimeric protein complex takes the form of any of the schematics of FIGS. 18A-F.

In various embodiments, the Fc-based chimeric protein complex takes the form of any of the schematics of FIGS. 19A-F.

In various embodiments, the Fc-based chimeric protein complex takes the form of any of the schematics of FIGS. 20A-E.

In some embodiments, the signaling agents are linked to the targeting moieties and the targeting moieties are linked to the Fc domain on the same terminus (see FIGS. 1A-F). In some embodiments, the Fc domain is homodimeric.

In some embodiments, the signaling agents and targeting moieties are linked to the Fc domain, wherein the targeting moieties and signaling agents are linked on the same terminus (see FIGS. 1A-F). In some embodiments, the Fc domain is homodimeric.

In some embodiments, the targeting moieties are linked to signaling agents and the signaling agents are linked to the Fc domain on the same terminus (see FIGS. 1A-F). In some embodiments, the Fc domain is homodimeric.

In some embodiments, the homodimeric Fc-based chimeric protein complex has two or more targeting moieties.

In some embodiments, there are four targeting moieties and two signaling agents, the targeting moieties are linked to the Fc domain and the signaling agents are linked to targeting moieties on the same terminus (see FIGS. 2A-H). In some embodiments, the Fc domain is homodimeric. In some embodiments, where there are four targeting moieties and two signaling agents, two targeting moieties are linked to the Fc domain and two targeting moieties are linked to the signaling agents, which are linked to the Fc domain on the same terminus (see FIGS. 2A-H). In some embodiments, the Fc domain is homodimeric. In some embodiments, where there are four targeting moieties and two signaling agents, two targeting moieties are linked to each other and one of the targeting moieties of from each pair is linked to the Fc domain on the same terminus and the signaling agents are linked to the Fc domain on the same terminus (see FIGS. 2A-H). In some embodiments, the Fc domain is homodimeric. In some embodiments, where there are four targeting moieties and two signaling agents, two targeting moieties are linked to each other, wherein one of the targeting moieties of from each pair is linked to a signaling agent, e.g. IFNα1 and the other targeting moiety of the pair is linked the Fc domain, wherein the targeting moieties linked to the Fc domain are linked on the same terminus (see FIGS. 2A-H). In some embodiments, the Fc domain is homodimeric.

In some embodiments, the homodimeric Fc-based chimeric protein complex has two or more signaling agents. In some embodiments, where there are four signaling agents and two targeting moieties, two signaling agents are linked to each other and one of the signaling agents of from pair is linked to the Fc domain on the same terminus and the targeting moieties are linked to the Fc domain on the same terminus (see FIGS. 3A-H). In some embodiments, the Fc domain is homodimeric. In some embodiments, where there are four signaling agents and two targeting moieties, two signaling agents are linked to the Fc domain one the same terminus and two of the signaling agents are each linked to a targeting moiety, wherein the targeting moieties are linked to the Fc domain at the same terminus (see FIGS. 3A-H). In some embodiments, the Fc domain is homodimeric. In some embodiments, where there are four signaling agents and two targeting moieties, two signaling agents are linked to each other and one of the signaling agents of from pair is linked to a targeting moiety and the targeting moieties are linked to the Fc domain on the same terminus (see FIGS. 3A-H). In some embodiments, the Fc domain is homodimeric.

By way of example, in some embodiments, the Fc-based chimeric protein complex comprise a Fc domain, wherein the Fc domain comprises ionic pairing mutation(s) and/or knob-in-hole mutation(s), at least one signaling agent, e.g. IFNα1, and at least one targeting moiety, wherein the ionic pairing motif and/or a knob-in-hole motif, signaling agent, e.g. IFNα1, and targeting moiety are selected from any of the ionic pairing motif and/or a knob-in-hole motif, signaling agents, and targeting moieties disclosed herein. In some embodiments, the Fc domain is heterodimeric. In some embodiments, the Fc domain comprises a mutation that reduces or eliminates its effector function.

In some embodiments, the signaling agent, e.g. IFNα1 is linked to the targeting moiety, which is linked to the Fc domain (see FIGS. 10A-F and 13A-F). In some embodiments, the targeting moiety is linked to the signaling agent, e.g. IFNα1, which is linked to the Fc domain (see FIGS. 10A-F and 13A-F). In some embodiments, the Fc domain is heterodimeric. In some embodiments, the Fc domain comprises a mutation that reduces or eliminates its effector function.

In some embodiments, the signaling agent, e.g. IFNα1 and targeting moiety are linked to the Fc domain (see FIGS. 4A-D, 7A-D, 10A-F, and 13A-F). In some embodiments, the targeting moiety and the signaling agent, e.g. IFNα1 are linked to different Fc chains on the same terminus (see FIGS. 4A-D and 7A-D). In some embodiments, the targeting moiety and the signaling agent, e.g. IFNα1 are linked to different Fc chains on different termini (see FIGS. 4A-D and 7A-D). In some embodiments, the targeting moiety and the signaling agent, e.g. IFNα1 are linked to the same Fc chain (see FIGS. 10A-F and 13A-F). In some embodiments, the Fc domain is heterodimeric. In some embodiments, the Fc domain comprises a mutation that reduces or eliminates its effector function.

In some embodiments, where there are one signaling agent, e.g. IFNα1 and two targeting moieties, the signaling agent, e.g. IFNα1 is linked to the Fc domain and two targeting moieties can be: 1) linked to each other with one of the targeting moieties linked to the Fc domain; or 2) each linked to the Fc domain (see FIGS. 5A-F, 8A-F, 11A-L, 14A-L, 16A-J, and 17A-J). In some embodiments, the targeting moieties are linked on one Fc chain and the signaling agent, e.g. IFNα1 is on the other Fc chain (see FIGS. 5A-F and 8A-F). In some embodiments, the paired targeting moieties and the signaling agent, e.g. IFNα1 are linked to the same Fc chain (see FIGS. 11A-L and 14A-L). In some embodiments, a targeting moiety is linked to the Fc domain and the other targeting moiety is linked to the signaling agent, e.g. IFNα1, and the paired targeting moiety is linked to the Fc domain (see FIGS. 11A-L, 14A-L, 16A-J, and 17A-J). In some embodiments, the unpaired targeting moiety and paired targeting moiety are linked to the same Fc chain (see FIGS. 11A-L and 14A-L). In some embodiments, the unpaired targeting moiety and paired targeting moiety are linked to different Fc chains (see FIGS. 16A-J and 17A-J). In some embodiments, the unpaired targeting moiety and paired targeting moiety are linked on the same terminus (see FIGS. 16A-J and 17A-J).

In some embodiments, the Fc domain is heterodimeric. In some embodiments, the Fc domain comprises a mutation that reduces or eliminates its effector function.

In some embodiments, where there are one signaling agent, e.g. IFNα1 and two targeting moieties, a targeting moiety is linked to the signaling agent, e.g. IFNα1, which is linked to the Fc domain, and the unpaired targeting moiety is linked the Fc domain (see FIGS. 11A-L, 14A-L, 16A-J, and 17A-J). In some embodiments, the paired signaling agent, e.g. IFNα1 and unpaired targeting moiety are linked to the same Fc chain (see FIGS. 11A-L and 14A-L). In some embodiments, the paired signaling agent, e.g. IFNα1 and unpaired targeting moiety are linked to different Fc chains (see FIGS. 16A-J and 17A-J). In some embodiments, the paired signaling agent, e.g. IFNα1 and unpaired targeting moiety are linked on the same terminus (see FIGS. 16A-J and 17A-J). In some embodiments, the Fc domain is heterodimeric. In some embodiments, the Fc domain comprises a mutation that reduces or eliminates its effector function.

In some embodiments, where there are one signaling agent, e.g. IFNα1 and two targeting moieties, the targeting moieties are linked together and the signaling agent, e.g. IFNα1 is linked to one of the paired targeting moieties, wherein the targeting moiety not linked to the signaling agent, e.g. IFNα1 is linked to the Fc domain (see FIGS. 11A-L and 14A-L). In some embodiments, the Fc domain is heterodimeric. In some embodiments, the Fc domain comprises a mutation that reduces or eliminates its effector function.

In some embodiments, where there are one signaling agent, e.g. IFNα1 and two targeting moieties, the targeting moieties are linked together and the signaling agent, e.g. IFNα1 is linked to one of the paired targeting moieties, wherein the signaling agent, e.g. IFNα1 is linked to the Fc domain (see FIGS. 11A-L and 14A-L). In some embodiments, the Fc domain is heterodimeric. In some embodiments, the Fc domain comprises a mutation that reduces or eliminates its effector function.

In some embodiments, where there are one signaling agent, e.g. IFNα1 and two targeting moieties, the targeting moieties are both linked to the signaling agent, e.g. IFNα1, wherein one of the targeting moieties is linked to the Fc domain (see FIGS. 11A-L and 14A-L). In some embodiments, the Fc domain is heterodimeric. In some embodiments, the Fc domain comprises a mutation that reduces or eliminates its effector function.

In some embodiments, where there are one signaling agent, e.g. IFNα1 and two targeting moieties, the targeting moieties and the signaling agent, e.g. IFNα1 are linked to the Fc domain (see FIGS. 16A-J and 17A-J). In some embodiments, the targeting moieties are linked on the terminus (see FIGS. 16A-J and 17A-J). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked to the Fc domain on the same terminus and the targeting moiety is linked to the Fc domain (see FIGS. 6A-J and 9A-J). In some embodiments, the signaling agents are linked to the Fc domain on the same Fc chain and the targeting moiety is linked on the other Fc chain (see FIGS. 18A-F and 19A-F). In some embodiments, the Fc domain is heterodimeric. In some embodiments, the Fc domain comprises a mutation that reduces or eliminates its effector function.

In some embodiments, where there are two signaling agents and one targeting moiety, a signaling agent, e.g. IFNα1 is linked to the targeting moiety, which is linked to the Fc domain and the other signaling agent, e.g. IFNα1 is linked to the Fc domain (see FIGS. 6A-J, 9A-J, 12A-L, and 15A-L). In some embodiments, the targeting moiety and the unpaired signaling agent, e.g. IFNα1 are linked to different Fc chains (see FIGS. 6A-J and 9A-J). In some embodiments, the targeting moiety and the unpaired signaling agent, e.g. IFNα1 are linked to different Fc chains on the same terminus (see FIGS. 6A-J and 9A-J). In some embodiments, the targeting moiety and the unpaired signaling agent, e.g. IFNα1 are linked to different Fc chains on different termini (see FIGS. 6A-J and 9A-J). In some embodiments, the targeting moiety and the unpaired signaling agent, e.g. IFNα1 are linked to the same Fc chains (see FIGS. 12A-L and 15A-L). In some embodiments, the Fc domain is heterodimeric. In some embodiments, the Fc domain comprises a mutation that reduces or eliminates its effector function.

In some embodiments, where there are two signaling agents and one targeting moiety, the targeting moiety is linked to a signaling agent, e.g. IFNα1, which is linked to the Fc domain and the other signaling agent, e.g. IFNα1 is linked to the Fc domain (see FIGS. 6A-J and 9A-J). In some embodiments, the paired signaling agent, e.g. IFNα1 and the unpaired signaling agent, e.g. IFNα1 are linked to different Fc chains (see FIGS. 6A-J and 9A-J). In some embodiments, the paired signaling agent, e.g. IFNα1 and the unpaired signaling agent, e.g. IFNα1 are linked to different Fc chains on the same terminus (see FIGS. 6A-J and 9A-J). In some embodiments, the paired signaling agent, e.g. IFNα1 and the unpaired signaling agent, e.g. IFNα1 are linked to different Fc chains on different termini (see FIGS. 6A-J and 9A-J). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and the targeting moiety is linked to one of the paired signaling agents, wherein the targeting moiety is linked to the Fc domain (see FIGS. 12A-L and 15A-L). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and one of the signaling agents is linked to the Fc domain and the targeting moiety is linked to the Fc domain (see FIGS. 12A-L, 15A-L, 18A-F, and 19A-F). In some embodiments, the paired signaling agents and targeting moiety are linked to the same Fc chain (see FIGS. 12A-L and 15A-L). In some embodiments, the paired signaling agents and targeting moiety are linked to different Fc chains (see FIGS. 18A-F and 19A-F). In some embodiments, the paired signaling agents and targeting moiety are linked to different Fc chains on the same terminus (see FIGS. 18A-F and 19A-F). In some embodiments, the Fc domain is heterodimeric. In some embodiments, the Fc domain comprises a mutation that reduces or eliminates its effector function.

In some embodiments, where there are two signaling agents and one targeting moiety, the signaling agents are both linked to the targeting moiety, wherein one of the signaling agents is linked to the Fc domain (see FIGS. 12A-L and 15A-L). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and one of the signaling agents is linked to the targeting moiety and the other signaling agent, e.g. IFNα1 is linked to the Fc domain (see FIGS. 12A-L and 15A-L).

In some embodiments, where there are two signaling agents and one targeting moiety, each signaling agent, e.g. IFNα1 is linked to the Fc domain and the targeting moiety is linked to one of the signaling agents (see FIGS. 12A-L and 15A-L). In some embodiments, the signaling agents are linked to the same Fc chain (see FIGS. 12A-L and 15A-L).

In some embodiments, a targeting moiety or signaling agent, e.g. IFNα1 is linked to the Fc domain, comprising one or both of $C_H2$ and $C_H3$ domains, and optionally a hinge region. For example, vectors encoding the targeting moiety, signaling agent, e.g. IFNα1, or combination thereof, linked as a single nucleotide sequence to an Fc domain can be used to prepare such polypeptides.

In some embodiments, the Fc-based chimeric protein complex comprises a polypeptide having an amino acid sequence having at least 95%, or at least 98%, or at least 99% identity with any one of SEQ ID NOs: 290, 291, 293-303. In embodiments, the Fc-based chimeric protein complex comprises a polypeptide having an amino acid sequence selected from SEQ ID NOs: 290, 291, 293-303 and less than 10 mutations to the amino acid sequence. In embodiments, the Fc-based chimeric protein complex comprises a polypeptide having an amino acid sequence selected from SEQ ID NOs: 290, 291, 293-303, and less than 5 mutations to the amino acid sequence. In some embodiments, the Fc-based chimeric protein complex comprises a polypeptide having an amino acid sequence selected from SEQ ID NOs: 290, 291, 293-303.

In some embodiments, the Fc-based chimeric protein complex comprises a first amino acid sequence having at least 95%, or at least 98%, or at least 99% identity to SEQ ID NO: 290 and a second amino acid sequence having at least 95%, or at least 98%, or at least 99% identity to SEQ ID NO: 291. In some embodiments, the Fc-based chimeric protein complex comprises a first amino acid sequence having at least 95%, or at least 98%, or at least 99% identity to SEQ ID NO: 293 and a second amino acid sequence having at least 95%, or at least 98%, or at least 99% identity to any one of SEQ ID NO: 294, 295, 296, 297, 298, or 299. In embodiments, the Fc-based chimeric protein complex comprises a first amino acid sequence having at least 95%, or at least 98%, or at least 99% identity to any one of SEQ ID NO: 300, 301, 302, 303 and a second amino acid sequence having at least 95%, or at least 98%, or at least 99% identity to SEQ ID NO: 294.

Additional Signaling Agents

In one aspect, the present invention provides a chimeric proteins or chimeric protein complexes such as Fc-based chimeric protein complex comprising one or more signaling agents (for instance, an immune-modulating agent) in addition to the IFNα1 or a variant thereof described herein. In illustrative embodiments, the chimeric proteins or chimeric protein complexes such as Fc-based chimeric protein complex may comprise two, three, four, five, six, seven, eight, nine, ten or more signaling agents in addition to the IFNα1 or a variant thereof described herein. In various embodiments, the additional signaling agent is modified to have reduced affinity or activity for one or more of its receptors, which allows for attenuation of activity (inclusive of agonism or antagonism) and/or prevents non-specific signaling or undesirable sequestration of the chimeric proteins or chimeric protein complexes such as Fc-based chimeric protein complex.

In various embodiments, the additional signaling agent is antagonistic in its wild type form and bears one or more mutations that attenuate its antagonistic activity. In various embodiments, the additional signaling agent is antagonistic due to one or more mutations, e.g. an agonistic signaling agent is converted to an antagonistic signaling agent and, such a converted signaling agent, optionally, also bears one or more mutations that attenuate its antagonistic activity (e.g. as described in WO 2015/007520, the entire contents of which are hereby incorporated by reference).

In various embodiments, the additional signaling agent is selected from modified versions of cytokines, growth factors, and hormones. Illustrative examples of such cytokines, growth factors, and hormones include, but are not limited to, lymphokines, monokines, traditional polypeptide hormones, such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and tumor necrosis factor-β; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-β; insulin-like growth factor-I and -II; osteo inductive factors; interferons such as, for example, interferon-α, interferon-β and interferon-y (and interferon type I, II, and III), colony stimulating factors (CSFs) such as macrophage-CSF (M-CSF); granulocyte-macrophage-CSF (GM-CSF); and granulocyte-CSF (G-CSF); interleukins (ILs) such as, for example, IL-1β, IL-1α, IL-2, IL-3, IL-4, IL-5, IL-6, IL-7, IL-8, IL-9, IL-10, IL-11, IL-12, IL-13, and IL-18; a tumor necrosis factor such as, for example, TNF-α or TNF-β; and other polypeptide factors including, for example, LIF and kit ligand (KL). As used herein, cytokines, growth factors, and hormones include proteins obtained from natural sources or produced from recombinant bacterial, eukaryotic or mammalian cell culture systems and biologically active equivalents of the native sequence cytokines.

In some embodiments, the additional signaling agent is a modified version of a growth factor selected from, but not limited to, transforming growth factors (TGFs) such as TGF-α and TGF-β, epidermal growth factor (EGF), insulin-like growth factor such as insulin-like growth factor-I and -II, fibroblast growth factor (FGF), heregulin, platelet-derived growth factor (PDGF), vascular endothelial growth factor (VEGF).

In an embodiment, the growth factor is a modified version of a fibroblast growth factor (FGF). Illustrative FGFs include, but are not limited to, FGF1, FGF2, FGF3, FGF4, FGF5, FGF6, FGF7, FGF8, FGF9, FGF10, FGF11, FGF12, FGF13, FGF14, murine FGF15, FGF16, FGF17, FGF18, FGF19, FGF20, FGF21, FGF22, and FGF23.

In an embodiment, the growth factor is a modified version of a vascular endothelial growth factor (VEGF). Illustrative VEGFs include, but are not limited to, VEGF-A, VEGF-B, VEGF-C, VEGF-D, and PGF and isoforms thereof including the various isoforms of VEGF-A such as $VEGF_{121}$, $VEGF_{121}b$, $VEGF_{145}$, $VEGF_{165}$, $VEGF_{165}b$, $VEGF_{189}$, and $VEGF_{206}$.

In an embodiment, the growth factor is a modified version of a transforming growth factor (TGF). Illustrative TGFs include, but are not limited to, TGF-α and TGF-β and subtypes thereof including the various subtypes of TGF-β including TGβ1, TGβ2, and TGβ3.

In some embodiments, the additional signaling agent is a modified version of a hormone selected from, but not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, calcitriol, calciferol, atrial-natriuretic peptide, gastrin, secretin, cholecystokinin, neuropeptide Y, ghrelin, PYY3-36, insulin-like growth factor (IGF), leptin, thrombopoietin, erythropoietin (EPO), and angiotensinogen.

In some embodiments, the additional signaling agent is an immune-modulating agent, e.g. one or more of an interleukin, interferon, and tumor necrosis factor.

In some embodiments, the additional signaling agent is an interleukin, including for example IL-1β; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; IL-36 or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. Interleukin activity can be determined using assays known in the art: Matthews et al., in *Lymphokines and Interferens: A Practical Approach*, Clemens et al., eds, IRL Press, Washington, D.C. 1987, pp. 221-225; and Orencole & Dinarello (1989) Cytokine 1, 14-20.

In some embodiments, the signaling agent is a modified version of an interferon such as interferon types I, II, and III. Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon $\overline{\omega}$.

In embodiments, the additional signaling agent is a type I interferon. In embodiments, the type I interferon is selected from IFN-α2, IFNα1, IFN-β, IFN-γ, Consensus IFN, IFN-ε, IFN-κ, IFN-τ, IFN-δ, and IFN-ν.

In some embodiments, the additional signaling agent is a modified version of a tumor necrosis factor (TNF) or a protein in the TNF family, including but not limited to, TNF-α, TNF-β, LT-β, CD40L, CD27L, CD3OL, FASL, 4-1BBL, OX40L, and TRAIL.

In various embodiments, the additional signaling agent is a modified (e.g. mutant) form of the signaling agent having one or more mutations. In various embodiments, the mutations allow for the modified signaling agent to have one or more of attenuated activity such as one or more of reduced binding affinity, reduced endogenous activity, and reduced specific bioactivity relative to unmodified or unmutated, i.e. the wild type form of the signaling agent (e.g. comparing the same signaling agent in a wild type form versus a modified (e.g. mutant) form). In various embodiments, the mutations allow for the modified signaling agent to have one or more of attenuated activity such as one or more of reduced binding affinity, reduced endogenous activity, and reduced specific bioactivity relative to unmodified or unmutated, i.e. the unmutated IFNα1. In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in various embodiments, the mutations allow for the signaling agent to be more safe, e.g. have reduced systemic toxicity, reduced side effects, and reduced off-target effects relative to unmutated, i.e. wild type, signaling agent (e.g. comparing the same signaling agent in a wild type form versus a modified (e.g. mutant) form). In various embodiments, the mutations allow for the signaling agent to be safer, e.g. have reduced systemic toxicity, reduced side effects, and reduced off-target effects relative to unmutated interferon, e.g. the unmutated sequence of IFNα1.

In various embodiments, the additional signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In various embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or more mutations that reduce its binding affinity or activity for one or more of its receptors or that substantially reduce or ablate binding affinity or activity for one or more of its receptors.

In some embodiments, the reduced affinity or activity at the receptor is inducible or restorable by attachment with one or more of the targeting moieties or upon inclusion in the Fc-based chimeric protein complex disclosed herein. In other embodiments, the reduced affinity or activity at the receptor is not substantially inducible or restorable by the activity of one or more of the targeting moieties or upon inclusion in the Fc-based chimeric protein complex disclosed herein.

In various embodiments, the additional signaling agent is active on target cells because the targeting moiety(ies) compensates for the missing/insufficient binding (e.g., without limitation and/or avidity) required for substantial activation. In various embodiments, the modified signaling agent is substantially inactive en route to the site of therapeutic activity and has its effect substantially on specifically targeted cell types which greatly reduces undesired side effects.

In some embodiments, the additional signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor. In some embodiments, the mutation(s) that reduce binding and/or activity at one receptor is the same as the mutation(s) that substantially reduce or ablate at another receptor. In some embodiments, the present chimeric proteins or chimeric protein complexes such as Fc-based chimeric protein complexes have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially inducible or restorable with a targeting moiety or upon inclusion in the Fc-based chimeric protein complex disclosed herein. In some embodiments, the substantial reduction or ablation of binding or activity is inducible or restorable with a targeting moiety or upon inclusion in the Fc-based chimeric protein complex disclosed herein. In various embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins or chimeric protein complexes such as Fc-based chimeric protein complexes away from the site of therapeutic action. For instance, in some embodiments, this obviates the need of high doses of the chimeric proteins or chimeric protein complexes such as Fc-based chimeric protein complexes that compensate for loss at the other receptor. Such ability to reduce dose further provides a lower likelihood of side effects.

In various embodiments, the additional modified signaling agent comprises one or more mutations that cause the signaling agent to have reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_I$ and/or $IC_{50}$), for one or more of its receptors. In various embodiments, the reduced affinity at the signaling agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent (including, by way of non-limitation, relative to the unmutated IFNα1).

In embodiments wherein the chimeric proteins or chimeric protein complexes such as Fc-based chimeric protein complex has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the additional modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent (including, by way of non-limitation, relative to the unmutated IFNα1).

In various embodiments, the additional modified signaling agent comprises one or more mutations that cause the signaling agent to have reduced affinity and/or activity for a receptor of any one of the cytokines, growth factors, and hormones as described herein.

In some embodiments, the additional modified signaling agent comprises one or more mutations that cause the signaling agent to have reduced affinity for its receptor that is lower than the binding affinity of the targeting moiety(ies) for its(their) receptor(s). In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

The amino acid sequences of the wild type signaling agents described herein are well known in the art. Accordingly, in various embodiments the additional modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the additional modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the additional modified signaling agent comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions as described herein.

As described herein, the additional modified signaling agents bear mutations that affect affinity and/or activity at one or more receptors. In various embodiments, there is reduced affinity and/or activity at a therapeutic receptor, e.g. a receptor through which a desired therapeutic effect is mediated (e.g. agonism or antagonism). In various embodiments, the modified signaling agents bear mutations that substantially reduce or ablate affinity and/or activity at a receptor, e.g. a receptor through which a desired therapeutic effect is not mediated (e.g. as the result of promiscuity of binding). The receptors of any modified signaling agents, e.g. one of the cytokines, growth factors, and hormones as described herein, are known in the art.

Illustrative mutations which provide reduced affinity and/or activity (e.g. agonistic) at a receptor are found in WO 2013/107791 (e.g. with regard to interferons), WO 2015/007542 (e.g. with regard to interleukins), and WO 2015/007903 (e.g. with regard to TNF), the entire contents of each of which are hereby incorporated by reference. Illustrative mutations which provide reduced affinity and/or activity (e.g. antagonistic) at a therapeutic receptor are found in WO 2015/007520, the entire contents of which are hereby incorporated by reference.

In some embodiments, the additional modified signaling agent comprises one or more mutations that cause the signaling agent to have reduced affinity and/or activity for a type I cytokine receptor, a type II cytokine receptor, a chemokine receptor, a receptor in the Tumor Necrosis Factor Receptor (TNFR) superfamily, TGF-beta Receptors, a receptor in the immunoglobulin (Ig) superfamily, and/or a receptor in the tyrosine kinase superfamily.

In various embodiments, the receptor for the additional signaling agent is a Type I cytokine receptor. Type I cytokine receptors are known in the art and include, but are not limited to receptors for IL2 (beta-subunit), IL3, IL4, IL5, IL6, IL7, IL9, IL11, IL12, GM-CSF, G-CSF, LIF, CNTF, and also the receptors for Thrombopoietin (TPO), Prolactin, and Growth hormone. Illustrative type I cytokine receptors include, but are not limited to, GM-CSF receptor, G-CSF receptor, LIF receptor, CNTF receptor, TPO receptor, and type I IL receptors.

In various embodiments, the receptor for the additional signaling agent is a Type II cytokine receptor. Type II cytokine receptors are multimeric receptors composed of heterologous subunits, and are receptors mainly for interferons. This family of receptors includes, but is not limited to, receptors for interferon-α, interferon-β and interferon-γ, IL10, IL22, and tissue factor. Illustrative type II cytokine receptors include, but are not limited to, IFN-α receptor (e.g. IFNAR1 and IFNAR2), IFN-β receptor, IFN-γ receptor (e.g. IFNGR1 and IFNGR2), and type II IL receptors.

In various embodiments, the receptor for the additional signaling agent is a G protein-coupled receptor. Chemokine receptors are G protein-coupled receptors with seven transmembrane structure and coupled to G-protein for signal transduction. Chemokine receptors include, but are not limited to, CC chemokine receptors, CXC chemokine receptors, CX3C chemokine receptors, and XC chemokine receptor (XCR1). Illustrative chemokine receptors include, but are not limited to, CCR1, CCR2, CCR3, CCR4, CCR5, CCR6, CCR7, CCR8, CCR9, CCR10, CXCR1, CXCR2, CXCR3, CXCR3B, CXCR4, CXCR5, CSCR6, CXCR7, XCR1, and CX3CR1.

In various embodiments, the receptor for the additional signaling agent is a TNFR family member. Tumor necrosis factor receptor (TNFR) family members share a cysteine-rich domain (CRD) formed of three disulfide bonds surrounding a core motif of CXXCXXC creating an elongated molecule. Illustrative tumor necrosis factor receptor family members include: CDI 20a (TNFRSFIA), CD 120b (TNFRSFIB), Lymphotoxin beta receptor (LTBR, TNFRSF3), CD 134 (TNFRSF4), CD40 (CD40, TNFRSF5), FAS (FAS, TNFRSF6), TNFRSF6B (TNFRSF6B), CD27 (CD27, TNFRSF7), CD30 (TNFRSF8), CD137 (TNFRSF9), TNFRSFIOA (TNFRSFIOA), TNFRSFIOB, (TNFRSFIOB), TNFRSFIOC (TNFRSFIOC), TNFRSFIOD (TNFRSFIOD), RANK (TNFRSFI IA), Osteoprotegerin (TNFRSFI IB), TNFRSF12A (TNFRSF12A), TNFRSF13B (TNFRSF13B), TNFRSF13C (TNFRSF13C), TNFRSF14 (TNFRSF14), Nerve growth factor receptor (NGFR, TNFRSF16), TNFRSF17 (TNFRSF17), TNFRSF18 (TNFRSF18), TNFRSF19 (TNFRSF19), TNFRSF21 (TNFRSF21), and TNFRSF25 (TNFRSF25).

In various embodiments, the receptor for the additional signaling agent is a TGF-beta receptor. TGF-beta receptors are single pass serine/threonine kinase receptors. TGF-beta receptors include, but are not limited to, TGFBR1, TGFBR2, and TGFBR3.

In various embodiments, the receptor for the additional signaling agent is an Ig superfamily receptor. Receptors in the immunoglobulin (Ig) superfamily share structural homology with immunoglobulins. Receptors in the Ig superfamily include, but are not limited to, interleukin-1 receptors, CSF-1R, PDGFR (e.g. PDGFRA and PDGFRB), and SCFR.

In various embodiments, the receptor for the additional signaling agent is a tyrosine kinase superfamily receptor. Receptors in the tyrosine kinase superfamily are well known in the art. There are about 58 known receptor tyrosine kinases (RTKs), grouped into 20 subfamilies. Receptors in the tyrosine kinase superfamily include, but are not limited to, FGF receptors and their various isoforms such as FGFR1, FGFR2, FGFR3, FGFR4, and FGFR5.

In an embodiment, the additional modified signaling agent is interferon α. In such embodiments, the modified IFN-α agent has reduced affinity and/or activity for the IFN-α/β receptor (IFNAR), i.e., IFNAR1 and/or IFNAR2 chains.

In some embodiments, the modified IFN-α agent has substantially reduced or ablated affinity and/or activity for the IFN-α/β receptor (IFNAR), i.e., IFNAR1 and/or IFNAR2 chains.

Mutant forms of interferon a are known to the person skilled in the art. In an illustrative embodiment, the modified signaling agent is the allelic form IFN-α2a having the amino acid sequence of SEQ ID NO:233.

In an illustrative embodiment, the modified signaling agent is the allelic form IFN-α2b having the amino acid sequence of SEQ ID NO:234 (which differs from IFN-α2a at amino acid position 23).

In some embodiments, said IFN-α2 mutant (IFN-α2a or IFN-α2b) is mutated at one or more amino acids at positions 144-154, such as amino acid positions 148, 149 and/or 153. In some embodiments, the IFN-α2 mutant comprises one or more mutations selected from L153A, R149A, and M148A. Such mutants are described, for example, in WO2013/107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wildtype IFN-α2 activity. In such embodiments, said mutant IFN-α2 has reduced affinity and/or activity for IFNAR1 while affinity and/or activity of IFNR2 is retained.

In some embodiments, the human IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In an embodiment, the human IFN-α2 mutant comprises R120E and L153A.

In some embodiments, the human IFN-α2 mutant comprises one or more mutations selected from, L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885. In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885. In some embodiments, the human IFN-α2 mutant comprises one or more mutations selected from R144$X_1$, A145$X_2$, and R33A, wherein $X_1$ is selected from A, S, T, Y, L, and I, and wherein X2 is selected from G, H, Y, K, and D. In some embodiments, the human IFN-α2 mutant comprises one or more mutations selected from R33A, T106$X_3$, R120E, R144$X_1$ A145$X_2$, M148A, R149A, and L153A with respect to amino acid sequence of SEQ ID NO: 233 or 234, wherein $X_1$ is selected from A, S, T, Y, L, and I, wherein X2 is selected from G, H, Y, K, and D, and wherein X3 is selected from A and E.

In an embodiment, the additional modified signaling agent is interferon β. In such embodiments, the modified interferon β agent also has reduced affinity and/or activity for the IFN-α/β receptor (IFNAR), i.e., IFNAR1 and/or IFNAR2 chains. In some embodiments, the modified interferon β agent has substantially reduced or ablated affinity and/or activity for the IFN-α/β receptor (IFNAR), i.e., IFNAR1 and/or IFNAR2 chains.

In an illustrative embodiment, the modified additional signaling agent is IFN-β. In various embodiments, the IFN-β encompasses functional derivatives, analogs, precursors, isoforms, splice variants, or fragments of IFN-β. In various embodiments, the IFN-β encompasses IFN-β derived from any species. In an embodiment, the chimeric proteins or chimeric protein complexes such as Fc-based chimeric protein complex comprises a modified version of mouse IFN-β. In another embodiment, the chimeric proteins or chimeric protein complexes such as Fc-based chimeric protein complex comprises a modified version of human IFN-β. Human IFN-β is a polypeptide with a molecular weight of about 22 kDa comprising 166 amino acid residues. The amino acid sequence of human IFN-β is SEQ ID NO: 277.

In some embodiments, the human IFN-β is IFN-β-1a which is a glycosylated form of human IFN-β. In some embodiments, the human IFN-β is IFN-β-1b which is a non-glycosylated form of human IFN-β that has a Met-1 deletion and a Cys-17 to Ser mutation.

In various embodiments, the modified IFN-β has one or more mutations that reduce its binding to or its affinity for the IFNAR1 subunit of IFNAR. In one embodiment, the modified IFN-β has reduced affinity and/or activity at IFNAR1. In various embodiments, the modified IFN-β is human IFN-β and has one or more mutations at positions F67, R71, L88, Y92, I95, N96, K123, and R124. In some embodiments, the one or more mutations are substitutions selected from F67G, F67S, R71A, L88G, L88S, Y92G, Y92S, 195A, N96G, K123G, and R124G. In an embodiment, the modified IFN-β comprises the F67G mutation. In an embodiment, the modified IFN-β comprises the K123G mutation. In an embodiment, the modified IFN-β comprises the F67G and R71A mutations. In an embodiment, the modified IFN-β comprises the L88G and Y92G mutations. In an embodiment, the modified IFN-β comprises the Y92G, 195A, and N96G mutations. In an embodiment, the modified IFN-β comprises the K123G and R124G mutations. In an embodiment, the modified IFN-β comprises the F67G, L88G, and Y92G mutations. In an embodiment, the modified IFN-β comprises the F67S, L88S, and Y92S mutations.

In some embodiments, the modified IFN-β has one or more mutations that reduce its binding to or its affinity for the IFNAR2 subunit of IFNAR. In one embodiment, the modified IFN-β has reduced affinity and/or activity at IFNAR2. In various embodiments, the modified IFN-β is human IFN-β and has one or more mutations at positions W22, R27, L32, R35, V148, L151, R152, and Y155. In some embodiments, the one or more mutations are substitutions selected from W22G, R27G, L32A, L32G, R35A, R35G, V148G, L151G, R152A, R152G, and Y155G. In an embodiment, the modified IFN-β comprises the W22G mutation. In an embodiment, the modified IFN-β comprises the L32A mutation. In an embodiment, the modified IFN-β comprises the L32G mutation. In an embodiment, the modified IFN-β comprises the R35A mutation. In an embodiment, the modified IFN-β comprises the R35G mutation. In an embodiment, the modified IFN-β comprises the V148G mutation. In an embodiment, the modified IFN-β comprises the R152A mutation. In an embodiment, the modified IFN-β comprises the R152G mutation. In an embodiment, the modified IFN-β comprises the Y155G mutation. In an embodiment, the modified IFN-β comprises the W22G and R27G mutations. In an embodiment, the modified IFN-β comprises the L32A and R35A mutation. In an embodiment, the modified IFN-β comprises the L151G and R152A mutations. In an embodiment, the modified IFN-β comprises the V148G and R152A mutations.

In some embodiments, the modified IFN-β has one or more of the following mutations: R35A, R35T, E42K, M62I, G78S, A141Y, A142T, E149K, and R152H. In some embodiments, the modified IFN-β has one or more of the following mutations: R35A, R35T, E42K, M62I, G78S, A141Y, A142T, E149K, and R152H in combination with C17S or C17A.

In some embodiments, the modified IFN-β has one or more of the following mutations: R35A, R35T, E42K, M62I, G78S, A141Y, A142T, E149K, and R152H in combination with any of the other IFN-β mutations described herein. The crystal structure of human IFN-β is known and is described in Karpusas et al., (1998) PNAS, 94(22): 11813-11818. Specifically, the structure of human IFN-β has been shown to include five a-helices (i.e., A, B, C, D, and E) and four loop regions that connect these helices (i.e., AB, BC, CD, and DE loops). In various embodiments, the modified IFN-β has one or more mutations in the A, B, C, D, E helices and/or the AB, BC, CD, and DE loops which reduce its binding affinity or activity at a therapeutic receptor such as IFNAR. Illustrative mutations are described in WO2000/023114 and US20150011732, the entire contents of which are hereby incorporated by reference. In an illustrative embodiment, the modified IFN-β is human IFN-β comprising alanine substitutions at amino acid positions 15, 16, 18, 19, 22, and/or 23. In an illustrative embodiment, the modified IFN-β is human IFN-β comprising alanine substitutions at amino acid positions 28-30, 32, and 33. In an illustrative embodiment, the modified IFN-β is human IFN-β comprising alanine substitutions at amino acid positions 36, 37, 39, and 42. In an illustrative embodiment, the modified IFN-β is human IFN-β comprising alanine substitutions at amino acid positions 64 and 67 and a serine substitution at position 68. In an illustrative embodiment, the modified IFN-β is human IFN-β comprising alanine substitutions at amino acid positions 71-73. In an illustrative embodiment, the modified IFN-β is human IFN-β comprising alanine substitutions at amino acid positions 92, 96, 99, and 100. In an illustrative embodiment, the modified IFN-β is human IFN-β comprising alanine substitutions at amino acid positions 128, 130, 131, and 134. In an illustrative embodiment, the modified IFN-β is human IFN-β comprising alanine substitutions at amino acid positions 149, 153, 156, and 159. In some embodiments, the mutant IFNβ comprises SEQ ID NO:277 and a mutation at W22, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at R27, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at W22, the mutation being an aliphatic hydrophobic residue selected from glycine (G), alanine (A), leucine (L), isoleucine (I), methionine (M), and valine (V) and a mutation at R27, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at L32, the mutation being an aliphatic hydrophobic residue selected from glycine (G), alanine (A), isoleucine (I), methionine (M), and valine (V).

In some embodiments, the mutant IFNβ comprises SEQ ID NO:277 and a mutation at R35, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at L32, the mutation being an aliphatic hydrophobic residue selected from glycine (G), alanine (A), isoleucine (I), methionine (M), and valine (V) and a mutation at R35, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at F67, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at R71, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at F67, the mutation being an aliphatic hydrophobic residue selected from glycine (G), alanine (A), leucine (L), isoleucine (I), methionine (M), and valine (V) and a mutation at R71, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at L88, the mutation being an aliphatic hydrophobic residue selected from glycine (G), alanine (A), isoleucine (I), methionine (M), and valine (V).

In some embodiments, the mutant IFNβ comprises SEQ ID NO:277 and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at F67, the mutation being an aliphatic hydrophobic residue selected from glycine (G), alanine (A), leucine (L), isoleucine (I), methionine (M), and valine (V) and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at 195, the mutation being an aliphatic hydrophobic residue selected from glycine (G), alanine (A), leucine (L), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:277 and a mutation at N96, the mutation being an aliphatic hydrophobic residue selected from glycine (G), alanine (A), leucine (L), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at Y92, the mutation being an aliphatic hydrophobic residue selected from glycine (G), alanine (A), leucine (L), isoleucine (I), methionine (M), and valine (V) and a mutation at 195, the mutation being an aliphatic hydrophobic residue selected from glycine (G), alanine (A), leucine (L), methionine (M), and valine (V) and a mutation at N96, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at K123, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at R124, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at K123, the mutation being an aliphatic hydrophobic residue selected from glycine (G), alanine (A), leucine (L), isoleucine (I), methionine (M), and valine (V) and a mutation at R124, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at L151, the mutation being an aliphatic hydrophobic residue selected from glycine (G), alanine (A), isoleucine (I), methionine (M), and valine (V).

In some embodiments, the mutant IFNβ comprises SEQ ID NO: 277 and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at L151, the mutation being an aliphatic hydrophobic residue selected from glycine (G), alanine (A), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at V148, the mutation being an aliphatic hydrophobic residue selected from glycine (G), alanine (A), leucine (L), isoleucine (I), and methionine (M).

In some embodiments, the mutant IFNβ comprises SEQ ID NO: 277 and a mutation at V148, the mutation being an aliphatic hydrophobic residue selected from glycine (G), alanine (A), leucine (L), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO: 277 and a mutation at Y155, the mutation being an aliphatic hydrophobic residue selected from glycine (G), alanine (A), leucine (L), isoleucine (I), methionine (M), and valine (V).

In some embodiments, the present invention relates to a chimeric proteins or chimeric protein complexes such as Fc-based chimeric protein complex comprising: (a) a modified IFN-β, having the amino acid sequence of SEQ ID NO: 277 and a mutation at position W22, wherein the mutation is an aliphatic hydrophobic residue and a modified IL-2 or modified IL-2 variant disclosed here; and (b) one or more targeting moieties, said targeting moieties comprising recognition domains which specifically bind to antigens or receptors of interest, the modified IFN-β and the one or more targeting moieties are optionally connected with one or more linkers. In various embodiments the mutation at position W22 is aliphatic hydrophobic residue is selected from G, A, L, I, M, and V. In various embodiments the mutation at position W22 is G.

Additional illustrative IFNβ mutants are provided in PCT/EP2017/061544, the entire disclosure of which is incorporated by reference herein.

In some embodiments, the modified additional signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

In some embodiments, the modified additional signaling agent is a consensus interferon. The consensus interferon is generated by scanning the sequences of several human non-allelic IFN-α subtypes and assigning the most frequently observed amino acid in each corresponding position. The consensus interferon differs from IFN-α2b at 20 out of 166 amino acids (88% homology), and comparison with IFN-β shows identity at over 30% of the amino acid positions. In various embodiments, the consensus interferon comprises the following amino acid sequence of SEQ ID NO: 278.

In some embodiments, the consensus interferon comprises the amino acid sequence of SEQ ID NO: 279, which differs from the amino acid sequence of SEQ ID NO: 278 by one amino acid, i.e., SEQ ID NO: 279 lacks the initial methionine residue of SEQ ID NO: 278:

In various embodiments, the consensus interferon comprises a modified version of the consensus interferon, i.e., a consensus interferon variant, as a signaling agent. In various embodiments, the consensus interferon variant encompasses functional derivatives, analogs, precursors, isoforms, splice variants, or fragments of the consensus interferon.

In an embodiment, the consensus interferon variants are selected form the consensus interferon variants disclosed in U.S. Pat. Nos. 4,695,623, 4,897,471, 5,541,293, and 8,496, 921, the entire contents of all of which are hereby incorporated by reference. For example, the consensus interferon variant may comprise the amino acid sequence of IFN-$CON_2$ or IFN-$CON_3$ as disclosed in U.S. Pat. Nos. 4,695, 623, 4,897,471, and 5,541,293. In an embodiment, the consensus interferon variant comprises the amino acid sequence of IFN-$CON_2$: SEQ ID NO: 280. In an embodiment, the consensus interferon variant comprises the amino acid sequence of IFN-$CON_3$: SEQ ID NO: 281.

In an embodiment, the consensus interferon variant comprises the amino acid sequence of any one of the variants disclosed in U.S. Pat. No. 8,496,921. For example, the consensus variant may comprise the amino acid sequence of: SEQ ID NO: 282.

In another embodiment, the consensus interferon variant may comprise the amino acid sequence of: SEQ ID NO: 283.

In some embodiments, the consensus interferon variant may be PEGylated, i.e., comprises a PEG moiety. In an embodiment, the consensus interferon variant may comprise a PEG moiety attached at the S156C position of SEQ ID NO: 283.

In some embodiments, the engineered interferon is a variant of human IFN-α2a, with an insertion of Asp at approximately position 41 in the sequence Glu-Glu-Phe-Gly-Asn-Gln (SEQ ID NO: 284) to yield Glu-Glu-Phe-Asp-Gly-Asn-Gln (SEQ ID NO: 285) (which resulted in a renumbering of the sequence relative to IFN-α2a sequence) and the following mutations of Arg23Lys, Leu26Pro, Glu53Gln, Thr54Ala, Pro56Ser, Asp86Glu, Ile104Thr, Gly106Glu, Thr110Glu, Lys117Asn, Arg125Lys, and Lys136Thr. All embodiments herein that describe consensus interferons apply equally to this engineered interferon In some embodiments, the additional modified signaling agent is vascular endothelial growth factor (VEGF). VEGF is a potent growth factor that plays major roles in physiological but also pathological angiogenesis, regulates vascular permeability and can act as a growth factor on cells expressing VEGF receptors. Additional functions include, among others, stimulation of cell migration in macrophage lineage and endothelial cells. Several members of the VEGF family of growth factors exist, as well as at least three receptors (VEGFR-1, VEGFR-2, and VEGFR-3). Members of the VEGF family can bind and activate more than one VEGFR type. For example, VEGF-A binds VEGFR-1 and -2, while VEGF-C can bind VEGFR-2 and -3. VEGFR-1 and VEGFR-2 activation regulate angiogenesis while VEGFR-3 activation is associated with lymphangiogenesis. The major pro-angiogenic signal is generated from activation of VEGFR-2. VEGFR-1 activation has been reported to be possibly associated with negative role in angiogenesis. It has also been reported that VEGFR-1 signaling is important for progression of tumors in vivo via bone marrow-derived VEGFR-1 positive cells (contributing to formation of premetastatic niche in the bone). Several therapies based on VEGF-A directed/neutralizing therapeutic antibodies have been developed, primarily for use in treatment of various human tumors relying on angiogenesis. These are not without side effects though. This may not be surprising considering that these operate as general, non-cell/tissue specific VEGF/VEGFR interaction inhibitors. Hence, it would be desirable to restrict VEGF (e.g. VEGF-A)/VEGFR-2 inhibition to specific target cells (e.g. tumor vasculature endothelial cells).

In some embodiments, the VEGF is VEGF-A, VEGF-B, VEFG-C, VEGF-D, or VEGF-E and isoforms thereof including the various isoforms of VEGF-A such as $VEGF_{121}$, $VEGF_{121}$b, $VEGF_{145}$, $VEGF_{165}$, $VEGF_{165}$b, $VEGF_{189}$, and $VEGF_{206}$. In some embodiments, the modified signaling agent has reduced affinity and/or activity for VEGFR-1 (Flt-1) and/or VEGFR-2 (KDR/Flk-1). In some embodiments, the modified signaling agent has substantially reduced or ablated affinity and/or activity for VEGFR-1 (Flt-1) and/or VEGFR-2 (KDR/Flk-1). In an embodiment, the modified signaling agent has reduced affinity and/or activity for VEGFR-2 (KDR/Flk-1) and/or substantially reduced or ablated affinity and/or activity for VEGFR-1 (Flt-1). Such an embodiment finds use, for example, in wound healing methods or treatment of ischemia-related diseases (without wishing to be bound by theory, mediated by VEGFR-2's effects on endothelial cell function and angiogenesis). In various embodiments, binding to VEGFR-1 (Flt-1), which is linked to cancers and pro-inflammatory activities, is avoided. In various embodiments, VEGFR-1 (Flt-1) acts a decoy receptor and therefore substantially reduces or ablates affinity at this receptor avoids sequestration of the therapeutic agent. In an embodiment, the modified signaling agent has substantially reduced or ablated affinity and/or activity for VEGFR-1 (Flt-1) and/or substantially reduced or ablated affinity and/or activity for VEGFR-2 (KDR/Flk-1). In some embodiments, the VEGF is VEGF-C or VEGF-D. In such embodiments, the modified signaling agent has reduced affinity and/or activity for VEGFR-3. Alternatively, the modified signaling agent has substantially reduced or ablated affinity and/or activity for VEGFR-3.

Proangiogenic therapies are also important in various diseases (e.g. ischemic heart disease, bleeding etc.), and include VEGF-based therapeutics. Activation of VEGFR-2 is proangiogenic (acting on endothelial cells). Activation of VEFGR-1 can cause stimulation of migration of inflammatory cells (including, for example, macrophages) and lead to inflammation associated hypervascular permeability. Activation of VEFGR-1 can also promote bone marrow associated tumor niche formation. Thus, VEGF based therapeutic selective for VEGFR-2 activation would be desirable in this case. In addition, cell specific targeting, e.g. to endothelial cells, would be desirable.

In some embodiments, the additional modified signaling agent has reduced affinity and/or activity (e.g. antagonistic) for VEGFR-2 and/or has substantially reduced or ablated affinity and/or activity for VEGFR-1. When targeted to tumor vasculature endothelial cells via a targeting moiety that binds to a tumor endothelial cell marker (e.g. PSMA and others), such construct inhibits VEGFR-2 activation specifically on such marker-positive cells, while not activating VEGFR-1 en route and on target cells (if activity ablated), thus eliminating induction of inflammatory responses, for example. This would provide a more selective and safe anti-angiogenic therapy for many tumor types as compared to VEGF-A neutralizing therapies.

In some embodiments, the additional modified signaling agent has reduced affinity and/or activity (e.g. agonistic) for VEGFR-2 and/or has substantially reduced or ablated affinity and/or activity for VEGFR-1. Through targeting to vascular endothelial cells, such construct, in some embodiments, promotes angiogenesis without causing VEGFR-1 associated induction of inflammatory responses. Hence, such a construct would have targeted proangiogenic effects with substantially reduced risk of side effects caused by systemic activation of VEGFR-2 as well as VEGR-1.

In an illustrative embodiment, the modified signaling agent is $VEGF_{165}$, which has the amino acid sequence of SEQ ID NO:235.

In another illustrative embodiment, the additional modified signaling agent is $VEGF_{165}$b, which has the amino acid sequence of SEQ ID NO:236.

In these embodiments, the modified signaling agent has a mutation at amino acid I83 (e.g., a substitution mutation at I83, e.g., I83K, I83R, or I83H). Without wishing to be bound by theory, it is believed that such mutations may result in reduced receptor binding affinity. See, for example, U.S. Pat. No. 9,078,860, the entire contents of which are hereby incorporated by reference.

In an embodiment, the additional modified signaling agent is TNF-α. TNF is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFkB pathway). Administration of TNF is systemically toxic, and this is largely due to TNFR1 engagement. However, it should be noted that activation of TNFR2 is also associated with a broad range of activities and, as with TNFR1, in the context of developing TNF based therapeutics, control over TNF targeting and activity is important.

In some embodiments, the additional modified signaling agent has reduced affinity and/or activity for TNFR1 and/or TNFR2. In some embodiments, the modified signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly, in embodiments directed to methods of treating cancer, the modified signaling agent has reduced affinity and/or activity for TNFR1 and/or substantially reduced or ablated affinity and/or activity for TNFR2. In these embodiments, the chimeric proteins or chimeric protein complexes such as Fc-based chimeric protein complex may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified signaling agent has reduced affinity and/or activity for TNFR2 and/or substantially reduced or ablated affinity and/or activity for TNFR1. Stated another way, the present chimeric proteins or chimeric protein complexes such as Fc-based chimeric protein complex, in some embodiments, comprise modified TNF-α agent that allows of favoring either death or survival signals.

In some embodiments, the chimeric proteins or chimeric protein complexes such as Fc-based chimeric protein complex has a modified TNF having reduced affinity and/or activity for TNFR1 and/or substantially reduced or ablated affinity and/or activity for TNFR2. Such a chimera, in some embodiments, is a more potent inducer of apoptosis as compared to a wild type TNF and/or a chimera bearing only mutation(s) causing reduced affinity and/or activity for TNFR1. Such a chimera, in some embodiments, finds use in inducing tumor cell death or a tumor vasculature endothelial cell death (e.g. in the treatment of cancers). Also, in some embodiments, these chimeras avoid or reduce activation of $T_{reg}$ cells via TNFR2, for example, thus further supporting TNFR1-mediated antitumor activity in vivo.

In some embodiments, the chimeric proteins or chimeric protein complexes such as Fc-based chimeric protein complex has a modified TNF having reduced affinity and/or activity for TNFR2 and/or substantially reduced or ablated affinity and/or activity for TNFR1. Such a chimera, in some embodiments, is a more potent activator of cell survival in some cell types, which may be a specific therapeutic objective in various disease settings, including without limitation, stimulation of neurogenesis. In addition, such a TNFR2-favoring chimeras also are useful in the treatment of autoimmune diseases (e.g. Crohn's, diabetes, MS, colitis etc. and many others described herein). In some embodiments, the chimera is targeted to auto-reactive T cells. In some embodiments, the chimera promotes $T_{reg}$ cell activation and indirect suppression of cytotoxic T cells.

In some embodiments, the chimera causes the death of auto-reactive T cells, e.g. by activation of TNFR2 and/or avoidance of TNFR1 (e.g. a modified TNF having reduced affinity and/or activity for TNFR2 and/or substantially reduced or ablated affinity and/or activity for TNFR1). Without wishing to be bound by theory these auto-reactive T cells, have their apoptosis/survival signals altered e.g. by NFkB pathway activity/signaling alterations.

In some embodiments, a TNFR2 based chimera has additional therapeutic applications in diseases, including various autoimmune diseases, heart disease, de-myelinating and neurodegenerative disorders, and infectious disease, among others.

In an embodiment, the wild type TNF-α has the amino acid sequence of SEQ ID NO:237.

In such embodiments, the modified TNF-α agent has mutations at one or more amino acid positions 29, 31, 32, 84, 85, 86, 87, 88, 89, 145, 146 and 147 which produces a modified TNF-α with reduced receptor binding affinity. See, for example, U.S. Pat. No. 7,993,636, the entire contents of which are hereby incorporated by reference.

In some embodiments, the modified human TNF-α moiety has mutations at one or more amino acid positions R32, N34, Q67, H73, L75, T77, S86, Y87, V91, 197, T105, P106, A109, P113, Y115, E127, N137, D143, and A145, as described, for example, in WO/2015/007903, the entire contents of which is hereby incorporated by reference (numbering according to the human TNF sequence, Genbank accession number BAG70306, version BAG70306.1 GI: 197692685). In some embodiments, the modified human TNF-α moiety has substitution mutations selected from R32G, N34G, Q67G, H73G, L75G, L75A, L75S, T77A, S86G, Y87Q, Y87L, Y87A, Y87F, V91G, V91A, I97A, I97Q, I97S, T105G, P106G, A109Y, P113G, Y115G, Y115A, E127G, N137G, D143N, A145G and A145T. In an embodiment, the human TNF-α moiety has a mutation selected from Y87Q, Y87L, Y87A, and Y87F. In another embodiment, the human TNF-α moiety has a mutation selected from I97A, I97Q, and I97S. In a further embodiment, the human TNF-α moiety has a mutation selected from Y115A and Y115G.

In some embodiments, the modified TNF-α agent has one or more mutations selected from N39Y, S147Y, and Y87H, as described in WO2008/124086, the entire contents of which is hereby incorporated by reference.

In an embodiment, the additional modified signaling agent is TNF-β. TNF-β can form a homotrimer or a heterotrimer with LT-β (LT-α1β2). In some embodiments, the modified signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of SEQ ID NO:238.

In such embodiments, the modified TNF-β agent may comprise mutations at one or more amino acids at positions 106-113, which produce a modified TNF-β with reduced receptor binding affinity to TNFR2. In an embodiment, the modified signaling agent has one or more substitution mutations at amino acid positions 106-113. In illustrative embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified signaling agent has an insertion of about 1 to about 3 amino acids at positions 106-113.

In some embodiments, the additional modified agent is a TNF family member (e.g. TNF-alpha, TNF-beta) which can be a single chain trimeric version as described in WO 2015/007903, the entire contents of which are incorporated by reference.

In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified agent is a TNF family member (e.g. TNF-alpha, TNF-beta) which also, optionally, has substantially reduced or ablated affinity and/or activity for TNFR2. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2. In these embodiments, the modified agent is a TNF family member (e.g. TNF-alpha, TNF-beta) which also, optionally, has substantially reduced or ablated affinity and/or activity for TNFR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In an embodiment, the additional modified signaling agent is TRAIL. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of SEQ ID NO:239.

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP_003801, version 10 NP_003801.1, GI: 4507593; see above).

In an embodiment, the additional modified signaling agent is TGFα. In such embodiments, the modified TGFα agent has reduced affinity and/or activity for the epidermal growth factor receptor (EGFR). In some embodiments, the modified TGFα agent has substantially reduced or ablated affinity and/or activity for the epidermal growth factor receptor (EGFR).

In an embodiment, the additional modified signaling agent is TGFβ. In such embodiments, the modified signaling agent has reduced affinity and/or activity for TGFBR1 and/or TGFBR2. In some embodiments, the modified signaling agent has substantially reduced or ablated affinity and/or activity for TGFBR1 and/or TGFBR2. In some embodiments, the modified signaling agent optionally has reduced or substantially reduced or ablated affinity and/or activity for TGFBR3 which, without wishing to be bound by theory, may act as a reservoir of ligand for TGF-beta receptors. In some embodiments, the TGFβ may favor TGFBR1 over TGFBR2 or TGFBR2 over TGFBR1.

Similarly, LAP, without wishing to be bound by theory, may act as a reservoir of ligand for TGF-beta receptors. In some embodiments, the modified signaling agent has reduced affinity and/or activity for TGFBR1 and/or TGFBR2 and/or substantially reduced or ablated affinity and/or activity for Latency Associated Peptide (LAP). In some embodiments, such chimeras find use in Camurati-Engelmann disease, or other diseases associated with inappropriate TGFβ signaling.

In some embodiments, the additional modified agent is a TGF family member (e.g. TGFα, TGFβ) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at one or more of TGFBR1, TGFBR2, TGFBR3. In these embodiments, the modified agent is a TGF family member (e.g. TGFα, TGFβ) which also, optionally, has substantially reduced or ablated affinity and/or activity at one or more of TGFBR1, TGFBR2, TGFBR3.

In some embodiments, the additional modified agent is a TGF family member (e.g. TGFα, TGFβ) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TGFBR1 and/or TGFBR2. In these embodiments, the modified agent is a TGF family member (e.g. TGFα, TGFβ) which also, optionally, has substantially reduced or ablated affinity and/or activity at TGFBR3.

In an embodiment, the additional modified signaling agent is IL-1. In an embodiment, the modified signaling agent is IL-1α or IL-1β. In some embodiments, the modified signaling agent has reduced affinity and/or activity for IL-1R1 and/or IL-1RAcP. In some embodiments, the modified signaling agent has substantially reduced or ablated affinity and/or activity for IL-1R1 and/or IL-1RAcP. In some embodiments, the modified signaling agent has reduced affinity and/or activity for IL-1R2. In some embodiments, the modified signaling agent has substantially reduced or ablated affinity and/or activity for IL-1R2. For instance, in some embodiments, the present modified IL-1 agents avoid interaction at IL-1R2 and therefore substantially reduce its function as a decoy and/or sink for therapeutic agents. In an embodiment, the wild type IL-1β has the amino acid sequence of SEQ ID NO:240.

IL-1β is a proinflammatory cytokine and an important immune system regulator. It is a potent activator of CD4 T cell responses, increases proportion of Th17 cells and expansion of IFNγ and IL-4 producing cells. IL-1β is also a potent regulator of $CD8^+$ T cells, enhancing antigen-specific $CD8^+$ T cell expansion, differentiation, migration to periphery and memory. IL-1β receptors comprise IL-1R1 and IL-1R2. Binding to and signaling through the IL-1R1 constitutes the mechanism whereby IL-1β mediates many of its biological (and pathological) activities. IL1-R2 can function as a decoy receptor, thereby reducing IL-1β availability for interaction and signaling through the IL-1R1.

In some embodiments, the modified IL-1β has reduced affinity and/or activity (e.g. agonistic activity) for IL-1R1. In some embodiments, the modified IL-1β has substantially reduced or ablated affinity and/or activity for IL-1R2. In such embodiments, there is inducible or restorable IL-1β/IL-1R1 signaling and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating cancer, including, for example, stimulating the immune system to mount an anti-cancer response.

In some embodiments, the modified IL-1β has reduced affinity and/or activity (e.g. antagonistic activity, e.g. natural antagonistic activity or antagonistic activity that is the result of one or more mutations, see, e.g., WO 2015/007520, the entire contents of which are hereby incorporated by reference) for IL-1R1. In some embodiments, the modified IL-1β has substantially reduced or ablated affinity and/or activity for IL-1R2. In such embodiments, there is the IL-1β/IL-1R1 signaling is not inducible or restorable and prevention of loss of therapeutic chimeras at IL-R2 and therefore a reduction in dose of IL-1β that is required (e.g. relative to wild type or a chimera bearing only an attenuation mutation for IL-R1). Such constructs find use in, for example, methods of treating autoimmune diseases, including, for example, suppressing the immune system.

In such embodiments, the modified signaling agent has a deletion of amino acids 52-54 which produces a modified human IL-1β with reduced binding affinity for type I IL-1R and reduced biological activity. See, for example, WO 1994/000491, the entire contents of which are hereby incorporated by reference. In some embodiments, the modified human IL-1β has one or more substitution mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, I172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO2015/007542 and WO/2015/007536, the entire contents of which is hereby incorporated by reference (numbering base on the human IL-1 β sequence, Genbank accession number NP_000567, version NP-000567.1, GI: 10835145). In some embodiments, the modified human IL-1β may have one or more mutations selected from R120A, R120G, Q130A, Q130W, H146A, H146G, H146E, H146N, H146R, Q148E, Q148G, Q148L, K209A, K209D, K219S, K219Q, E221S and E221K. In an embodiment, the modified human IL-1β comprises the mutations Q131G and Q148G. In an embodiment, the modified human IL-1β comprises the mutations Q148G and K208E. In an embodiment, the modified human IL-1β comprises the mutations R120G and Q131G. In an embodiment, the modified human IL-1β comprises the mutations R120G and H146G. In an embodiment, the modified human IL-1β comprises the mutations R120G and K208E. In an embodiment, the modified human IL-1β comprises the mutations R120G, F162A, and Q164E.

In an embodiment, the additional modified signaling agent is IL-2. In such an embodiment, the modified signaling agent has reduced affinity and/or activity for IL-2Rα and/or IL-2Rβ and/or IL-2Rγ. In some embodiments, the modified signaling agent has reduced affinity and/or activity for IL-2Rβ and/or IL-2Rγ. In some embodiments, the modified signaling agent has substantially reduced or ablated affinity and/or activity for IL-2Rα. Such embodiments may be relevant for treatment of cancer, for instance when the modified IL-2 is agonistic at IL-2Rβ and/or IL-2Rγ. For instance, the present constructs may favor attenuated activation of $CD8^+$ T cells (which can provide an anti-tumor effect), which have IL2 receptors β and γ and disfavor $T_{regs}$ (which can provide an immune suppressive, pro-tumor effect), which have IL2 receptors α, β, and γ. Further, in some embodiments, the preferences for IL-2Rβ and/or IL-2Rγ over IL-2Rα avoid IL-2 side effects such as pulmonary edema. Also, IL-2-based chimeras are useful for the treatment of autoimmune diseases, for instance when the modified IL-2 is antagonistic (e.g. natural antagonistic activity or antagonistic activity that is the result of one or more mutations, see, e.g., WO 2015/007520, the entire contents of which are hereby incorporated by reference) at IL-2Rβ and/or IL-2Rγ. For instance, the present constructs may favor attenuated suppression of $CD8^+$ T cells (and therefore dampen the immune response), which have IL2 receptors β and γ and disfavor $T_{regs}$ which have IL2 receptors α, β, and γ. Alternatively, in some embodiments, the chimeras bearing IL-2 favor the activation of $T_{regs}$, and therefore immune suppression, and activation of disfavor of $CD8^+$ T cells. For instance, these constructs find use in the treatment of diseases or diseases that would benefit from immune suppression, e.g. autoimmune disorders.

In some embodiments, the chimeric proteins or chimeric protein complexes such as Fc-based chimeric protein complex has targeting moieties as described herein directed to $CD8^+$ T cells as well as a modified IL-2 agent having reduced affinity and/or activity for IL-2Rβ and/or IL-2Rγ and/or substantially reduced or ablated affinity and/or activity for IL-2Rα. In some embodiments, these constructs provide targeted $CD8^+$ T cell activity and are generally inactive (or have substantially reduced activity) towards $T_{reg}$ cells. In some embodiments, such constructs have enhanced immune stimulatory effect compared to wild type IL-2 (e.g., without wishing to be bound by theory, by not stimulating Tregs), whilst eliminating or reducing the systemic toxicity associated with IL-2.

In an embodiment, the wild type IL-2 has the amino acid sequence of SEQ ID NO:241.

In such embodiments, the modified IL-2 agent has one or more mutations at amino acids L72 (L72G, L72A, L72S, L72T, L72Q, L72E, L72N, L72D, L72R, or L72K), F42 (F42A, F42G, F42S, F42T, F42Q, F42E, F42N, F42D, F42R, or F42K) and Y45 (Y45A, Y45G, Y45S, Y45T, Y45Q, Y45E, Y45N, Y45D, Y45R or Y45K). Without wishing to be bound by theory, it is believed that these modified IL-2 agents have reduced affinity for the high-affinity IL-2 receptor and preserves affinity to the intermediate-affinity IL-2 receptor, as compared to the wild-type IL-2. See, for example, US Patent Publication No. 2012/0244112, the entire contents of which are hereby incorporated by reference.

In an embodiment, the additional modified signaling agent is IL-3. In some embodiments, the modified signaling agent has reduced affinity and/or activity for the IL-3 receptor, which is a heterodimer with a unique alpha chain paired with the common beta (beta c or CD131) subunit. In some embodiments, the modified signaling agent has substantially reduced or ablated affinity and/or activity for the IL-3 receptor, which is a heterodimer with a unique alpha chain paired with the common beta (beta c or CD131) subunit.

In an embodiment, the additional modified signaling agent is IL-4. In such an embodiment, the modified signaling agent has reduced affinity and/or activity for type 1 and/or type 2 IL-4 receptors. In such an embodiment, the modified signaling agent has substantially reduced or ablated affinity and/or activity for type 1 and/or type 2 IL-4 receptors. Type 1 IL-4 receptors are composed of the IL-4Ra subunit with a common γ chain and specifically bind IL-4. Type 2 IL-4 receptors include an IL-4Ra subunit bound to a different subunit known as IL-13Rα1. In some embodiments, the modified signaling agent has substantially reduced or ablated affinity and/or activity the type 2 IL-4 receptors.

In an embodiment, the wild type IL-4 has the amino acid sequence of SEQ ID NO:242.

In such embodiments, the modified IL-4 agent has one or more mutations at amino acids R121 (R121A, R121D, R121E, R121F, R121H, R121I, R121K, R121N, R121P, R121T, R121W), E122 (E122F), Y124 (Y124A, Y124Q, Y124R, Y124S, Y124T) and S125 (S125A). Without wishing to be bound by theory, it is believed that these modified IL-4 agents maintain the activity mediated by the type I receptor, but significantly reduces the biological activity mediated by the other receptors. See, for example, U.S. Pat. No. 6,433,157, the entire contents of which are hereby incorporated by reference.

In an embodiment, the additional modified signaling agent is IL-6. IL-6 signals through a cell-surface type I cytokine receptor complex including the ligand-binding IL-6R chain (CD126), and the signal-transducing component gp130. IL-6 may also bind to a soluble form of IL-6R (sIL-6R), which is the extracellular portion of IL-6R. The sIL-6R/IL-6 complex may be involved in neurites outgrowth and survival of neurons and, hence, may be important in nerve regeneration through remyelination. Accordingly, in some embodiments, the modified signaling agent has reduced affinity and/or activity for IL-6R/gp130 and/or sIL-6R. In some embodiments, the modified signaling agent has substantially reduced or ablated affinity and/or activity for IL-6R/gp130 and/or sIL-6R.

In an embodiment, the wild type IL-6 has the amino acid sequence of SEQ ID NO:243.

In such embodiments, the modified signaling agent has one or more mutations at amino acids 58, 160, 163, 171 or 177. Without wishing to be bound by theory, it is believed that these modified IL-6 agents exhibit reduced binding affinity to IL-6Ralpha and reduced biological activity. See, for example, WO 97/10338, the entire contents of which are hereby incorporated by reference.

In an embodiment, the additional modified signaling agent is IL-10. In such an embodiment, the modified signaling agent has reduced affinity and/or activity for IL-10 receptor-1 and IL-10 receptor-2. In some embodiments, the modified signaling agent has substantially reduced or ablated affinity and/or activity for IL-10 receptor-1 and IL-10 receptor-2

In an embodiment, the additional modified signaling agent is IL-11. In such an embodiment, the modified signaling agent has reduced affinity and/or activity for IL-11Rα and/or IL-11Rβ and/or gp130. In such an embodiment, the modified signaling agent has substantially reduced or ablated affinity and/or activity for IL-11Rα and/or IL-11Rβ and/or gp130.

In an embodiment, the additional modified signaling agent is IL-12. In such an embodiment, the modified signaling agent has reduced affinity and/or activity for IL-12Rβ1 and/or IL-12Rβ2. In such an embodiment, the modified signaling agent has substantially reduced or ablated affinity and/or activity for IL-12Rβ1 and/or IL-12Rβ2.

In an embodiment, the additional modified signaling agent is IL-13. In such an embodiment, the modified signaling agent has reduced affinity and/or activity for the IL-4 receptor (IL-4Rα) and IL-13Rα1. In some embodiments, the modified signaling agent has substantially reduced or ablated affinity and/or activity for IL-4 receptor (IL-4Rα) or IL-13Rα1.

In an embodiment, the wild type IL-13 has the amino acid sequence of SEQ ID NO:244.

In such embodiments, the modified IL-13 agent has one or more mutations at amino acids 13, 16, 17, 66, 69, 99, 102, 104, 105, 106, 107, 108, 109, 112, 113 and 114. Without wishing to be bound by theory, it is believed that these modified IL-13 agents exhibit reduced biological activity. See, for example, WO 2002/018422, the entire contents of which are hereby incorporated by reference.

In an embodiment, the signaling agent is a wild type or modified IL-15. In embodiments, the modified IL-15 has reduced affinity and/or activity for interleukin 15 receptor.

In an embodiment, the wild type IL-15 has the amino acid sequence of:

```
                                        (SEQ ID NO: 292)
NWVNVISDLKKIEDLIQSMHIDATLYTESDVHPSCKVTAMKCFLLELQVI

SHESGDTDIHDTVENLIILANNILSSNGNITESGCKECEELEEKNIKEFL

QSFVHIVQMFINTS.
```

In such embodiments, the modified IL-15 agent has one or more mutations at amino acids S7, D8, K10, K11, E46, L47, V49, I50, D61, N65, L66, I67, I68, L69, N72, Q108 with respect to SEQ ID NO: 292.

In an embodiment, the additional modified signaling agent is IL-18. In some embodiments, the modified signaling agent has reduced affinity and/or activity for IL-18Rα and/or IL-18Rβ. In some embodiments, the modified signaling agent has substantially reduced or ablated affinity and/or activity for IL-18Rα and/or IL-18Rβ. In some embodiments, the modified signaling agent has substantially reduced or ablated affinity and/or activity for IL-18Rα type II, which is an isoform of IL-18Rα that lacks the TIR domain required for signaling.

In an embodiment, the wild type IL-18 has the amino acid sequence of SEQ ID NO:245.

In such embodiments, the modified IL-18 agent may comprise one or more mutations in amino acids or amino acid regions selected from Y37-K44, R49-Q54, D59-R63, E67-C74, R80, M87-A97, N 127-K129, Q139-M149, K165-K171, R183 and Q190-N191, as described in WO/2015/007542, the entire contents of which are hereby incorporated by reference (numbering based on the human IL-18 sequence, Genbank accession number AAV38697, version AAV38697.1, GI: 54696650).

In an embodiment, the additional modified signaling agent is IL-33. In such an embodiment, the modified signaling agent has reduced affinity and/or activity for the ST-2 receptor and IL-1RAcP. In some embodiments, the modified signaling agent has substantially reduced or ablated affinity and/or activity for the ST-2 receptor and IL-1RAcP.

In an embodiment, the wild type IL-33 has the amino acid sequence of SEQ ID NO:246.

In such embodiments, the modified IL-33 agent may comprise one or more mutations in amino acids or amino acid regions selected from I113-Y122, S127-E139, E144-D157, Y163-M183, E200, Q215, L220-C227 and T260-E269, as described in WO/2015/007542, the entire contents of which are hereby incorporated by reference (numbering based on the human sequence, Genbank accession number NP_254274, version NP_254274.1, GI:15559209).

In an embodiment, the modified signaling agent is epidermal growth factor (EGF). EGF is a member of a family of potent growth factors. Members include EGF, HB-EGF, and others such as TGFalpha, amphiregulin, neuregulins, epiregulin, betacellulin. EGF family receptors include EGFR (ErbB1), ErbB2, ErbB3 and ErbB4. These may function as homodimeric and/or heterodimeric receptor subtypes. The different EGF family members exhibit differential selectivity for the various receptor subtypes. For example, EGF associates with ErbB1/ErbB1, ErbB1/ErbB2, ErbB4/ErbB2 and some other heterodimeric subtypes. HB-EGF has a similar pattern, although it also associates with ErbB4/4. Modulation of EGF (EGF-like) growth factor signaling, positively or negatively, is of considerable therapeutic interest. For example, inhibition of EGFRs signaling is of interest in the treatment of various cancers where EGFR signaling constitutes a major growth promoting signal. Alternatively, stimulation of EGFRs signaling is of therapeutic interest in, for example, promoting wound healing (acute and chronic), oral mucositis (a major side-effect of various cancer therapies, including, without limitation radiation therapy).

In some embodiments, the additional modified signaling agent has reduced affinity and/or activity for ErbB1, ErbB2, ErbB3, and/or ErbB4. Such embodiments find use, for example, in methods of treating wounds. In some embodiments, the modified signaling agent binds to one or more ErbB1, ErbB2, ErbB3, and ErbB4 and antagonizes the activity of the receptor. In such embodiments, the modified signaling agent has reduced affinity and/or activity for ErbB1, ErbB2, ErbB3, and/or ErbB4 which allows for the activity of the receptor to be antagonized in an attenuated fashion. Such embodiments find use in, for example, treatments of cancer. In an embodiment, the modified signaling agent has reduced affinity and/or activity for ErbB1. ErbB1 is the therapeutic target of kinase inhibitors—most have side effects because they are not very selective (e.g., gefitinib, erlotinib, afatinib, brigatinib and icotinib). In some embodiments, attenuated antagonistic ErbB1 signaling is more on-target and has less side effects than other agents targeting receptors for EGF.

In some embodiments, the additional modified signaling agent has reduced affinity and/or activity (e.g. antagonistic e.g. natural antagonistic activity or antagonistic activity that is the result of one or more mutations, see, e.g., WO 2015/007520, the entire contents of which are hereby incorporated by reference) for ErbB1 and/or substantially reduced or ablated affinity and/or activity for ErbB4 or other subtypes it may interact with. Through specific targeting via the targeting moiety, cell-selective suppression (antagonism e.g. natural antagonistic activity or antagonistic activity that is the result of one or more mutations, see, e.g., WO 2015/007520, the entire contents of which are hereby incorporated by reference) of ErbB1/ErbB1 receptor activation would be achieved —while not engaging other receptor subtypes potentially associated with inhibition-associated side effects. Hence, in contrast to EGFR kinase inhibitors, which inhibit EGFR activity in all cell types in the body, such a construct would provide a cell-selective (e.g., tumor cell with activated EGFR signaling due to amplification of receptor, overexpression etc.) anti-EGFR (ErbB1) drug effect with reduced side effects.

In some embodiments, the additional modified signaling agent has reduced affinity and/or activity (e.g. agonistic) for ErbB4 and/or other subtypes it may interact with. Through targeting to specific target cells through the targeting moiety, a selective activation of ErbB1 signaling is achieved (e.g. epithelial cells). Such a construct finds use, in some embodiments, in the treatment of wounds (promoting would healing) with reduced side effects, especially for treatment of chronic conditions and application other than topical application of a therapeutic (e.g. systemic wound healing).

In an embodiment, the modified signaling agent is insulin or insulin analogs. In some embodiments, the modified insulin or insulin analog has reduced affinity and/or activity for the insulin receptor and/or IGF1 or IGF2 receptor. In some embodiments, the modified insulin or insulin analog has substantially reduced or ablated affinity and/or activity for the insulin receptor and/or IGF1 or IGF2 receptor. Attenuated response at the insulin receptor allows for the control of diabetes, obesity, metabolic disorders and the like while directing away from IGF1 or IGF2 receptor avoids pro-cancer effects.

In an embodiment, the modified signaling agent is insulin-like growth factor-I or insulin-like growth factor-II (IGF-1 or IGF-2). In an embodiment, the modified signaling agent is IGF-1. In such an embodiment, the modified signaling agent has reduced affinity and/or activity for the insulin receptor and/or IGF1 receptor. In an embodiment, the modified signaling agent may bind to the IGF1 receptor and antagonize the activity of the receptor. In such an embodiment, the modified signaling agent has reduced affinity and/or activity for IGF1 receptor which allows for the activity of the receptor to be antagonized in an attenuated fashion. In some embodiments, the modified signaling agent has substantially reduced or ablated affinity and/or activity for the insulin receptor and/or IGF1 receptor. In some embodiments, the modified signaling agent has reduced affinity and/or activity for IGF2 receptor which allows for the activity of the receptor to be antagonized in an attenuated fashion. In an embodiment, the modified signaling agent has substantially reduced or ablated affinity and/or activity for the insulin receptor and accordingly does not interfere with insulin signaling. In various embodiments, this applies to cancer treatment. In various embodiments, the present agents may prevent IR isoform A from causing resistance to cancer treatments.

In an embodiment, the modified signaling agent is EPO. In various embodiments, the modified EPO agent has reduced affinity and/or activity for the EPO receptor (EPOR) receptor and/or the ephrin receptor (EphR) relative to wild type EPO or other EPO based agents described herein. In some embodiments, the modified EPO agent has substantially reduced or ablated affinity and/or activity for the EPO receptor (EPOR) receptor and/or the Eph receptor (EphR). Illustrative EPO receptors include, but are not limited to, an EPOR homodimer or an EPOR/CD131 heterodimer. Also included as an EPO receptor is beta-common receptor (βcR). Illustrative Eph receptors include, but are not limited to, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, and EPHB6. In some embodiments, the modified EPO protein comprises one or more mutations that cause the EPO protein to have reduced affinity for receptors that comprise one or more different EPO receptors or Eph receptors (e.g. heterodimer, heterotrimers, etc., including by way of non-limitation: EPOR-EPHB4, EPOR-βcR-EPOR). Also provided are the receptors of EP Patent Publication No. 2492355 the entire contents of which are hereby incorporated by reference, including by way of non-limitation, NEPORs.

In an embodiment, the human EPO has the amino acid sequence of SEQ ID NO:247 (first 27 amino acids are the signal peptide).

In an embodiment, the human EPO protein is the mature form of EPO (with the signal peptide being cleaved off) which is a glycoprotein of 166 amino acid residues having the sequence of SEQ ID NO:248.

The structure of the human EPO protein is predicted to comprise four-helix bundles including helices A, B, C, and D. In various embodiments, the modified EPO protein comprises one or more mutations located in four regions of the EPO protein which are important for bioactivity, i.e., amino acid residues 10-20, 44-51, 96-108, and 142-156. In some embodiments, the one or more mutations are located at residues 11-15, 44-51, 100-108, and 147-151. These residues are localized to helix A (Val11, Arg14, and Tyr15), helix C (Ser100, Arg103, Ser104, and Leu108), helix D (Asn147, Arg150, Gly151, and Leu155), and the NB connecting loop (residues 42-51). In some embodiments, the modified EPO protein comprises mutations in residues between amino acids 41-52 and amino acids 147, 150, 151, and 155. Without wishing to be bound by theory, it is believed that mutations of these residues have substantial effects on both receptor binding and in vitro biological activity. In some embodiments, the modified EPO protein comprises mutations at residues 11, 14, 15, 100, 103, 104, and 108. Without wishing to be bound by theory, it is believed that mutations of these residues have modest effects on receptor binding activity and much greater effects on in vitro biological activity. Illustrative substitutions include, but are not limited to, one or more of Val11Ser, Arg14Ala, Arg14Gln, Tyr15Ile, Pro42Asn, Thr44Ile, Lys45Asp, Val46Ala, Tyr51Phe, Ser100Glu, Ser100Thr, Arg103Ala, Ser104Ile, Ser104Ala, Leu108Lys, Asn147Lys, Arg150Ala, Gly151Ala, and Leu155Ala.

In some embodiments, the modified EPO protein comprises mutations that effect bioactivity and not binding, e.g. those listed in Eliot, et al. Mapping of the Active Site of Recombinant Human Erythropoietin Jan. 15, 1997; *Blood:* 89 (2), the entire contents of which are hereby incorporated by reference.

In some embodiments, the modified EPO protein comprises one or more mutations involving surface residues of the EPO protein which are involved in receptor contact. Without wishing to be bound by theory, it is believed that mutations of these surface residues are less likely to affect protein folding thereby retaining some biological activity. Illustrative surface residues that may be mutated include, but are not limited to, residues 147 and 150. In illustrative embodiments, the mutations are substitutions including, one or more of N147A, N147K, R150A and R150E.

In some embodiments, the modified EPO protein comprises one or more mutations at residues N59, E62, L67, and L70, and one or more mutations that affect disulfide bond formation. Without wishing to be bound by theory, it is believed that these mutations affect folding and/or are predicted be in buried positions and thus affects biological activity indirectly.

In an embodiment, the modified EPO protein comprises a K20E substitution which significantly reduces receptor binding. See Elliott, et al., (1997) *Blood,* 89:493-502, the entire contents of which are hereby incorporated by reference.

Additional EPO mutations that may be incorporated into the chimeric EPO protein of the invention are disclosed in, for example, Elliott, et al., (1997) *Blood,* 89:493-502, the entire contents of which are hereby incorporated by reference and Taylor et al., (2010) *PEDS,* 23(4): 251-260, the entire contents of which are hereby incorporated by reference.

In various embodiments, the signaling agent is a toxin or toxic enzyme. In some embodiments, the toxin or toxic enzyme is derived from plants and bacteria. Illustrative toxins or toxic enzymes include, but are not limited to, the diphtheria toxin, Pseudomonas toxin, anthrax toxin, ribosome-inactivating proteins (RIPs) such as ricin and saporin, modeccin, abrin, gelonin, and poke weed antiviral protein. Additional toxins include those disclosed in Mathew et al., (2009) Cancer Sci 100(8): 1359-65, the entire disclosures are hereby incorporated by reference. In such embodiments, the chimeric proteins or chimeric protein complexes such as Fc-based chimeric protein complex of the invention may be utilized to induce cell death in cell-type specific manner. In such embodiments, the toxin may be modified, e.g. mutated, to reduce affinity and/or activity of the toxin for an attenuated effect, as described with other signaling agents herein.

Linkers and Functional Groups

In some embodiments, the present chimeric proteins or chimeric protein complexes such as Fc-based chimeric protein complex optionally comprises one or more linkers. In some embodiments, the present chimeric proteins or chimeric protein complexes such as Fc-based chimeric protein complex comprises a linker connecting the targeting moiety and the signaling agent (e.g., IFNα1 or a variant thereof). In some embodiments, the present chimeric proteins or chimeric protein complexes such as Fc-based chimeric protein complex comprises a linker within the signaling agent (e.g., IFNα1 or a variant thereof). In some embodiments, the linker may be utilized to link various functional groups, residues, or moieties as described herein to the chimeric proteins or chimeric protein complexes such as Fc-based chimeric protein complex. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

In some embodiments vectors encoding the present chimeric proteins or chimeric protein complexes such as Fc-based chimeric protein complex linked as a single nucleotide sequence to any of the linkers described herein are provided and may be used to prepare such chimeric proteins or chimeric protein complexes such as Fc-based chimeric protein complex. In embodiments, the substituents of the Fc-based chimeric protein complex are expressed as nucleotide sequences in a vector.

In some embodiments, the linker length allows for efficient binding of a targeting moiety and the signaling agent (e.g., IFNα1 or a variant thereof) to their receptors. For instance, in some embodiments, the linker length allows for efficient binding of one of the targeting moieties and the signaling agent to receptors on the same cell.

In some embodiments the linker length is at least equal to the minimum distance between the binding sites of one of the targeting moieties and the signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the targeting moieties and the signaling agent to receptors on the same cell.

As described herein, the linker length allows for efficient binding of one of the targeting moieties and the signaling agent to receptors on the same cell, the binding being sequential, e.g. targeting moiety/receptor binding preceding signaling agent/receptor binding.

In some embodiments, there are two linkers in a single chimera, each connecting the signaling agent to a targeting moiety. In various embodiments, the linkers have lengths that allow for the formation of a site that has a disease cell and an effector cell without steric hindrance that would prevent modulation of the either cell.

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present chimeric proteins or chimeric protein complexes such as Fc-based chimeric protein complex.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments directed to chimeric proteins or chimeric protein complexes such as Fc-based chimeric protein complexes having two or more targeting moieties, a linker connects the two targeting moieties to each other and this linker has a short length and a linker connects a targeting moiety and a signaling agent this linker is longer than the linker connecting the two targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8 (SEQ ID NO:249-SEQ ID NO:256, respectively). In an embodiment, the linker sequence is GGSGGSGGGGSGGGGS (SEQ ID NO:257). Additional illustrative linkers include, but are not limited to, linkers having the sequence LE, GGGGS (SEQ ID NO:249), $(GGGGS)_n$ (n=1-4) (SEQ ID NO:249-SEQ ID NO:252), $(Gly)_8$ (SEQ ID NO:258), $(Gly)_6$ (SEQ ID NO:259), $(EAAAK)_n$ (n=1-3) (SEQ ID NO:260-SEQ ID NO:262), $A(EAAAK)_nA$ (n=2-5) (SEQ ID NO:263-SEQ ID NO:266), AEAAAKEAAAKA (SEQ ID NO:263), $A(EAAAK)_4ALEA(EAAAK)_4A$ (SEQ ID NO:267), PAPAP (SEQ ID NO:268), KESGSVSSEQLAQFRSLD (SEQ ID NO:269), EGKSSGSGSESKST (SEQ ID NO:270), GSAGSAAGSGEF (SEQ ID NO:271), and $(XP)_n$, with X designating any amino acid, e.g., Ala, Lys, or Glu. In various embodiments, the linker is GGS.

In some embodiments, the linker is one or more of GGGSE (SEQ ID NO: 272), GSESG (SEQ ID NO: 273), GSEGS (SEQ ID NO: 274), GEGGSGEGSSGEGSSSEGGGSEGGGSEGGGSEGGS (SEQ ID NO: 275), and a linker of randomly placed G, S, and E every 4 amino acid intervals.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys (SEQ ID NO: 276), which when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin.

In various embodiments, the linker of the present invention comprises one or more glycosylation sites. In various embodiments, the linker is a hinge-CH2-CH3 domain of a human IgG4 antibody.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present chimeric proteins or chimeric protein complexes such as Fc-based chimeric protein complex. In another example, the linker may function to target the chimeric proteins or chimeric protein complexes such as Fc-based chimeric protein complex to a particular cell type or location.

In various embodiments, the present chimeric proteins or chimeric protein complexes such as Fc-based chimeric protein complex may include one or more functional groups, residues, or moieties. In various embodiments, the one or more functional groups, residues, or moieties are attached or genetically fused to any of the signaling agents or targeting moieties described herein. In some embodiments, such functional groups, residues or moieties confer one or more desired properties or functionalities to the chimeric proteins or chimeric protein complexes such as Fc-based chimeric protein complex of the invention. Examples of such functional groups and of techniques for introducing them into the chimeric proteins or chimeric protein complexes such as Fc-based chimeric protein complex are known in the art, for example, see *Remington's Pharmaceutical Sciences,* 16th ed., Mack Publishing Co., Easton, Pa. (1980).

In various embodiments, each of the chimeric proteins or chimeric protein complexes such as Fc-based chimeric protein complex may by conjugated and/or fused with another agent to extend half-life or otherwise improve pharmacodynamic and pharmacokinetic properties. In some embodiments, the chimeric proteins or chimeric protein complexes such as Fc-based chimeric protein complex may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In various embodiments, each of the individual chimeric proteins or chimeric protein complexes such as Fc-based chimeric protein complex is fused to one or more of the agents described in BioDrugs (2015) 29:215-239, the entire contents of which are hereby incorporated by reference.

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG). In some embodiments, attachment of the PEG moiety increases the half-life and/or reduces the immunogenicity of the chimeric proteins or chimeric protein complexes such as Fc-based chimeric protein complex. Generally, any suitable form of pegylation can be used, such as the pegylation used in the art for antibodies and antibody fragments (including but not limited to single domain antibodies such as VHHs); see, for example, Chapman, *Nat. Biotechnol.,* 54, 531-545 (2002); by Veronese and Harris, *Adv. Drug Deliv. Rev.* 54, 453-456 (2003), by Harris and Chess, *Nat. Rev. Drug. Discov.,* 2, (2003) and in WO04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). In some embodiments, the chimeric proteins or chimeric protein complexes such as Fc-based chimeric protein complex of the invention is modified so as to suitably introduce one or more cysteine residues for attachment of PEG, or an amino acid sequence comprising one or more cysteine residues for attachment of PEG may be fused to the amino- and/or carboxy-terminus of the chimeric proteins or chimeric protein complexes such as Fc-based chimeric protein complex, using techniques known in the art.

In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VHHs and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the chimeric proteins or chimeric protein complexes such as Fc-based chimeric protein complex. In some embodiments, the chimeric proteins or chimeric protein complexes such as Fc-based chimeric protein complex may include a single tag or multiple tags. The tag for example is a peptide, sugar, or DNA molecule that does not inhibit or prevent binding of the chimeric proteins or chimeric protein complexes such as Fc-based chimeric protein complex to its target or any other antigen of interest such as tumor antigens. In various embodiments, the tag is at least about: three to five amino acids long, five to eight amino acids long, eight to twelve amino acids long, twelve to fifteen amino acids long, or fifteen to twenty amino acids long. Illustrative tags are described for example, in U.S. Patent Publication No. US2013/0058962. In some embodiment, the tag is an affinity tag such as glutathione-S-transferase (GST) and histidine (His) tag. In an embodiment, the chimeric proteins or chimeric protein complexes such as Fc-based chimeric protein complex comprises a His tag.

In some embodiments, the functional groups, residues, or moieties comprise a chelating group, for example, to chelate one of the metals or metallic cations. Suitable chelating groups, for example, include, without limitation, diethylenetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the chimeric proteins or chimeric protein complexes such as Fc-based chimeric protein complex of the invention to another protein, polypeptide or chemical compound that is bound to the other half of the binding pair, i.e., through formation of the binding pair. For example, a chimeric proteins or chimeric protein complexes such as Fc-based chimeric protein complex of the invention may be conjugated to biotin, and linked to another protein, polypeptide, compound or carrier conjugated to avidin or streptavidin. For example, such a conjugated chimeric proteins or chimeric protein complexes such as Fc-based chimeric protein complex may be used as a reporter, for example, in a diagnostic system where a detectable signal-producing agent is conjugated to avidin or streptavidin. Such binding pairs may, for example, also be used to bind the chimeric proteins or chimeric protein complexes such as Fc-based chimeric protein complex to a carrier, including carriers suitable for pharmaceutical purposes. One non-limiting example are the liposomal formulations described by Cao and Suresh, *Journal of Drug Targeting,* 8, 4, 257 (2000). Such binding pairs may also be used to link a therapeutically active agent to the chimeric proteins or chimeric protein complexes such as Fc-based chimeric protein complex of the invention.

Production of Chimeric Proteins or Chimeric Protein Complexes Such as Fc-Based Chimeric Protein Complex Methods for producing the chimeric proteins or chimeric protein complexes such as Fc-based chimeric protein complex of the invention are described herein. For example, DNA sequences encoding the chimeric proteins or chimeric protein complexes such as Fc-based chimeric protein complex of the invention (e.g., DNA sequences encoding the signaling agent (e.g., IFNα1 or a variant thereof) and the targeting moiety and the linker) can be chemically synthesized using methods known in the art. Synthetic DNA sequences can be ligated to other appropriate nucleotide sequences, including, e.g., expression control sequences, to produce gene expression constructs encoding the desired chimeric proteins or chimeric protein complexes such as Fc-based chimeric protein complex. Accordingly, in various embodiments, the present invention provides for isolated nucleic acids comprising a nucleotide sequence encoding the chimeric proteins or chimeric protein complexes such as Fc-based chimeric protein complex of the invention.

Nucleic acids encoding the chimeric proteins or chimeric protein complexes such as Fc-based chimeric protein complex of the invention can be incorporated (ligated) into expression vectors, which can be introduced into host cells through transfection, transformation, or transduction techniques. For example, nucleic acids encoding the chimeric proteins or chimeric protein complexes such as Fc-based chimeric protein complex of the invention can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the chimeric proteins or chimeric protein complexes such as Fc-based chimeric protein complex of the invention. Accordingly, in various embodiments, the present invention provides expression vectors comprising nucleic acids that encode the chimeric proteins or chimeric protein complexes such as Fc-based chimeric protein complex of the invention.

In various embodiments, the present invention additional provides host cells comprising such expression vectors. Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The chimeric proteins or chimeric protein complexes such as Fc-based chimeric protein complex of the invention can be produced by growing a host cell transfected with an expression vector encoding the chimeric proteins or chimeric protein complexes such as Fc-based chimeric protein complex under conditions that permit expression of the protein. Following expression, the protein can be harvested and purified using techniques well known in the art, e.g., affinity tags such as glutathione-S-transferase (GST) and histidine tags or by chromatography.

Accordingly, in various embodiments, the present invention provides for a nucleic acid encoding a chimeric proteins or chimeric protein complexes such as Fc-based chimeric protein complex of the present invention. In various embodiments, the present invention provides for a host cell comprising a nucleic acid encoding a chimeric proteins or chimeric protein complexes such as Fc-based chimeric protein complex of the present invention.

In various embodiments, IFNα1, its variant, or a chimeric proteins or chimeric protein complexes such as Fc-based chimeric protein complex comprising the IFNα1 or its variant may be expressed in vivo, for instance, in a patient. For example, in various embodiments, the IFNα1, its variant, or a chimeric proteins or chimeric protein complexes such as Fc-based chimeric protein complex comprising the IFNα1 or its variant may administered in the form of nucleic acid which encodes for the IFNα1 or its variant or chimeric proteins or chimeric protein complexes such as Fc-based chimeric protein complex comprising IFNα1 or its variant. In various embodiments, the nucleic acid is DNA or RNA. In some embodiments, the IFNα1, its variant, or a chimeric proteins or chimeric protein complexes such as Fc-based chimeric protein complex comprising the IFNα1 or its variant is encoded by a modified mRNA, i.e. an mRNA comprising one or more modified nucleotides. In some embodiments, the modified mRNA comprises one or modifications found in U.S. Pat. No. 8,278,036, the entire contents of which are hereby incorporated by reference. In some embodiments, the modified mRNA comprises one or more of m5C, m5U, m6A, s2U, ψ, and 2'-O-methyl-U. In some embodiments, the present invention relates to administering a modified mRNA encoding one or more of the present chimeric proteins or chimeric protein complexes such as Fc-based chimeric protein complex. In some embodiments, the present invention relates to gene therapy vectors comprising the same. In some embodiments, the present invention relates to gene therapy methods comprising the same. In various embodiments, the nucleic acid is in the form of an oncolytic virus, e.g. an adenovirus, reovirus, measles, herpes simplex, Newcastle disease virus or vaccinia.

In various embodiments, the chimeric proteins or chimeric protein complexes such as Fc-based chimeric protein complex comprises a targeting moiety that is a VHH. In various embodiments, the VHH is not limited to a specific biological source or to a specific method of preparation. For example, the VHH can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized VHH domain; (4) by "camelization" of a naturally occurring VH domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the chimeric proteins or chimeric protein complexes such as Fc-based chimeric protein complex comprises a VHH that corresponds to the $V_HH$ domains of naturally occurring heavy chain antibodies directed against a target of interest. In some embodiments, such $V_HH$ sequences can generally be generated or obtained by suitably immunizing a species of Camelid with a molecule of based on the target of interest (e.g., XCR1, Clec9a, CD8, SIRP1α, FAP, etc.) (i.e., so as to raise an immune response and/or heavy chain antibodies directed against the target of interest), by obtaining a suitable biological sample from the Camelid (such as a blood sample, or any sample of B-cells), and by generating $V_HH$ sequences directed against the target of interest, starting from the sample, using any suitable known techniques. In some embodiments, naturally occurring $V_HH$ domains against the target of interest can be obtained from naive libraries of Camelid $V_HH$ sequences, for example, by screening such a library using the target of interest or at least one part, fragment, antigenic determinant or epitope thereof using one or more screening techniques known in the art. Such libraries and techniques are, for example, described in WO 9937681, WO 0190190, WO 03025020 and WO 03035694, the entire contents of which are hereby incorporated by reference. In some embodiments, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as for example, described in WO 0043507, the entire contents of which are hereby incorporated by reference. In some embodiments, another technique for obtaining $V_HH$ sequences directed against a target of interest involves suitably immunizing a transgenic mammal that is capable of expressing heavy chain antibodies (i.e., so as to raise an immune response and/or heavy chain antibodies directed against the target of interest), obtaining a suitable biological sample from the transgenic mammal (such as a blood sample, or any sample of B-cells), and then generating $V_HH$ sequences directed against XCR1 starting from the sample, using any suitable known techniques. For example, for this purpose, the heavy chain antibody-expressing mice and the further methods and techniques described in WO 02085945 and in WO 04049794 (the entire contents of which are hereby incorporated by reference) can be used.

In an embodiment, the chimeric proteins or chimeric protein complexes such as Fc-based chimeric protein complex comprises a VHH that has been "humanized" i.e., by replacing one or more amino acid residues in the amino acid sequence of the naturally occurring $V_HH$ sequence (and in particular in the framework sequences) by one or more of the amino acid residues that occur at the corresponding position (s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the invention may become more "human-like," while still retaining favorable properties such as a reduced immunogenicity, compared to the corresponding naturally occurring $V_HH$ domains. In various embodiments, the humanized VHHs of the invention can be obtained in any suitable manner known in the art and thus are not strictly limited to polypeptides that have been obtained using a polypeptide that comprises a naturally occurring $V_HH$ domain as a starting material.

In an embodiment, the chimeric proteins or chimeric protein complexes such as Fc-based chimeric protein complex comprises a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a $V_HH$ domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In various embodiments, the camelized VHHs can be obtained in any suitable manner known in the art (i.e., as indicated under points (1)-(8) above) and thus are not strictly limited to polypeptides that have been obtained using a polypeptide that comprises a naturally occurring VH domain as a starting material.

In various embodiments, both "humanization" and "camelization" can be performed by providing a nucleotide sequence that encodes a naturally occurring $V_HH$ domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the invention. Alternatively, based on the amino acid sequence of a naturally occurring $V_HH$ domain or VH domain, respectively, the amino acid sequence of the desired humanized or camelized VHH of the invention, respectively, can be designed and then synthesized de novo using techniques for peptide synthesis known in the art. Also, based on the amino acid sequence or nucleotide sequence of a naturally occurring $V_HH$ domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the invention. Other suitable methods and techniques for obtaining the VHHs of the invention and/or nucleic acids encoding the same, starting from naturally occurring VH sequences or $V_HH$ sequences, are known in the art, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a VHH of the invention or a nucleotide sequence or nucleic acid encoding the same.

Pharmaceutically Acceptable Salts and Excipients

The chimeric proteins or chimeric protein complexes such as Fc-based chimeric protein complex described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, a-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to pharmaceutical compositions comprising the chimeric proteins or chimeric protein complexes such as Fc-based chimeric protein complex described herein and a pharmaceutically acceptable carrier or excipient. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the chimeric proteins or chimeric protein complexes such as Fc-based chimeric protein complex described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any chimeric proteins or chimeric protein complexes such as Fc-based chimeric protein complex described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the chimeric proteins or chimeric protein complexes such as Fc-based chimeric protein complex to be administered according to the present invention will vary according to the particular dosage form, and the mode of administration. Many factors that may modify the action of the chimeric proteins or chimeric protein complexes such as Fc-based chimeric protein complex (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the chimeric proteins or chimeric protein complexes such as Fc-based chimeric protein complex is in a range of about 0.01 μg/kg to about 100 mg/kg of body weight of the subject, about 0.01 μg/kg to about 10 mg/kg of body weight of the subject, or about 0.01 μg/kg to about 1 mg/kg of body weight of the subject for example, about 0.01 μg/kg, about 0.02 μg/kg, about 0.03 μg/kg, about 0.04 μg/kg, about 0.05 μg/kg, about 0.06 μg/kg, about 0.07 μg/kg, about 0.08 μg/kg, about 0.09 μg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, or about 100 mg/kg body weight, inclusive of all values and ranges therebetween.

Individual doses of the chimeric proteins or chimeric protein complexes such as Fc-based chimeric protein complex can be administered in unit dosage forms (e.g., tablets, capsules, or liquid formulations) containing, for example, from about 1 μg to about 100 mg, from about 1 μg to about 90 mg, from about 1 μg to about 80 mg, from about 1 μg to about 70 mg, from about 1 μg to about 60 mg, from about 1 μg to about 50 mg, from about 1 μg to about 40 mg, from about 1 μg to about 30 mg, from about 1 μg to about 20 mg, from about 1 μg to about 10 mg, from about 1 μg to about 5 mg, from about 1 μg to about 3 mg, from about 1 μg to about 1 mg per unit dosage form, or from about 1 μg to about 50 μg per unit dosage form. For example, a unit dosage form can be about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29, about 30 μg, about 35 μg, about 40 μg, about 45 μg, about 50 μg, about 60 μg, about 70 μg, about 80 μg, about 90 μg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween.

In one embodiment, the chimeric proteins or chimeric protein complexes such as Fc-based chimeric protein complex is administered at an amount of from about 1 μg to about 100 mg daily, from about 1 μg to about 90 mg daily, from about 1 μg to about 80 mg daily, from about 1 μg to about 70 mg daily, from about 1 μg to about 60 mg daily, from about 1 μg to about 50 mg daily, from about 1 μg to about 40 mg daily, from about 1 μg to about 30 mg daily, from about 1 μg to about 20 mg daily, from about 01 μg to about 10 mg daily, from about 1 μg to about 5 mg daily, from about 1 μg to about 3 mg daily, or from about 1 μg to about 1 mg daily. In various embodiments, the chimeric proteins or chimeric protein complexes such as Fc-based chimeric protein complex is administered at a daily dose of about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29, about 30 μg, about 35 μg, about 40 μg, about 45 μg, about 50 μg, about 60 μg, about 70 μg, about 80 μg, about 90 μg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween.

In accordance with certain embodiments of the invention, the pharmaceutical composition comprising the chimeric proteins or chimeric protein complexes such as Fc-based chimeric protein complex may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year. In an embodiment, the pharmaceutical composition comprising the chimeric proteins or chimeric protein complexes such as Fc-based chimeric protein complex is administered about three times a week.

In various embodiments, the present chimeric proteins or chimeric protein complexes such as Fc-based chimeric protein complex may be administered for a prolonged period. For example, the chimeric proteins or chimeric protein complexes such as Fc-based chimeric protein complex may be administered as described herein for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. For example, the chimeric proteins or chimeric protein complexes such as Fc-based chimeric protein complex may be administered for 12 weeks, 24 weeks, 36 weeks or 48 weeks. In some embodiments, the chimeric proteins or chimeric protein complexes such as Fc-based chimeric protein complex is administered for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. n some embodiments, the chimeric proteins or chimeric protein complexes such as Fc-based chimeric protein complex may be administered for at least about 1 year, at least about 2 years, at least about 3 years, at least about 4 years, or at least about 5 years.

Combination Therapy and Additional Therapeutic Agents

In various embodiments, the pharmaceutical composition of the present invention is co-administered in conjunction with additional therapeutic agent(s). Co-administration can be simultaneous or sequential.

In one embodiment, the additional therapeutic agent and the chimeric proteins or chimeric protein complexes such as Fc-based chimeric protein complex of the present invention are administered to a subject simultaneously. The term "simultaneously" as used herein, means that the additional therapeutic agent and the chimeric proteins or chimeric protein complexes such as Fc-based chimeric protein complex are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the chimeric proteins or chimeric protein complexes such as Fc-based chimeric protein complex can be by simultaneous administration of a single formulation (e.g., a formulation comprising the additional therapeutic agent and the chimeric proteins or chimeric protein complexes such as Fc-based chimeric protein complex) or of separate formulations (e.g., a first formulation including the additional therapeutic agent and a second formulation including the chimeric proteins or chimeric protein complexes such as Fc-based chimeric protein complex).

Co-administration does not require the therapeutic agents to be administered simultaneously, if the timing of their administration is such that the pharmacological activities of the additional therapeutic agent and the chimeric proteins or chimeric protein complexes such as Fc-based chimeric protein complex overlap in time, thereby exerting a combined therapeutic effect. For example, the additional therapeutic agent and the chimeric proteins or chimeric protein complexes such as Fc-based chimeric protein complex can be administered sequentially. The term "sequentially" as used herein means that the additional therapeutic agent and the chimeric proteins or chimeric protein complexes such as Fc-based chimeric protein complex are administered with a time separation of more than about 60 minutes. For example, the time between the sequential administration of the additional therapeutic agent and the chimeric proteins or chimeric protein complexes such as Fc-based chimeric protein complex can be more than about 60 minutes, more than about 2 hours, more than about 5 hours, more than about 10 hours, more than about 1 day, more than about 2 days, more than about 3 days, more than about 1 week apart, more than about 2 weeks apart, or more than about one month apart. The optimal administration times will depend on the rates of metabolism, excretion, and/or the pharmacodynamic activity of the additional therapeutic agent and the chimeric proteins or chimeric protein complexes such as Fc-based chimeric protein complex being administered. Either the additional therapeutic agent or the chimeric proteins or chimeric protein complexes such as Fc-based chimeric protein complex cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the chimeric proteins or chimeric protein complexes such as Fc-based chimeric protein complex described herein acts synergistically when co-administered with another therapeutic agent. In such embodiments, the chimeric proteins or chimeric protein complexes such as Fc-based chimeric protein complex and the additional therapeutic agent may be administered at doses that are lower than the doses employed when the agents are used in the context of monotherapy.

In some embodiments, the present invention pertains to chemotherapeutic agents as additional therapeutic agents. For example, without limitation, such combination of the present chimeric proteins or chimeric protein complexes such as Fc-based chimeric protein complex and chemotherapeutic agent find use in the treatment of cancers, as described elsewhere herein. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-5 norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, inclusive of, without limitation, infectious disease applications, the present invention pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In illustrative embodiments, the present invention pertains to the use of hepatitis therapeutics as additional therapeutic agents. In various embodiments, the hepatitis therapeutics include, but are not limited to, IFN-α such as INTRON A or pegylated IFN-α such as Pegasys or PEG-INTRON, ribavirin, boceprevir, simeprevir, sofosbuvir, simeprevir, daclatasvir, ledipasvir/sofosbuvir (Harvoni), ombitasvir/paritaprevir/ritonavir (Technivie), ombitasvir/paritaprevir/ritonavir/dasabuvir (Viekira Pak), lamivudine, adefovir, entecavir, telbivudine, entecavir, tenofovir, velpatasvir, elbasvir, grazoprevir, dasabuvir, and any combinations thereof. In an embodiment, the additional therapeutic agent is IFN-α (e.g., INTRON A) or pegylated IFN-α (e.g., Pegasys or PEG-INTRON). In another embodiment, the additional therapeutic agent is ribavirin.

In some embodiments, the present invention relates to combination therapies using the chimeric proteins or chimeric protein complexes such as Fc-based chimeric protein complex and an immunosuppressive agent. In some embodiments, the present invention relates to administration of the Clec9A binding agent to a patient undergoing treatment with an immunosuppressive agent.

In an embodiment, the immunosuppressive agent is TNF. In illustrative embodiments, the chimeric proteins or chimeric protein complexes such as Fc-based chimeric protein complex act synergistically when co-administered with TNF. In an illustrative embodiment, the chimeric proteins or chimeric protein complexes such as Fc-based chimeric protein complex acts synergistically when co-administered with TNF for use in treating tumor or cancer. For example, co-administration of the chimeric proteins or chimeric protein complexes such as Fc-based chimeric protein complex of the present invention and TNF may act synergistically to reduce or eliminate the tumor or cancer, or slow the growth and/or progression and/or metastasis of the tumor or cancer. In some embodiments, the combination of the chimeric proteins or chimeric protein complexes such as Fc-based chimeric protein complex and TNF may exhibit improved safety profiles when compared to the agents used alone in the context of monotherapy. In some embodiments, the chimeric proteins or chimeric protein complexes such as Fc-based chimeric protein complex and TNF may be administered at doses that are lower than the doses employed when the agents are used in the context of monotherapy.

In some embodiments, inclusive, without limitation, of autoimmune applications, the additional therapeutic agent is an immunosuppressive agent that is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluorometha-lone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosuppressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin). Additional anti-inflammatory agents are described, for example, in U.S. Pat. No. 4,537,776, the entire contents of which is incorporated by reference herein.

In some embodiments, the present invention pertains to various agents used for treating obesity as additional therapeutic agents. Illustrative agents used for treating obesity include, but are not limited to, orlistat (e.g. ALL1, XENICAL), loracaserin (e.g. BELVIQ), phentermine-topiramate (e.g. QSYMIA), sibutramme (e.g. REDUCTIL or MERJDIA), rimonabant (ACOMPLLA), exenatide (e.g. BYETTA), pramlintide (e.g. SYMLIN) phentermine, benzphetamine, diethylpropion, phendimetrazme, bupropion, and metformin. Agents that interfere with the body's ability to absorb specific nutrients in food are among the additional agents, e.g. orlistat (e.g. ALU, XENICAL), glucomannan, and guar gum. Agents that suppress appetite are also among the additional agents, e.g. catecholamines and their derivatives (such as phenetamine and other amphetamine-based drugs), various antidepressants and mood stabilizers (e.g. bupropion and topiramate), anorectics (e.g. dexedrine, digoxin). Agents that increase the body's metabolism are also among the additional agents.

In some embodiments, additional therapeutic agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NK1) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; dipeptidyl peptidase 4 (DPP-4) antagonists, agents for treating cardiovascular disease, agents for treating elevated triglyceride levels, agents for treating low HDL, agents for treating hypercholesterolemia, and agents for treating hypertension. Some agents for cardiovascular disease include statins (e.g. lovastatin, atorvastatin, fluvastatin, rosuvastatin, simvastatin and pravastatin) and omega-3 agents (e.g. LOVAZA, EPANQVA, VASCEPA, esterified omega-3's in general, fish oils, krill oils, algal oils). In some embodiments, additional agents may be selected from among amphetamines, benzodiazepines, sulfonyl ureas, meglitinides, thiazolidinediones, biguanides, beta-blockers, XCE inhibitors, diuretics, nitrates, calcium channel blockers, phentermine, sibutramine, iorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, repaglinide, nateglinide, glimepiride, metformin, pioglitazone, rosiglitazone, and sitagliptin.

In some embodiments, the present invention pertains to an agent used for treating diabetes as additional therapeutic agents. Illustrative anti-diabetic agents include, but are not limited to, sulfonylurea (e.g., DYMELOR (acetohexamide), DIABINESE (chlorpropamide), ORINASE (tolbutamide), and TOLINASE (tolazamide), GLUCOTROL (glipizide), GLUCOTROL XL (extended release), DIABETA (glyburide), MICRONASE (glyburide), GLYNASE PRESTAB (glyburide), and AMARYL (glimepiride)); a Biguanide (e.g. metformin (GLUCOPHAGE, GLUCOPHAGE XR, RIOMET, FORTAMET, and GLUMETZA)); a thiazolidinedione (e.g. ACTOS (pioglitazone) and AVANDIA (rosiglitazone); an alpha-glucosidase inhibitor (e.g., PRECOSE (acarbose) and GLYSET (miglitol); a Meglitinide (e.g., PRANDIN (repaglinide) and STARLIX (nateglinide)); a Dipeptidyl peptidase IV (DPP-IV) inhibitor (e.g., JANUVIA (sitagliptin), NESINA (alogliptin), ONGLYZA (saxagliptin), and TRADJENTA (linagliptin)); Sodium-glucose co-transporter 2 (SGLT2) inhibitor (e.g. INVOKANA (canagliflozin)); and a combination pill (e.g. GLUCOVANCE, which combines glyburide (a sulfonylurea) and metformin, METAGLIP, which combines glipizide (a sulfonylurea) and metformin, and AVANDAMET, which uses both metformin and rosiglitazone (AVANDIA) in one pill, KAZANO (alogliptin and metformin), OSENI (alogliptin plus pioglitazone), METFORMIN oral, ACTOS oral, BYETTA subcutaneous, JANUVIA oral, WELCHOL oral, JANUMET oral, glipizide oral, glimepiride oral, GLUCOPHAGE oral, LANTUS subcutaneous, glyburide oral, ONGLYZA oral, AMARYI oral, LANTUS SOLOSTAR subcutaneous, BYDUREON subcutaneous, LEVEMIR FLEXPEN subcutaneous, ACTOPLUS MET oral, GLUMETZA oral, TRADJENTA oral, bromocriptine oral, KOMBIGLYZE XR oral, INVOKANA oral, PRANDIN oral, LEVEMIR subcutaneous, PARLODEL oral, pioglitazone oral, NOVOLOG subcutaneous, NOVOLOG FLEXPEN subcutaneous, VICTOZA 2-PAK subcutaneous, HUMALOG subcutaneous, STARLIX oral, FORTAMET oral, GLUCOVANCE oral, GLUCOPHAGE XR oral, NOVOLOG Mix 70-30 FLEXPEN subcutaneous, GLYBURIDE-METFORMIN oral, acarbose oral, SYMLINPEN 60 subcutaneous, GLUCOTROI XL oral, NOVOLIN R inj, GLUCOTROL oral, DUETACT oral, sitagliptin oral, SYMLINPEN 120 subcutaneous, HUMALOG KWIKPEN subcutaneous, JANUMET XR oral, GLIPIZIDE-METFORMIN oral, CYCLOSET oral, HUMALOG MIX 75-25 subcutaneous, nateglinide oral, HUMALOG Mix 75-25 KWIKPEN subcutaneous, HUMULIN 70/30 subcutaneous, PRECOSE oral, APIDRA subcutaneous, Humulin R inj, Jentadueto oral, Victoza 3-Pak subcutaneous, Novolin 70/30 subcutaneous, NOVOLIN N subcutaneous, insulin detemir subcutaneous, glyburide micronized oral, GLYNASE oral, HUMULIN N subcutaneous, insulin glargine subcutaneous, RIOMET oral, pioglitazone-metformin oral, APIDRA SOLOSTAR subcutaneous, insulin lispro subcutaneous, GLYSET oral, HUMULIN 70/30 Pen subcutaneous, colesevelam oral, sitagliptin-metformin oral, DIABETA oral, insulin regular human inj, HUMULIN N Pen subcutaneous, exenatide subcutaneous, HUMALOG Mix 50-50 KWIKPEN subcutaneous, liraglutide subcutaneous, KAZANO oral, repaglinide oral, chlorpropamide oral, insulin aspart subcutaneous, NOVOLOG Mix 70-30 subcutaneous, HUMALOG Mix 50-50 subcutaneous, saxagliptin oral, ACTOPLUS Met XR oral, miglitol oral, NPH insulin human recomb subcutaneous, insulin NPH and regular human subcutaneous, tolazamide oral, mifepristone oral, insulin aspart protam-insulin aspart subcutaneous, repaglinide-metformin oral, saxagliptin-metformin oral, linagliptin-metformin oral, NESINA oral, OSENI oral, tolbutamide oral, insulin lispro protamine and lispro subcutaneous, pramlintide subcutaneous, insulin glulisine subcutaneous, pioglitazone-glimepiride oral, PRANDIMET oral, NOVOLOG PenFill subcutaneous, linagliptin oral, exenatide microspheres subcutaneous, KORLYM oral, alogliptin oral, alogliptin-pioglitazone oral, alogliptin-metformin oral, canagliflozin oral, Lispro (HUMALOG); Aspart (NOVOLOG); Glulisine (APIDRA); Regular (NOVOLIN R or HUMULIN R); NPH (NOVOLIN N or HUMULIN N); Glargine (LANTUS); Detemir (LEVEMIR); HUMULIN or NOVOLIN 70/30; and NOVOLOG Mix 70/30 HUMALOG Mix 75/25 or 50/50.

In some embodiments, the chimeric proteins or chimeric protein complexes such as Fc-based chimeric protein complex of the present invention act synergistically when used in combination with Chimeric Antigen Receptor (CAR) T-cell therapy. In an illustrative embodiment, the chimeric proteins or chimeric protein complexes such as Fc-based chimeric protein complex acts synergistically when used in combination with CAR T-cell therapy in treating tumor or cancer. In an embodiment, the chimeric proteins or chimeric protein complexes such as Fc-based chimeric protein complex agent acts synergistically when used in combination with CAR T-cell therapy in treating blood-based tumors. In an embodiment, the chimeric proteins or chimeric protein complexes such as Fc-based chimeric protein complex acts synergistically when used in combination with CAR T-cell therapy in treating solid tumors. For example, use of the chimeric proteins or chimeric protein complexes such as Fc-based chimeric protein complex and CAR T-cells may act synergistically to reduce or eliminate the tumor or cancer, or slow the growth and/or progression and/or metastasis of the tumor or cancer. In various embodiments, the chimeric proteins or chimeric protein complexes such as Fc-based chimeric protein complex of the invention induces CAR T-cell division. In various embodiments, the chimeric proteins or chimeric protein complexes such as Fc-based chimeric protein complex of the invention induces CAR T-cell proliferation. In various embodiments, the chimeric proteins or chimeric protein complexes such as Fc-based chimeric protein complex of the invention prevents anergy of the CAR T cells.

In various embodiments, the CAR T-cell therapy comprises CAR T cells that target antigens (e.g., tumor antigens) such as, but not limited to, carbonic anhydrase IX (CAIX), 5T4, CD19, CD20, CD22, CD30, CD33, CD38, CD47, CS1, CD138, Lewis-Y, L1-CAM, MUC16, ROR-1, IL13Rα2, gp100, prostate stem cell antigen (PSCA), prostate-specific membrane antigen (PSMA), B-cell maturation antigen (BCMA), human papillomavirus type 16 E6 (HPV-16 E6), CD171, folate receptor alpha (FR-α), GD2, human epidermal growth factor receptor 2 (HER2), mesothelin, EGFRvIII, fibroblast activation protein (FAP), carcinoembryonic antigen (CEA), and vascular endothelial growth factor receptor 2 (VEGF-R2), as well as other tumor antigens well known in the art. Additional illustrative tumor antigens include, but are not limited to MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD37, CD56, CD70, CD74, CD138, AGS16, MUC1, GPNMB, Ep-CAM, PD-L1, and PD-L2.

Illustrative CAR T-cell therapy include, but are not limited to, JCAR014 (Juno Therapeutics), JCAR015 (Juno Therapeutics), JCAR017 (Juno Therapeutics), JCAR018 (Juno Therapeutics), JCAR020 (Juno Therapeutics), JCAR023 (Juno Therapeutics), JCAR024 (Juno Therapeutics), CTL019 (Novartis), KTE-C19 (Kite Pharma), BPX-401 (Bellicum Pharmaceuticals), BPX-501 (Bellicum Pharmaceuticals), BPX-601 (Bellicum Pharmaceuticals), bb2121 (Bluebird Bio), CD-19 Sleeping Beauty cells (Ziopharm Oncology), UCART19 (Cellectis), UCART123 (Cellectis), UCART38 (Cellectis), UCARTCS1 (Cellectis), OXB-302 (Oxford BioMedica, MB-101 (Mustang Bio) and CAR T-cells developed by Innovative Cellular Therapeutics.

In some embodiments, the chimeric proteins or chimeric protein complexes such as Fc-based chimeric protein complex of the present invention is used in a method of treating multiple sclerosis (MS) in combination with one or more MS therapeutics including, but not limited to, 3-interferons, glatiramer acetate, T-interferon, IFN-R-2 (U.S. Patent Publication No. 2002/0025304), spirogermaniums (e.g., N-(3-dimethylaminopropyl)-2-aza-8,8-dimethyl-8-germanspiro [4:5] decane, N-(3-dimethylaminopropyl)-2-aza-8,8-diethyl-8-germaspiro [4:5] decane, N-(3-dimethylaminopropyl)-2-aza-8,8-dipropyl-8-germaspiro [4:5] decane, and N-(3-dimethylaminopropyl)-2-aza-8,8-dibutyl-8-germaspiro [4:5] decane), vitamin D analogs (e.g., 1,25 (OH) 2D3, (see, e.g., U.S. Pat. No. 5,716,946)), prostaglandins (e.g., latanoprost, brimonidine, PGE1, PGE2 and PGE3, see, e.g., U. S. Patent Publication No. 2002/0004525), tetracycline and derivatives (e.g., minocycline and doxycycline, see, e.g., U.S. Patent Publication No. 20020022608), a VLA-4 binding antibody (see, e.g., U.S. Patent Publication No. 2009/0202527), adrenocorticotrophic hormone, corticosteroid, prednisone, methylprednisone, 2-chlorodeoxyadenosine, mitoxantrone, sulphasalazine, methotrexate, azathioprine, cyclophosphamide, cyclosporin, fumarate, anti-CD20 antibody (e.g., rituximab), and tizanidine hydrochloride.

In some embodiments, the chimeric proteins or chimeric protein complexes such as Fc-based chimeric protein complex is used in combination with one or more therapeutic agents that treat one or more symptoms or side effects of MS. Such agents include, but are not limited to, amantadine, baclofen, papaverine, meclizine, hydroxyzine, sulfamethoxazole, ciprofloxacin, docusate, pemoline, dantrolene, desmopressin, dexamethasone, tolterodine, phenyloin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline.

In some embodiments, the chimeric proteins or chimeric protein complexes such as Fc-based chimeric protein complex is used in a method of treating multiple sclerosis in combination with one or more of the disease modifying therapies (DMTs) described herein (e.g. the agents of Table 6). In some embodiments, the present invention provides an improved therapeutic effect as compared to use of one or more of the DMTs described herein (e.g. the agents listed in Table 6 below) without the one or more disclosed binding agent. In an embodiment, the combination of the chimeric proteins or chimeric protein complexes such as Fc-based chimeric protein complex and the one or more DMTs produces synergistic therapeutic effects.

Illustrative disease modifying therapies include, but are not limited to:

TABLE 6

| Generic Name | Branded Name/Company | Frequency/Route of Delivery/Usual Dose |
|---|---|---|
| teriflunomide | AUBAGIO (GENZYME) | Every day; pill taken orally; 7 mg or 14 mg. |
| interferon beta-1a | AVONEX (BIOGEN IDEC) | Once a week; intramuscular (into the muscle) injection; 30 mcg |
| interferon beta-1b | BETASERON (BAYER HEALTHCARE PHARMACEUTICALS, INC.) | Every other day; subcutaneous (under the skin) injection; 250 mcg. |
| glatiramer acetate | COPAXONE (TEVA NEUROSCIENCE) | Every day; subcutaneous (under the skin) injection; 20 mg (20,000 mcg) OR Three times a week; subcutaneous (under the skin) injection; 40 mg (40,000 mcg) |
| interferon beta-1b | EXTAVIA (NOVARTIS PHARMACEUTICALS CORP.) | Every other day; subcutaneous (under the skin) injection; 250 mcg. |
| fingolimod | GILENYA (NOVARTIS PHARMACEUTICALS CORP.) | Every day; capsule taken orally; 0.5 mg. |
| Alemtuzumab (anti-CD52 monoclonal antibody) | LEMTRADA (GENZYME) | Intravenous infusion on five consecutive days, followed by intravenous infusion on three consecutive days one year later (12 mg) |
| mitoxantrone | NOVANTRONE(EMD SERONO) | Four times a year by IV infusion in a medical facility. Lifetime cumulative dose limit of approximately 8-12 doses over 2-3 years (140 mg/m2). |
| pegylated interferon beta-1a | PLEGRIDY (BIOGEN IDEC) | Every 14 days; subcutaneous (under the skin) injection; 125 mcg |
| interferon beta-1a | REBIF (EMD SERONO, INC.) | Three times a week; subcutaneous (under the skin) injection; 44 mcg |
| dimethyl fumarate (BG-12) | TECFIDERA (BIOGEN IDEC) | Twice a day; capsule taken orally; 120 mg for one week and 240 mg therafter |
| Natalizumab (humanized monoclonal antibody VLA-4 antagonist) | TYSABRI (BIOGEN IDEC) | Every four weeks by IV infusion in a registered infusion facility; 300 mg |

TABLE 6-continued

| Generic Name | Branded Name/Company | Frequency/Route of Delivery/Usual Dose |
|---|---|---|
| DMTs in Development | | |
| Amiloride (targets Acid-sensing ion channel-1 Epithelial sodium channel Na+/H+ exchanger) | PAR PHARMACEUTICAL, PERRIGO COMPANY, SIGMAPHARM LABORATORIES | Oral |
| ATX-MS-1467 (targets Major histocompatibility complex class II T cell responses to myelin basic protein) | APITOPE/MERCK SERONO | Intradermal Subcutaneous |
| BAF312 (targets Sphingosine 1-phosphate (S1P) receptor subtypes S1P1 and S1P5B cell distrubution T cell distribution) | NOVARTIS PHARMA | Oral |
| BGC20-0134 (targets Proinflammatory and anti-inflammatory cytokines) | BTG PLC | Oral |
| BHB033 (targets LINGO-1 (“leucine-rich repeat and immunoglobulin-like domain-containing, Nogo receptor-interacting protein”)) | BIOGEN | Intravenous infusion used in Phase I and Phase II trials Subcutaneous injection used in Phase I trial |
| Cladribine (targets CD4+ T cells DNA synthesis and repair E-selectin Intracellular adhesion molecule-1 Pro-inflammatory cytokines interleukin 2 and interleukin 2R Pro-inflammatory cytokines interleukin 8 and RANTES Cytokine secretion Monocyte and lymphocyte migration) | MERCK SERONO | Oral |
| Cyclophosphamide (targets T cells, particularly CD4+ helper T cells B cells) | BAXTER HEALTHCARE CORPORATION | Oral, monthly intravenous pulses |
| Daclizumab (humanized monoclonal antibody targeting CD25 Immune modulator of T cells) | BIOGEN IDEC/ABBVIE BIOTHERAPEUTICS | Projected to be IM injection once monthly |
| Dalfampridine (targets Voltage-gated potassium channels Degenerin/epithelial sodium channels L-type calcium channels that contain subunit Cavbeta3) | ACORDA THERAPEUTICS/ BIOGEN IDEC | One tablet every 12 hours (extended release), 10 mg twice a day |
| Dronabinol (targets Cannabinoid receptor CB1 Cannabinoid receptor CB2) | ABBVIE INC. | Oral |
| Firategrast (targets Alpha4beta1 integrin) | GLAXOSMITHKLINE | Oral |
| GNbACI MSRV-Env (targets envelope protein of the MS-associated retrovirus) | GENEURO SA/SERVIER | Intravenous infusion |
| Idebenone (targets Reactive oxygen species) | SANTHERA PHARMACEUTICALS | Oral Dose in clinical trial for PPMS is 2250 mg per day (750 mg dose, 3 times per day) |
| Imilecleucel-T (targets Myelin-specific, autoreactive T cells) | OPEXA THERAPEUTICS/ MERCK SERONO | Subcutaneous Given 5 times per year, according to information from the manufacturer |
| Laquinimod | TEVA | Projected to be 0.6 mg or 1.2 mg oral tablet taken daily |
| Masitinib (targets KIT (a stem cell factor, also called c-KIT) receptor as well as select other tyrosine kinases Mast cells) | AB SCIENCE | Oral |
| MEDI-551 (targets CD19, a B cell-specific antigen that is part of the B cell receptor complex and that functions in determining the threshold for B cell activation B cells Plasmablasts, B cells that express CD 19 (but not CD20) and that secrete large | MEDIMMUNE | Intravenous Subcutaneous |

TABLE 6-continued

| Generic Name | Branded Name/Company | Frequency/Route of Delivery/Usual Dose |
|---|---|---|
| quantities of antibodies; depletion of plasmablasts may be useful in autoimmune diseases involving pathogenic autoantibodies) | | |
| Minocycline (targets T cells Microglia Leukocyte migration Matrix metalloproteinases) | VARIOUS | Oral Available as pellet-filled capsules and an oral suspension |
| MIS416 (targets Innate immune system Pathogen-associated molecular pattern recognition receptors of the innate immune system Myeloid cells of the innate immune system, which might be able to remodel the deregulated immune system activity that occurs in SPMS) | INNATE IMMUNOTHERAPEUTICS | Intravenous |
| Mycophenolate mofetil (targets Purine synthesis) | MANUFACTURED BY GENENTECH | Oral |
| Naltrexone (targets Opioid receptors Toll-like receptor 4) | VARIOUS | Given at low doses (3 to 4.5 mg per day) in oral form as"Low-dose naltrexone" (or "LDN") |
| Ocrelizumab and Ofatumumab (humanized monoclonal antibodies targeting CD20 B cell suppression | ROCHE/GSK | Projected to be IV infusion |
| ONO-4641 (targets Sphingosine 1-phosphate receptor) | ONO PHARMACEUTICAL CO. | Oral |
| Phenytoin (targets Sodium channels) | PFIZER | Intravenous Intramuscular (less favored option) Oral |
| Ponesimod | ACTELION | To be determined |
| Raltegravir (targets Retroviral integrase Herpesvirus DNA packaging terminase) | MERCK | Oral 400 mg tablet twice daily, according to information from the manufacturer |
| RHB-104 | REDHILL BIOPHARMA LIMITED | 95 mg clarithromycin, 45 mg rifabutin, and 10 mg clofazimine |
| Riluzole (targets Glutamatergic neurotransmission Glutamate uptake and release Voltage-gated sodium channels Protein kinase C) | COVIS PHARMA/SANOFI | Oral |

In some embodiments, the present invention relates to combination therapy with a blood transfusion. For instance, the present compositions may supplement a blood transfusion. In some embodiments, the present invention relates to combination therapy with iron supplements.

In some embodiments, the present invention relates to combination therapy with one or more EPO-based agents. For example, the present compositions may be used as an adjuvant to other EPO-based agents. In some embodiments, the present compositions are used as a maintenance therapy to other EPO-based agents. Other EPO-based agents include the following: epoetin alfa, including without limitation, DARBEPOETIN (ARANESP), EPOCEPT (LUPIN PHARMA), NANOKINE (NANOGEN PHARMACEUTICAL), EPOFIT (INTAS PHARMA), EPOGEN (AMGEN), EPOGIN, EPREX, (JANSSEN-CILAG), BINOCRIT7 (SANDOZ), PROCRIT; epoetin beta, including without limitation, NEORECORMON (HOFFMANN-LA ROCHE), RECORMON, Methoxy polyethylene glycol-epoetin beta (MIRCERA, ROCHE); epoetin delta, including without limitation, DYNEPO (erythropoiesis stimulating protein, SHIRE PLC); epoetin omega, including without limitation, EPOMAX; epoetin zeta, including without limitation, SILAPO (STADA) and RETACRIT (HOSPIRA) and other EPOs, including without limitation, EPOCEPT (LUPIN PHARMACEUTICALS), EPOTRUST (PANACEA BIOTEC LTD), ERYPRO SAFE (BIOCON LTD.), REPOITIN (SERUM INSTITUTE OF INDIA LIMITED), VINTOR (EMCURE PHARMACEUTICALS), EPOFIT (INTAS PHARMA), ERYKINE (INTAS BIOPHARMACEUTICA), WEPDX (WOCKHARDT BIOTECH), ESPOGEN (LG LIFE SCIENCES), RELIPOIETIN (RELIANCE LIFE SCIENCES), SHANPOIETIN (SHANTHA BIOTECHNICS LTD), ZYROP (CADILA HEALTHCARE LTD.), EPIAO (RHUEPO) (SHENYANG SUNSHINE PHARMACEUTICAL CO. LTD), CINNAPOIETIN (CINNAGEN).

In some embodiments, the present invention relates to combination therapy with one or more immune-modulating agents, for example, without limitation, agents that modulate immune checkpoint. In various embodiments, the immune-modulating agent targets one or more of PD-1, PD-L1, and PD-L2. In various embodiments, the immune-modulating agent is PD-1 inhibitor. In various embodiments, the immune-modulating agent is an antibody specific for one or more of PD-1, PD-L1, and PD-L2. For instance, in some embodiments, the immune-modulating agent is an antibody such as, by way of non-limitation, nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE). In some embodiments, the immune-modulating agent targets one or more of CD137 or CD137L. In various embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the present chimeric proteins or chimeric protein complexes such as Fc-based chimeric protein complex is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an agent that targets one or more of CTLA-4, AP2M1, CD80, CD86, SHP-2, and PPP2R5A. In various embodiments, the immune-modulating agent is an antibody specific for one or more of CTLA-4, AP2M1, CD80, CD86, SHP-2, and PPP2R5A. For instance, in some embodiments, the immune-modulating agent is an antibody such as, by way of non-limitation, ipilimumab (MDX-010, MDX-101, Yervoy, BMS) and/or tremelimumab (Pfizer). In some embodiments, the present chimeric proteins or chimeric protein complexes such as Fc-based chimeric protein complex is combined with ipilimumab (optionally with bavituximab) for the treatment of one or more of melanoma, prostate cancer, and lung cancer. In various embodiments, the immune-modulating agent targets CD20. In various embodiments, the immune-modulating agent is an antibody specific CD20. For instance, in some embodiments, the immune-modulating agent is an antibody such as, by way of non-limitation, Ofatumumab (GENMAB), obinutuzumab (GAZYVA), AME-133v (APPLIED MOLECULAR EVOLUTION), Ocrelizumab (GENENTECH), TRU-015 (TRUBION/EMERGENT), veltuzumab (IMMU-106).

In some embodiments, the present invention relates to combination therapy with one or more chimeric agents described in WO 2013/10779, WO 2015/007536, WO 2015/007520, WO 2015/007542, and WO 2015/007903, the entire contents of which are hereby incorporated by reference in their entireties.

In some embodiments, the chimeric proteins or chimeric protein complexes such as Fc-based chimeric protein complex described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the chimeric proteins or chimeric protein complexes such as Fc-based chimeric protein complex described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The chimeric proteins or chimeric protein complexes such as Fc-based chimeric protein complex described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and Pseudomonas toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the chimeric proteins or chimeric protein complexes such as Fc-based chimeric protein complex, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment

Methods and compositions described herein have application to treating various diseases and disorders, including, but not limited to cancer, infections, immune disorders, anemia, autoimmune diseases, cardiovascular diseases, wound healing, ischemia-related diseases, neurodegenerative diseases, metabolic diseases and many other diseases and disorders.

Further, any of the present agents may be for use in the treating, or the manufacture of a medicament for treating, various diseases and disorders, including, but not limited to cancer, infections, immune disorders, inflammatory diseases or conditions, and autoimmune diseases.

In some embodiments, the present invention relates to the treatment of, or a patient having one or more of chronic granulomatous disease, osteopetrosis, idiopathic pulmonary fibrosis, Friedreich's ataxia, atopic dermatitis, Chagas disease, cancer, heart failure, autoimmune disease, sickle cell disease, thalassemia, blood loss, transfusion reaction, diabetes, vitamin B12 deficiency, collagen vascular disease, Shwachman syndrome, thrombocytopenic purpura, Celiac disease, endocrine deficiency state such as hypothyroidism or Addison's disease, autoimmune disease such as Crohn's Disease, systemic lupus erythematosis, rheumatoid arthritis or juvenile rheumatoid arthritis, ulcerative colitis immune disorders such as eosinophilic fasciitis, hypoimmunoglobulinemia, or thymoma/thymic carcinoma, graft versus host disease, preleukemia, Nonhematologic syndrome (e.g. Down's, Dubowwitz, Seckel), Felty syndrome, hemolytic uremic syndrome, myelodysplasic syndrome, nocturnal paroxysmal hemoglobinuria, osteomyelofibrosis, pancytopenia, pure red-cell aplasia, Schoenlein-Henoch purpura, malaria, protein starvation, menorrhagia, systemic sclerosis, liver cirrhosis, hypometabolic states, and congestive heart failure.

In some embodiments, the present invention is related to a method for treating cancer, comprising administering an effective amount of i) the chimeric protein, the chimeric protein complex and/or the Fc-based chimeric protein complex to a patient in need thereof; ii) a recombinant nucleic acid encoding the chimeric protein, the chimeric protein complex and/or the Fc-based chimeric protein complex to a patient in need thereof; or iii) a host cell comprising the recombinant nucleic acid encoding the chimeric protein, the chimeric protein complex and/or the Fc-based chimeric protein complex to a patient in need thereof.

In some embodiments, the present invention relates to the treatment of, or a patient having one or more of chronic granulomatous disease, osteopetrosis, idiopathic pulmonary fibrosis, Friedreich's ataxia, atopic dermatitis, Chagas disease, mycobacterial infections, cancer, scleroderma, hepatitis, hepatitis C, septic shock, and rheumatoid arthritis.

In some embodiments, the present invention relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma (e.g., Kaposi's sarcoma); skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome. In an embodiment, the present invention relates to the treatment of leukemia including hairy cell leukemia. In another embodiment, the present invention relates to the treatment of melanoma including malignant melanoma. In a further embodiment, the present invention relates to the treatment of Kaposi's sarcoma including AIDS-related Kaposi's sarcoma.

In some embodiments, the present invention relates to the treatment of, or a patient having a microbial infection and/or chronic infection. Illustrative infections include, but are not limited to, Chagas disease, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

In some embodiments, the present invention relates to the treatment of hepatitis. Illustrative hepatitis that may be treated include, but is not limited to, hepatitis A, hepatitis B, hepatitis C, hepatitis D, hepatitis E, autoimmune hepatitis, alcoholic hepatitis, acute hepatitis, and chronic hepatitis.

In an illustrative embodiment, the present invention relates to the treatment of chronic hepatitis C. In an embodiment, the chimeric proteins or chimeric protein complexes such as Fc-based chimeric protein complex of the invention may be utilized to treat a patient infected with any one of the hepatitis C genotypes, including genotype 1 (e.g., 1a, 1b), genotype 2 (e.g. 2a, 2b, 2c and 2d), genotype 3 (e.g., 3a, 3b, 3c, 3d, 3e, and 3f), genotype 4 (e.g., 4a, 4b, 4c, 4d, 4e, 4f, 4g, 4h, 4i and 4j), genotype 5a, and genotype 6a.

In various embodiments, the chimeric proteins or chimeric protein complexes such as Fc-based chimeric protein complex of the invention may be utilized to treat patients who are poorly or non-responsive to standard of care anti-viral therapy or who are otherwise difficult to treat with standard of care hepatitis C treatment. In an embodiment, the chimeric proteins or chimeric protein complexes such as Fc-based chimeric protein complex may be utilized to treat a patient who shows low or no response to IFN-α therapy (e.g., IFN-α2a or IFN-α2b or pegylated IFN-α) with or without ribavirin. In an embodiment, the chimeric proteins or chimeric protein complexes such as Fc-based chimeric protein complex may be utilized to treat a patient who shows low or no response to combination therapy of pegylated interferon and ribavirin. In an embodiment, the present invention is directed to the treatment of patients infected with hepatitis C genotype 1 or any other genotype who did not respond to previous IFN-α therapy. In an embodiment, the chimeric proteins or chimeric protein complexes such as Fc-based chimeric protein complex of the invention may be used to treat a patient with high baseline viral load (e.g., greater than 800,000 IU/mL). In an embodiment, the chimeric proteins or chimeric protein complexes such as Fc-based chimeric protein complex of the invention may be utilized to treat patients with severe liver damage including those patients with advanced liver fibrosis and/or liver cirrhosis.

In some embodiments, the present invention relates to the treatment of patients who are naive to antiviral therapy.

In other embodiments, the present invention relates to the treatment of patients who did not respond to previous antiviral therapy. In some embodiments, the present chimeric proteins or chimeric protein complexes such as Fc-based chimeric protein complex may be used to treat relapsed patients.

In some embodiments, the present chimeric proteins or chimeric protein complexes such as Fc-based chimeric protein complex may be effective in treating hepatitis infection in all ethnic groups including white, African-American, Hispanic, and Asian. In an embodiment, the present chimeric proteins or chimeric protein complexes such as Fc-based chimeric protein complex may be particularly effective in treating African-Americans who are otherwise poorly responsive to IFN-α therapy with or without ribavirin.

In various embodiments, the targeted chimeric proteins or chimeric protein complexes such as Fc-based chimeric protein complex of the invention provides improved safety compared to, e.g., untargeted IFNα1 or an unmodified, wildtype IFNα1 or a modified IFNα1 (e.g., pegylated IFNα1). In illustrative embodiments, administration of the present chimeric proteins or chimeric protein complexes such as Fc-based chimeric protein complex is associated with minimal side effects such as those side effects associated with the use of the untargeted IFNα1 or an unmodified, wildtype IFN-a or a modified IFN-a (e.g., influenza-like symptoms, myalgia, leucopenia, thrombocytopenia, neutropenia, depression, and weight loss).

In some embodiments, the targeted chimeric proteins or chimeric protein complexes such as Fc-based chimeric protein complex of the invention shows improved therapeutic activity compared to untargeted IFNα1 or an unmodified, wildtype IFNα1, or a modified IFNα1 (e.g., pegylated IFNα1). In some embodiments, the targeted chimeric proteins or chimeric protein complexes such as Fc-based chimeric protein complex of the invention shows improved pharmacokinetic profile (e.g., longer serum half-life and stability) compared to untargeted IFNα1 or an unmodified, wildtype IFNα1 or a modified IFNα1 (e.g., pegylated IFNα1).

Without wishing to be bound by theory, it is believed that due to such advantageous safety and pharmacokinetic and therapeutic profiles, the present chimeric proteins or chimeric protein complexes such as Fc-based chimeric protein complex may be used to treat patients at high dosages and/or for prolonged periods of time. For example, the present chimeric proteins or chimeric protein complexes such as Fc-based chimeric protein complex may be used at high dosages for initial induction therapy against chronic hepatitis C infection. In another example, the present chimeric proteins or chimeric protein complexes such as Fc-based chimeric protein complex may be used for long-term maintenance therapy to prevent disease relapse.

In various embodiments, the present compositions are used to treat or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses. In various embodiments, the present compositions are used to treat or prevent one or more autoimmune diseases or conditions, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

In various embodiments, the present compositions are used to treat, control or prevent cardiovascular disease, such as a disease or condition affecting the heart and vasculature, including but not limited to, coronary heart disease (CHD), cerebrovascular disease (CVD), aortic stenosis, peripheral vascular disease, atherosclerosis, arteriosclerosis, myocardial infarction (heart attack), cerebrovascular diseases (stroke), transient ischemic attacks (TIA), angina (stable and unstable), atrial fibrillation, arrhythmia, valvular disease, and/or congestive heart failure.

In various embodiments, the present compositions are used to treat or prevent one or more metabolic-related disorders. In various embodiments, the present invention is useful for the treatment, controlling or prevention of diabetes, including Type 1 and Type 2 diabetes and diabetes associated with obesity. The compositions and methods of the present invention are useful for the treatment or prevention of diabetes-related disorders, including without limitation diabetic nephropathy, hyperglycemia, impaired glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflamatory bowel disease, including Crohn's disease and ulcerative colitis, other inflammatory conditions, pancreatitis, abdominal obesity, neurodegenerative disease, retinopathy, neoplastic conditions, adipose cell tumors, adipose cell carcinomas, such as liposarcoma, prostate cancer and other cancers, including gastric, breast, bladder and colon cancers, angiogenesis, Alzheimer's disease, psoriasis, high blood pressure, Metabolic Syndrome (e.g. a person has three or more of the following disorders: abdominal obesity, hypertriglyceridemia, low HDL cholesterol, high blood pressure, and high fasting plasma glucose), ovarian hyperandrogenism (polycystic ovary syndrome), and other disorders where insulin resistance is a component, such as sleep apnea. The compositions and methods of the present invention are useful for the treatment, control, or prevention of obesity, including genetic or environmental, and obesity-related disorders. The obesity-related disorders herein are associated with, caused by, or result from obesity. Examples of obesity-related disorders include obesity, diabetes, overeating, binge eating, and bulimia, hypertension, elevated plasma insulin concentrations and insulin resistance, dyslipidemia, hyperlipidemia, endometrial, breast, prostate, kidney and colon cancer, osteoarthritis, obstructive sleep apnea, gallstones, heart disease, abnormal heart rhythms and arrythmias, myocardial infarction, congestive heart failure, coronary heart disease, sudden death, stroke, polycystic ovary disease, craniopharyngioma, Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are Metabolic Syndrome, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, lower back pain, gallbladder disease, hyperuricemia, gout, and kidney cancer, and increased anesthetic risk. The compositions and methods of the present invention are also useful to treat Alzheimer's disease.

In various embodiments, the present compositions are used to treat or prevent one or more respiratory diseases, such as idiopathic pulmonary fibrosis (IPF), asthma, chronic obstructive pulmonary disease (COPD), bronchiectasis, allergic rhinitis, sinusitis, pulmonary vasoconstriction, inflammation, allergies, impeded respiration, respiratory distress syndrome, cystic fibrosis, pulmonary hypertension, pulmonary vasoconstriction, emphysema, Hantavirus pulmonary syndrome (HPS), Loeffler's syndrome, Goodpasture's syndrome, Pleurisy, pneumonitis, pulmonary edema, pulmonary fibrosis, Sarcoidosis, complications associated with respiratory syncitial virus infection, and other respiratory diseases.

In some embodiments, the present invention is used to treat or prevent one or more neurodegenerative disease. Illustrative neurodegenerative diseases include, but are not limited to, Friedreich's Ataxia, multiple sclerosis (including without limitation, benign multiple sclerosis; relapsing-remitting multiple sclerosis (RRMS); secondary progressive multiple sclerosis (SPMS); progressive relapsing multiple sclerosis (PRMS); and primary progressive multiple sclerosis (PPMS)), Alzheimer's. disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

In various embodiments, the present chimeric proteins or chimeric protein complexes such as Fc-based chimeric protein complex finds use in treating wounds, e.g., a non-healing wound, an ulcer, a burn, or frostbite, a chronic or acute wound, open or closed wound, internal or external wound (illustrative external wounds are penetrating and non-penetrating wound.

In various embodiments, the present chimeric proteins or chimeric protein complexes such as Fc-based chimeric protein complexes find use in treating ischemia, by way of non-limiting example, ischemia associated with acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, frostbite, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, or wounds to tissues or organs In various embodiments, the present invention relates to the treatment of one or more of anemia, including anemia resulting from chronic kidney disease (e.g. from dialysis) and/or an anti-cancer agent (e.g. chemotherapy and/or HIV treatment (e.g. Zidovudine (INN) or azidothymidine (AZT)), inflammatory bowel disease (e.g. Crohn's disease and ulcer colitis), anemia linked to inflammatory conditions (e.g. arthritis, lupus, IBD), anemia linked to diabetes, schizophrenia, cerebral malaria, as aplastic anemia, and myelodysplasia from the treatment of cancer (e.g. chemotherapy and/or radiation), and various myelodysplastic syndrome diseases (e.g. sickle cell anemia, hemoglobin SC disease, hemoglobin C disease, alpha- and beta-thalassemias, neonatal anemia after premature birth, and comparable conditions).

In some embodiments, the present invention relates to the treatment of, or a patient having anemia, i.e. a condition in which the number of red blood cells and/or the amount of hemoglobin found in the red blood cells is below normal. In various embodiments, the anemia may be acute or chronic. For example, the present anemias include but are not limited to iron deficiency anemia, renal anemia, anemia of chronic diseases/inflammation, pernicious anemia such as macrocytic achylic anemia, juvenile pernicious anemia and congenital pernicious anemia, cancer-related anemia, anti-cancer-related anemia (e.g. chemotherapy-related anemia, radiotherapy-related anemia), pure red cell aplasia, refractory anemia with excess of blasts, aplastic anemia, X-lined siderobalstic anemia, hemolytic anemia, sickle cell anemia, anemia caused by impaired production of ESA, myelodysplasia syndromes, hypochromic anemia, microcytic anemia, sideroblastic anemia, autoimmune hemolytic anemia, Cooley's anemia, Mediterranean anemia, Diamond Blackfan anemia, Fanconi's anemia and drug-induced immune hemolytic anemia. Anemia may cause serious symptoms, including hypoxia, chronic fatigue, lack of concentration, pale skin, low blood pressure, dizziness and heart failure.

In some embodiments, the present invention relates to the treatment of anemia resulting from chronic renal failure. In some embodiments, the present invention relates to the treatment of anemia resulting from the use of one or more renal replacement therapies, inclusive of dialysis, hemodialysis, peritoneal dialysis, hemofiltration, hemodiafiltration, and renal transplantation.

In some embodiments, the present invention relates to the treatment of anemia in patients with chronic kidney disease who are not on dialysis. For instance, the present invention relates to patients in stage 1 CKD, or stage 2 CKD, or stage 3 CKD, or stage 4 CKD, or stage 5 CKD. In some embodiments, the present patient is stage 4 CKD or stage 5 CKD. In some embodiments, the present patient has undergone a kidney transplant. In some embodiments, the present invention relates to the treatment of anemia is a patient having an acute kidney injury (AKI).

In some embodiments, the anemia is induced by chemotherapy. For instance, the chemotherapy may be any myelosuppressive chemotherapy. In some embodiment, the chemotherapy is one or more of Revlimid, Thalomid, dexamethasone, Adriamycin and Doxil. In some embodiments, the chemotherapy is one or more platinum-based drugs including cisplatin (e.g. PLATINOL) and carboplatin (e.g. PARAPLATIN). In some embodiments, the chemotherapy is any one of the chemotherapeutic agents described herein. In some embodiments, the chemotherapy is any agent described in Groopman et al. J Natl Cancer Inst (1999) 91 (19): 1616-1634, the contents of which are hereby incorporated by reference in their entireties. In some embodiments, the present compositions and methods are used in the treatment of chemotherapy-related anemia in later stage cancer patients (e.g. a stage IV, or stage III, or stage II cancer). In some embodiments, the present compositions and methods are used in the treatment of chemotherapy-related anemia in cancer patients receiving dose-dense chemotherapy or other aggressive chemotherapy regimens.

In some embodiments, the present invention relates to the treatment of anemia in a patient having one or more blood-based cancers, such as leukemia, lymphoma, and multiple myeloma. Such cancers may affect the bone marrow directly. Further, the present invention relates to metastatic cancer that has spread to the bone or bone marrow. In some embodiments, the present invention relates to the treatment of anemia in a patient undergoing radiation therapy. Such radiation therapy may damage the bone marrow, lowering its ability to make red blood cells. In further embodiments, the present invention relates to the treatment of anemia in a patient having a reduction or deficiency of one or more of iron, vitamin B12, and folic acid. In further embodiments, the present invention relates to the treatment of anemia in a patient having excessive bleeding including without limitation, after surgery or from a tumor that is causing internal bleeding. In further embodiments, the present invention relates to the treatment of anemia in a patient having anemia of chronic disease.

In some embodiments, the present methods and compositions stimulate red blood cell production. In some embodiments, the present methods and compositions stimulate division and differentiation of committed erythroid progenitors in the bone marrow.

Certain embodiments of the present invention are particularly useful for treating chemotherapy-induced anemia in cancer patients. In some embodiments, the present methods and compositions allows for continued administration of the chimeric proteins or chimeric protein complexes such as Fc-based chimeric protein complex after a cancer patient's chemotherapy is finished. In some embodiments, the present methods and compositions allows for treatment of a cancer patient without dose reduction relative to a non-cancer patient. In some embodiments, the present methods and compositions allows for treatment of a cancer patient receiving chemotherapy and considered curable. In various embodiments, the cancer patient has one or more of a history of blood clots, recent surgery, prolonged periods of bed rest or limited activity, and treatment with a chemotherapeutic agent.

Kits

The invention also provides kits for the administration of any agent described herein (e.g. the chimeric proteins or chimeric protein complexes such as Fc-based chimeric protein complex with or without various additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired outcome, such as to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Unless specifically stated or obvious from context, as used herein, the term "or" is understood to be inclusive and covers both "or" and "and".

Further, the term "about" when used in connection with a referenced numeric indication means the referenced numeric indication plus or minus up to 10% of that referenced numeric indication, e.g., within (plus or minus) 10%, 9%, 8%, 7%, 6%, 5%, 4%, 3%, 2%, 1%, 0.5%, 0.1%, 0.05%, or 0.01% of the stated value. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred.

A therapeutically effective dose can be estimated initially from in vitro assays, including, for example, cell culture assays. Also, a dose can be formulated in animal models to achieve a circulating plasma concentration range that includes the 1050 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein. This invention is further illustrated by the following non-limiting examples.

EXAMPLES

The term "AcTaferon" or "AFN" is occasionally used herein to reference an INFα1-based chimeric protein or chimeric protein complex described herein (details are provided in the Examples regarding the format of the chimeric protein, occasionally an INFα2-based chimeric protein or chimeric protein complex is described, as noted).

"IFNα1" and "IFNα1" may be used interchangeably to refer to interferon alpha 1.

"IFNα2" and "IFNα2" may be used interchangeably to refer to interferon alpha 2.

Example 1: Generation, Production and Purification of IFNα1 AcTaferons (AFNs)

To generate AFNs based on IFNα1 fusion proteins, a nucleic acid sequence encoding for IFNα1 was linked, via a nucleic acid sequence encoding a flexible 20*GGS flexible linker, to a nucleic acid sequence encoding a VHH targeting human CD20 in pHEN6C vector (under control of the PelB signal peptide) for bacterial expression. A $His_6$ tag was added at the end for purification.

AFN expression was induced overnight with 1 mM IPTG, cells were pelleted, and periplasmic extracts prepared using TES (0.2 M Tris pH 8.0, 0.5 mM EDTA, 0.5 M sucrose) and TES/4 buffers. Proteins were purified from extracts using the TALON Metal affinity resin according to the manufacturer's guidelines and imidazole was removed from the samples using PD10 columns (GE HEALTHCARE).

A similar process was used to generate AFNs based on IFN-α2.

Structure and Sequence of IFNα1 AFN

The structure of the IFNα1 AFN is shown below:

CD20 VHH-$(GGS)_{20}$-hIFNα1—$His_6$

The amino acid sequence of the IFNα1 AFN is shown below (the sequence of CD20 VHH is shown in bold letters, the sequence of $(GGS)_{20}$ is shown in italicized letters, and the sequence of hIFNα1 is shown in underlined letters):

(SEQ ID NO: 286)

QVQLQESGGGLAQAGGSLRLSCAASGRTFSMGWFRQAPGKEREFVAAIT

YSGGSPYYASSVRGRFTISRDNAKNTVYLQMNSLKPEDTAVYYCAANPT

YGSDWNAENWGQGTQVTVSSVD*GGSGGSGGSGGSGGSGGSRSGGSGGSG*

*GSGGSGGSGGSGGSGGSGGSGGSGGSGGSGGS*AAACDLPETHSLDNRRT

LMLLAQMSRISPSSCLMDRHDFGFPQEEFDGNQFQKAPAISVLHELIQQ

IFNLFTTKDSSAAWDEDLLDKFCTELYQQLNDLEACVMQEERVGETPLM

NADSILAVKKYFRRITLYLTEKKYSPCAWEWRAEIMRSLSLSTNLQERL

RRKELEHHHHHH.

Structure and Sequence of IFN-α2 AFN

The structure of the IFN-α2 AFN is shown below:

CD20 VHH - $(GGS)_{20}$ - hIFNα2 - $His_6$

The amino acid sequence of the IFN-α2 AFN is shown below (the sequence of CD20 VHH is shown in bold letters, the sequence of $(GGS)_{20}$ is shown in italicized letters, and the sequence of hIFNα2 is shown in underlined letters):

(SEQ ID NO: 287)

QVQLQESGGGLAQAGGSLRLSCAASGRTFSMGWFRQAPGKEREFVAAIT

YSGGSPYYASSVRGRFTISRDNAKNTVYLQMNSLKPEDTAVYYCAANPT

YGSDWNAENWGQGTQVTVSSVD*GGSGGSGGSGGSGGSGGSRSGGSGGSG*

*GSGGSGGSGGSGGSGGSGGSGGSGGSGGSGGS*AAAMCDLPQTHSLGSRR

TLMLLAQMRRISLFSCLKDRHDFGFPQEEFGNQFQKAETIPVLHEMIQQ

IFNLFSTKDSSAAWDETLLDKFYTELYQQLNDLEACVIQGVGVTETPLM

KEDSILAVRKYFQRITLYLKEKKYSPCAWEVVRAEIMRSFSLSTNLQES

LRSKELEHHHHHH.

Example 2: Methods for STAT1 Phosphorylation in Peripheral Blood Mononuclear Cells (PBMCs) and IFN-Responsive Reporter Activity in HL116 Cells PBMCs from buffy coats of healthy donors were isolated using density gradient centrifugation using Lymphoprep (STEMCELL TECHNOLOGIES). Cells were washed twice with FACS buffer (2% FBS, 1 mM EDTA in PBS) and stained with anti-human CD20 FITC (SINOBIOLOGICALS) for 20 minutes at 4° C. After two washes, cells were stimulated with a serial dilution wild type IFNα2, CD20 VHH-IFNα2, IFNα1 and CD20 VHH-IFNα1 for 15 minutes at 37° C. After fixation (10 minutes, 37° C., Fix Buffer I; BD BIOSCIENCES), permeabilization (30 minutes, on ice, Perm III Buffer I; BD BIOSCIENCES) and washing, cells were stained with anti-STAT1 pY701 Ab (BD Biosciences). Samples were acquired with a Macsquant X instrument (MILTENYI BIOTEC) and analyzed using the FlowLogic software (MILTENYI BIOTEC). Induction of pSTAT1 reflects activation of IFNAR by interferons. The HL116 clone is derived from the human HT1080 cell line (ATCC CCL-121). It contains the firefly luciferase gene controlled by the IFN-inducible 6-16 promoter. Thus, induction of luciferase reporter expression reflects activation of IFNAR by interferons. Parental HL116 cells were transfected with an expression vector encoding the human CD20 sequence. Stable transfected clones were selected in G418-containing medium. Parental HL116 and HL116-huCD20 cells were seeded overnight at 20.000 cells per 96-well, before stimulation with a serial dilution of IFNα2 and IFNα1 variants for 6 hours. Luciferase activity in cell lysates was measured on an EnSight Multimode Plate Reader (Perkin Elmer).

Example 3: STAT1 Phosphorylation in Peripheral Blood Mononuclear Cells (PBMCs) and IFN-Responsive Reporter Activity in HL116 Cells Data in FIGS. 21A-D, FIGS. 22A-D and Table 7 clearly illustrate that incorporation of wild type IFNα1 into a chimeric fusion protein, exemplified here by linking IFNα1 to an anti-CD20 VHH, results in reduced IFNAR-stimulatory activity of IFNα1 compared to wild type IFNα1 (as shown here for CD20 negative cells, both for PBMCs and HL116). However, IFNα1 activity was induced/restored specifically on target cells (CD20 positive, for both PBMC and HL116-huCD20). Importantly, the activation of IFNAR signaling was highly selective for targeted (CD20-positive) versus non-targeted (CD20-negative) cells, with about a 200-600 fold targeting selectivity. Instead, in the case of IFNα2, a targeting selectivity of only 20-60-fold was observed in CD20-positive versus CD20 negative PBMCs and HL116 cells, thus approximately 10-fold less favorable for the intended target (CD20-positive cells) than observed for the comparable IFNα1 constructs. Furthermore, it is notable that targeted IFNα1 chimeric fusion protein was substantially more potent than wild type IFNα1 itself in activating IFNAR signaling in target cells (CD20-positive). Indeed, and remarkably, IFNα1 chimeric protein was 30-150 fold more potent than wild type IFNα1 on target cells (depending on cell type). Surprisingly also, both CD20 VHH-IFNα1 and CD20 VHH-IFNα2 chimeric proteins have a similar potency on CD20-positive target cells, while IFNα1 without fusion is significantly less potent compared to IFNα2. Stated another way, wild type IFNα1 is far less potent than IFNα2; however, unexpectedly, when coupled to a targeting moiety, such as a VHH, its on-target activity is similar to the on-target activity of targeted IFNα2, while the off-target activity is higher for targeted IFNα2. Thus, IFNAR activators that combine high potency and high selectivity may be created de novo by incorporating wild type IFNα1 in targeted chimeric fusion proteins—in a way and with a potency/selectivity index that is not achieved through use of wild type IFNα2.

TABLE 7

IFNα1, IFNα2 and variants signalling in PBMC and HL116 cells that express (positive) or do not express (negative) CD20. Note that in the first experiment on PBMC the curves for IFNα2 did not reach a bottom and hence the EC50 needed to be extrapolated.

| | Biological activity IFNα1 AFN's | | | | | |
|---|---|---|---|---|---|---|
| | EC50 pSTAT1 in PBMC's (ng/ml) | | ratio | EC50 6-16 reporter activity (ng/ml) | | ratio |
| | CD20 negative | CD20 positive | CD20 neg/pos | HL116 | HL116-huCD20 | CD20 neg/pos |
| Exp 1 | | | | | | |
| IFNα2 | 0.103 | ±0.019 | ±5 | 0.1756 | 0.4598 | 0.4 |
| CD20-IFNα2 | 3.019 | 0.149 | 20 | 0.9641 | 0.01567 | 62 |
| IFNα1 | 7.515 | 3.966 | 2 | 2.375 | 3.249 | 0.7 |
| CD20-IFNα1 | 24.57 | 0.1144 | 215 | 14.12 | 0.02408 | 586 |

TABLE 7-continued

IFNα1, IFNα2 and variants signalling in PBMC and HL116 cells that express (positive) or do not express (negative) CD20. Note that in the first experiment on PBMC the curves for IFNα2 did not reach a bottom and hence the EC50 needed to be extrapolated.

| | Biological activity IFNα1 AFN's | | | | | |
|---|---|---|---|---|---|---|
| | EC50 pSTAT1 in PBMC's (ng/ml) | | ratio | EC50 6-16 reporter activity (ng/ml) | | ratio |
| | CD20 negative | CD20 positive | CD20 neg/pos | HL116 | HL116-huCD20 | CD20 neg/pos |
| Exp 2 | | | | | | |
| IFNα2 | 0.106 | 0.039 | 3 | | | |
| CD20-IFNα2 | 2.786 | 0.109 | 26 | | | |
| IFNα1 | 6.774 | 2.723 | 2.5 | | | |
| CD20-IFNα1 | 27.67 | 0.085 | 325 | | | |

Data in FIGS. 22A-D and Table 7 for induction of luciferase activity in HL116 cells are qualitatively comparable with data for pSTAT1 induction in PBMCs data in FIGS. 21A-D. That is CD20 targeting of IFNα1 results in a more pronounced relative increase in IFNAR signalling compared to CD20 targeting wild type IFNα2 (586 versus 62-fold respectively in HL116 cells, and 215 versus 20-fold, respectively, in PBMCs). Remarkably, both CD20-IFNα1 and CD20-IFNα2 have a similar potency on respective CD20-positive PBMC and HL116 target cells, while IFNα1 without fusion is significantly less potent compared to IFNα2 in CD20-positive cells (as well as CD20-negative cells).

Surprisingly, without limitation, the data show an IFNα1-based fusion/chimeric protein to be as potent as a comparable fusion/chimeric protein based on WT IFNα2, despite the reduced activity of IFNα1 as compared to IFNα2 in an unfused, non-chimeric protein setting. Moreover, without limitation, the data show that the IFNα1 fusion is superior over the IFNα2 fusion regarding degree of selectivity for intended target cells versus non-target cells.

Example 4: Generation, Production, Purification and Characterization of Mutant IFNα1 AcTaFerons (AFNs)

Chimeric proteins based on mutant IFNα1 are generated using the following protocol. A nucleic acid sequence encoding for mutant IFNα1 is fused/linked, via a nucleic acid sequence encoding a flexible 20*GGS flexible linker, to a nucleic acid sequence encoding a VHH antibody targeting human CD20 in pHEN6C vector (under control of the PelB signal peptide) for bacterial expression. A sequence encoding a His tag is added at the end for purification. AFN expression is induced overnight with 1 mM IPTG, cells were pelleted, and periplasmic extracts prepared using TES (0.2 M Tris pH 8.0, 0.5 mM EDTA, 0.5 M sucrose) and TES/4 buffers. Proteins were purified from extracts using the TALON Metal affinity resin according to the manufacturer's guidelines and imidazole is removed from the samples using PD10 columns (GE HEALTHCARE).

The mutants for IFNα1 that are prepared are shown in Table 8 below:

| | |
|---|---|
| Reduced Cysteine Based | C86S, C88Y, or C86A (knocking out unpaired cysteine) |

-continued

| | |
|---|---|
| Aggregation Mutants | |
| Attenuated Mutants (or variants) for IFNa1 with single mutations | L15A, A19W, R23A, S25A, L30A, L30V, D32A, R33K, R33A, R33Q, H34A, Q40A, D115R, L118A, K121A, K121E, R126A, R126E, E133A, K134A, K135A, R145A, R145D, R145E, R145G, R145H, R145I, R145K, R145L, R145N, R145Q, R145S, R145T, R145V, R145Y, A146D, A146E, A146G, A146H, A1 461, A146K, A146L, A146M, A146N, A146Q, A146R, A146S, A146T, A146V, A146Y, M149A, R150A, S153A, L154A, N157A |
| Attenuated Mutants (or variants) for IFNa1 with multiple mutations | L30A/H58Y/E59N/Q62S, R33A/H58Y/E59N/Q62S, M149A/H58Y/E59N/Q62S, L154A/H58Y/E59N/Q62S, R145A/H58Y/E59N/Q62S, D115A/R121A, L118A/R121A, L118A/R121A/K122A, R121A/K122A, R121E/K122E |

The STAT1 phosphorylation in PBMCs for each of these mutants, in the context of chimeras, identified in Table 8, is assessed using the protocol specified in Example 2. Similarly, reporter activity in HL116 wells is characterized for each of the mutants identified in Table 8 using the protocol identified in Example 2.

Example 5: Generation, Production, Purification and Characterization of Further Mutant IFNα1 AFNs In this example, we evaluated the activity of IFNα1 fused to a non-antibody type of targeting moiety—specifically FLT3L, which is a known ligand for FLT3, the receptor for FLT3L. The resulting chimeric molecule is therefore also an example of a bifunctional IFNα1 chimeric fusion protein, in the sense that it comprises two effector domains (IFNα1 and FLT3L), of which one of them (FLT3L) also serves as a targeting moiety. FLT3 is expressed on human dendritic cells, such a cDC1 dendritic cells. cDC1 cells are potent activators of T cells and important in promoting immune system-mediated antitumor responses. To evaluate the in vivo efficacy of Flt3-targeted IFNα1 in a humanized mouse (mouse with a human immune system), a Flt3L_Iinker_humanIFNα1_GGS_his9 fusion protein was expressed in HEKT cells and purified by metal affinity chromatography.

The sequence of the fusion protein contains the sequence of the extracellular domain of Flt3L (bold below; the final 21 residues of the bold residues are part of an extracellular region and not part of receptor binding domain):

Mature Sequence Flt3L (bold) linker (underline) humanIFNα1_(bold and underline)LEGGS_his9

(SEQ ID NO: 289)

TQDCSFQHSPISSDFAVKIRELSDYLLQDYPVTVASNLQDEELCGGLWR

LVLAQRWMERLKTVAGSKMQGLLERVNTEIHFVTKCAFQPPPSCLRFVQ

TNISRLLQETSEQLVALKPWITRQNFSRCLELQCQPDSSTLPPPWSPRP

LEATAPTAVDGGSGGSGGSGGSGGSGGSGGSGGSGGSGGSGGSGGSGGS

GGSGGSGGSGGSGGSGGSAAACDLPETHSLDNRRTLMLLAQMSRISPSS

-continued

CLMDRHDFGFPQEEFDGNQFQKAPAISVLHELIQQIFNLFTTKDSSAAW

DEDLLDKFCTELYQQLNDLEACVMQEERVGETPLMNADSILAVKKYFRR

ITLYLTEKKYSPCAWEVVRAEIMRSLSLSTNLQERLRRKELEGGSHHHH

HHHHH.

The purified protein was subsequently evaluated in a tumor model in a humanized mouse. In brief, newborn NSG mice (1-2 days of age) were sublethal irradiated with 100 cGy prior to intrahepatic delivery of $1\times10^5$ CD34+ human stem cells (from HLA-A2 positive cord bloods). At week 13 after stem cell transfer mice were subcutaneously inoculated with $25\times10^5$ human RL follicular lymphoma cells (ATCC CRL-2261; not sensitive to the direct antiproliferative effect of IFN). Mice were treated daily intraperitoneally with 30 μg of human Flt3L protein, from day 8 to day 18 after tumor inoculation. Daily perilesional injection with buffer or Flt3L-IFNα1 (30 μg) was initiated at day 10 after tumor inoculation, when a palpable tumor was visible (n=5 or 6 mice per group). Tumor size (caliper measurements), body weight and temperature were assessed daily.

Figure 23:
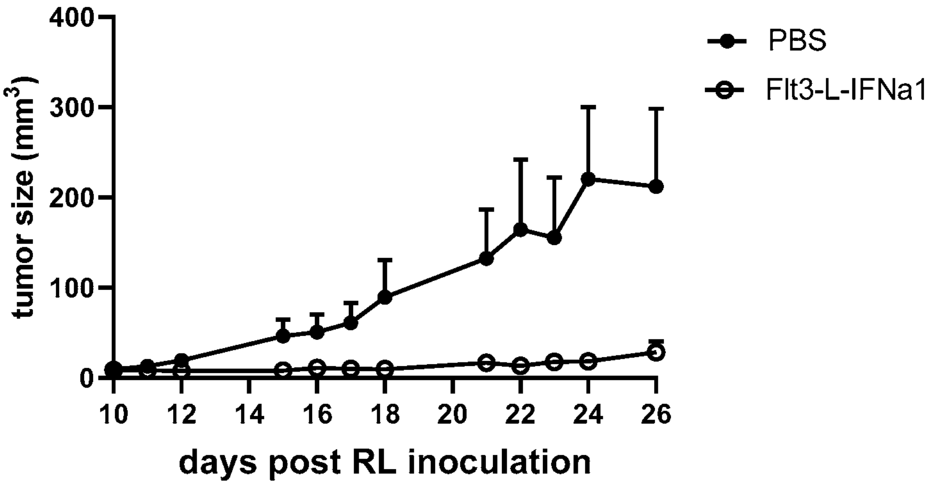
FIG. 23 shows tumor growth curves in humanized mice after treatment with buffer or Flt3L-IFNα1. Average values (in $mm^3$) of 5 or 6 animals per time point time (+SEM) are plotted.
Figure 24A:
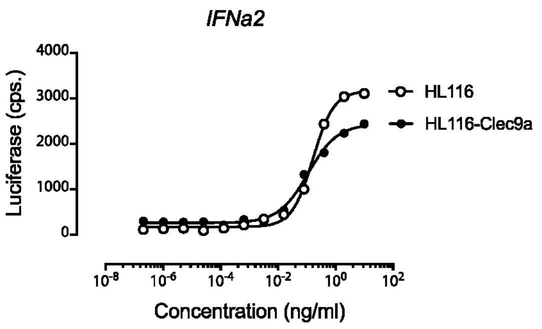
FIGS. 24A-G show biological activity of IFNα1 AFNs on the HL116 reporter. HL116 or HL116-Clec9A cells were stimulated for 6 hours with serial dilution wild type IFNα2 or IFNα1 AFNs. Average luciferase activities (±STDEV) are plotted.
Figure 24B:
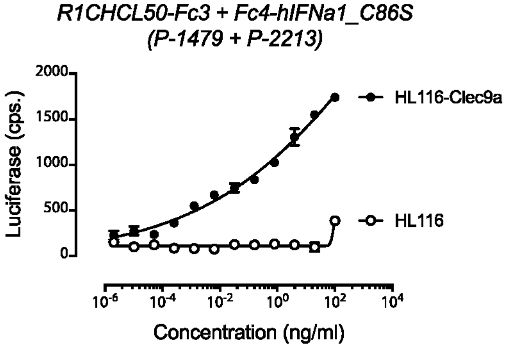
Figure 24C:
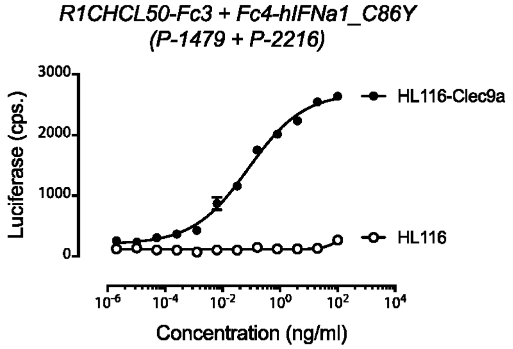
Figure 24D:
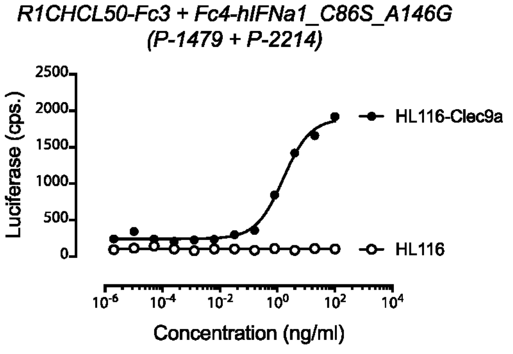
Figure 24E:
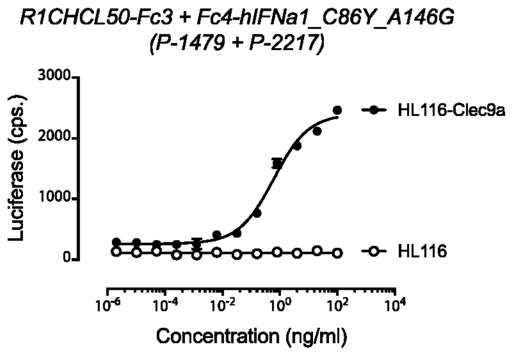
Figure 24F:
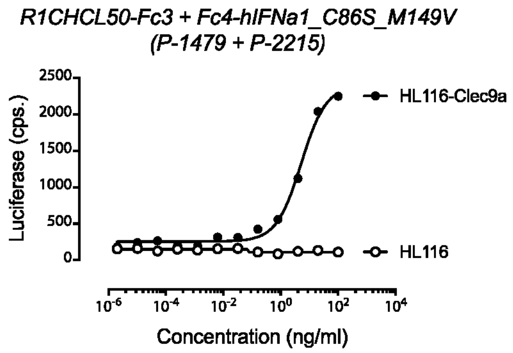
Figure 24G:
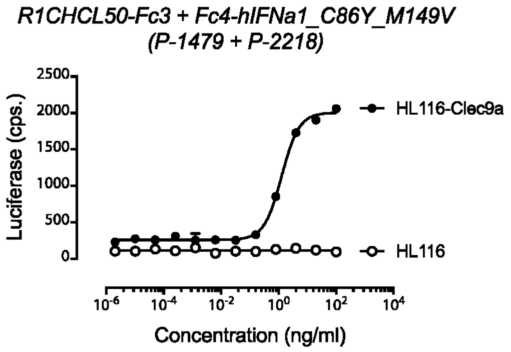
Figure 25A:
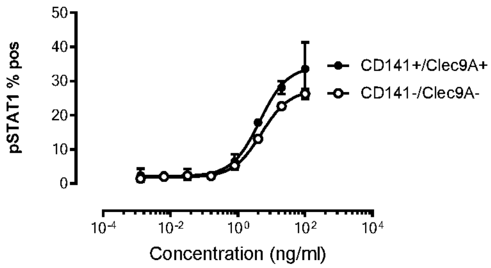
FIGS. 25A-E show pSTAT1 activity in Clec9A−/CD141− and Clec9A+/CD141+PBMC's by IFNα2 or IFNα1 based AFN.
Figure 25B:
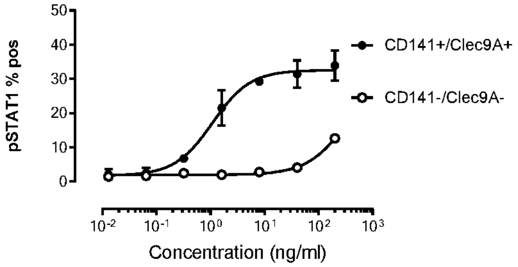
Figure 25C:
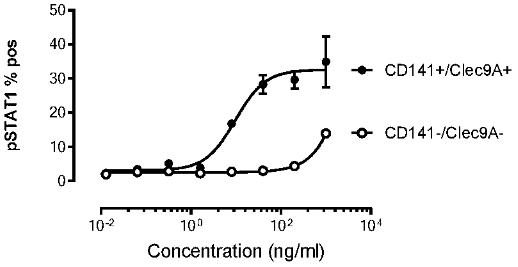
Figure 25D:
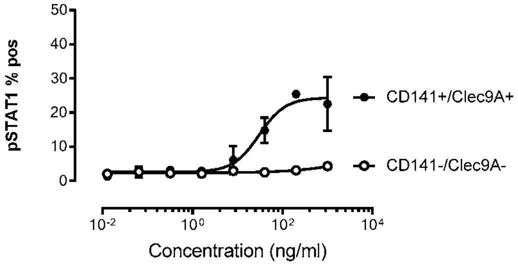
Figure 25E:
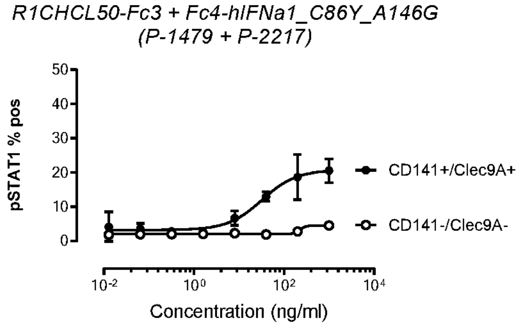

Data in FIG. 23 show the tumor growth until 2 days after the last treatment and demonstrates that targeted-IFNα1 strongly suppresses tumor growth. Data on body weight and temperature did not show any major difference between buffer treatment and IFNα1 treatment supporting that the IFNα1 treatment was well tolerated.

Example 6: Fc-Based Chimeric Protein Complexes with Interferon Alpha 1

This Example evaluates and generates chimer protein complexes based on wild type interferon alpha 1 (IFNα1) and targeted via a human Clec9A specific VHH (clone R1CHCL50). For this purpose, a heterodimeric Fc protein based on knob-into-hole technology was designed.

Constructs:

R1CHCL50-20*GGS-human IgG1 Fc (with hole mutations and effector knock-out mutations) (P-1451)

(SEQ ID NO: 290)

QVQLVESGGGLVHPGGSLRLSCAASGSFSSINVMGWYRQAPGKERELVA

RITNLGLPNYADSVTGRFTISRDNAKNTVYLQMNSLKPEDTAVYYCYLV

ALKAEYWGQGTQVTVSSGGSGGSGGSGGSGGSGGSGGSGGSGGSGGSGG

SGGSGGSGGSGGSGGSGGSGGSGGSGGSDKTHTCPPCPAPEAAGGPSVF

LFPPKPKDTLMISRTPEVTCVVVDVSHEDPEVKFNWYVDGVEVHNAKTK

PREEQYNSTYRVVSVLTVLHQDWLNGKEYKCQVSNKALPAPIEKTISKA

KGQPREPQVCTLPPSRDELTKNQVSLSCAVKGFYPSDIAVEWESNGQPE

NNYKTTPPVLDSDGSFFLVSKLTVDKSRWQQGNVFSCSVMHEALHNHYT

QKSLSLSPGK human IgG1 Fc (with knob mutations and effector knock-out mutations)-20*GGS-IFNα1 (P-1852)

(SEQ ID NO: 291)

DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCQVSNKALPAPIEKTISKAKGQPREPQVYTLPPCRDELTKNQVSLWC

LVKGFYPSDIAVEWESNGQPENNYKTTPPVLDSDGSFFLYSKLTVDKSR

-continued

WQQGNVFSCSVMHEALHNHYTQKSLSLSPGKGGSGGSGGSGGSGGSGGS

GGSGGSGGSGGSGGSGGSGGSGGSGGSGGSGGSGGSGGSGGSCDLPETH

SLDNRRTLMLLAQMSRISPSSCLMDRHDFGFPQEEFDGNQFQKAPAISV

LHELIQQIFNLFTTKDSSAAWDEDLLDKFCTELYQQLNDLEACVMQEER

VGETPLMNADSILAVKKYFRRITLYLTEKKYSPCAWEVVRAEIMRSLSL

STNLQERLRRKE

Production and Purification of IFNα1 AFN

Figure 7A:
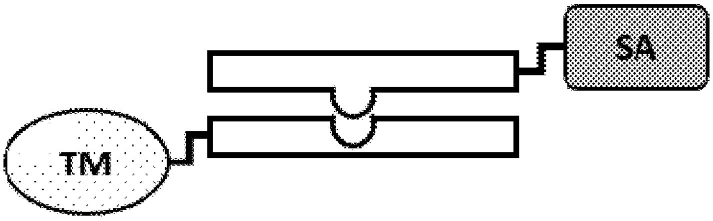
Figure 7B:
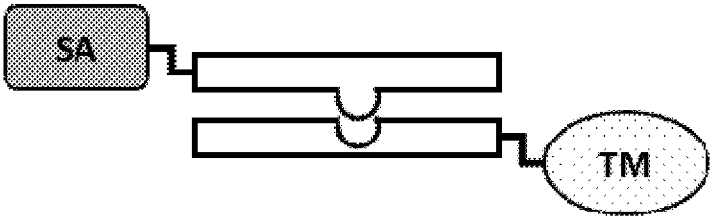
Figure 7C:
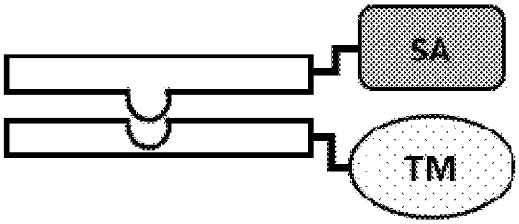
Figure 7D:
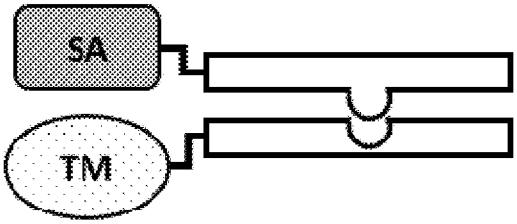
Figure 8A:
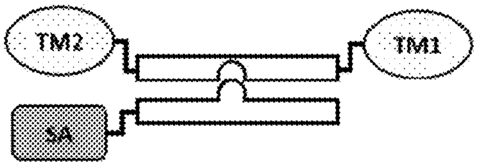
Figure 8B:
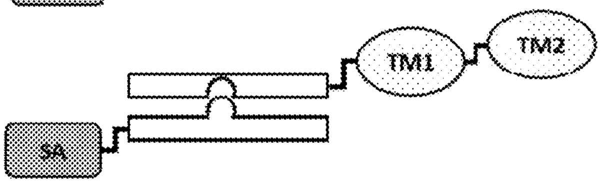
Figure 8C:
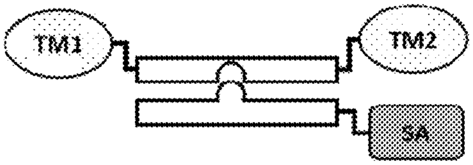
Figure 8D:
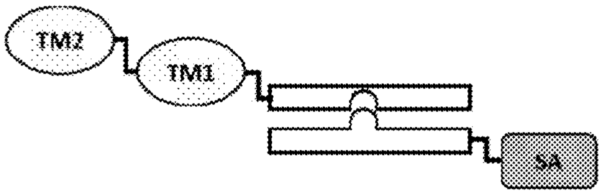
Figure 8E:
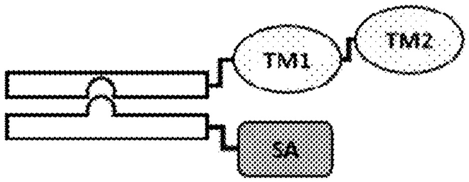
Figure 8F:
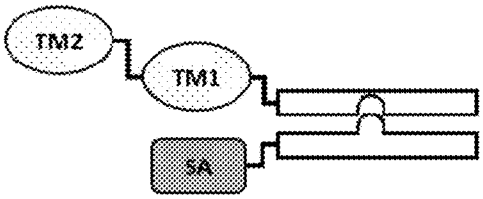
Figure 9A:
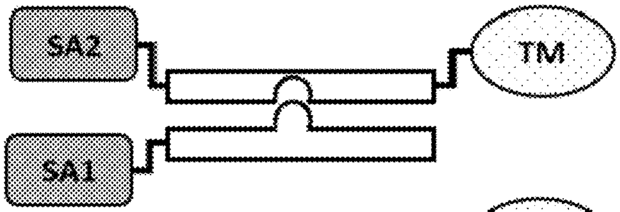
Figure 9B:
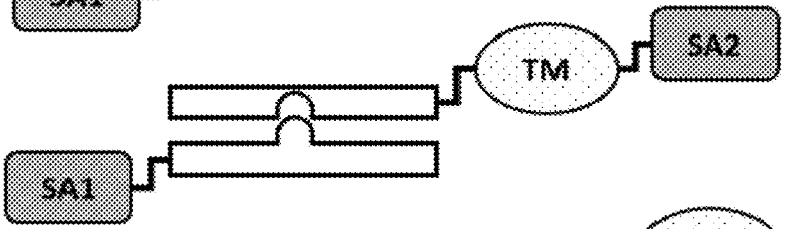
Figure 9C:
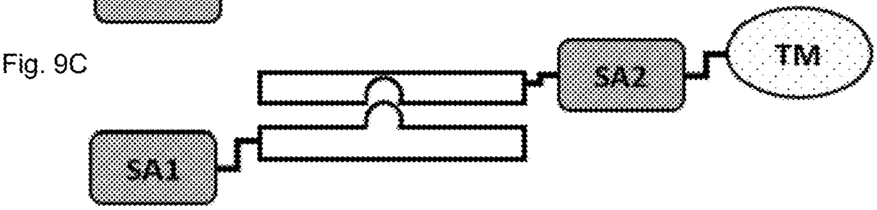
Figure 9D:
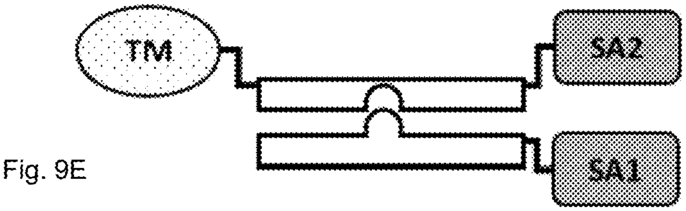
Figure 9E:
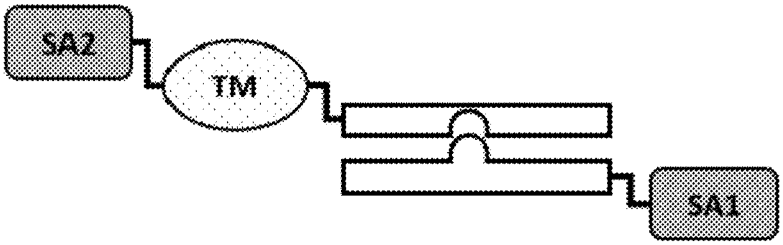
Figure 9F:
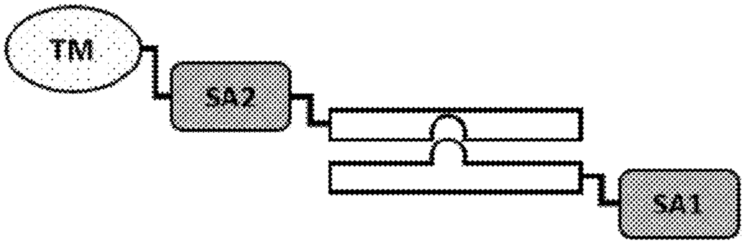
Figure 9G:
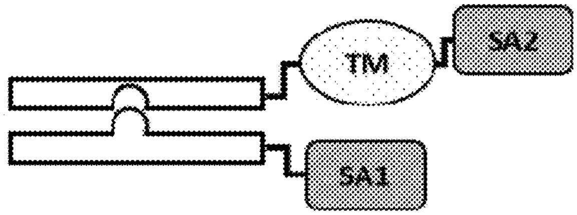
Figure 9H:
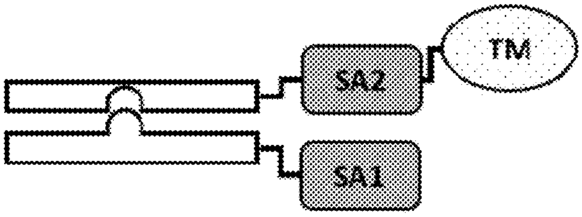
Figure 9I:
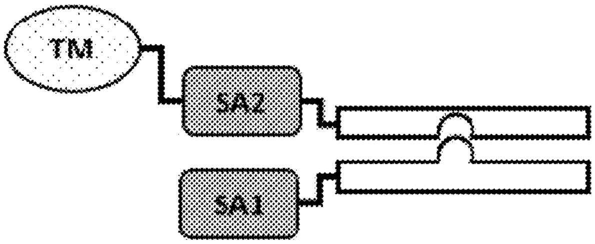
Figure 9J:
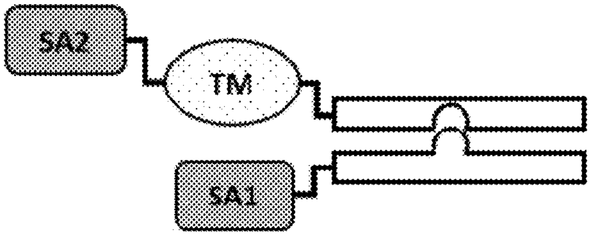
Figure 10A:
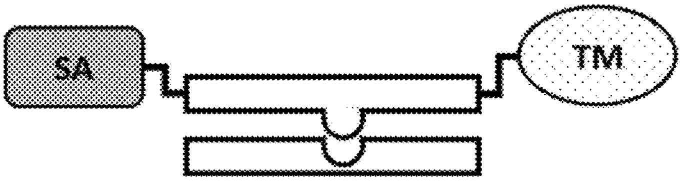
Figure 10B:
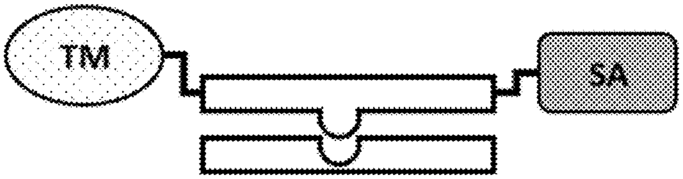
Figure 10C:
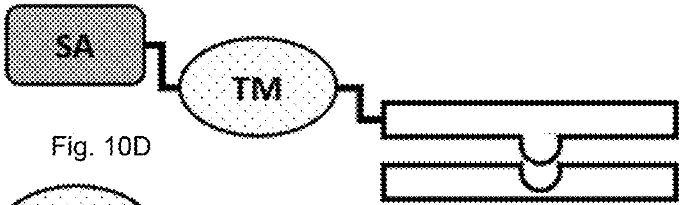
Figure 10D:
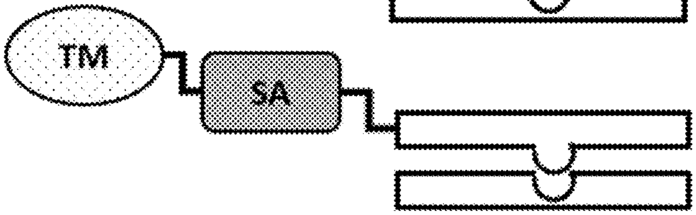
Figure 10E:
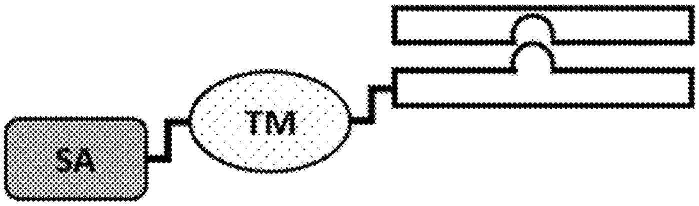
Figure 10F:
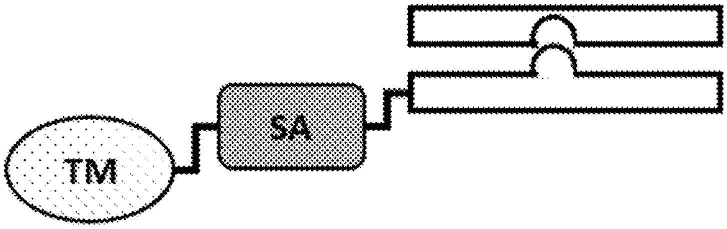
Figure 11A:
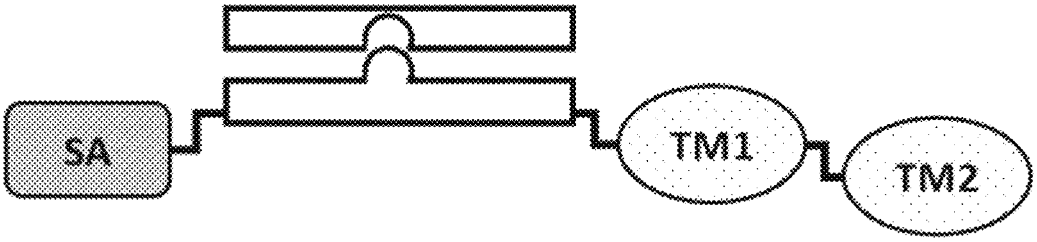
Figure 11B:
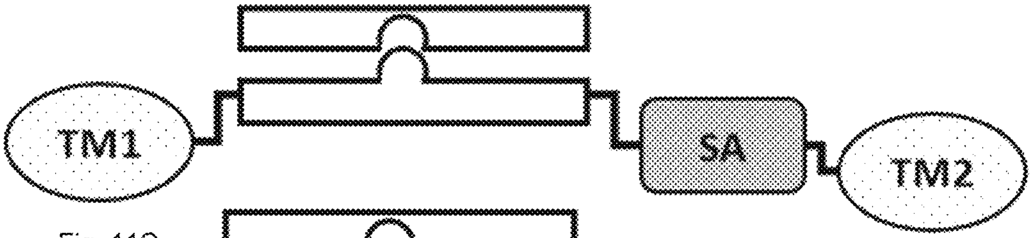
Figure 11C:
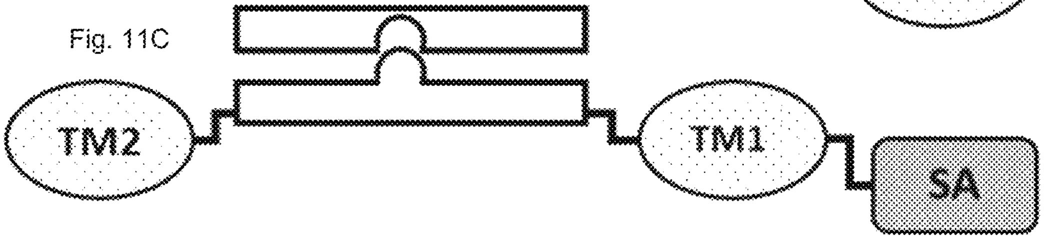
Figure 11D:
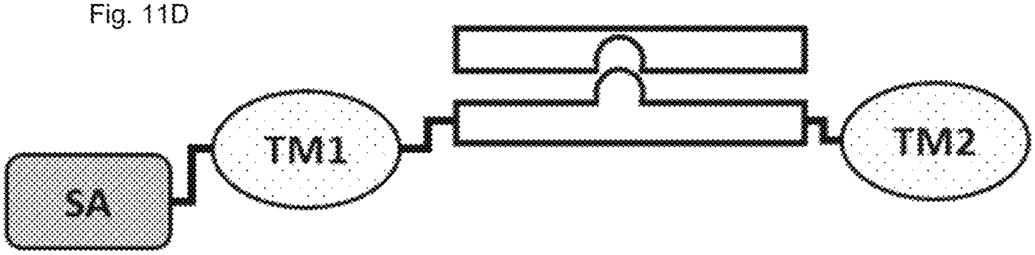
Figure 11E:
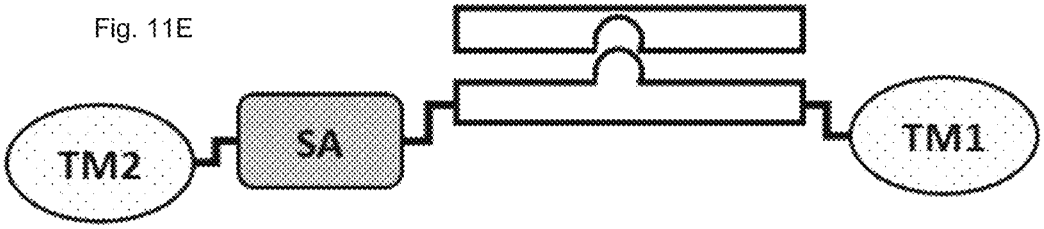
Figure 11F:
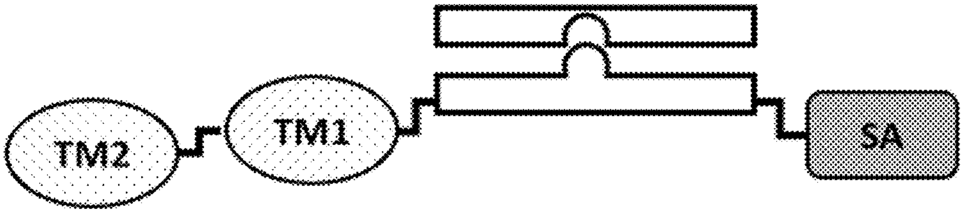
Figure 11G:
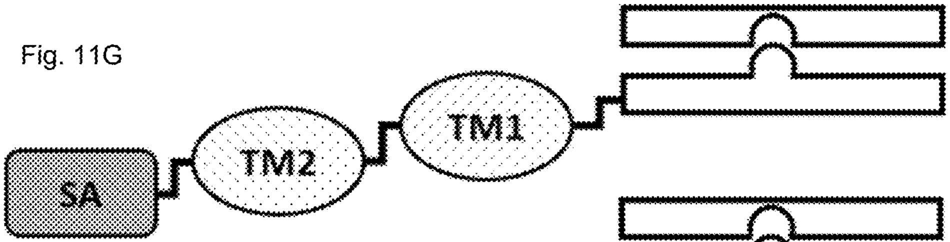
Figure 11H:
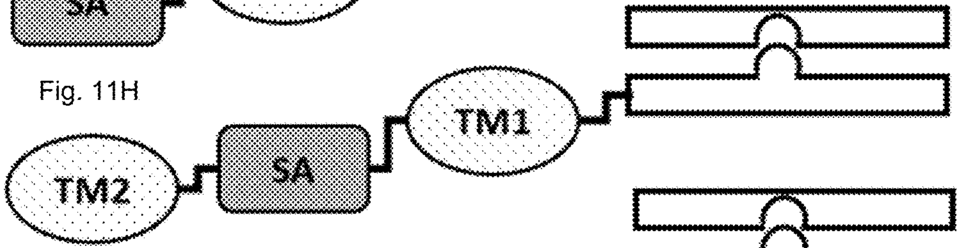
Figure 11I:
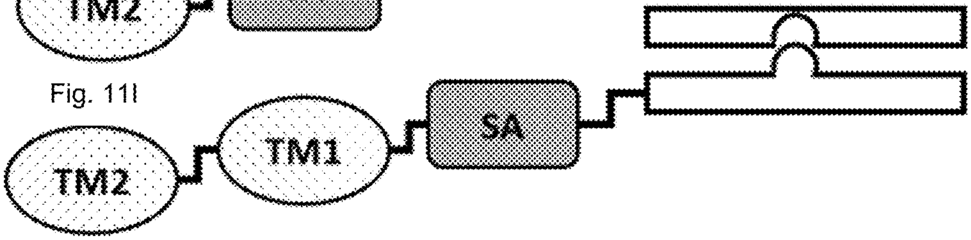
Figure 11J:
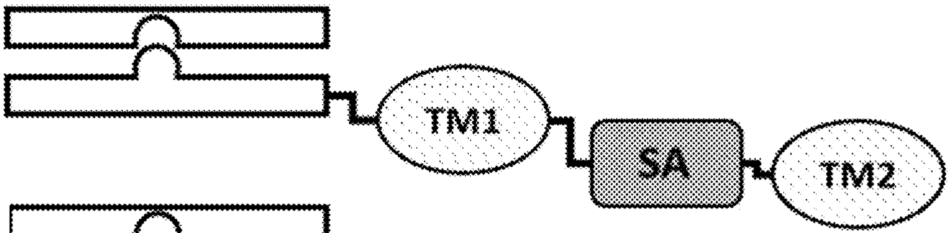
Figure 11K:
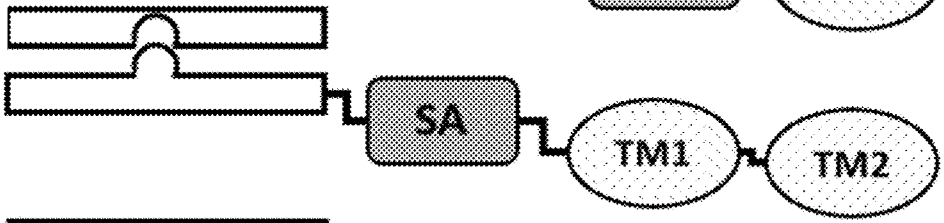
Figure 11L:
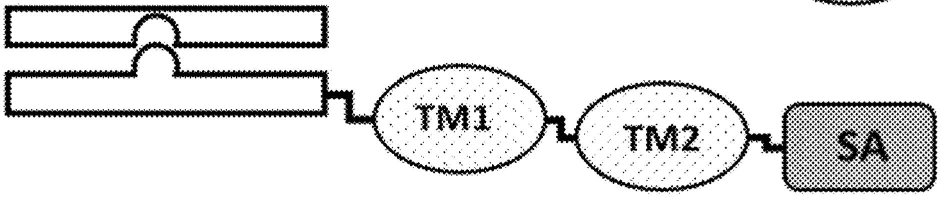
Figure 12A:
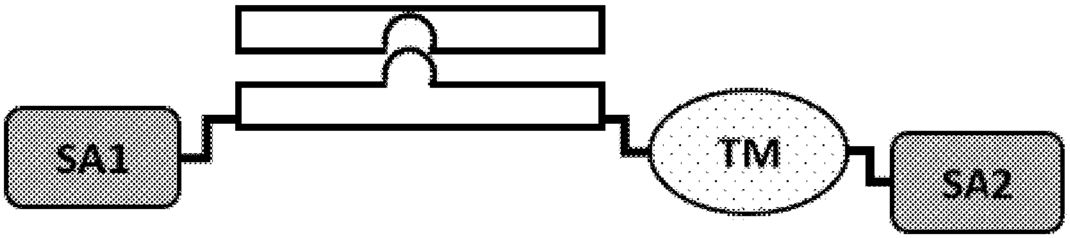
Figure 12B:
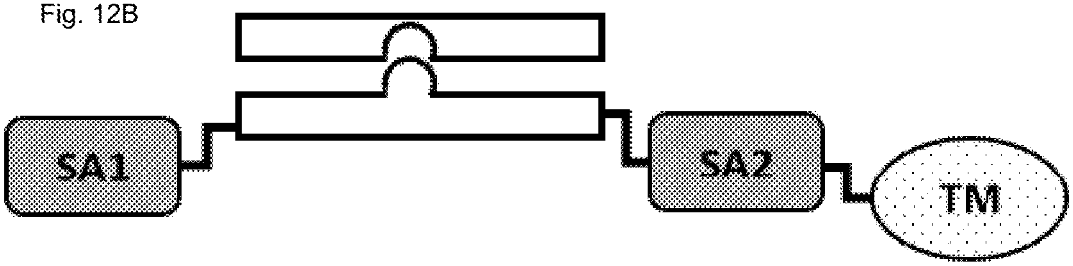
Figure 12C:
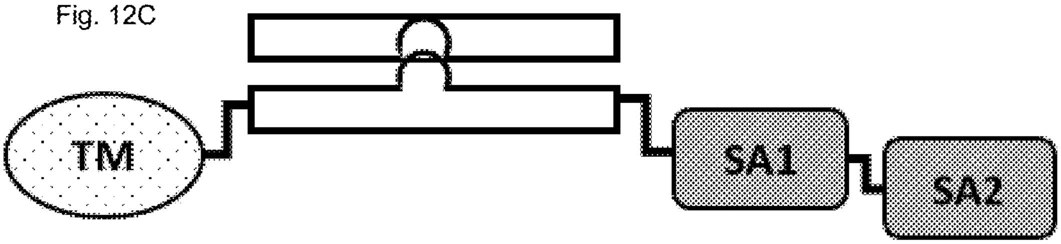
Figure 12D:
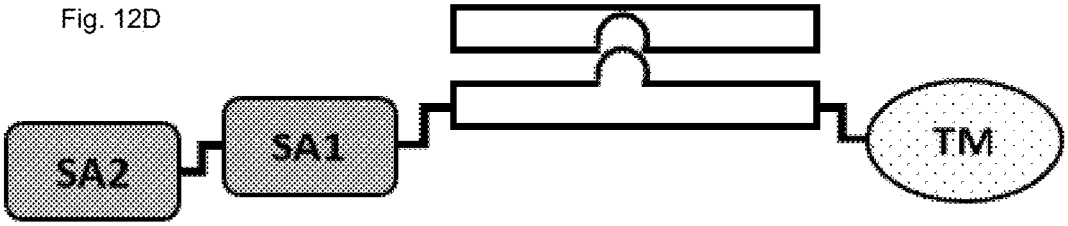
Figure 12E:
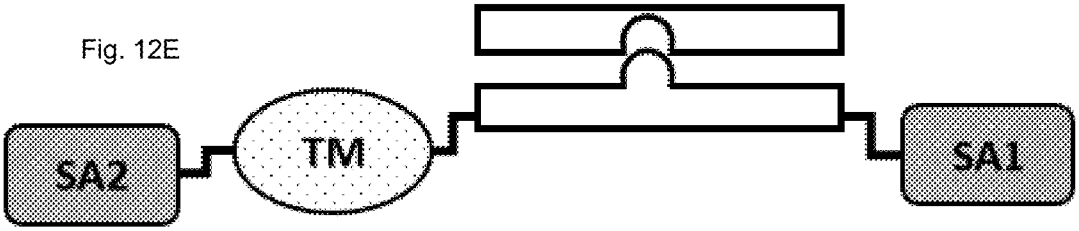
Figure 12F:
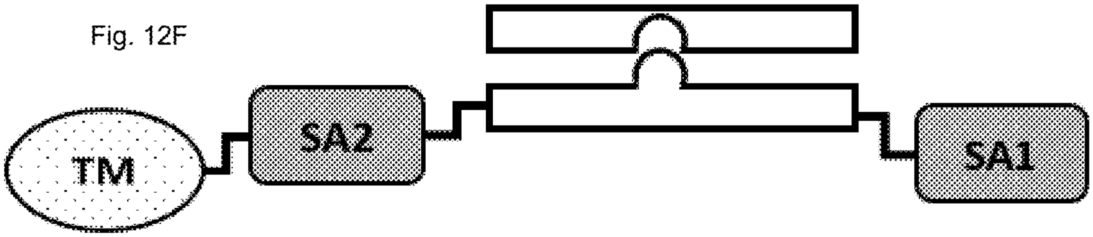
Figure 12G:
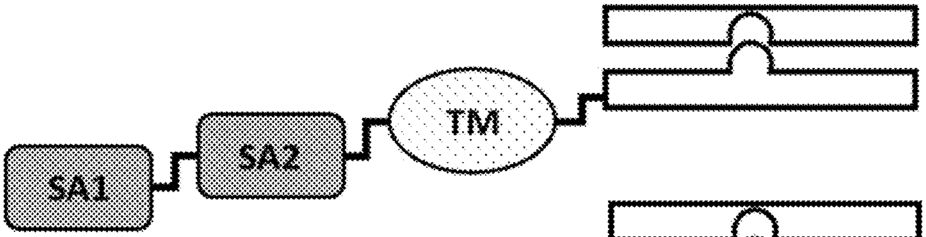
Figure 12H:
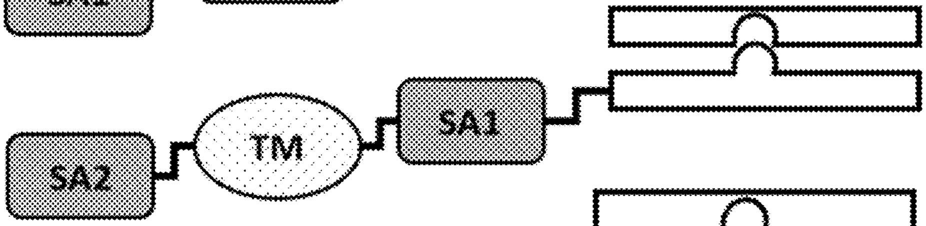
Figure 12I:
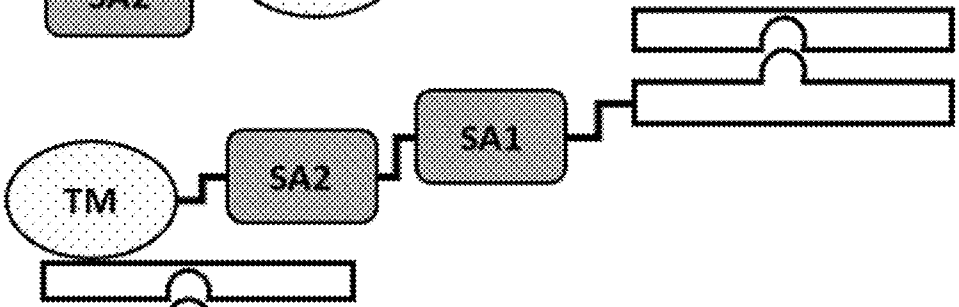
Figure 12J:
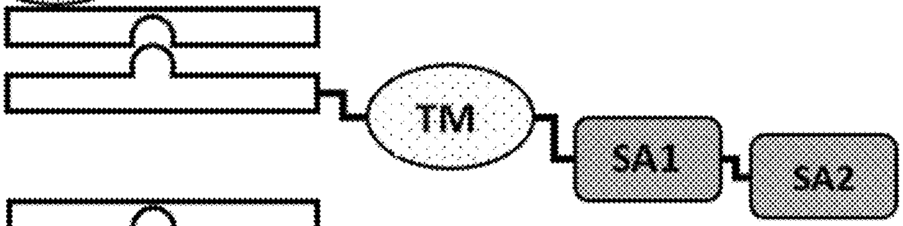
Figure 12K:
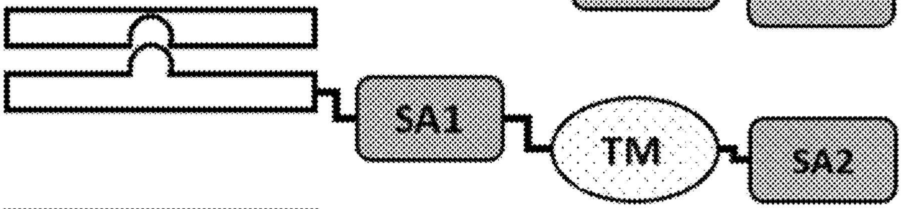
Figure 12L:
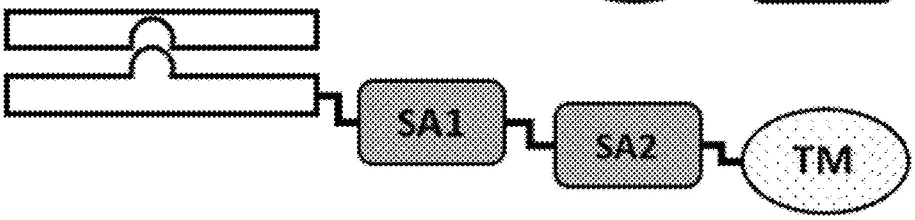
Figure 13A:
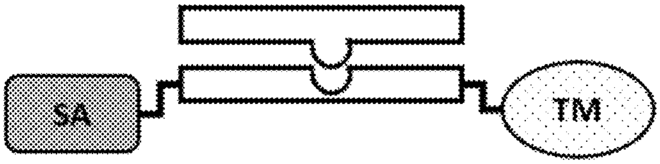
Figure 13B:
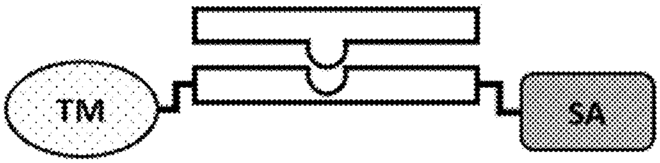
Figure 13C:
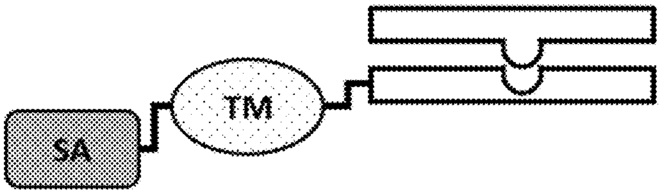
Figure 13D:
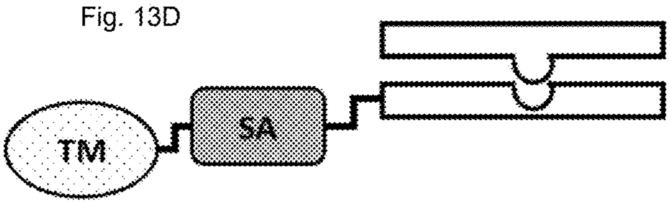
Figure 13E:
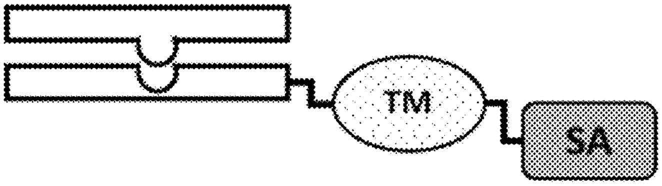
Figure 13F:
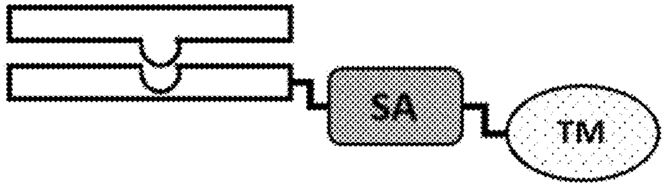
Figure 14A:
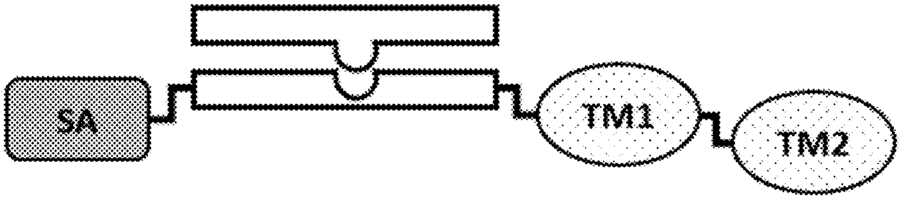
Figure 14B:
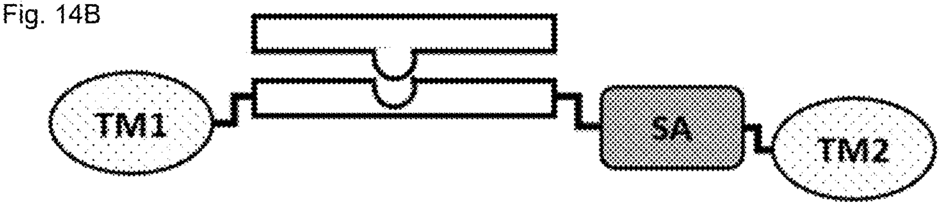
Figure 14C:
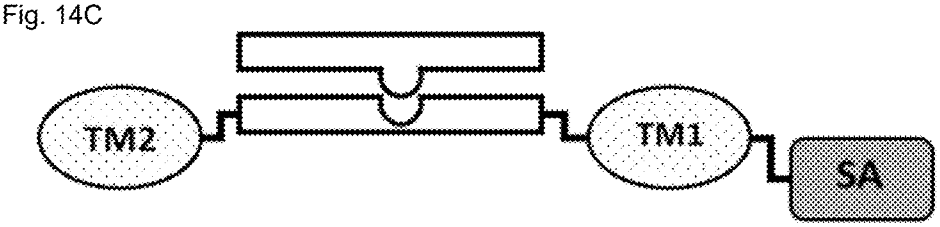
Figure 14D:
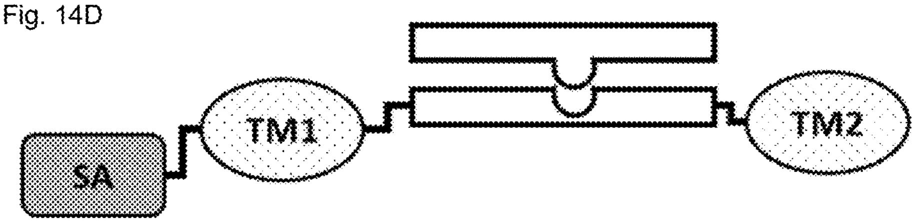
Figure 14E:
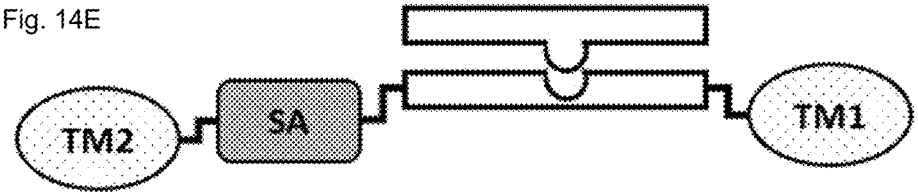
Figure 14F:
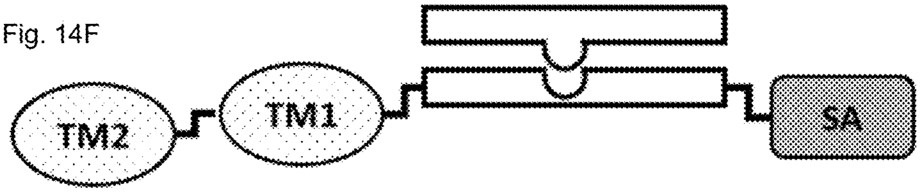
Figure 14G:
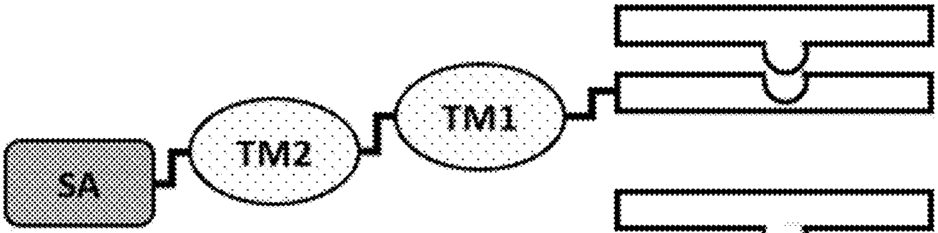
Figure 14H:
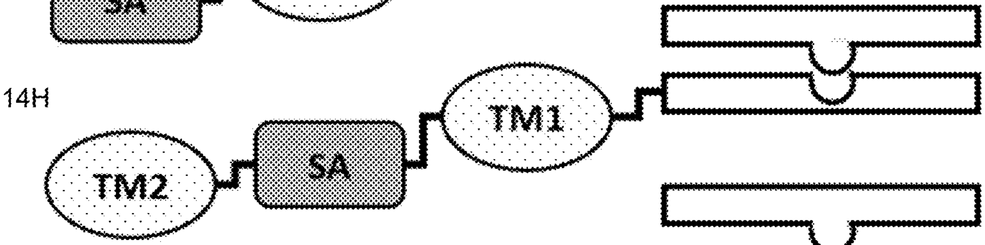
Figure 14I:
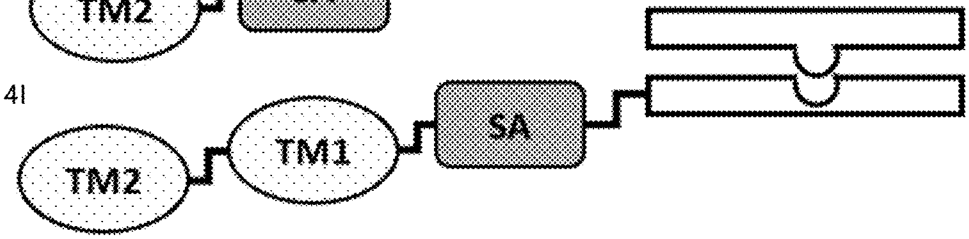
Figure 14J:
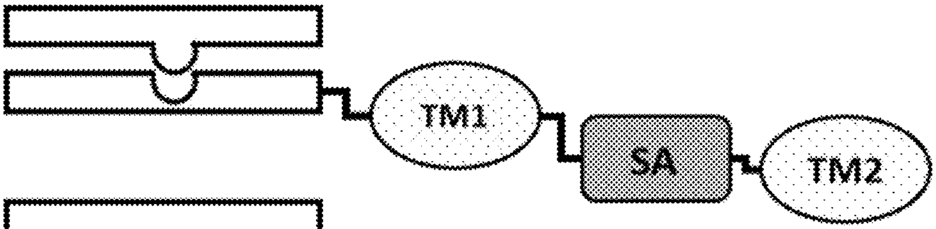
Figure 14K:
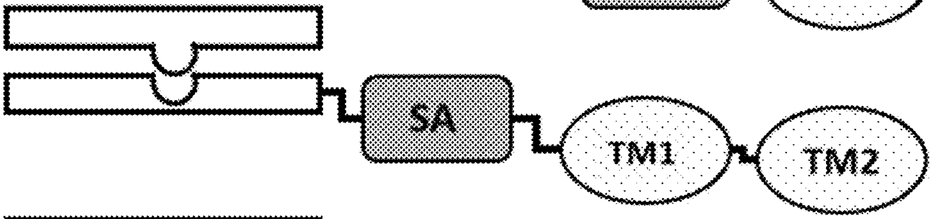
Figure 14L:
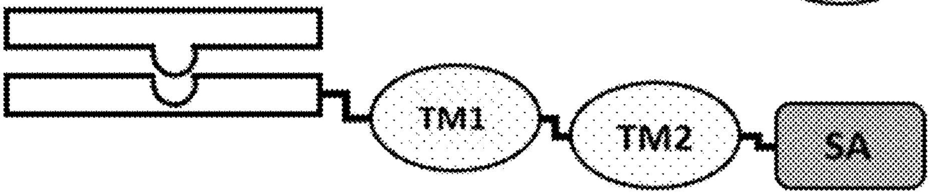
Figure 15A:
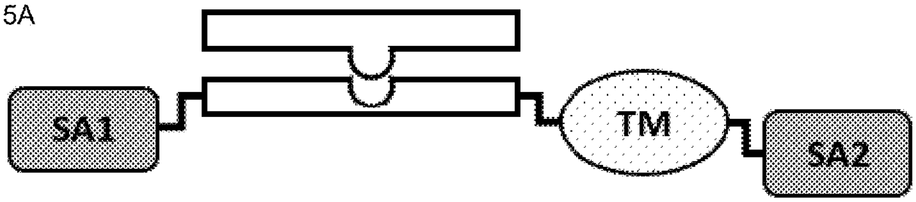
Figure 15B:
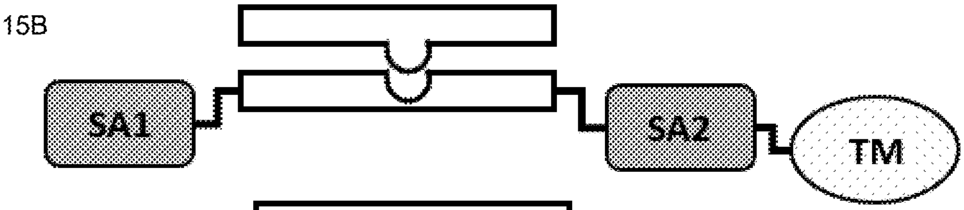
Figure 15C:
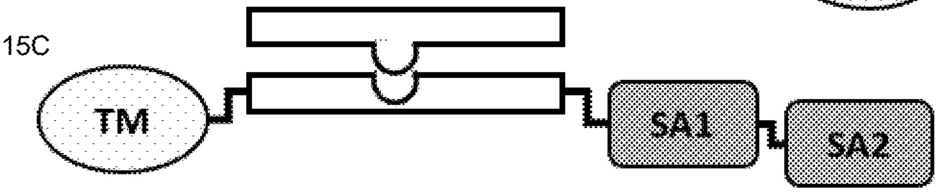
Figure 15D:
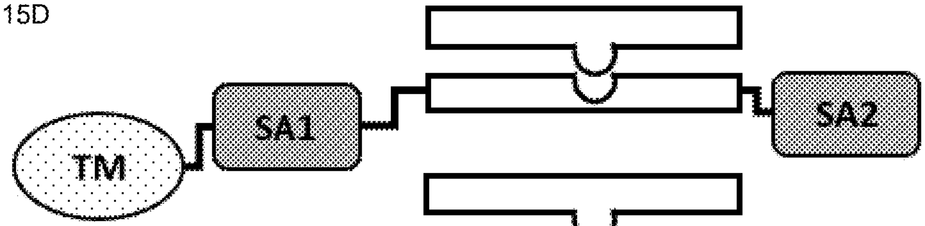
Figure 15E:
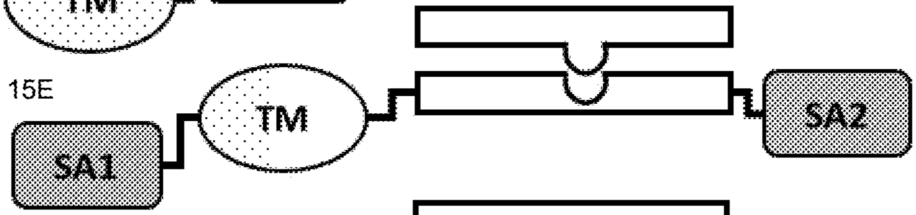
Figure 15F:
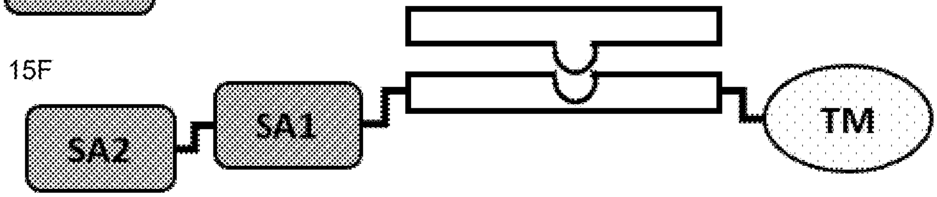
Figure 15G:
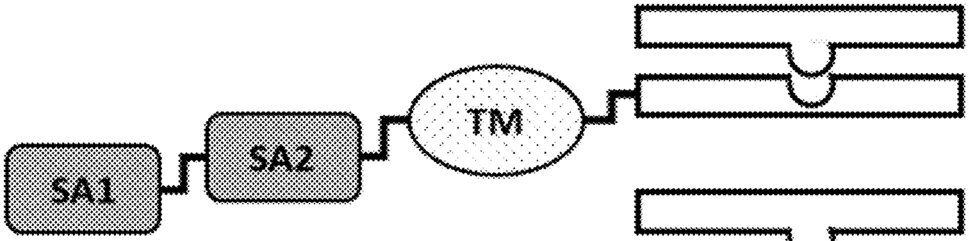
Figure 15H:
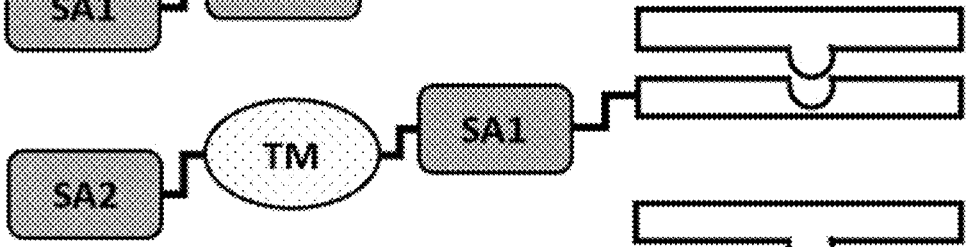
Figure 15I:
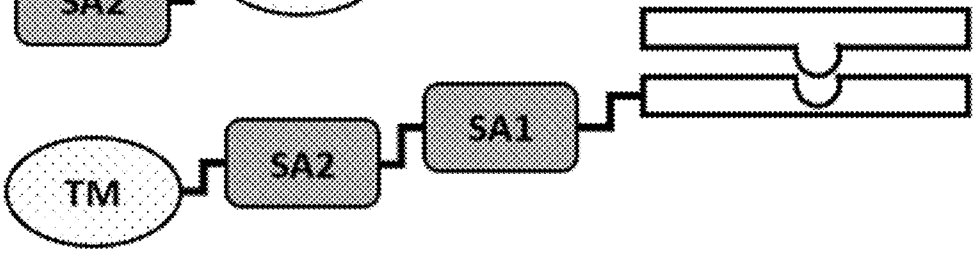
Figure 15J:
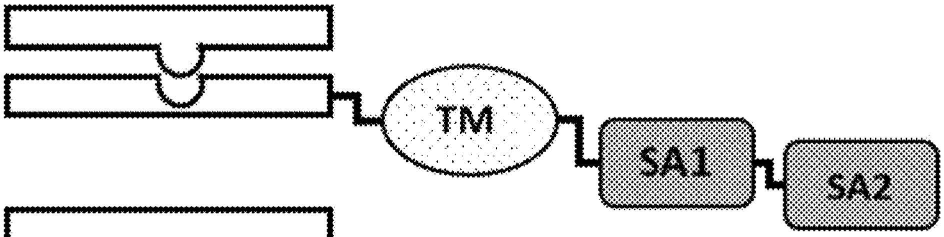
Figure 15K:
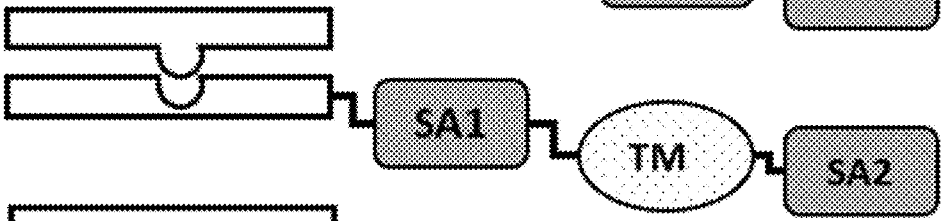
Figure 15L:
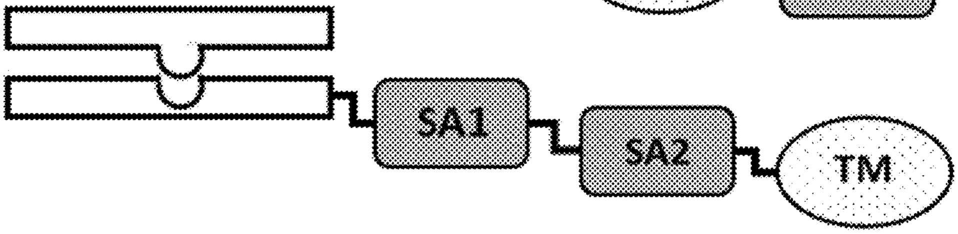
Figure 16A:
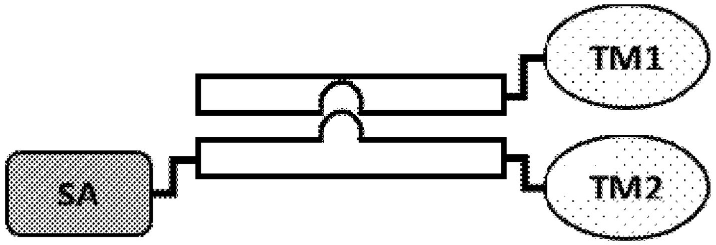
Figure 16B:
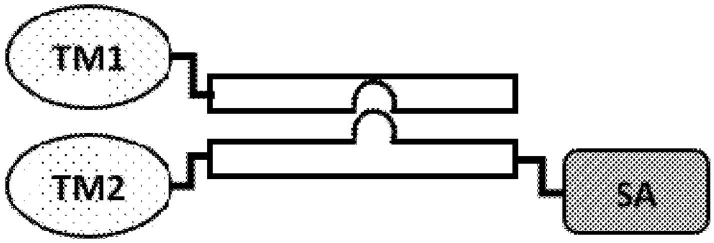
Figure 16C:
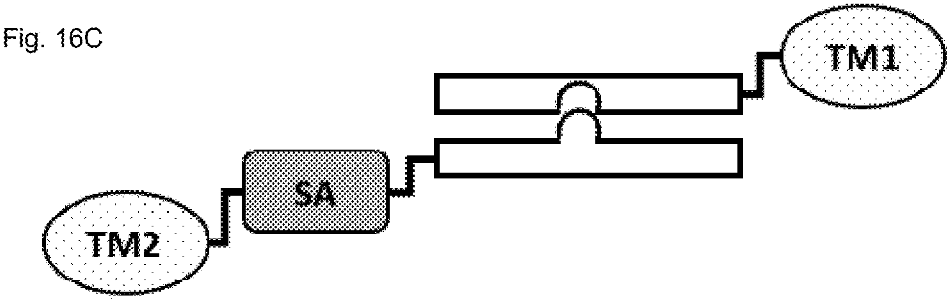
Figure 16D:
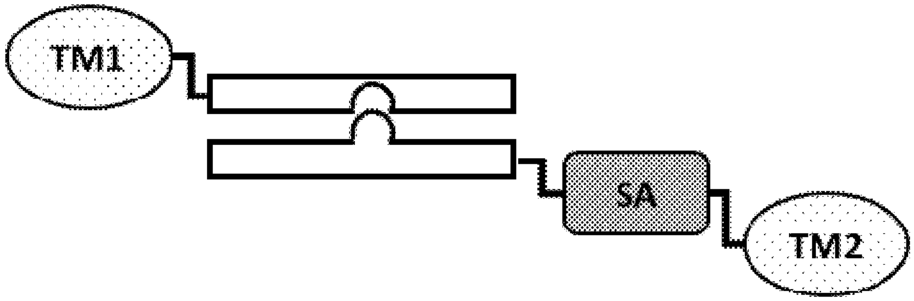
Figure 16E:
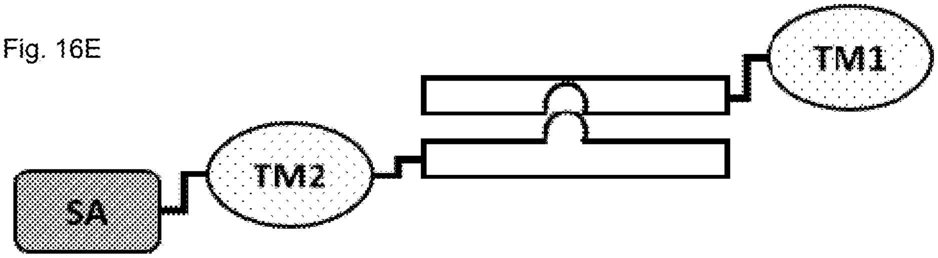
Figure 16F:
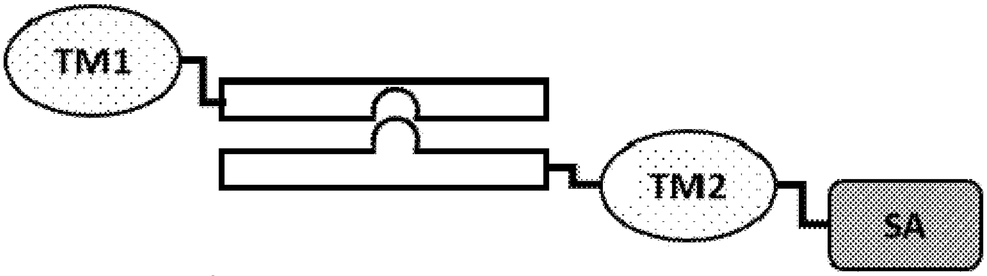
Figure 16G:
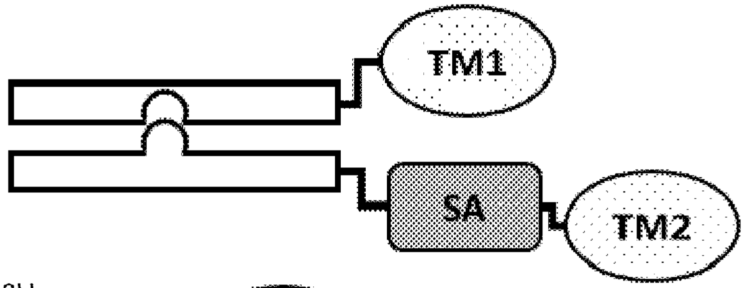
Figure 16H:
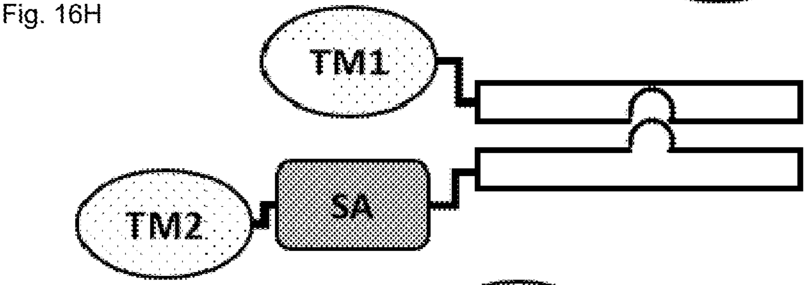
Figure 16I:
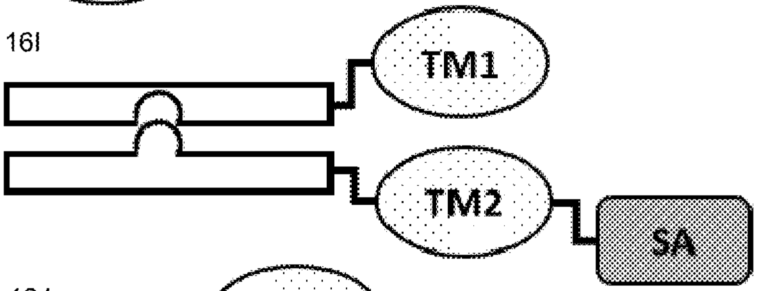
Figure 16J:
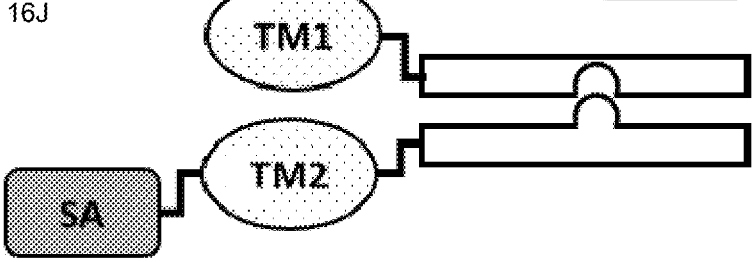
Figure 17A:
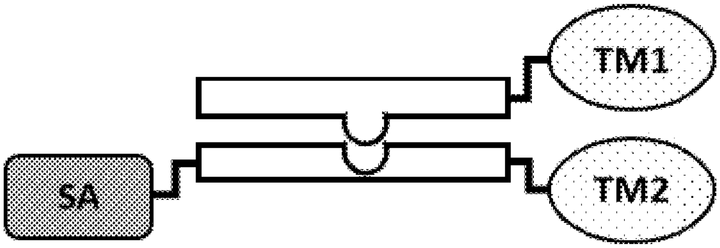
Figure 17B:
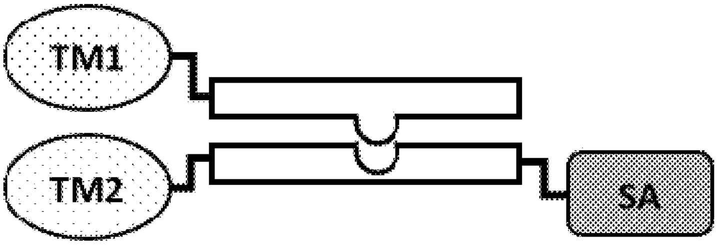
Figure 17C:
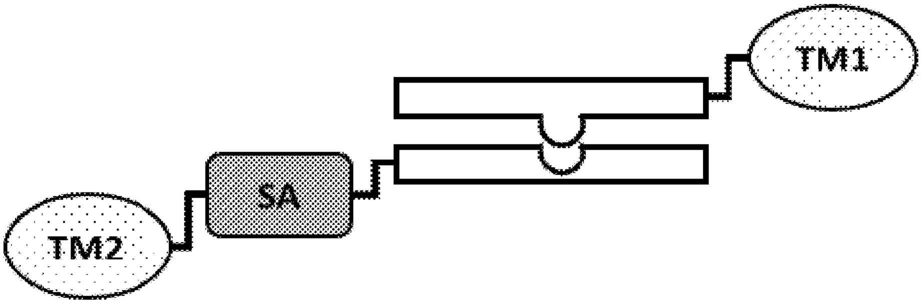
Figure 17D:
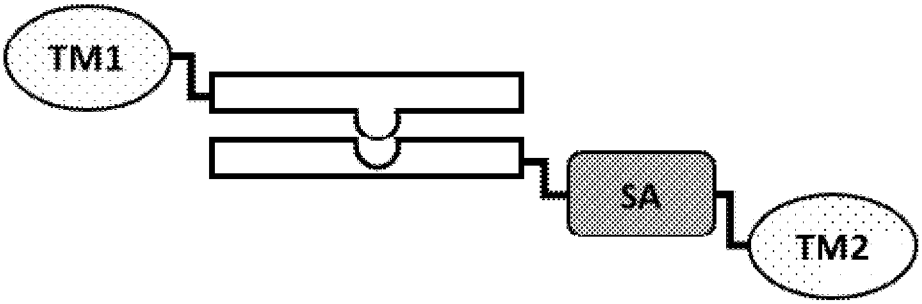
Figure 17E:
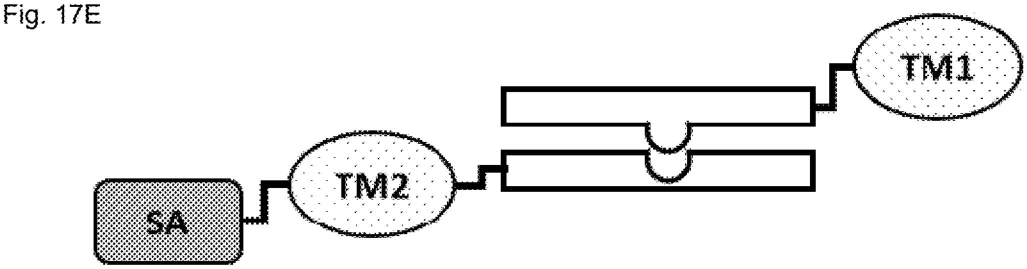
Figure 17F:
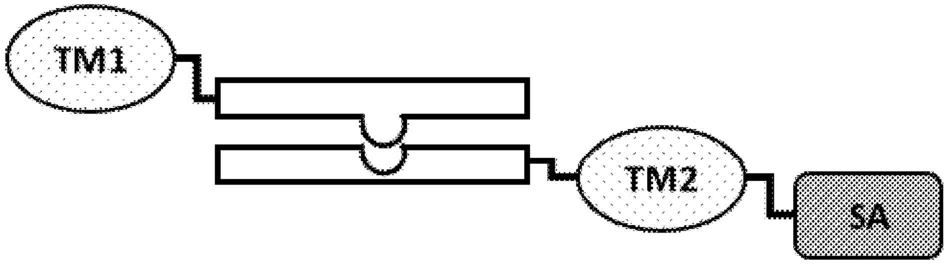
Figure 17G:
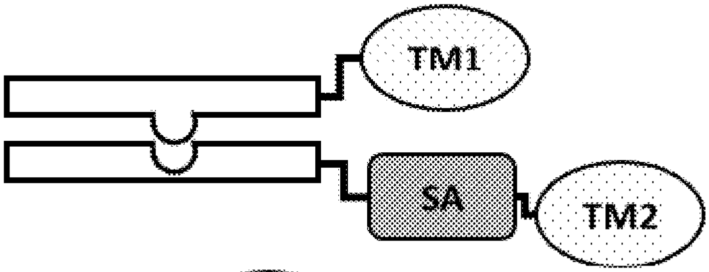
Figure 179H:
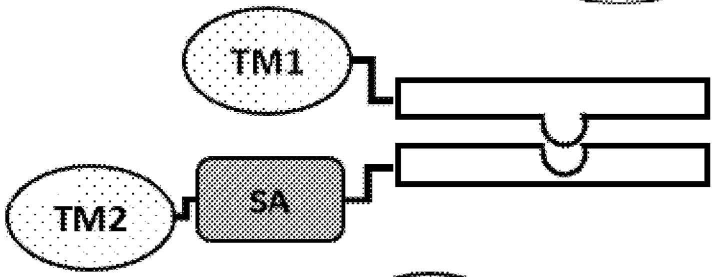
Figure 17I:
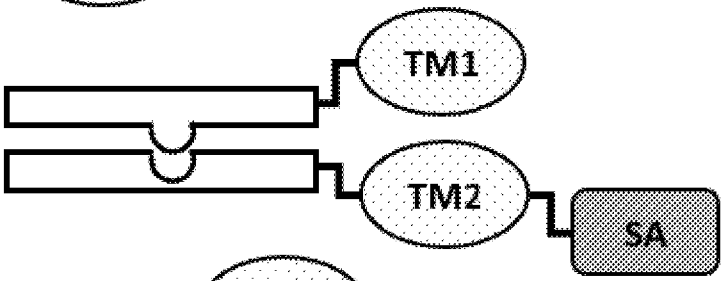
Figure 17J:
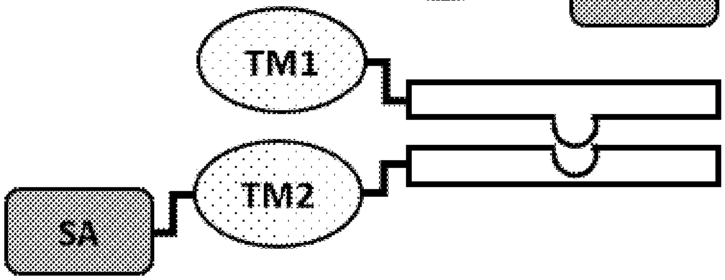
Figure 18A:
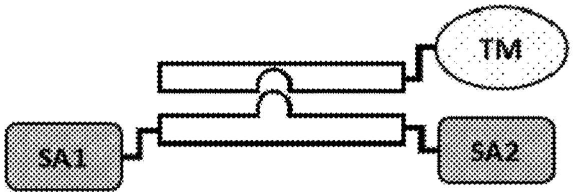
Figure 18B:
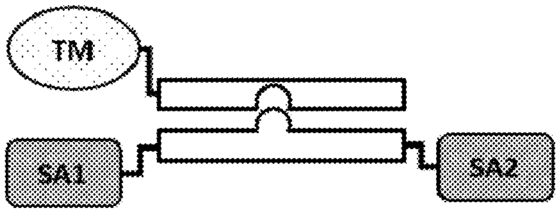
Figure 18C:
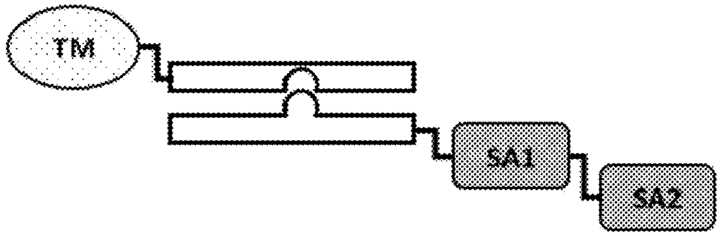
Figure 18D:
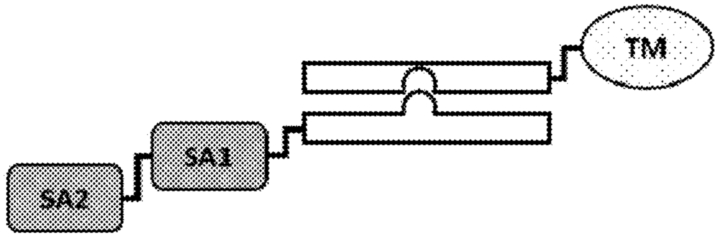
Figure 18E:
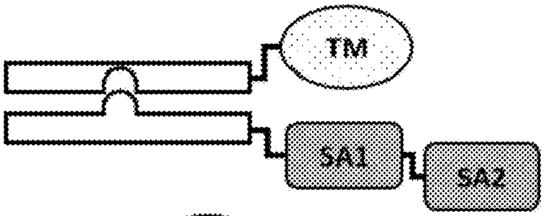
Figure 18F:
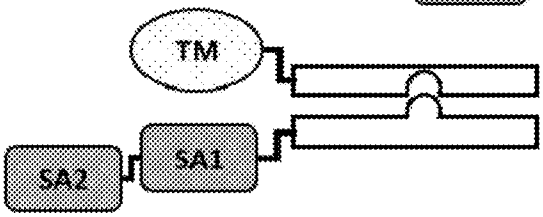
Figure 19A:
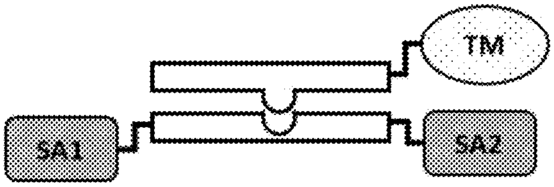
Figure 19B:
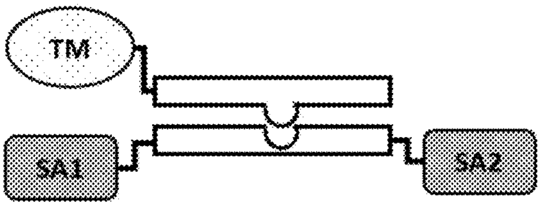
Figure 19C:
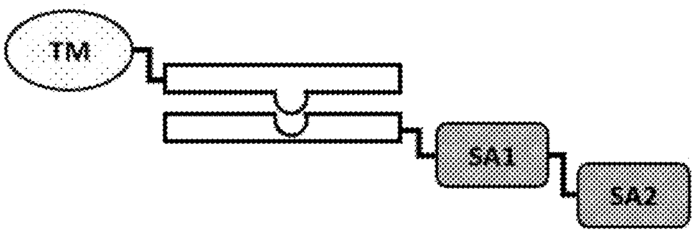
Figure 19D:
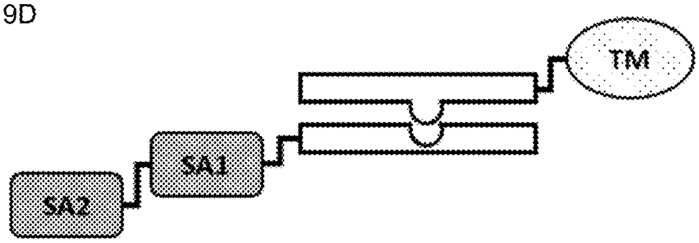
Figure 19E:
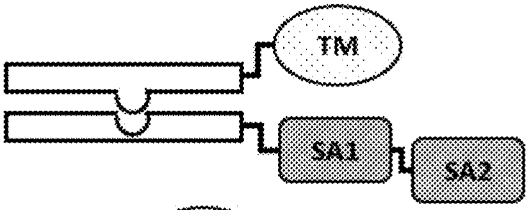
Figure 19F:
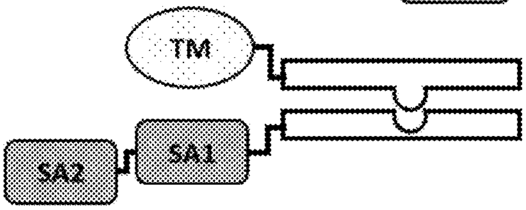

Constructs R1CHCL50-20*GGS-Fc and Fc-20*GGS-IFNα1 were combined, resulting in an AFN with a structure outlined in FIG. 7B, and transiently expressed in the ExpiCHO expression system (Thermo Fisher) according to the manufacturer's guidelines. One week after transfection, supernatant was collected, and cells removed by centrifugation. Recombinant proteins were purified from the supernatant using the Pierce Protein A spin plates (Thermo Fisher).

Biological Activity on HL116 Reporter Cell-Lines

Figure 20:
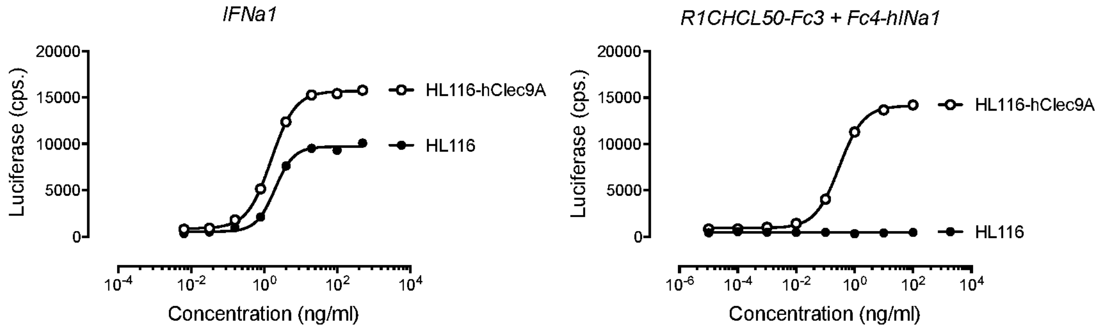
FIG. 20 shows biological activity of IFNα1 and Clec9A VHH Fc ActaFeron (AFN) on HL116 and HL116-hClec9A cells. Parental HL116 or the derived HL116-hClec9A cells were stimulated for 6 hours with a serial dilution of Fc AFNs. Average luciferase values (±STDEV) of triplicate measurements are plotted.
Figure 21A:
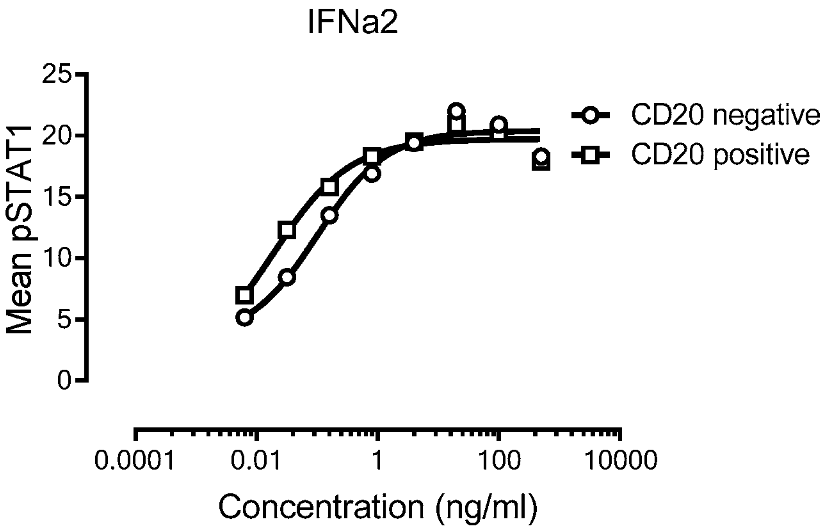
FIGS. 21A-D show IFNα1 (also represented herein as IFNα1) and IFN-α2 (also represented herein as IFNα2) signaling in peripheral blood mononuclear cells (PBMC) upon targeting. PBMCs from buffy coats of healthy donors were stained for CD20 and subsequently stimulated with a serial dilution of IFNα2 (i.e. without a targeting moiety), CD20 VHH-IFNα2 (a chimera of a CD20-directed VHH targeting moiety and wild type IFNα2), IFNα1 (i.e. without a targeting moiety), or CD20 VHH-IFNα1 (a chimera of a CD20-directed VHH targeting moiety and wild type IFNα1) for 15 minutes. STAT1 phosphorylation was quantified in FACS and plotted for CD20 positive and CD20 negative PBMCs. The data for IFN-α2 is shown in FIG. 21A, the data for CD20 VHH-IFNα2 is shown in FIG. 21B, the data for IFNα1 is shown in FIG. 21C and the data for CD20 VHH-IFNα1 is shown in FIG. 21D.
Figure 21B:
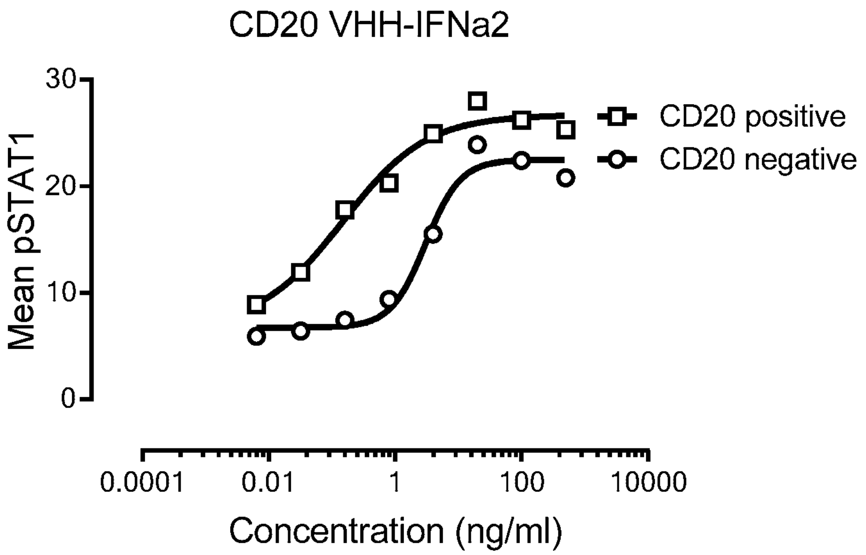
Figure 21C:
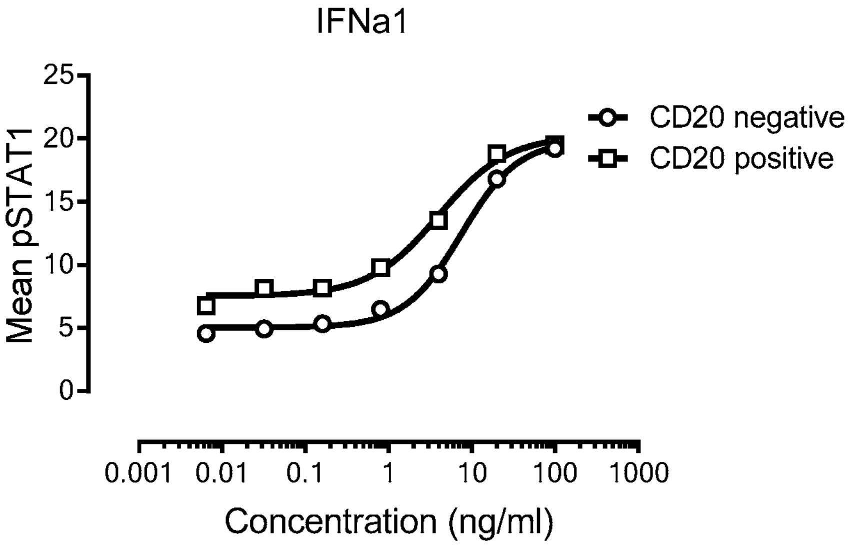
Figure 21D:
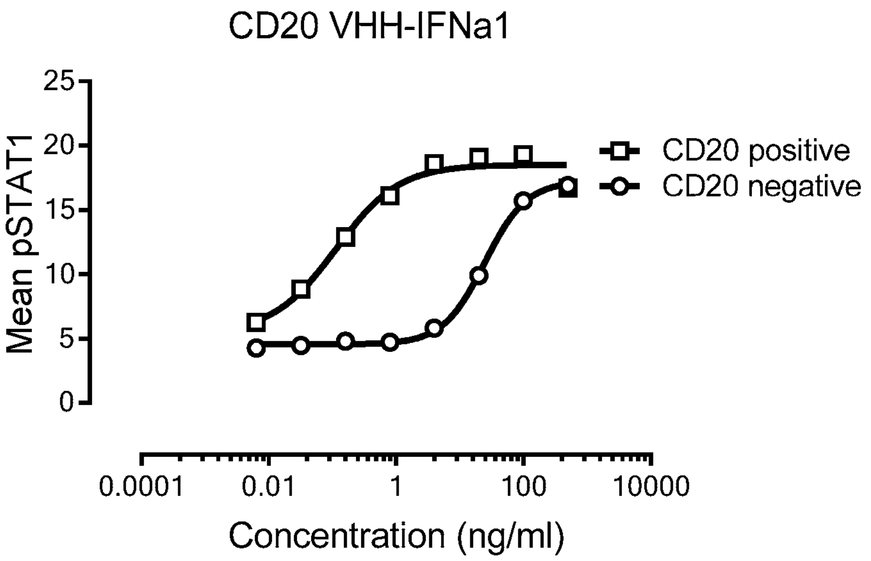

The HL116 clone is derived from the human HT1080 cell line (ATCC CCL-121). It contains the firefly luciferase gene controlled by the IFN-inducible 6-16 promoter. Parental HL116 cells were transfected with an expression vector encoding the human Clec9A sequence. Stable transfected clones were selected in G418-containing medium. Parental HL116 and HL116-hClec9A (target) cells were seeded overnight at 20,000 cells per 96-well and subsequently stimulated with a serial dilution of wild type human IFNα1 or the Fc-based CLEC9A targeted IFNα1 construct for 6 hours. Luciferase activity was measured in cell lysates. Data in the FIG. 20 illustrate that both cell-lines are comparably sensitive to wild type IFNα1. The EC50 of IFNα1-based Fc AFN signaling in targeted cells is 0.3 ng/ml, while no luciferase induction could be measured in parental HL116 cells.

Without wishing to be bound by theory, multiple surprising observations can be made from data shown in FIG. 20. While wild type IFNα1 is comparably active on both cell lines (HL116 and HL116-hClec9A cells), the IFNα1-based Fc AFN is in comparison substantially inactive in HLL16 parental cells (no detectable signal at 100 ng/ml, while the EC50 for wild type IFNα1 on these cells is about 2 ng/ml). This shows, inter alia, that fusion of or linking of wild type IFNα1 to an Fc polypeptide and incorporating IFNα1 in a Fc-based chimeric protein complex, leads to a substantial loss of IFNα1 potency in IFNAR-activation. This is similar to observations made for other forms of IFNα1 fusions/chimeric proteins, as shown in Example 2 and Example 3. However, as also observed for other forms of IFNα1 fusions and chimeric proteins, IFNα1 activity is induced and/or restored on target cells (HL116-hClec9A cells). Furthermore, and surprisingly, the Fc-based IFNα1, whose intrinsic IFNα1 activity is severely reduced (to undetectable levels in dose range tested on HL116 cells), is even more potent than wild type IFNa on target cells (while wild type IFNα1 has an EC50 of about 1.6 ng/ml on HL116-CLEC9A cells this improves to 0.3 ng/ml for the fusion protein or 84 and 3.3 pM respectively). In summary, IFNAR activators that combine high potency and high selectivity may be created de novo by incorporating wild type IFNα1 in a targeted (Fc-based chimeric) fusion protein complex—in a way and with a potency/selectivity index that is not achieved through use of wild type IFNα2.

Example 7: Fc-Based Chimeric Protein Complexes Having Interferon Alpha 1 Variants This Example evaluates and generates chimeric proteins and chimeric protein complexes based on interferon alpha 1 (IFNα1), including modified and activity-attenuated variants thereof, and targeted via a human Clec9A antigen-specific VHH antibody (clone R1CHCL50) to Clec9A-positive cells. For this purpose, illustrative heterodimeric Fc-based proteins based on knob-into-hole Fc-technology were designed, made and evaluated for bioactivity characteristics. This includes IFNα1 variants that comprise one of different mutations that cause change of a cysteine residue (C86) to reduce undesired disulfide pairing, to improve product homogeneity and pharmaceutical properties of the chimeric protein and chimeric protein complexes. The objective was to also evaluate whether such modifications would not substantially interfere with induction of, and/or allow for maintaining or avoiding substantial loss of induction of IFNAR-activation at the target cell (for both IFNα1 attenuated by fusion alone, and IFNα1 that is activity-attenuated by additional mutation). The results show that a unique combination of highly potent and highly cell target-selective IFNAR-signaling activation can be achieved with IFNα1 compositions, and variants thereof, described herein.

Constructs:

R1CHCL50-5*GGS-human IgG1 Fc (with hole mutations and effector knock-out mutations); P-1479

(SEQ ID NO: 293)

qvqlvesggglvhpggslrlscaasgsfssinvmgwyrqapgkerelvaritnlglpnyadsvtgrftisrdnakn tvylqmnslkpedtavyycylvalkaeywgqgtqvtvssGGSGGSGGSGGSGGSDKTHTCPPCPAPEAAGGPSVF

LFPPKPKDTLMISRTPEVTCVVVDVSHEDPEVKFNWYVDGVEVHNAKTKPREEQYNSTYRWVSVLTVLHQDWLN

GKEYKCQVSNKALPAPIEKTISKAKGQPREPQVCTLPPSRDELTKNQVSLSCAVKGFYPSDIAVEWESNGQPEN

NYKTTPPVLDSDGSFFLVSKLTVDKSRWQQGNVFSCSVMHEALHNHYTQKSLSLSPGK human IgG1 Fc (with knob mutations and effector knock-out mutations) -10*GGS-IFNα1(C86S); P-2213

(SEQ ID NO: 294)

DKTHTCPPCPAPEAAGGPSVFLFPPKPKDTLMISRTPEVTCVWVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSCDLPETHSLDNRRTLMLLAQMSRISPSSCLMDRHD

-continued

FGFPQEEFDGNQFQKAPAISVLHELIQQIFNLFTTKDSSAAWDEDLLDKFSTELYQQLNDLEACVMQEERVGETP

LMNADSILAVKKYFRRITLYLTEKKYSPCAWEVVRAEIMRSLSLSTNLQERLRRKE human IgG1 Fc (with knob mutations and effector knock-out mutations) -10*GGS-IFNα1(C86S, A146G); P-2214

(SEQ ID NO: 295)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSCDLPETHSLDNRRTLMLLAQMSRISPSSCLMDRHD

FGFPQEEFDGNQFQKAPAISVLHELIQQIFNLFTTKDSSAAWDEDLLDKFSTELYQQLNDLEACVMQEERVGETP

LMNADSILAVKKYFRRITLYLTEKKYSPCAWEVVRGEIMRSLSLSTNLQERLRRKE human IgG1 Fc (with knob mutations and effector knock-out mutations) -10*GGS-IFNα1(C86S, M149V); P-2215

(SEQ ID NO: 296)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSCDLPETHSLDNRRTLMLLAQMSRISPSSCLMDRHD

FGFPQEEFDGNQFQKAPAISVLHELIQQIFNLFTTKDSSAAWDEDLLDKFSTELYQQLNDLEACVMQEERVGETP

LMNADSILAVKKYFRRITLYLTEKKYSPCAWEVVRAEIVRSLSLSTNLQERLRRKE human lgG1 Fc (with knob mutations and effector knock-out mutations) -10*GGS-IFNα1(C86Y); P-2216

(SEQ ID NO: 297)

DKTHTCPPCPAPEAAGGPSVFLFPPKPKDTLMISRTPEVTCVWVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSCDLPETHSLDNRRTLMLLAQMSRISPSSCLMDRHD

FGFPQEEFDGNQFQKAPAISVLHELIQQIFNLFTTKDSSAAWDEDLLDKFYTELYQQLNDLEACVMQEERVGETP

LMNADSILAVKKYFRRITLYLTEKKYSPCAWEVVRAEIMRSLSLSTNLQERLRRKE human IgG1 Fc (with knob mutations and effector knock-out mutations -10*GGS-IFNα1(C86Y, A146G); P-2217

(SEQ ID NO: 298)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSCDLPETHSLDNRRTLMLLAQMSRISPSSCLMDRHD

FGFPQEEFDGNQFQKAPAISVLHELIQQIFNLFTTKDSSAAWDEDLLDKFYTELYQQLNDLEACVMQEERVGETP

LMNADSILAVKKYFRRITLYLTEKKYSPCAWEVVRGEIMRSLSLSTNLQERLRRKE human IgG1 Fc (with knob mutations and effector knock-out mutations) -10*GGS-IFNα1(C86Y, M149V); P-2218

(SEQ ID NO: 299)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSCDLPETHSLDNRRTLMLLAQMSRISPSSCLMDRHD

FGFPQEEFDGNQFQKAPAISVLHELIQQIFNLFTTKDSSAAWDEDLLDKFYTELYQQLNDLEACVMQEERVGETP

LMNADSILAVKKYFRRITLYLTEKKYSPCAWEVVRAEIVRSLSLSTNLQERLRRKE

The construct R1CHCL50-5*GGS-Fc is combined with each of the Fc-10*GGS-IFNα1 variants, resulting in six different AFNs with a structure outlined in FIG. 7B, and transiently expressed in the ExpiCHO expression system (Thermo Fisher) according to the manufacturer's guidelines. One week after transfection, supernatant is collected, and cells removed by centrifugation. Recombinant proteins are purified from the supernatant using the Pierce Protein A spin plates (Thermo Fisher) and potency tested as described in Example 6.

Data in FIGS. 24A-G and Table 8 clearly illustrate, inter alia, that:

- (i) Parental HL116 and the derived HL116-Clec9A cells (expressing human Clec9A) are comparably responsive/sensitive to wild type IFNα2a with an EC50 of 8 pM and 6 pM for reporter induction observed in HL116 and HL116-hCLEC9A, respectively. The same was previously observed for IFNα1 (as shown in Example 6, FIG. 20), with IFNα1 being approximately 10-15-fold less potent compared to IFNα2 (IFNα1 EC50 of 105 pM and 85 pM for reporter induction in HL116 and HL116-hCLEC9A, respectively).
- (ii) All tested IFNα1 construct variants are substantially less active compared to wild type IFNα2 (and IFNα1 when comparing to Example 6, FIG. 20) on non-target cells (HL116).
- (iii) Activity of all tested IFNα1 protein variants can be induced and/or restored at the target cells (Clec9A-positive), being markedly more active on targeted (i.e., Clec9A expressing) cells compared to non-targeted cells (i.e., exhibit high selectivity for target cells).
- (iv) Remarkably, induction of IFNAR-activation in target cells by IFNα1 proteins harboring mutation of the free C86 (C to S, or C to Y), and otherwise wild type for IFNα1, is far superior to that obtained with wild type IFNα1 (non-fused, unmodified IFNα1). Even more surprising, activity on target cells is similar to that observed for IFNα2, which is among the most potent type I interferons. Similar observations were made for an Fc-based IFNα1 construct incorporating wild type IFNα1 that does not incorporate a mutation in C86 (see FIG. 20), as also observed for non-Fc chimeric proteins incorporating IFNα1 (see Table 7 for example).
- (v) All the Fc-IFNα1 constructs exhibit remarkable selectivity for target cells (which is not observed for non-fused, unmodified wild type IFNα1 or IFNα2).
- (vi) IFNα1 constructs with mutation of the free C86, to either S or Y (one amino acid change being conservative, the other non-conservative), have similar bioactivity, and similar to that of equivalent construct without mutation of C86 (see FIG. 20).
- (vii) The activity of IFNα1 constructs with mutations A146G or M149V in IFNα1, while further attenuated for IFNAR-activation compared to a fusion without these mutations, is induced and/or restorable at a target cell (Clec9-positive cells). Remarkably, potency of IFNAR-activation is similar to or greater than potency of wild type IFNα1 at target cells.
- (viii) IFNα1 chimeric constructs incorporating mutation of the free C86 to S or Y are highly inducible and active at target cells, including constructs harboring additional mutation A146G or M149V.

TABLE 8

EC50 of IFNAR signaling in HL116 cells expressed in pM. If the reporter activity at the highest concentration was detectable but did not reach EC50 levels this is indicated with ">>". In case at the highest concentration no reporter activity was detected this is indicated by ">>".

| | EC50 6-16 reporter activity (pM) | | |
|---|---|---|---|
| | HL116 | HL116-CLEC9A | ratio |
| IFNa1(Example 6) | 105 | 84 | 1.2 |
| R1CHCL50-Fc3 + Fc-hIFNa1 (Example 6) | >1000 | 3 | >330 |
| IFNa2 | 8 | 6 | 1.3 |
| R1CHCL50-Fc3 + Fc-hIFNa1(C86S) | >1000 | curve does not allow EC50 calculation | |
| R1CHCL50-Fc3 + Fc-hIFNa1(C86Y) | >1000 | 1 | >1000 |
| R1CHCL50-Fc3 + Fc-hIFNa1(C86S-A146G) | >>1000 | 19 | >>50 |
| R1CHCL50-Fc3 + Fc-hIFNa1(C86Y-A146G) | >>1000 | 7 | >>140 |
| R1CHCL50-Fc3 + Fc-hIFNa1(C86S-M149V) | >>1000 | 60 | >>15 |
| R1CHCL50-Fc3 + Fc-hIFNa1(C86Y-M149V) | >>1000 | 15 | >>65 |

In a second series of experiments, IFNα1 AFNs were tested for ability to promote STAT1 phosphorylation in primary human cDC1 cells (naturally express Clec9A, and the target of the IFNα1 chimeric constructs) compared to other PBMC populations (Clec9A negative cells). In brief, PBMCs from buffy coats of healthy donors were isolated using density gradient centrifugation using Lymphoprep (StemCell technologies). Cells were washed twice with FACS buffer (2% FBS, 1 mM EDTA in PBS) and stained with anti-Clec9A and anti-CD141 Ab's (both Miltenyi) to identify the cDC1 population for 20 minutes at 4° C. After two washes, cells were stimulated with a serial dilution of wild type IFNα2 or IFNα1 AFNs for 15 minutes at 37° C. After fixation (10 minutes, 37° C., Fix Buffer I; BD Biosciences), permeabilization (30 minutes, on ice, Perm III Buffer I; BD Biosciences) and washing, cells were stained with anti-STAT1 pY701 Ab (BD Biosciences). Samples were acquired with a MACSQuant X instrument (Miltenyi Biotec) and analyzed using the FlowLogic software (Miltenyi Biotec). Data in FIGS. 25A-E are qualitatively comparable to results obtained with the HL-116/HL-116-hClec9A reporter cell lines (see FIGS. 24A-G), and similar overall conclusion can be drawn from these data. For example, without limitation, the data show that (i) Clec9A−/CD141- and Clec9A+/CD141+ cells are comparably responsive/sensitive to wild type IFN, (ii) all tested targeted IFNα1 variants instead are markedly more active on targeted Clec9A+/CD141+ cells compared to non-targeted (Clec9A−/CD141−) cells, i.e., high targeting and selectivity index is observed, (iii) induction of IFNAR-activation in target cells by IFNα1 proteins harboring mutation of the free C86 (C to S, or C to Y), and otherwise wild type for IFNα1, is far superior to that obtained with wild type, non-fused, unmodified IFNα2. Even more surprising, activity on target cells is similar to that observed for IFNα2, which is among the most potent type I interferons, (iv) IFNα1 activity for IFN1a chimeric constructs harboring mutation A146G, while intrinsically attenuated, is induced and/or restored in target cells. v) IFNα1 chimeric constructs incorporating mutation of the free C86 to S or Y are highly inducible and active at target cells, including constructs harboring an additional mutation such as A146G.

Together, both datasets illustrate, inter alia, that it is possible to selectively target IFNα1 activity to Clec9A expressing target cells including primary human cells, and achieve high potency of IFNAR-activation, without detectable IFNAR-activation and signaling in non-target cells at equivalent dose/concentration. Both C86S and C86Y mutations allow for removal of the free cysteine residue in the IFNα1 sequence, and hence undesired disulfide pairing, and still achieve a maximum signaling restoration. Surprisingly, on primary cDC1 which are the key target cells for a CLEC9A-targeted construct, the potency of the C86Y IFNα1 variant construct matched the potency of wild type IFNα2 (EC50 of 350 pM for P-1479/P-2216 versus 240 pM for IFNα2) while the selectivity window of the C86Y IFNα1 construct versus non-cDC1 cells was >100 fold.

Even more surprisingly is the finding that on primary cDC1 the potency of the C86S IFNα1 variant construct exceeded the potency of wild type IFNα2 (EC50 of 20 pM for P-1479/P-2213 versus 240 pM for IFNα2) while the selectivity window of the C86S IFNα1 construct versus non-cDC1 cells was about >300 fold.

In summary, the results show that a unique combination of high potency and high cell target-selectivity for IFNAR-signaling activation can be achieved with IFNα1 chimeric protein and protein complex compositions, and variants thereof.

Example 8: PD-L1 Targeted IFNα1 and Variants Thereof

In this example, constructs for Fc-based IFNα1, and variants thereof, and their targeting to PD-L1 expressing cells was evaluated. This includes constructs that incorporate wild type IFNα1 with a C86S mutation (as in some constructs in previous Example 7) and PD-L1 direct VHH antibodies. Two PD-L1-specific VHHs, termed 2LIG99 and 2LIG189, were used in different constructs. Comparable constructs based on use of an activity-attenuated and target-specific restorable mutant IFNα2 were also included, for comparison. Illustrative chimeric proteins and protein complexes were generated that are based on a heterodimeric, ‘knob-in-hole’ Fc-based AFN format. In the pcDNA3.4 expression vector, the sequence encoding one or two PD-L1 VHHs was, via a flexible 5*GGS-linker, fused/linked to the human IgG1 Fc sequence containing the L234A_L235A_K322Q effector mutations and the ‘hole’ modifications Y349C_T366S_L368A_Y407V (see sequence below). The second polypeptide that is part of and incorporated into the chimeric Fc-based protein complex, was also cloned in the pcDNA3.4 vector, and consists of the fusion/linkage between the human IgG1 Fc sequence containing the L234A_L235A_K322Q effector mutations and the ‘knob’ modifications S354C_T366W and the C86S variant of IFNα1.

To produce heterodimeric ‘knob-in-hole’ Fc-based chimeric protein and protein complexes, the following combinations of both ‘hole’ and ‘knob’ plasmids was transfected in ExpiCHO cells (ThermoFisher) according to the manufacturer's instructions:

P-1542: Fc3+P-2213: Fc4-10*GGS-hIFNα1_C86S;

P-2204: 2LIG99-5*GGS-Fc3+P-2213: Fc4-10*GGS-hIFNα1_C86S;

P-2206: 2LIG189-5*GGS-Fc3+P-2213: Fc4-10*GGS-hIFNα1_C86S;

P-2399: 2LIG99-20*GGS-2LIG99-5*GGS-Fc3+P-2213: Fc4-10*GGS-hIFNα1_C86S; (note: in this construct the PD-L1 VHH 2LIGG99 is repeated in tandem)

In addition, the equivalent constructs for the IFNα2 mutant were generated:

P-1542: Fc3+Fc4-10*GGS-hIFNα2_mut;

P-2204: 2LIG99-5*GGS-Fc3+Fc4-10*GGS-hIFNα2_mut;

P-2206: 2LIG189-5*GGS-Fc3+Fc4-10*GGS-hIFNα2_mut;

P-2399: 2LIG99-20*GGS-2LIG99-5*GGS-Fc3++Fc4-10*GGS-hIFNα2_mut;

(note: in this construct the PD-L1 VHH 2LIGG99 is repeated in tandem)

Seven days post transfection, recombinant protein complexes were sequentially purified on a Protein A column and a Superdex 200 Increase 10/300 column (both GE Healthcare) on an AKTA pure instrument (GE Healthcare). Proteins were quantified and purity checked on SDS-PAGE. Biological activity of the Fc-based constructs was tested on HL116 cells (an IFN responsive cell-line stably transfected with an IFN-inducible p6-16 luciferase reporter gene) that express PD-L1. Cells were seeded overnight and stimulated for 6 hours with a serial dilution of the different protein construct preparations. Luciferase activity was measured on an EnSight Multimode Plate Reader (Perkin Elmer).

Figure 22A:
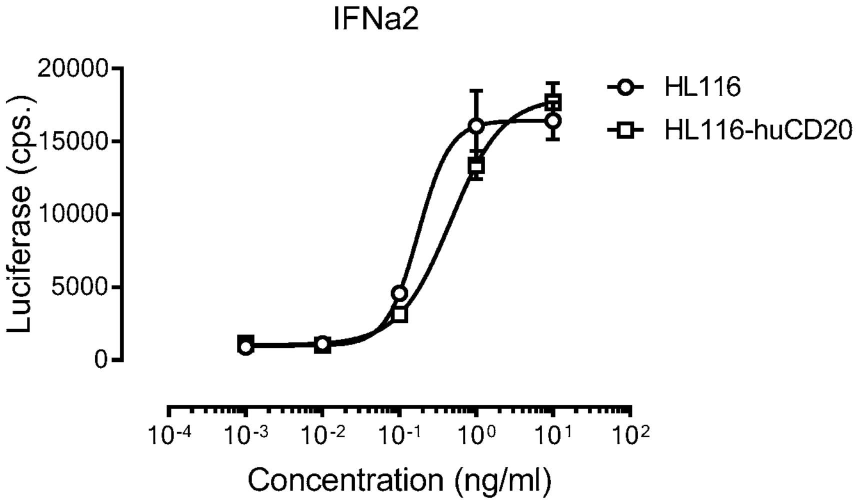
FIGS. 22A-D show IFNα1 and IFN-α2 signalling in HL116 and HL116-hCD20 cells upon targeting. Parental HL116 or the derived HL116-huCD20 cells were stimulated with a serial dilution of IFNα2 (i.e. without a targeting moiety), CD20 VHH-IFNα2 (a chimera of a CD20-directed VHH targeting moiety and wild type IFNα2), IFNα1 (i.e. without a targeting moiety), or CD20 VHH-IFNα1 for 6 hours. Average luciferase values (±STDEV) of triplicate measurements are plotted. The data for IFN-α2 is shown in FIG. 22A, the data for CD20 VHH-IFNα2 is shown in FIG. 22B, the data for IFNα1 is shown in FIG. 22C and the data for CD20 VHH-IFNα1 is shown in FIG. 22D.
Figure 22B:
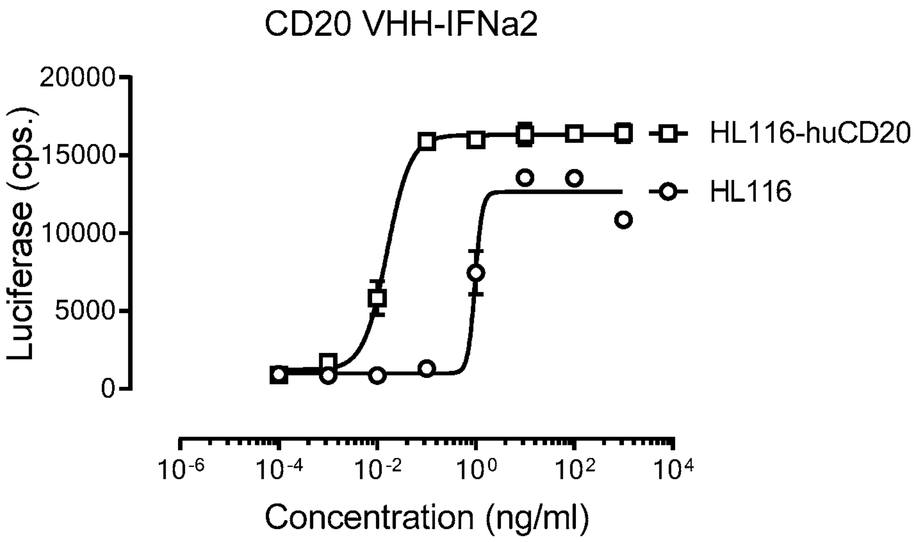
Figure 22C:
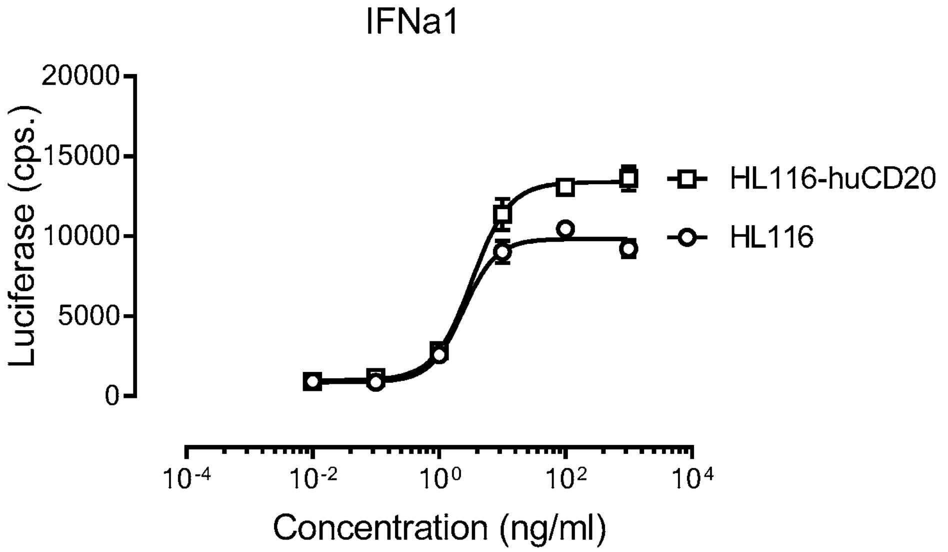
Figure 22D:
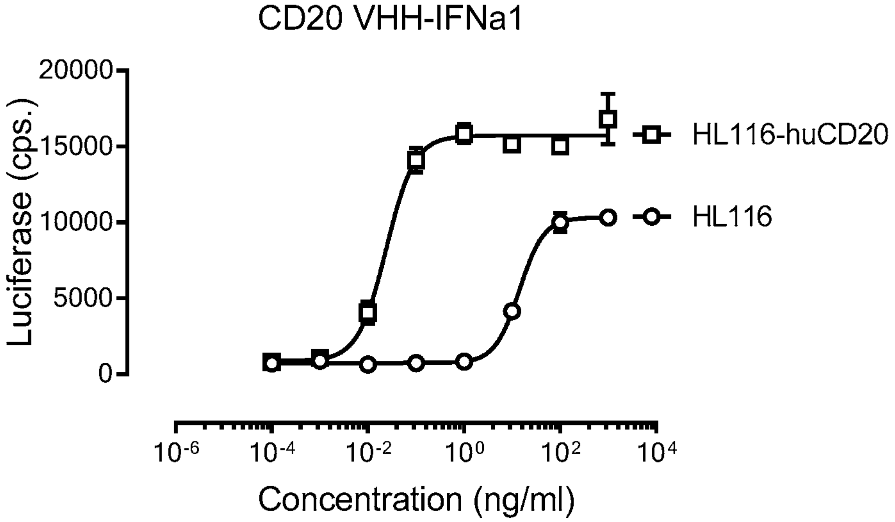
Figure 26A:
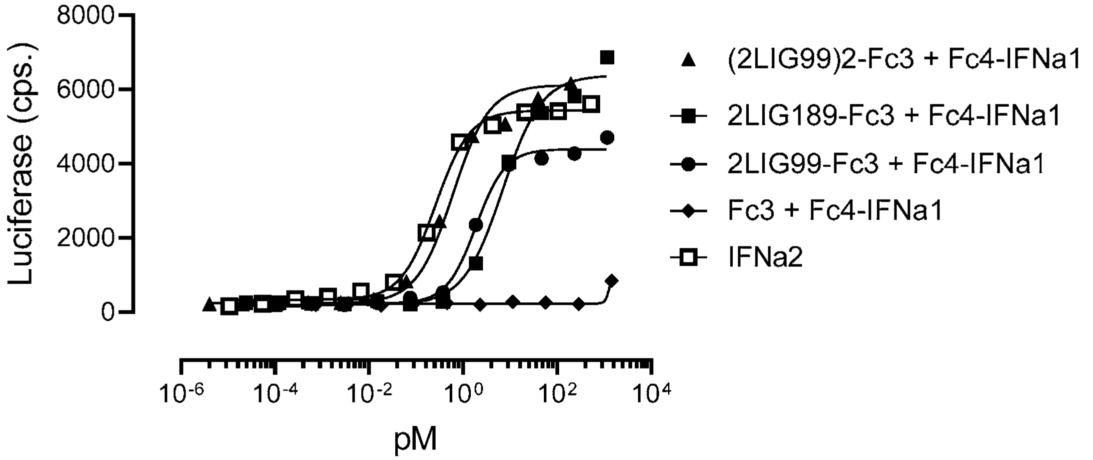
FIGS. 26A-B show biological activity of PD-L1 targeted IFNα1 (FIG. 26A) and IFNα2 (FIG. 26B) AFNs on the HL116 reporter. HL116 cells were stimulated for 6 hours with serial dilution wild type IFNα2 or IFNα1 AFNs. Average luciferase activities (±STDEV) are plotted.

Data in FIG. 26A illustrates clearly that Fc-based, PD-L1 targeted IFNα1 constructs are far more active than the untargeted variant, which is substantially inactive, also compared to wild type IFNα1 (unfused, unmodified as shown in Tables 7 and 8 and FIGS. 20 and 22C). Thus, PD-L1 targeting induces and/or restores IFNα1-mediated IFNAR activation. This behavior is similar to that observed with targeting of IFNα1 that is incorporated into chimeric proteins or protein complexes, and variants thereof, to other target antigens (e.g., Clec9A and CD20: see Examples 2, 3, 7 and Tables 7 and 8), indicating that targeting is a generic approach to induce quenched or attenuated IFNα1 activity at target cells in a selective manner. Most surprisingly, induction of activity can reach or substantially overshoot that of wild type IFNα1. Interestingly, activity may be further enhanced by creating constructs that incorporate more than one copy of a targeting moiety, as shown for the (2LIG99) 2-Fc3+Fc4-IFNα1 construct (which comprises two copies of the PD-L1 VHH 2LIG99), which was able to reach potency of wild type human IFNα2 for IFNAR activation (while an untargeted Fc-IFNα1 construct has no significantly detectable activity over a large concentration range.

Figure 26B:
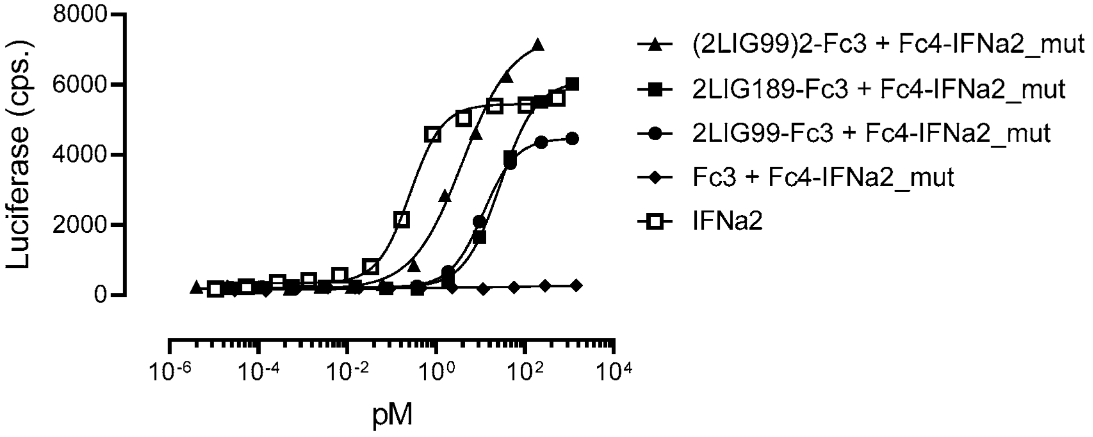

FIG. 26B shows similar analysis for constructs that incorporate a mutant form of IFNα2 instead of IFNα1. The mutant IFNα2 is a variant of IFNα2 that is substantially attenuated for IFNAR binding and activity, as indicated by the loss in IFNAR-activation and signaling activity of the untargeted Fc-based IFNα2 mutant (e.g., compared to wild type IFNα2 or other constructs). When targeted to PD-L1, IFNα2 activity is induced and/or restored. This is enhanced by integrating two copies of the PD-L1 VHH in the construct. Surprisingly, all comparable IFNα1 Fc-based constructs were more potent than the respective constructs incorporating mutant IFNα2: with EC50s on average 6-fold lower than those for respective IFNα2_mut constructs.

These findings, in conjunction with similar findings for various IFNα1 chimeric protein and chimeric protein complex constructs, and variants thereof, further demonstrate the extraordinary, unexpected and unique combination of potency and selectivity for IFNAR-activation that can be achieved on target cells when incorporating IFNα1, and variants thereof, in chimeric proteins and protein complexes. Sequences:

1. P-1542: Fc3

(SEQ ID NO: 300)

DKTHTCPPCPAPEAAGGPSVFLFPPKPKDTLMISRTPEVTCVVVDVSH
EDPEVKFNWYVDGVEVHNAKTKPREEQYNSTYRVVSVLTVLHQDWLNG
KEYKCQVSNKALPAPIEKTISKAKGQPREPQVCTLPPSRDELTKNQVS
LSCAVKGFYPSDIAVEWESNGQPENNYKTTPPVLDSDGSFFLVSKLTV
DKSRWQQGNVFSCSVMHEALHNHYTQKSLSLSPGK

2. P-2204: 2LIG99-**5*GGS**-Fc3

(SEQ ID NO: 301)

DVQLVESGGGLVQPGGSLRLSCTASGTIFSINRMDWFRQAPGKQRELV
ALITSGGTPAYADSAKGRFTISRDNSKNTVYLQMNSLRPEDTAVYYCH
VSSGVYNYWGQGTLVTVSSGGSGGSGGSGGSGGSDKTHTCPPCPAPEA
AGGPSVFLFPPKPKDTLMISRTPEVTCVVVDVSHEDPEVKFNWYVDGV
EVHNAKTKPREEQYNSTYRVVSVLTVLHQDWLNGKEYKCQVSNKALPA
PIEKTISKAKGQPREPQVCTLPPSRDELTKNQVSLSCAVKGFYPSDIA
VEWESNGQPENNYKTTPPVLDSDGSFFLVSKLTVDKSRWQQGNVFSCS
VMHEALHNHYTQKSLSLSPGK

3. P-2206: 2LIG189-**5*GGS**-Fc3

(SEQ ID NO: 302)

DVQLVESGGGLVQPGGSLRLSCAASGKIFSGNHMGWYRQAPGKQRELV
GIITSGGITDYADSVKGRFTISRDNSKNTVYLQMNSLRPEDTAVYYCN
VRDRTIWWGQGTLVTVSSGGSGGSGGSGGSGGSDKTHTCPPCPAPEAA
GGPSVFLFPPKPKDTLMISRTPEVTCVVVDVSHEDPEVKFNWYVDGVE
VHNAKTKPREEQYNSTYRVVSVLTVLHQDWLNGKEYKCQVSNKALPAP
IEKTISKAKGQPREPQVCTLPPSRDELTKNQVSLSCAVKGFYPSDIAV
EWESNGQPENNYKTTPPVLDSDGSFFLVSKLTVDKSRWQQGNVFSCSV
MHEALHNHYTQKSLSLSPGK

4. P-2399: 2LIG99-**20*GGS-2LIG99-5*GGS**-Fc3

(SEQ ID NO: 303)

DVQLQESGGGLVQPGGSLRLSCTASGTIFSINRMDWFRQAPGKQRELV
ALITSGGTPAYADSAKGRFTISRDNSKNTVYLQMNSLRPEDTAVYYCH
VSSGVYNYWGQGTLVTVSSGGSGGSGGSGGSGGSGGSGGSGGSGGSGG

-continued

SGGSGGSGGSGGSGGSGGSGGSGGSGGSGGSDVQLVESGGGLVQPGGS
LRLSCTASGTIFSINRMDWFRQAPGKQRELVALITSGGTPAYADSAKG
RFTISRDNSKNTVYLQMNSLRPEDTAVYYCHVSSGVYNYWGQGTLVTV
SSGGSGGSGGSGGSGGSDKTHTCPPCPAPEAAGGPSVFLFPPKPKDTL
MISRTPEVTCVVVDVSHEDPEVKFNWYVDGVEVHNAKTKPREEQYNST
YRVVSVLTVLHQDWLNGKEYKCQVSNKALPAPIEKTISKAKGQPREPQ
VCTLPPSRDELTKNQVSLSCAVKGFYPSDIAVEWESNGQPENNYKTTP
PVLDSDGSFFLVSKLTVDKSRWQQGNVFSCSVMHEALHNHYTQKSLSL
SPGK

5. P-2213: Fc4-**10*GGS**-hIFNα1_C86S (SEQ ID NO: 294)

DKTHTCPPCPAPEAAGGPSVFLFPPKPKDTLMISRTPEVTCVVVDVSH
EDPEVKFNWYVDGVEVHNAKTKPREEQYNSTYRVVSVLTVLHQDWLNG
KEYKCQVSNKALPAPIEKTISKAKGQPREPQVYTLPPCRDELTKNQVS
LWCLVKGFYPSDIAVEWESNGQPENNYKTTPPVLDSDGSFFLYSKLTV
DKSRWQQGNVFSCSVMHEALHNHYTQKSLSLSPGKGGSGGSGGSGGSG
GSGGSGGSGGSGGSGGSCDLPETHSLDNRRTLMLLAQMSRISPSSCLM
DRHDFGFPQEEFDGNQFQKAPAISVLHELIQQIFNLFTTKDSSAAWDE
DLLDKFSTELYQQLNDLEACVMQEERVGETPLMNADSILAVKKYFRRI
TLYLTEKKYSPCAWEVVRAEIMRSLSLSTNLQERLRRKE

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A chimeric protein complex comprising:

(a) a human interferon alpha 1 (IFNα1) comprising an amino acid sequence having at least 98% identity with SEQ ID NO: 1 and having a substitution selected from C86S, C86A, and C86Y, (b) a targeting moiety comprising a recombinant heavy-chain-only antibody (VHH) that specifically binds to a cellular target selected from Cluster of differentiation 20 (CD20), C-type lectin domain containing 9A (Clec9A), and Programmed death-ligand 1 (PD-L1), or a targeting moiety comprising FMS-like tyrosine kinase 3 ligand (Flt3L); wherein:

the IFNα1 of the chimeric protein complex exhibits attenuated activity as compared to wild type IFNα1 having SEQ ID NO: 1; and (c) an Fc domain connecting the IFNα1 and the one or more targeting moieties, the Fc domain having one or more mutations that reduce or eliminate one or more effector functions of the Fc domain, promotes Fc chain pairing in the Fc domain, or stabilizes a hinge region in the Fc domain, and being derived from a human IgG, selected from human IgG1, IgG2, IgG3, and IgG4, wherein the chimeric protein complex is a heterodimer having a trans orientation/configuration, as relates to any targeting moiety and IFNα1, relative to each other.

2. The chimeric protein complex of claim 1, wherein the IFNα1 of the chimeric protein complex comprises an amino acid sequence having at least 99% identity with SEQ ID NO: 1.

3. The chimeric protein complex of claim 1, wherein the IFNα1 of the chimeric protein complex exhibits reduced affinity or activity for interferon-a/β receptor (IFNAR).

4. The chimeric protein complex of claim 3, wherein the IFNα1 of the chimeric protein complex exhibits reduced affinity or activity for IFNAR1 or IFNAR2.

5. The chimeric protein complex of claim 1, wherein the Fc is a human IgG1 Fc and comprises one or more mutations selected from L234A, L235A, and K322Q (according to EU numbering) and/or one or more mutations selected from L234, L235, K322, D265, P329, and P331 (according to EU numbering).

6. The chimeric protein complex of claim 1, wherein the human IFNα1 comprises one or two additional mutations at a position selected from L15, A19, R23, S25, L30, D32, R33, H34, Q40, D115, L118, K121, R126, E133, K134, K135, R145, A146, M149, R150, S153, L154, and N157 or a combination thereof, wherein the positions are in reference to SEQ ID NO: 1.

7. The chimeric protein complex of claim 6, wherein the one or two additional mutations is selected from L15A, A19W, R23A, S25A, L30A, L30V, D32A, R33K, R33A, R33Q, H34A, Q40A, D115R, L118A, K121A, K121E, R126A, R126E, E133A, K134A, K135A, R145A, R145D, R145E, R145G, R145H, R145I, R145K, R145L, R145N, R145Q, R145S, R145T, R145V, R145Y, A146D, A146E, A146G, A146H, A146I, A146K, A146L, A146M, A146N, A146Q, A146R, A146S, A146T, A146V, A146Y, M149A, M149V, R150A, S153A, L154A, N157A, D115A-R121A, L118A-R121A, R121A-K122A, and R121E-K122E.

8. A composition comprising a recombinant nucleic acid encoding the chimeric protein complex of claim 1.

9. An isolated host cell comprising the nucleic acid of claim 8.

* * * * *